United States Patent
Lynch et al.

(10) Patent No.: US 10,668,118 B2
(45) Date of Patent: **\*Jun. 2, 2020**

(54) MICROBIAL CONSORTIUM AND USES THEREOF

(71) Applicant: The Regents of the University of California, San Francisco, CA (US)

(72) Inventors: Susan Lynch, Piedmont, CA (US); Nikole Kimes, San Francisco, CA (US); Din Lin, San Francisco, CA (US); Ricardo Valladares, San Francisco, CA (US); Kei Fujimura, San Francisco, CA (US)

(73) Assignee: The Regents of the University of California, Oakland, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 15/946,031

(22) Filed: Apr. 5, 2018

(65) Prior Publication Data

US 2018/0264053 A1 Sep. 20, 2018

Related U.S. Application Data

(63) Continuation of application No. PCT/US2017/020809, filed on Mar. 3, 2017.

(60) Provisional application No. 62/304,087, filed on Mar. 4, 2016.

(51) Int. Cl.
| | |
|---|---|
| *A61K 35/745* | (2015.01) |
| *A61K 39/35* | (2006.01) |
| *A61K 39/02* | (2006.01) |
| *A61K 39/00* | (2006.01) |
| *A23L 29/00* | (2016.01) |
| *A61P 1/14* | (2006.01) |
| *A61K 9/00* | (2006.01) |
| *A61K 35/747* | (2015.01) |
| *A61K 35/00* | (2006.01) |

(52) U.S. Cl.
CPC .......... *A61K 35/745* (2013.01); *A23L 29/065* (2016.08); *A61K 9/0031* (2013.01); *A61K 9/0053* (2013.01); *A61K 35/747* (2013.01); *A61K 39/0008* (2013.01); *A61K 39/02* (2013.01); *A61K 39/35* (2013.01); *A61P 1/14* (2018.01); *A61K 2035/11* (2013.01); *A61K 2039/58* (2013.01)

(58) Field of Classification Search
None
See application file for complete search history.

(56) References Cited

U.S. PATENT DOCUMENTS

| | | | |
|---|---|---|---|
| 9,011,834 B1 | 4/2015 | McKenzie et al. | |
| 9,439,953 B2 | 9/2016 | De Simone | |
| 2008/0193373 A1 | 8/2008 | Stritzker et al. | |
| 2010/0196340 A1* | 8/2010 | Graf | A23L 2/382 424/93.45 |
| 2014/0363397 A1* | 12/2014 | Allen-Vercoe | C12N 1/20 424/93.3 |
| 2015/0110834 A1* | 4/2015 | Underhill | A61K 36/06 424/195.16 |
| 2015/0246081 A1 | 9/2015 | Morris | |
| 2015/0306152 A1 | 10/2015 | Cani et al. | |
| 2016/0022592 A1* | 1/2016 | Kabadi | A61K 9/4808 424/463 |
| 2016/0068890 A1 | 3/2016 | Pichaud et al. | |
| 2016/0113971 A1 | 4/2016 | Kaplan et al. | |
| 2016/0143961 A1 | 5/2016 | Berry et al. | |
| 2016/0199424 A1 | 7/2016 | Berry et al. | |
| 2016/0235792 A1 | 8/2016 | Berry et al. | |
| 2016/0256383 A1* | 9/2016 | Allio | A61K 36/9066 |
| 2016/0271188 A1 | 9/2016 | Berry et al. | |
| 2016/0271189 A1 | 9/2016 | Cutcliffe et al. | |
| 2016/0317653 A1 | 11/2016 | Cook et al. | |
| 2017/0027996 A1 | 2/2017 | Cutcliffe et al. | |
| 2017/0151291 A1 | 6/2017 | Henn et al. | |
| 2017/0173086 A1 | 6/2017 | Boyle et al. | |
| 2017/0224745 A1 | 8/2017 | Dart | |
| 2017/0235902 A1 | 8/2017 | Almonacid et al. | |
| 2017/0296596 A1 | 10/2017 | Allen-Vercoe et al. | |
| 2017/0368108 A1 | 12/2017 | Kaplan et al. | |

FOREIGN PATENT DOCUMENTS

| | | |
|---|---|---|
| CA | 2 938 790 A1 | 8/2015 |
| CN | 102132788 B | 11/2012 |
| WO | WO-2007/138011 A1 | 12/2007 |
| WO | WO-2011/094579 A2 | 8/2011 |
| WO | WO-2011/094579 A3 | 8/2011 |
| WO | WO-2012/039615 A2 | 3/2012 |

(Continued)

OTHER PUBLICATIONS

Herbst et al., Am. J. Respir. Crit. Care Med., 184:198-205 (2011) (Year: 2011).*
Couturier-Maillard (J. Clin. Invest., 123(2):700-711 (2013) (Year: 2013).*
Hilty et al., PLoS One 5(1): e8578 (2010) (Year: 2010).*
Munoz et al., J. Exp. Med., 206(13):3047-3059 (2009).*
Punchard et al., J. Inflamm., 1(1):1-4 (2004).*
Pamer, Nature, 7(2):210-214 (2014) (Year: 2014).*
Garber, Nature Biotechnol., 33(3):228-231 (2015) (Year: 2015).*

(Continued)

*Primary Examiner* — Thomas J. Visone
(74) *Attorney, Agent, or Firm* — Mintz, Levin, Cohn, Ferris, Glovsky and Popeo, P.C.

(57) ABSTRACT

Provided herein are, inter alia, microbial compositions and methods of using the same. The microbial compositions provided include, inter alia, therapeutically effective amounts of *Lactobacillus johnsonii, Faecalibacterium prausnitzii, Akkermansia muciniphila, Myxococcus xanthus* and *Pediococcus pentosaceus* and are particularly useful for methods of treating and preventing inflammatory diseases.

27 Claims, 60 Drawing Sheets
Specification includes a Sequence Listing.

(56) References Cited

FOREIGN PATENT DOCUMENTS

| WO | WO-2012/039615 A3 | 3/2012 |
|---|---|---|
| WO | WO-2014/121302 A2 | 8/2014 |
| WO | WO-2014/121302 A3 | 8/2014 |
| WO | WO-2017/134240 A1 | 8/2017 |

OTHER PUBLICATIONS

Aichbhaumik, N. et al. (Nov. 2008, e-published Aug. 11, 2008). "Prenatal exposure to household pets influences fetal immunoglobulin E production," *Clin Exp Allergy* 38(11):1787-1794.

Arrieta, M.C. et al. (Sep. 30, 2015). "Early infancy microbial and metabolic alterations affect risk of childhood asthma," *Sci Transl Med* 7(307):307ra152.

Asher, M.I. et al. (Aug. 26, 2006). "Worldwide time trends in the prevalence of symptoms of asthma, allergic rhinoconjunctivitis, and eczema in childhood: ISAAC Phases One and Three repeat multicountry cross-sectional surveys," *Lancet* 368(9537):733-743.

Atarashi, et al. (Jan. 21, 2011). "Induction of colonic regulatory T cells by indigenous *clostridium* species," *Science* 331(6015):337-341.

Bamias G. et al. (May 2011). "Cytokines in the pathogenesis of ulcerative colitis," *Discov Med* 11(60):459-467.

Chehoud C. et al. (Aug. 2015). "Fungal Signature in the Gut Microbiota of Pediatric Patients With Inflammatory Bowel Disease," Inflamm Bowel Dis 21(8):1948-1956.

Dello S.A. et al. (2013). "Systematic review of ophthalmate as a novel bio-marker of hepatic glutathione depletion," *Clin Nutr* 32(3):325-330.

Frank, D.N. et al. (Jan. 2011, e-published Sep. 13, 2010). "Disease phenotype and genotype are associated with shifts in intestinal-associated microbiota in inflammatory bowel diseases," *Inflamm Bowel Dis* 17(1):179-184.

Fujimura, K.E. et al. (Jan. 14, 2014, e-published Dec. 16, 2013). House dust exposure mediates gut microbiome Lactobacillus enrichment and airway immune defense against allergens and virus infection *Proc. Natl. Acad. Sci.* 111(2) 805-810.

Fujimura, K.E. et al. (Oct. 2016). "Neonatal gut microbiota associates with childhood multisensitized atopy and T cell differentiation," *Nature Medicine* 22(10):1187-1191.

Gevers, D. et al. (Mar. 12, 2014). "The treatment-naive microbiome in new-onset Crohn's disease," *Cell Host Microbe* 15(3):382-392.

Henricks, P.A. et al. (Jan. 1991). "9- and 13-hydroxy-linoleic acid possess chemotactic activity for bovine and human polymorphonuclear leukocytes," *Prostaglandins* 41(1):21-27.

Hoffmann, C. et al. (2013). "Archaea and fungi of the human gut microbiome: correlations with diet and bacterial residents," *PLoS One* 8(6):e66019.

Hogan, D.A. et al. (Dec. 2004). "A Pseudomonas aeruginosa quorum-sensing molecule influences Candida albicans morphology," *Mol Microbiol* 54(5):1212-1223.

Hou, Y.C. et al. (Apr. 2013, e-published Jul. 31, 2012). Effects of alanyl-glutamine dipeptide on the expression of colon-inflammatory mediators during the recovery phase of colitis induced by dextran sulfate sodium, *Eur J Nutr* 52(3):1089-1098.

International Search Report dated Jun. 9, 2017, for PCT Application No. PCT/US2017/020809, filed Mar. 3, 2017, 5 pages.

Jensen, S.S. et al. (Jul. 27, 2010). "Differential induction of inflammatory cytokines by dendritic cells treated with novel TLR-agonist and cytokine based cocktails: targeting dendritic cells in autoimmunity," *J Inflamm* 7:37.

Juyal G. et al. (Jan. 31, 2011). "An investigation of genome-wide studies reported susceptibility loci for ulcerative colitis shows limited replication in north Indians," *PLoS One* 6:e16565.

Levy, M. et al. (Dec. 3, 2015). "Microbiota-Modulated Metabolites Shape the Intestinal Microenvironment by Regulating NLRP6 Inflammasome Signaling," *Cell* 163(6):1428-1443.

Lewis J.D. et al. (Oct. 14, 2015). "Inflammation, Antibiotics, and Diet as Environmental Stressors of the Gut Microbiome in Pediatric Crohn's Disease," *Cell Host Microbe* 18(4):489-500.

Li Q. et al. (Jul. 2014). "Dysbiosis of gut fungal microbiota is associated with mucosal inflammation in Crohn's disease," *J Clin Gastroenterol* 48(6):513-523.

Liao, J. et al. (Feb. 2007, e-published Sep. 14, 2006). "Inhibition of chronic ulcerative colitis associated adenocarcinoma development in mice by inositol compounds," *Carcinogenesis* 28(2):446-454.

Mar, J.S. et al. (Aug. 16, 2016). "Disease Severity and Immune Activity Relate to Distinct Interkingdom Gut Microbiome States in Ethnically Distinct Ulcerative Colitis Patients," *mBio* 7(4):e01072-16, pp. 1-11.

Mistry, D. et al. (Aug. 2010). "Gamma-glutamyl transferase: the silent partner?" *COPD* 7(4):285-290.

Morgan, X.C. et al. (Apr. 16, 2012). "Dysfunction of the intestinal microbiome in inflammatory bowel disease and treatment," *Genome Biol* 13(9):R79.

Nagalingam, N.A. et al. (May 2012, e-published Sep. 20, 2011). "Role of the microbiota in inflammatory bowel diseases," *Inflamm Bowel Dis* 18(5):968-984.

Nascimento N.R. et al (Jan. 3, 2006, Dec. 22, 2005). "Inositols prevent and reverse endothelial dysfunction in diabetic rat and rabbit vasculature metabolically and by scavenging superoxide," *PNAS USA* 103(1):218-223.

Neuman M.G. et al. (Jul. 2012, e-published Sep. 24, 2011). "Inflammatory bowel disease: role of diet, microbiota, life style," *Transl Res* 160(1):29-44.

Noverr. M.C. et al. (Sep. 2004). "Role of antibiotics and fungal microbiota in driving pulmonary allergic responses," *Infect Immun* 72(9):4996-5003.

Ohkusa, T. et al. (May 2009). "Commensal bacteria can enter colonic epithelial cells and induce proinflammatory cytokine secretion: a possible pathogenic mechanism of ulcerative colitis," *J Med Microbiol* 58(Pt 5):535-545.

Park, S.K. et al. (Apr. 2012, e-published May 13, 2011). "*Blautia stercoris* sp. nov., isolated from human faeces," *Int J Syst Evol Microbiol* 62(Pt 4):776-779.

Park, J. et al. (Jan. 2015, e-published Jun. 11, 2014). "Short-chain fatty acids induce both effector and regulatory T cells by suppression of histone deacetylases and regulation of the mTOR-S6K pathway," *Mucosal Immunol* 8(1):80-93.

Patel, K.P. et al. (Jun. 2012, e-published Apr. 5, 2012). "The production of p-cresol sulfate and indoxyl sulfate in vegetarians versus omnivores," *Clin J Am Soc Nephrol* 7(6):982-928.

Prindiville, T.P. et al. (Mar.-Apr. 2000). "Bacteroides fragilis enterotoxin gene sequences in patients with inflammatory bowel disease," *Emerg Infect Dis* 6(2):171-174.

Qin, X. et al. (May-Jun. 2014, e-published May 2, 2014). "Lysophosphatidylcholine perpetuates macrophage polarization toward classically activated phenotype in inflammation," *Cell Immunol* 289(1-2):185-190.

Rath, H.C. et al. (Jun. 1999). "Differential induction of colitis and gastritis in HLA-B27 transgenic rats selectively colonized with Bacteroides vulgatus or *Escherichia coli*," *Infect Immun* 67(6):2969-2974.

Riedel, C.U. et al. (Jun. 21, 2006). "Anti-inflammatory effects of bifidobacteria by inhibition of LPS-induced NF-kappaB activation," *World J Gastroenterol* 12(23):3729-3735.

Rolin, J. et al. (Jun. 2013, e-published Oct. 26, 2012). "Oxidized lipids and lysophosphatidylcholine induce the chemotaxis and intracellular calcium influx in natural killer cells," *Immunobiology* 218(6):875-883.

Sakanaka, A. et al. (Aug. 28, 2015, e-published Jun. 17, 2015). "Arginine-Ornithine Antiporter ArcD Controls Arginine Metabolism and Interspecies Biofilm Development of *Streptococcus gordonii*," *J Biol Chem* 290(35):21185-21198.

Schepers, E. et al. (Feb. 2007, e-published Oct. 13, 2006). "P-cresylsulphate, the main in vivo metabolite of p-cresol, activates leucocyte free radical production," *Nephrol Dial Transplant* 22(2):592-596.

(56) References Cited

OTHER PUBLICATIONS

Shenker, B.J. et al. (Dec. 1991). "Immunosuppressive effects of Prevotella intermedia on in vitro human lymphocyte activation," *Infect Immun* 59(12):4583-4589.

Simpson, A. et al. (Jun. 1, 2010, e-published Feb. 18, 2010). "Beyond atopy: multiple patterns of sensitization in relation to asthma in a birth cohort study," *Am J Respir Crit Care Med* 181(11):1200-1206.

Sokol, H. et al. (Oct. 28, 2008, e-published Oct. 20, 2008). "*Faecalibacterium prausnitzii* is an anti-inflammatory commensal bacterium identified by gut microbiota analysis of Crohn disease patients," *PNAS USA* 105(43):16731-16736.

Totani, Y. et al. (Jan. 2000). "Leukotoxin and its diol induce neutrophil chemotaxis through signal transduction different from that of fMLP," *Eur Respir J* 15(1):75-79.

Trompette, A. et al. (Feb. 2014, e-published Jan. 5, 2014). "Gut microbiota metabolism of dietary fiber influences allergic airway disease and hematopoiesis," *Nat Med* 20(2):159-166.

Walmsley, R.S. et al. (Jul. 1998). "A simple clinical colitis activity index," 43(1):29-32.

Walters, J.D. et al. (May 1995). "Polyamines found in gingival fluid enhance the secretory and oxidative function of human polymorphonuclear leukocytes in vitro," *J Periodontal Res* 30(3):167-171.

Weingarden, A.R. et al. (Feb. 15, 2014, e-published Nov. 27, 2013). "Microbiota transplantation restores normal fecal bile acid composition in recurrent Clostridium difficile infection," *Am J Physiol Gastrointest Liver Physiol* 306(4):G310-G319.

Wenzel, S.E. (May 4, 2012). "Asthma phenotypes: the evolution from clinical to molecular approaches," *Nat Med* 18(5):716-725.

Written Opinion dated Jun. 9, 2017, for PCT Application No. PCT/US2017/020809, filed Mar. 3, 2017, 11 pages.

Yatsunenko, T. et al. (May 9, 2012). "Human gut microbiome viewed across age and geography," *Nature* 486(7402):222-227.

Young, D. et al. (Feb. 2012, e-published Dec. 21, 2011). "Soy-derived di- and tripeptides alleviate colon and ileum inflammation in pigs with dextran sodium sulfate-induced colitis," *J Nutr* 142(2):363-368.

Zhang, W. et al. (Dec. 2013). "Soluble epoxide hydrolase deficiency inhibits dextran sulfate sodium-induced colitis and carcinogenesis in mice," 33(12):5261-5271.

Zwolinska-Wcislo et al. (Mar. 2009). "Effect of Candida colonization on human ulcerative colitis and the healing of inflammatory changes of the colon in the experimental model of colitis ulcerosa," *J Physiol Pharmacol* 60(1):107-118.

Remely, M. et al. (May 2015, e-published Mar. 13, 2015). "Increased gut microbiota diversity and abundance of Faecalibacterium prausnitzii and Akkermansia after fasting: a pilot study," *Wien Klin Wochenschr* 127(9-10):394-398.

Kumar, R.S. et al. (2016). "Pharmaceutical Suspensions: Patient Compliance Oral Dosage Forms," *World Journal of Pharmacy and Pharmaceutical Sciences* 5(12):1471-1537.

Rowe, R.C. et al. (2009). *Handbook of Pharmaceutical Excipients*, Sixth Edition pp. 283-286.

Stenman, L.K. et al. (Feb. 2016, e-published Nov. 13, 2015). "Establishing a causal link between gut microbes, body weight gain and glucose metabolism in humans—towards treatment with probiotics," *Benef Microbes* 7(1):11-22.

\* cited by examiner

FIG. 17

| Cockroach Allergen (CRA) | Gavage Intervention | Group |
|---|---|---|
| - (PBS) | PBS Vehicle | No CRA |
| + | PBS Vehicle | CRA+PBS |
| + | Therapeutic Consortium (TC) | CRA+TC |
| + | *L. johnsonii* (Lj) | CRA+Lj |
| + | Consortium without Lj (C) | CRA+C |
| + | Heat-Killed TC (HKTC) | CRA+HKTC |

FIG. 21

|  | DMM community states | | | RR (95% CI) | | | Overall P value |
|---|---|---|---|---|---|---|---|
|  | NGM1 (n = 70) | NGM2 (n = 49) | NGM3 (n = 11) | NGM2 versus NGM1 | NGM3 versus NGM1 | NGM3 versus NGM2 |  |
| Atopy (PM) | 13 (18.6%) | 13 (26.5%) | 6 (54.5%) | 1.43 (0.73–2.81) $P = 0.30$ | 2.94 (1.42–6.09) $P = 0.004$ | 2.06 (1.01–4.19) $P = 0.048$ | 0.034 |
| Parental report of doctor-diagnosed asthma[a,b] | 8 (13.6%) | 5 (11.9%) | 4 (40.0%) | 0.87 (0.31–2.50) $P = 0.81$ | 2.95 (1.09–7.98) $P = 0.033$ | 3.36 (1.10–10.3) $P = 0.034$ | 0.13 |
| Atopy (IgE > 0.35 IU ml$^{-1}$) | 29 (41.4%) | 25 (51%) | 7 (63.6%) | 1.23 (0.83–1.82) $P = 0.30$ | 1.54 (0.91–2.60) $P = 0.11$ | 1.25 (0.74–2.11) $P = 0.41$ | 0.30 |

[a] n = 19 missing information regarding doctor diagnosis of asthma; [b] average age at interview, 4.1 years (s.d. of 0.84).

| Allergen | n | Mean (SD) | Median | [Min, Max] |
|---|---|---|---|---|
| Alternaria | 292 | 0.21 (0.86) | 0.05 | [0.05, 12.8] |
| German cockroach (Bla g 2) | 296 | 0.22 (1.09) | 0.05 | [0.05, 14.7] |
| Dog (Can f 1) | 295 | 0.2 (0.65) | 0.05 | [0.05, 6.22] |
| House dust mite (Der f 1) | 295 | 0.18 (0.72) | 0.05 | [0.05, 7.55] |
| Egg | 298 | 1.48 (10.64) | 0.05 | [0.05, 170] |
| Cat (Fel d 1) | 295 | 0.23 (1.27) | 0.05 | [0.05, 14.8] |
| Milk | 296 | 0.79 (3.65) | 0.05 | [0.05, 59.0] |
| Peanut | 291 | 2.88 (34.07) | 0.05 | [0.05, 572] |
| Common ragweed | 292 | 0.08 (0.12) | 0.05 | [0.05, 1.08] |
| Timothy grass | 296 | 0.09 (0.23) | 0.05 | [0.05, 2.22] |

FIG. 27

| | DMM community state | | RR (95% CI) IGM2 versus IGM1 | P-value |
|---|---|---|---|---|
| | IGM1 (n = 89) | IGM2 (n = 79) | | |
| Atopy (PM) | 21 (23.6%) | 19 (24.1%) | 1.02 (0.59, 1.75) | 0.94 |
| Parental report of doctor diagnosed asthma | 15 (19.2%) | 7 (9.7%) | 0.51 (0.22, 1.17) | 0.11 |
| Atopy (IgE > 0.35 IU ml$^{-1}$) | 49 (55.1%) | 38 (48.1%) | 0.87 (0.65, 1.17) | 0.37 |

FIG. 28

| OTU | NGM1-NGM3 | q-value | Phylum | Order | Family | Genus |
|---|---|---|---|---|---|---|
| 1 | 7207.18 | 7.1E-11 | Ascomycota | Saccharomycetales | Unclassified | Unclassified |
| 17 | 803.31 | 6.7E-03 | Basidiomycota | Malasseziales | Incertae sedis | Malassezia |
| 430 | 188.46 | 6.7E-05 | Basidiomycota | Malasseziales | Incertae sedis | Malassezia |
| 25 | 150.36 | 6.2E-127 | Unclassified | Unclassified | Unclassified | Unclassified |
| 2188 | 82.78 | 3.2E-02 | Ascomycota | Capnodiales | Davidiellaceae | Unclassified |
| 997 | 42.42 | 1.7E-03 | Ascomycota | Eurotiales | Trichocomaceae | Unclassified |
| 109 | 22.28 | 2.2E-49 | Unclassified | Unclassified | Unclassified | Unclassified |
| 102 | 8.80 | 3.8E-11 | Basidiomycota | Trichosporonales | Trichosporonaceae | Unclassified |
| 228 | 4.21 | 1.0E-05 | Ascomycota | Chaetothyriales | Unclassified | Unclassified |
| 2111 | 2.72 | 1.0E-01 | Unclassified | Unclassified | Unclassified | Unclassified |
| 318 | 2.01 | 1.8E-01 | Basidiomycota | Malasseziales | Incertae sedis | Malassezia |
| 172 | 0.22 | 2.6E-02 | Ascomycota | Saccharomycetales | Incertae sedis | Candida |
| 2344 | -919.11 | 6.2E-04 | Basidiomycota | Sporidiobolales | Incertae sedis | Rhodotorula |
| 84 | -384.58 | 1.8E-29 | Ascomycota | Hypocreales | Nectriaceae | Unclassified |
| 145 | -171.96 | 2.6E-14 | Basidiomycota | Polyporales | Phanerochaetaceae | Phanerochaete |
| 94 | -70.57 | 3.5E-17 | Ascomycota | Pleosporales | Pleosporaceae | Unclassified |
| 23 | -52.81 | 3.1E-07 | Ascomycota | Unclassified | Unclassified | Unclassified |
| 107 | -35.81 | 1.4E-06 | Ascomycota | Saccharomycetales | Incertae sedis | Unclassified |
| 29 | -35.64 | 1.4E-06 | Ascomycota | Saccharomycetales | Incertae sedis | Candida |
| 69 | -32.10 | 1.9E-12 | Ascomycota | Saccharomycetales | Incertae sedis | Cyberlindnera |
| 62 | -31.93 | 1.2E-06 | Ascomycota | Saccharomycetales | Debaryomycetaceae | Meyerozyma |
| 273 | -31.29 | 3.9E-03 | Ascomycota | Unclassified | Unclassified | Unclassified |
| 260 | -10.47 | 3.0E-43 | Ascomycota | Pleosporales | Incertae sedis | Unclassified |
| 2018 | -9.79 | 2.7E-19 | Ascomycota | Saccharomycetales | Saccharomycetaceae | Saccharomyces |
| 637 | -7.64 | 5.1E-03 | Basidiomycota | Sporidiobolales | Incertae sedis | Rhodotorula |
| 367 | -7.60 | 2.4E-03 | Basidiomycota | Unclassified | Unclassified | Unclassified |
| 473 | -2.96 | 1.0E-03 | Ascomycota | Pleosporales | Cucurbitariaceae | Pyrenochaetopsis |
| 745 | -1.31 | 4.7E-03 | Ascomycota | Saccharomycetales | Incertae sedis | Candida |
| 1971 | -0.91 | 1.2E-02 | Ascomycota | Saccharomycetales | Saccharomycetaceae | Saccharomyces |

FIG. 29

| OTU | NGM2-NGM3 | q-value | Phylum | Order | Family | Genus |
|---|---|---|---|---|---|---|
| 17 | 1462.83 | 2.5E-05 | Basidiomycota | Malasseziales | Incertae sedis | Malassezia |
| 430 | 180.12 | 5.5E-05 | Basidiomycota | Malasseziales | Incertae sedis | Malassezia |
| 2113 | 88.31 | 1.9E-01 | Basidiomycota | Malasseziales | Incertae sedis | Malassezia |
| 656 | 80.83 | 4.9E-02 | Basidiomycota | Malasseziales | Incertae sedis | Malassezia |
| 2188 | 64.25 | 1.0E-01 | Ascomycota | Capnodiales | Davidiellaceae | Unclassified |
| 997 | 22.41 | 1.5E-02 | Ascomycota | Eurotiales | Trichocomaceae | Unclassified |
| 171 | 19.59 | 1.1E-140 | Unclassified | Unclassified | Unclassified | Unclassified |
| 102 | 12.02 | 1.6E-56 | Basidiomycota | Trichosporonales | Trichosporonaceae | Trichosporon |
| 2252 | 7.46 | 2.0E-01 | Basidiomycota | Malasseziales | Incertae sedis | Malassezia |
| 165 | 6.18 | 1.9E-01 | Ascomycota | Eurotiales | Trichocomaceae | Unclassified |
| 2111 | 3.01 | 1.8E-02 | Unclassified | Unclassified | Unclassified | Unclassified |
| 878 | 0.78 | 4.1E-05 | Unclassified | Unclassified | Unclassified | Unclassified |
| 2277 | 0.76 | 3.8E-03 | Unclassified | Unclassified | Unclassified | Unclassified |
| 1884 | 0.45 | 8.2E-02 | Unclassified | Unclassified | Unclassified | Unclassified |
| 1309 | 0.08 | 8.2E-02 | Unclassified | Unclassified | Unclassified | Unclassified |
| 2344 | -920.65 | 3.3E-04 | Basidiomycota | Sporidiobolales | Incertae sedis | Rhodotorula |
| 84 | -364.28 | 5.9E-70 | Ascomycota | Hypocreales | Nectriaceae | Unclassified |
| 963 | -178.30 | 1.1E-01 | Ascomycota | Saccharomycetales | Incertae sedis | Candida |
| 28 | -164.94 | 1.1E-15 | Ascomycota | Saccharomycetales | Incertae sedis | Debaryomyces |
| 23 | -52.77 | 1.6E-04 | Unclassified | Unclassified | Unclassified | Unclassified |
| 107 | -35.06 | 2.5E-22 | Ascomycota | Saccharomycetales | Incertae sedis | Unclassified |
| 62 | -29.90 | 1.7E-03 | Ascomycota | Saccharomycetales | Debaryomycetaceae | Meyerozyma |
| 187 | -20.35 | 1.0E-12 | Ascomycota | Trichosphaeriales | Incertae sedis | Nigrospora |
| 260 | -10.68 | 6.4E-20 | Ascomycota | Pleosporales | Incertae sedis | Unclassified |
| 2018 | -9.91 | 5.1E-13 | Ascomycota | Saccharomycetales | Saccharomycetaceae | Saccharomyces |
| 473 | -2.94 | 1.7E-03 | Ascomycota | Pleosporales | Cucurbitariaceae | Pyrenochaetopsis |
| 1505 | -2.15 | 1.7E-13 | Unclassified | Unclassified | Unclassified | Unclassified |
| 1944 | -1.80 | 1.8E-02 | Ascomycota | Unclassified | Unclassified | Unclassified |
| 745 | -1.27 | 1.7E-02 | Ascomycota | Saccharomycetales | Incertae sedis | Candida |
| 885 | -0.37 | 1.8E-02 | Unclassified | Unclassified | Unclassified | Unclassified |

| Comparison | r* (M²) | P-value |
|---|---|---|
| 16S rRNA versus PICRUSt | 0.72 (0.48) | < 0.001 |
| 16S rRNA versus Metabolomics | 0.87 (0.24) | < 0.001 |
| PICRUSt versus Metabolomics | 0.66 (0.56) | 0.010 |

*r = correlation between data sources. Unweighted UniFrac distance used for 16S rRNA; Canberra distance used for PICRUSt and Metabolomic datasets.

| | EU-Healthy | SA-Healthy | EU-UC | SA-UC |
|---|---|---|---|---|
| Healthy | 10 | 3 | 18 | 12 |
| Male:Female | 7:3 | 1:2 | 7:11 | 9:2 |
| Median Age (range) | 28.5 (26-67) | 38 (29-59) | 36.5 (22-67) | 43 (24-76) |
| Median BMI (range) | 21.9 (19.94-28.98) | 24.69 (23.06-26.83) | 24.94 (17.47-32.89) | 23.78 (18.47-28.06) |
| Medication History: | | | | |
| ASA Usage – Current:Unknown (MSC-1:-2:-3:-4) | NA | NA | 9:3 (5:3:0:NA) | 9:1 (3:1:3:2) |
| Corticosteroid Usage – Current: Unknown (MSC-1:-2:-3:-4) | NA | NA | 4:3 (2:1:1:NA) | 5:2 (2:0:1:2) |
| Antimetabolite Usage – Current: Unknown (MSC-1:-2:-3:-4) | NA | NA | 7:8 (4:3:0:NA) | 2:8 (0:0:1:1) |
| Biologics Usage – Current: Unknown (MSC-1:-2:-3:-4) | NA | NA | 5:12 (3:2:0:NA) | 1:10 (0:1:0:0) |

FIG. 38

| Type | Description | Purpose |
|---|---|---|
| MTRX | Large pool of human plasma maintained by Metabolon that has been characterized extensively. | Assure that all aspects of Metabolon process are operating within specifications. |
| CMTRX | Pool created by taking a small aliquot from every customer sample. | Assess the effect of a non-plasma matrix on the Metabolon process and distinguish biological variability from process variability. |
| PRCS | Aliquot of ultra-pure water | Process Blank used to assess the contribution to compound signals from the process. |
| SOLV | Aliquot of solvents used in extraction. | Solvent blank used to segregate contamination sources in the extraction. |

FIG. 39

| Type | Description | Purpose |
|---|---|---|
| DS | Derivatization Standard | Assess variability of derivatization for GC/MS samples. |
| IS | Internal Standard | Assess variability and performance of instrument. |
| RS | Recovery Standard | Assess variability and verify performance of extraction and instrumentation. |

MICROBIAL CONSORTIUM AND USES THEREOF

CROSS-REFERENCE TO RELATED APPLICATIONS

This application is a continuation of PCT International Application No. PCT/US2017/020809, filed Mar. 3, 2017, which claims the benefit of priority to U.S. Provisional Application No. 62/304,087, filed Mar. 4, 2016, the entire contents of each of which are hereby incorporated by reference in their entireties and for all purposes.

STATEMENT AS TO RIGHTS TO INVENTIONS MADE UNDER FEDERALLY SPONSORED RESEARCH AND DEVELOPMENT

This invention was made with government support under grant numbers R21 AT004732, P01 AI089473, and HL080074 awarded by the National Institutes of Health. The Government has certain rights in the invention.

INCORPORATION-BY-REFERENCE OF SEQUENCE LISTING

The content of the text file named "48536_575C01US_Sequence_Listing.txt", which was created on Apr. 5, 2018, and is 107,578 bytes in size, is hereby incorporated by reference in its entirety.

BACKGROUND OF THE INVENTION

Recent studies provide evidence that microbial communities residing in the human gut play a key role in the development and modulation of the host immune response. For instance, the presence of particular *Clostridium* species has been shown to induce specific T-cell repertoires [Atarashi, et al. (2011) Induction of colonic regulatory T cells by indigenous *Clostridium* species. Science 331(6015):337-341]. Despite the complexity of the gut microbiome, the presence or absence of specific bacterial species can dramatically alter the adaptive immune environment.

BRIEF SUMMARY OF THE INVENTION

Provided herein are novel methods and microbial compositions including *Lactobacillus johnsonii*, *Faecalibacterium prausnitzii*, *Akkermansia muciniphila*, *Myxococcus xanthus*, and *Pediococcus penrtosaceus*, which are surprisingly useful for the treatment of dysbiosis, infections, and inflammatory diseases.

An aspect provides methods and compositions comprising a bacterial population that comprises, consists essentially of, or consists of, 1, 2, 3, 4, 5, 6, 7, or 8 (or at least 1, 2, 3, 4, 5, 6, 7, or 8) bacterial species. In embodiments, the bacterial population comprises, consists essentially of, or consists of any 1, 2, 3, 4, 5, 6, 7, or 8 of *Lactobacillus* sp., *Faecalibacterium* sp., *Akkermansia* sp., *Myxococcus* sp., *Cysobacter* sp., *Pediococcus* sp., *Bifidobacterium* sp., and *Clostridium* sp. In embodiments, the bacterial population comprises *Lactobacillus* sp. and *Faecalibacterium prausnitzii*. In embodiments, the bacterial population comprises *Lactobacillus* sp. and *Akkermansia muciniphila*. In embodiments, the bacterial population comprises *Lactobacillus* sp., and *Myxococcus xanthus*. In embodiments, the bacterial population comprises *Lactobacillus* sp. and *Cystobacter fuscus*. In embodiments, the bacterial population comprises *Lactobacillus* sp. and *Pediococcus pentosaceus*, *Pediococcus acidilactici*, *Pediococcus damnosus*, *Pediococcus ethanolidurans*, or *Pediococcus parvulus*. In embodiments, the bacterial population comprises *Lactobacillus* sp. and *Bifidobacterium bifidum*, *Bifidobacterium pseudolongum*, *Bifidobacterium saeculare*, or *Bifidobacterium subtile*. In embodiments, the bacterial population comprises *Lactobacillus* sp. and *Clostridium hiranonis*. In embodiments, the *Lactobacillus* sp. is *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*. In embodiments, the *Lactobacillus* sp. is *Lactobacillus johnsonii*. In embodiments, the bacterial population comprises at least 1, 2, 3, 4, 5, 6, 7, 8, 9, or 10, or from 1-5, 1-10, 1-5, or 1-20 of any combination of the following: *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*. *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, *Lactococcus lactis*, *Faecalibacterium prausnitzii*, *Akkermansia muciniphila*, *Myxococcus xanthus*, *Cystobacter fuscus*, *Pediococcus pentosaceus*, *Pediococcus acidilactici*, *Pediococcus damnosus*, *Pediococcus ethanolidurans*, and *Pediococcus parvulus*. In embodiments, the bacterial population includes *Lactobacillus johnsonii*, *Faecalibacterium prausnitzii*, *Akkermansia muciniphila*, *Myxococcus xanthus*, and/or *Pediococcus pentosaceus*.

In an aspect, a method for administering isolated bacteria is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. In embodiments, the bacterial population includes *Lactobacillus johnsonii, Faecalibacterium prausnitzii, Akkermansia muciniphila, Myxococcus xanthus*, and/or *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect, a method of bacterial supplementation is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. In embodiments, the bacterial population includes *Lactobacillus johnsonii, Faecalibacterium prausnitzii, Akkermansia muciniphila, Myxococcus xanthus*, and/or *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect, a method of treating or preventing inflammation in a subject in need thereof is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. In embodiments, the bacterial population includes *Lactobacillus johnsonii, Faecalibacterium prausnitzii, Akkermansia muciniphila, Myxococcus xanthus*, and/or *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect, a microbial composition is provided. In embodiments, the microbial composition comprises *Lactobacillus* sp., *Faecalibacterium* sp., *Akkermansia* sp., *Myxococcus* sp., and/or *Pediococcus* sp. In embodiments, the microbial composition comprises *Lactobacillus* sp., *Faecalibacterium* sp., *Akkermansia* sp., *Cystobacter* sp., and/or *Pediococcus* sp. In embodiments, the composition includes *Lactobacillus johnsonii, Faecalibacterium prausnitzii, Akkermansia muciniphila, Myxococcus xanthus, Pediococcus pentosaceus* and a biological carrier suitable for administration to the gut. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect, a microbial composition is provided. In embodiments, the microbial composition comprises *Lactobacillus* sp., *Faecalibacterium* sp., *Akkermansia* sp., *Myxococcus* sp., and/or *Pediococcus* sp. In embodiments, the microbial composition comprises *Lactobacillus* sp., *Faecalibacterium* sp., *Akkermansia* sp., *Cystobacter* sp., and/or *Pediococcus* sp. In embodiments, the composition includes *Lactobacillus johnsonii, Faecalibacterium prausnitzii, Akkermansia muciniphila, Myxococcus xanthus* or *Pediococcus pentosaceus* and a biological carrier suitable for administration to the gut. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect a pharmaceutical composition is provided. In embodiments, the pharmaceutical composition comprises *Lactobacillus* sp., *Faecalibacterium* sp., *Akkermansia* sp., *Myxococcus* sp., and/or *Pediococcus* sp. In embodiments, the pharmaceutical composition comprises *Lactobacillus* sp., *Faecalibacterium* sp., *Akkermansia* sp., *Cystobacter* sp., and/or *Pediococcus* sp. In embodiments, the pharmaceutical composition includes a therapeutically effective amount of *Lactobacillus johnsonii, Faecalibacterium prausnitzii, Akkermansia muciniphila, Myxococcus xanthus*, and *Pediococcus pentosaceus* and a pharmaceutically acceptable excipient is provided. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect a method of treating or preventing an inflammatory disease in a subject in need thereof is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. The method includes administering to the subject a therapeutically effective amount of *Lactobacillus johnsonii, Faecalibacterium prausnitzii, Akkermansia muciniphila, Myxococcus xanthus* and *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect is provided a method of increasing an anti-inflammatory metabolite in a subject in need thereof is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. In embodiments, the method includes administering to the subject a therapeutically effective amount of *Lactobacillus johnsonii, Faecalibacterium prausnitzii, Akkermansia muciniphila, Myxococcus xanthus* and *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect is provided a method of decreasing a pro-inflammatory metabolite in a subject in need thereof is provided. In embodiments, the method comprises administering to the subject an effective amount of a bacterial population comprising *Lactobacillus* sp., *Faecalibacterium* sp., *Akkermansia* sp., *Myxococcus* sp., and/or *Pediococcus* sp. In embodiments, the method comprises administering to the subject an effective amount of a bacterial population comprising *Lactobacillus* sp., *Faecalibacterium* sp., *Akkermansia* sp., *Cystobacter* sp., and/or *Pediococcus* sp. In embodiments, the method includes administering to the subject a therapeutically effective amount of *Lactobacillus johnsonii, Faecalibacterium prausnitzii, Akkermansia muciniphila, Myxococcus xanthus* and *Pediococcus pentosaceus*. In embodiments, the bacterial population further comprises *Bifidobacterium* sp. or *Clostridium* sp. In embodiments, the bacterial population further comprises *Bifidobacterium* sp. or *Clostridium hiranonis*.

In an aspect a method of detecting an anti-inflammatory metabolite in a subject that has or is at risk for developing an inflammatory disease is provided. The method includes (i) obtaining a biological sample from the subject; and (ii) determining an expression level of an anti-inflammatory metabolite in the biological sample.

In an aspect a method of detecting a pro-inflammatory metabolite in a subject that has or is at risk for developing an inflammatory disease is provided. The method includes (i) obtaining a biological sample from the subject; and (ii) determining an expression level of a pro-inflammatory metabolite in the biological sample.

In an aspect, a method of determining whether a subject has or is at risk of developing an inflammatory disease is provided. The method includes (i) detecting an expression level of one or more anti-inflammatory metabolites or pro-inflammatory metabolites in a subject; (ii) determining whether the expression level is increased or decreased relative to a standard control, wherein an elevated expression level of an pro-inflammatory metabolite or a decreased expression level of an anti-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In an aspect, a method of determining whether a subject has or is at risk of developing an inflammatory disease is provided. The method includes (i) detecting an expression level of one or more pro-inflammatory metabolites in a subject; (ii) determining whether the expression level is increased or decreased relative to a standard control, wherein an increased expression level of an pro-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In an aspect, a method of determining whether a subject has or is at risk of developing an inflammatory disease is provided. The method includes (i) detecting an expression level of one or more anti-inflammatory metabolites in a subject; (ii) determining whether the expression level is increased or decreased relative to a standard control, wherein a decreased expression level of an anti-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In an aspect, a method of monitoring the effect of treatment for an inflammatory disease in a subject undergoing inflammatory disease therapy or a patient that has received inflammatory disease therapy is provided. The method includes (i) determining a first expression level of an anti-inflammatory metabolite in the subject at a first time point; (ii) determining a second expression level of an anti-inflammatory metabolite in the subject at a second time point; and (iii) comparing the second expression level of an anti-inflammatory metabolite to the first expression level of an anti-inflammatory metabolite, thereby determining the effect of treatment for an inflammatory disease in the subject.

In an aspect, a method of monitoring the effect of treatment for an inflammatory disease in a subject undergoing inflammatory disease therapy or a patient that has received inflammatory disease therapy is provided. The method includes (i) determining a first expression level of a pro-inflammatory metabolite in the subject at a first time point; (ii) determining a second expression level of a pro-inflammatory metabolite in the subject at a second time point; and (iii) comparing the second expression level of a pro-inflammatory metabolite to the first expression level of a pro-inflammatory metabolite, thereby determining the effect of treatment for an inflammatory disease in the subject.

In an aspect, a method of determining an inflammatory disease activity in a subject is provided. The method includes (i) detecting an expression level of one or more anti-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

In an aspect, a method of determining an inflammatory disease activity in a subject is provided. The method includes (i) detecting an expression level of one or more pro-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

BRIEF DESCRIPTION OF THE DRAWINGS

FIG. 1A: Representative images of PAS staining for each of the six groups clearly show that mucin secretion of goblet cells (stained) is induced in CRA challenged mice and that supplementation with *L. johnsonii* and microbial consortium is the only treatment group that protects against this induction. FIG. 1B: Image J was used to quantify the percentage of area in each image that is positive for PAS staining. Each data point is represented by an individual symbol generated in two independent murine studies. Statistical analyses of this data show significant reductions in the percentage of PAS staining associated with the C+Lj consortium supplemented mice compared to all other CRA treated groups.

and IL-17. Similarly, Applicants observed a significant decrease in cytokine expression associated with C+Lj supplementation for the Th2-associated cytokines (IL-4 and IL-13), as well as IL-10. Data from two independent replicate studies is presented.

Figure 4:
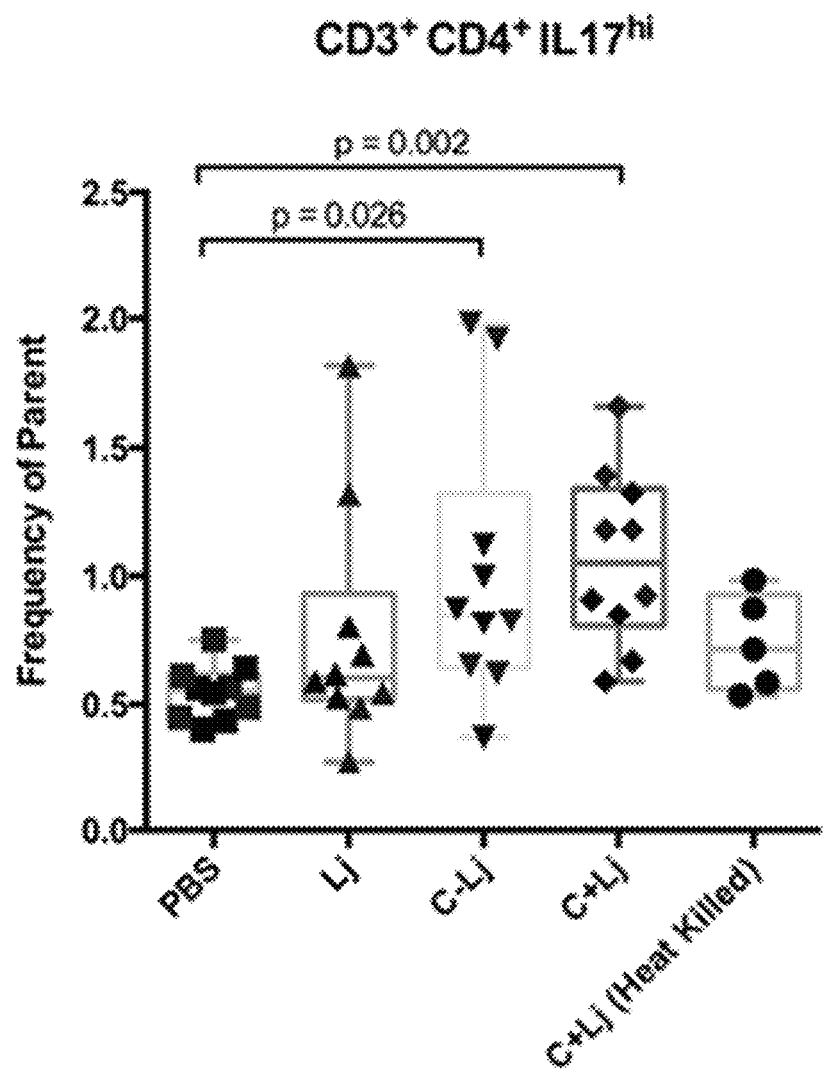

FIG. 4. Increased percentage of 11-17 secreting T helper cells (CD3+CD4+) is most significant in mice supplemented with C+Lj. Flow cytometry data from splenocytes reveal a significant increase in the percentage of CD4+ cells expressing IL-17, a cytokine associated with Th 17 cells. This observation held true across duplicated studies, and the data from both studies are shown here.

Figure 5A:
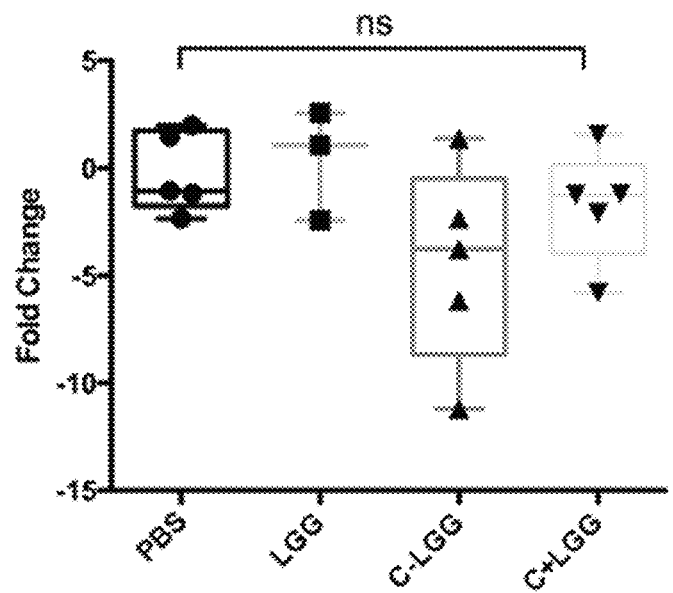
Figure 5B:
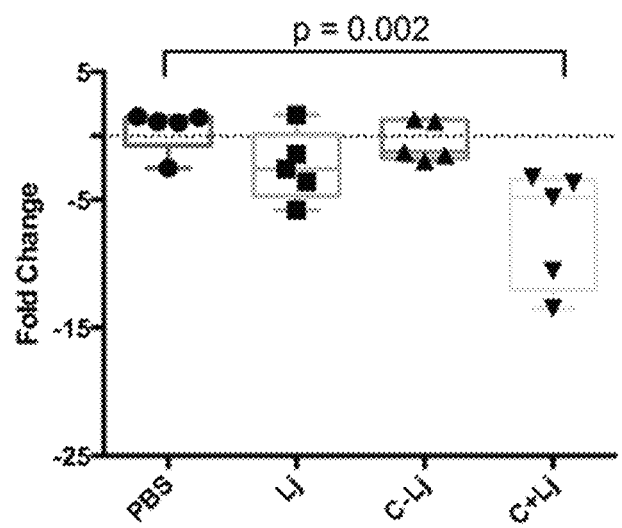

FIGS. 5A-5B. The bacterial consortium including *L. johnsonii*, but not *L. rhamnosus* LGG, provides attenuation of allergic sensitization. The CRA allergen mouse study was performed using either *L. rhamnosus* LGG (LGG) or *L. johnsonii* (Lj) as the *Lactobacillus* anchor species included in the bacterial consortium supplement. To evaluate the effect of each consortium on sensitization, the expression level of MUC5AC was determined in lung tissue using qPCR. The *L. johnsonii*-based consortium significantly decreased MUC5AC expression, whereas the *L. rhamnosus* LGG consortium failed decrease the expression of this allergic response biomarker.

Figure 6A:
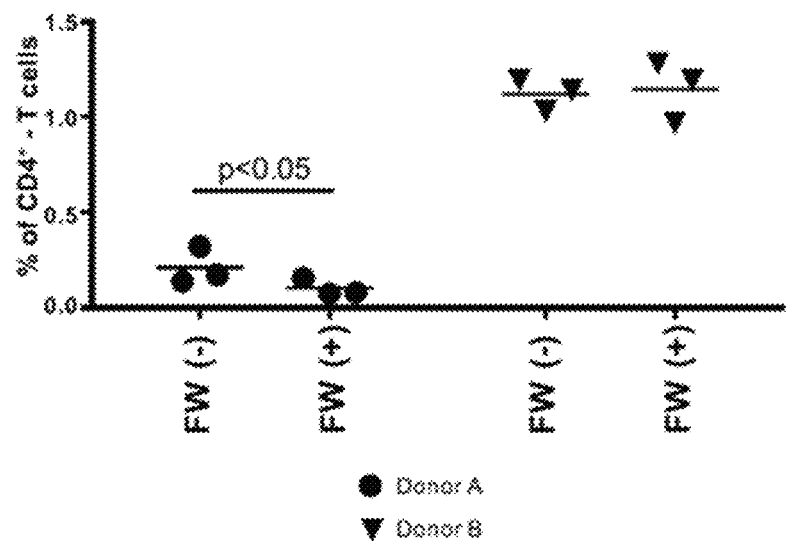
Figure 6B:
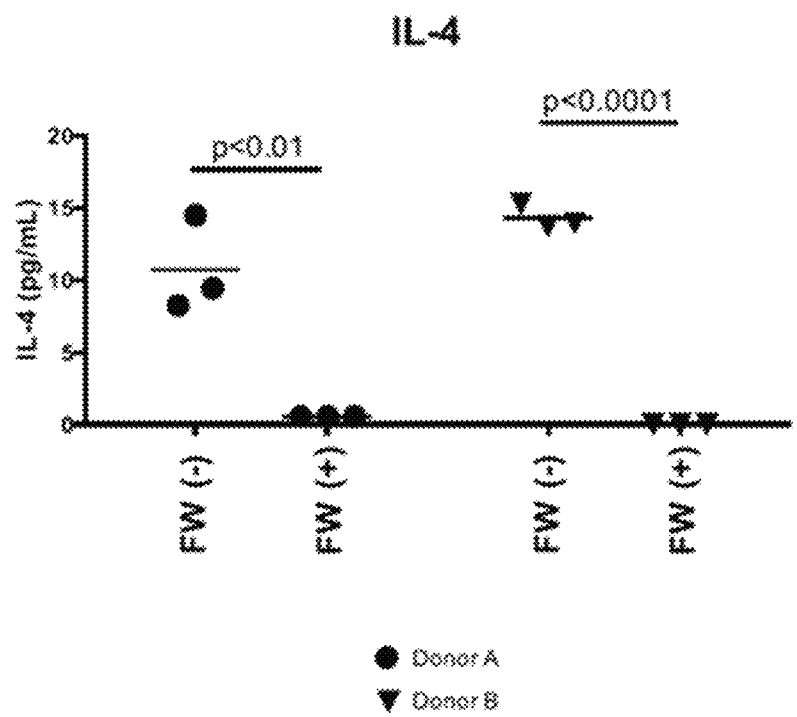
Figure 6C:
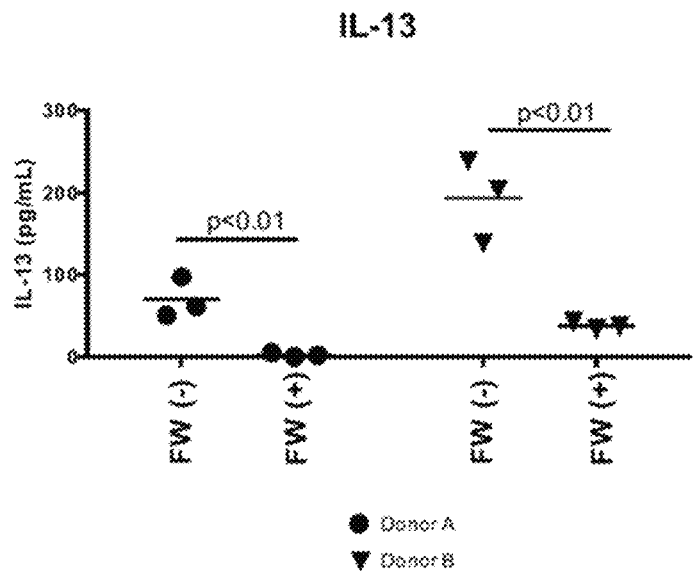

FIGS. 6A-6C. Fecal water from a non-atopic neonate significantly reduces expression of IL4 and IL13 responses. FIG. 6A: Fecal water exposure significantly decreases the number of CD4+ T-helper 2 cells in one but not both donors. FIG. 6B: IL4 expression is significantly reduced in both donors. FIG. 6C: IL13 expression is significantly reduced in both donors.

Figure 7A:
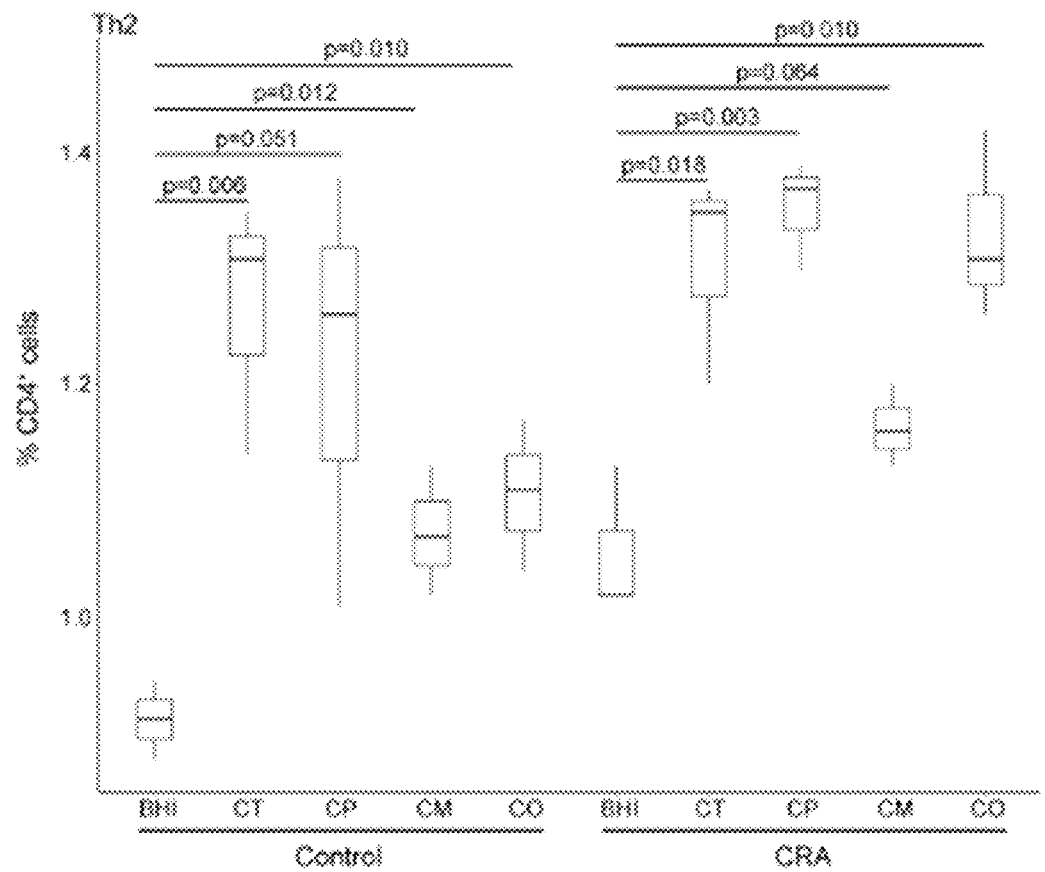
Figure 7B:
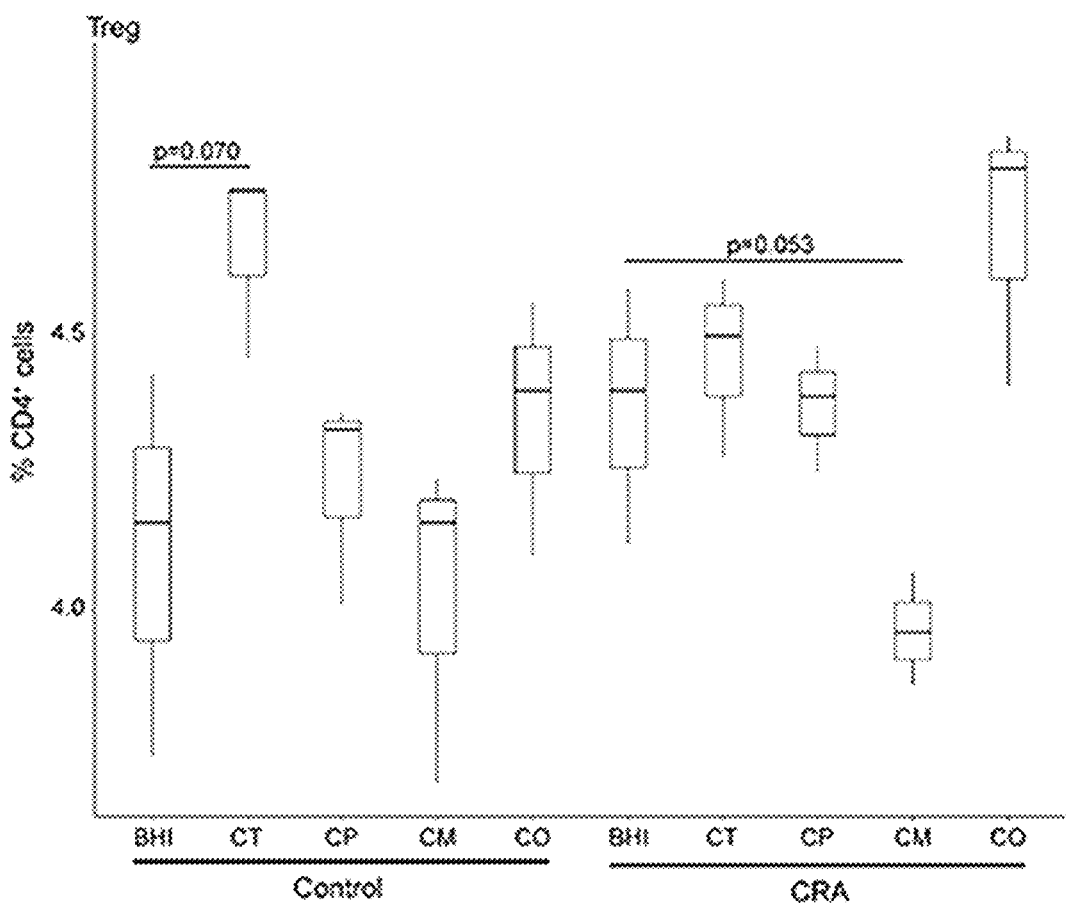

FIGS. 7A-7B. Cell-free supernatant from distinct neonatal gut microbiome isolates of *Candida* consistently induce CD4+ IL4+ (Th2) cells (FIG. 7A). Specific species induce or suppress CD4+ IL10+ (T-reg) cells (FIG. 7B). BHI, sterile brain heart infusion medium exposure (control); CT, *C. tropicalis*; CP, *C. parapsilosis*; CO, *C. orthopsilosis*; and CT, *C. tropicalis*; Control, non-antigen stimulated conditions; CRA, cockroach stimulated T-cells.

Figure 8A:
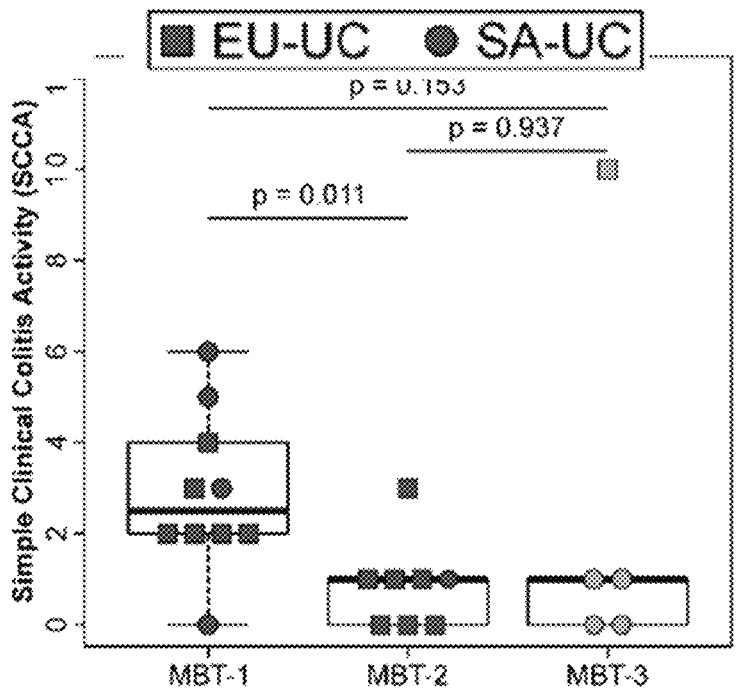
Figure 8B:
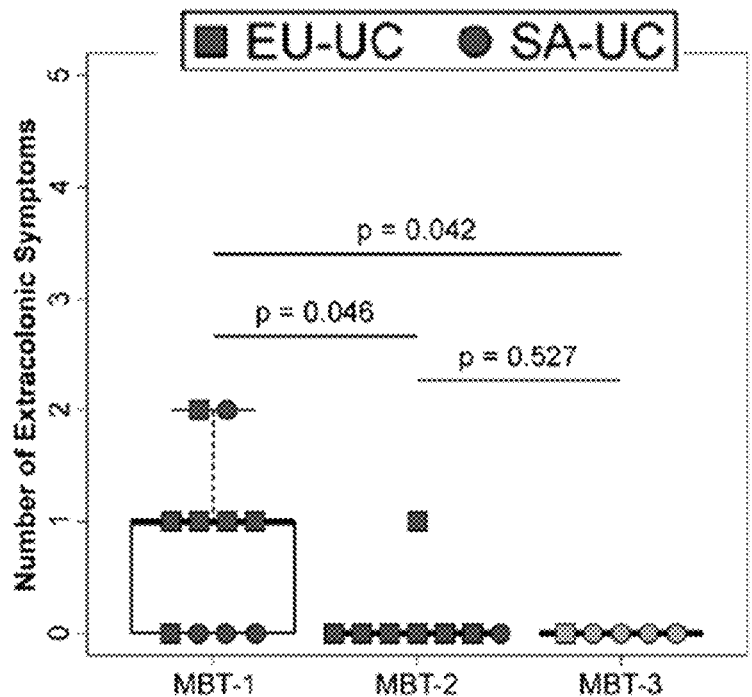
Figure 8C:
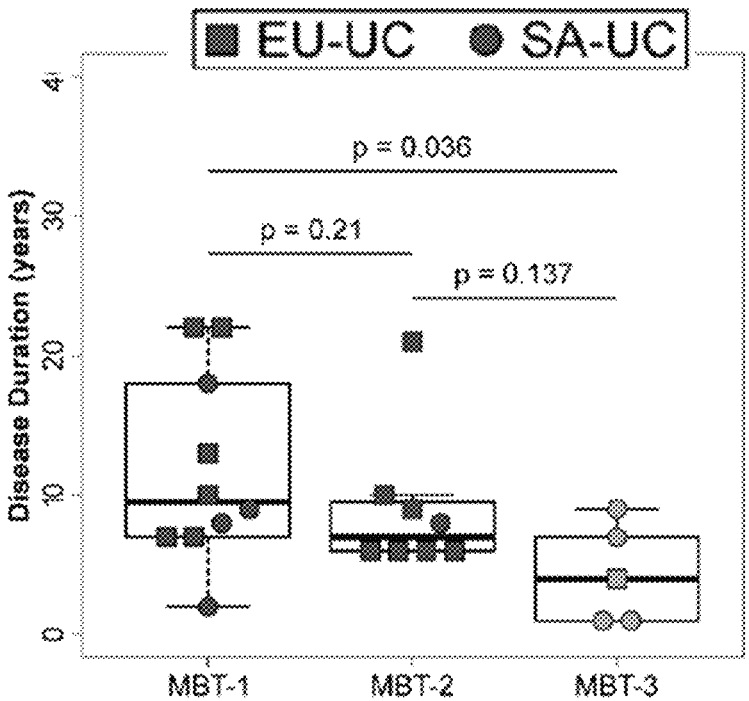
Figure 8D:
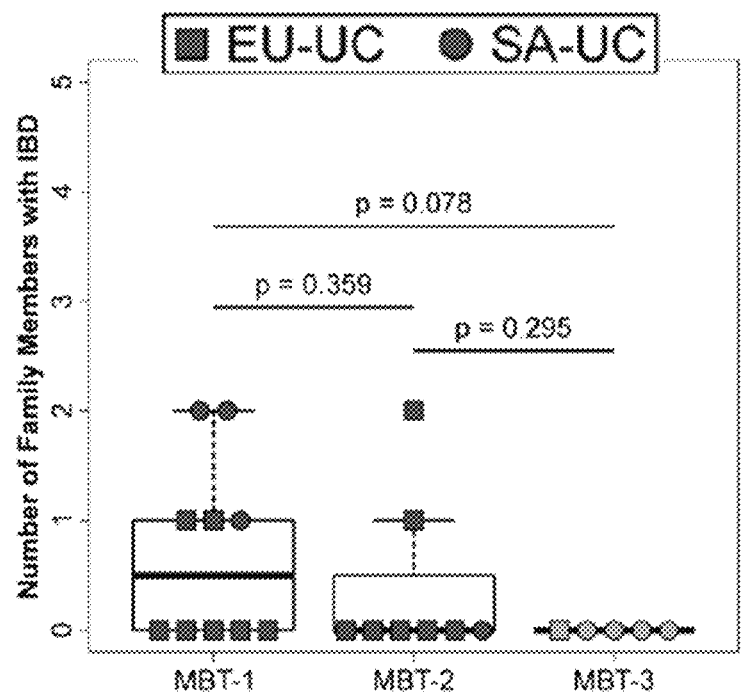

FIGS. 8A-8D. UC microbiotypes exhibit significantly different disease severity and duration. FIG. 8A: Simple *colitis* disease severity score. FIG. 8B: Number of extra-colonic manifestations. FIG. 8C: Disease duration. FIG. 8D: Number of family members with inflammatory bowel disease (IBD).

Figure 9A:
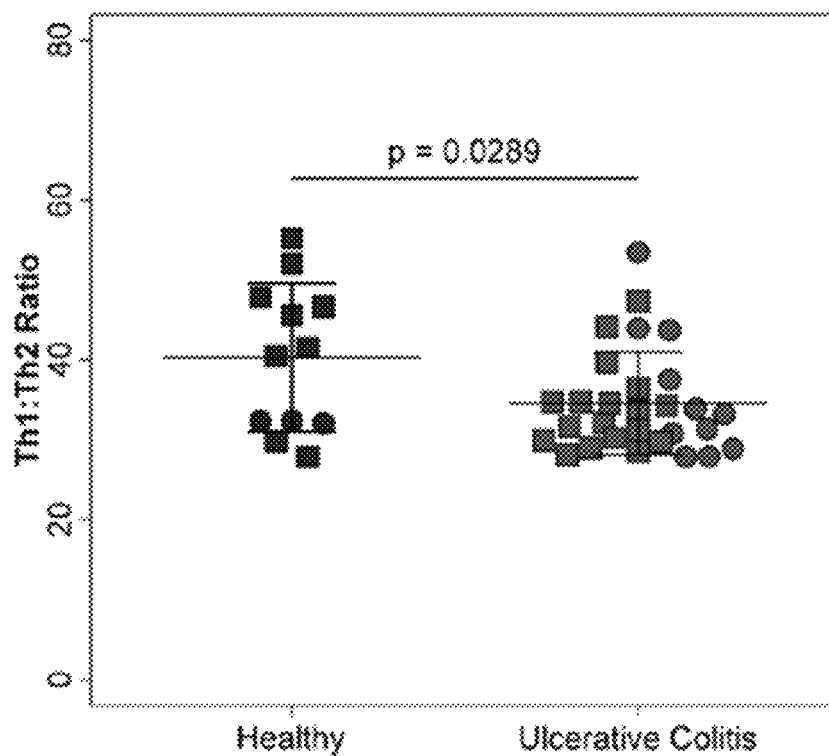
Figure 9B:
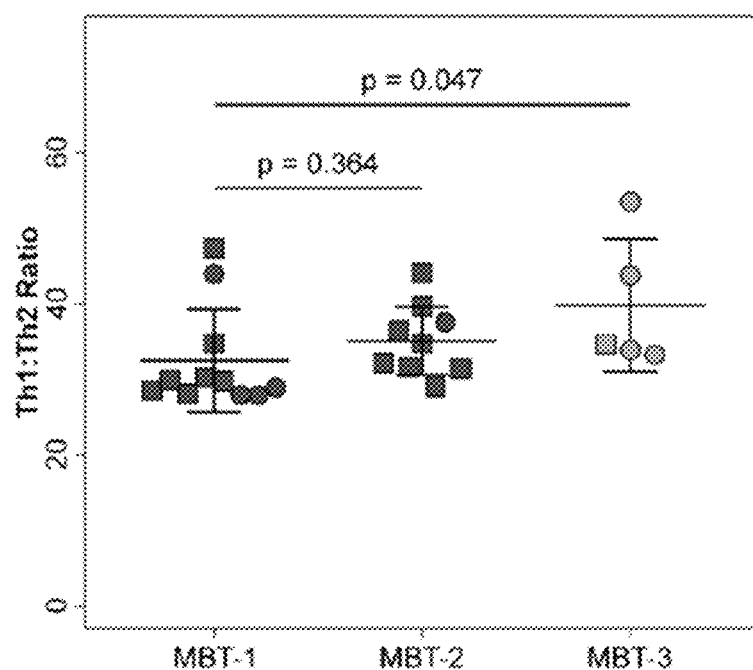
Figure 9C:
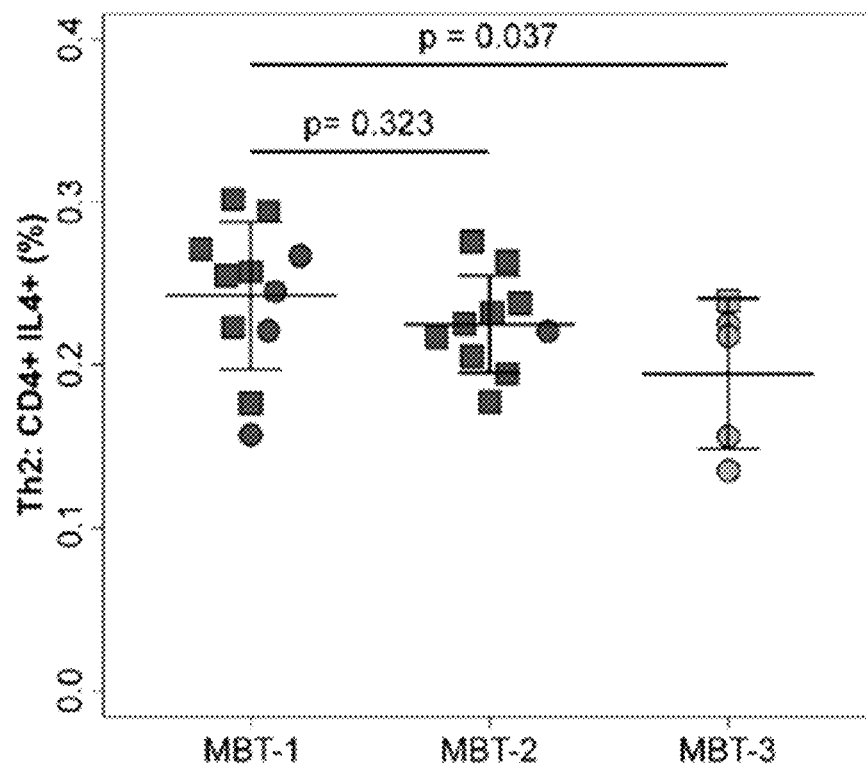
Figure 9D:
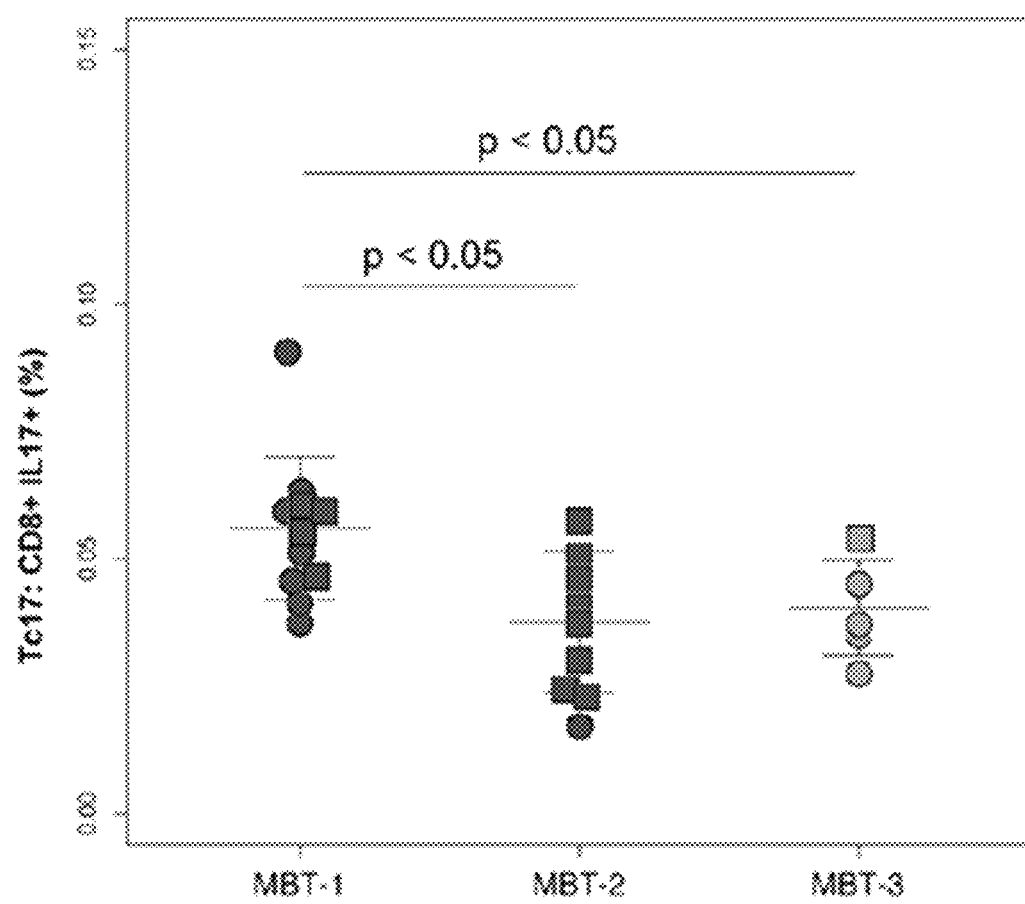

FIGS. 9A-9D. In vitro fecal water assays reveal that UC patients exhibit significantly distinct Th2 ratios, IL4 production and CD8+ IL17+ populations. FIG. 9A: A significant skew towards Th2 responses characterizes UC patients compared to healthy controls. FIG. 9B: UC microbiotypes exhibit significant differences in the degree of Th2 skew, with the most severe microbiotype (MBT-1) exhibiting the most profound Th2 skew. FIG. 9C: IL4 expression is significantly different across UC microbiotypes, with the MBT-1 group exhibiting significantly higher IL4 expression compared to the lowest disease severity group. FIG. 9D: MBT-1 patients exhibit significantly greater numbers of CD8+ IL17+ cells compared with the two other lower disease severity groups.

Figure 10:
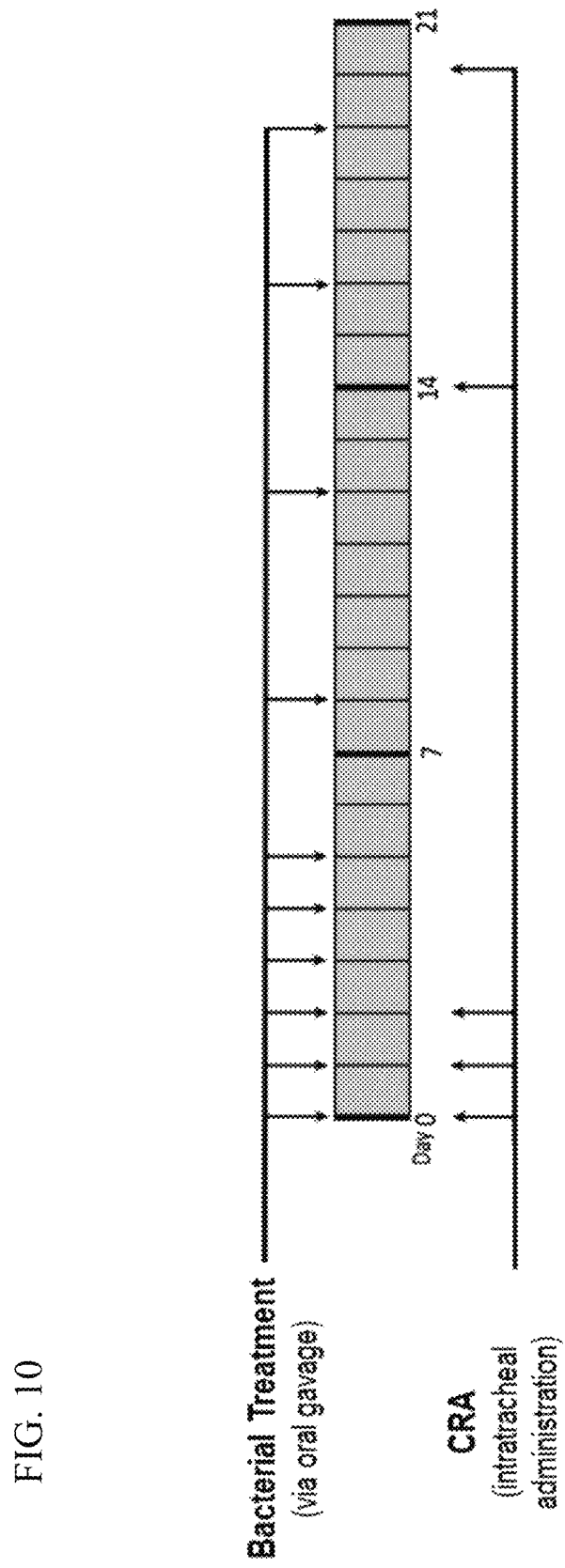

FIG. 10. Experimental timeline illustrating phosphate buffered saline (PBS) or the therapeutic consortium (TC) supplementation regime and CRA challenge schedule in a murine model of airway allergic sensitization.

Figure 11A:
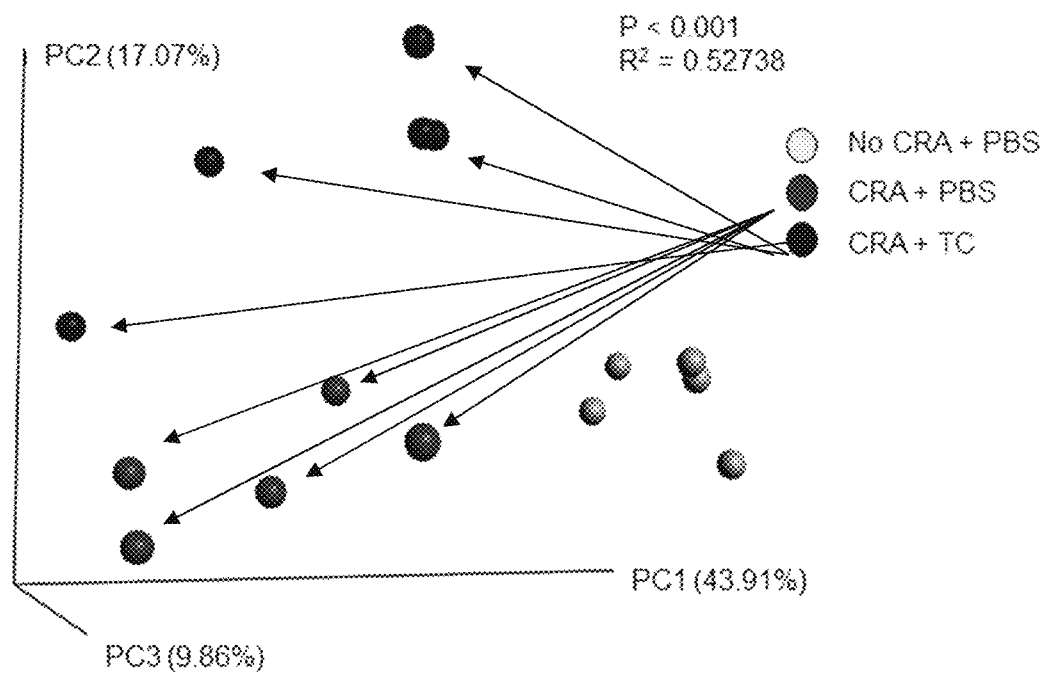
Figure 11B:
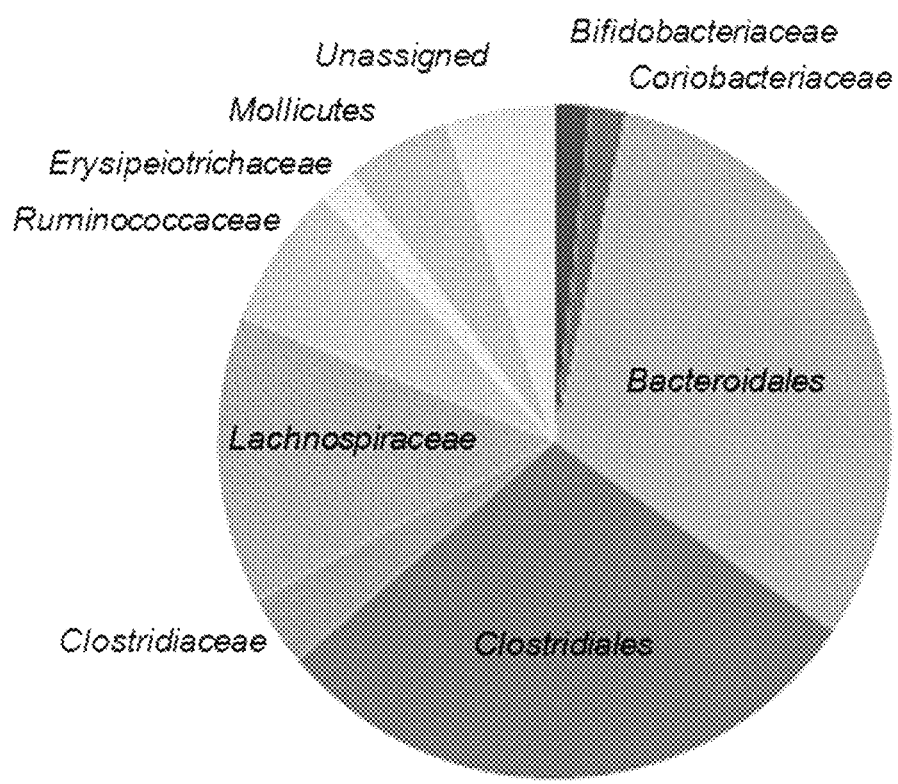

FIGS. 11A-11B. Oral supplementation of mice with the TC promotes increased relative abundance of genera associated with induction of immune tolerance. FIG. 11A: Microbiome composition was determined in the feces of the animals in the study using 16S rRNA sequencing. Cluster analysis revealed differences in microbiome composition across treatment groups. The TC-supplemented animals showed a significantly distinct composition compared with the control groups. Specifically, TC-supplemented animals were enriched for species with the potential for immunomodulatory activity (e.g., *Bifidobacterium*, *Clostridia* species belong to Clade IV and XIV, *Lachnospira*, and *Bacteroides*). FIG. 11B: Pie chart showing enriched taxa in CRA-TC treated animals.

Figure 12A:
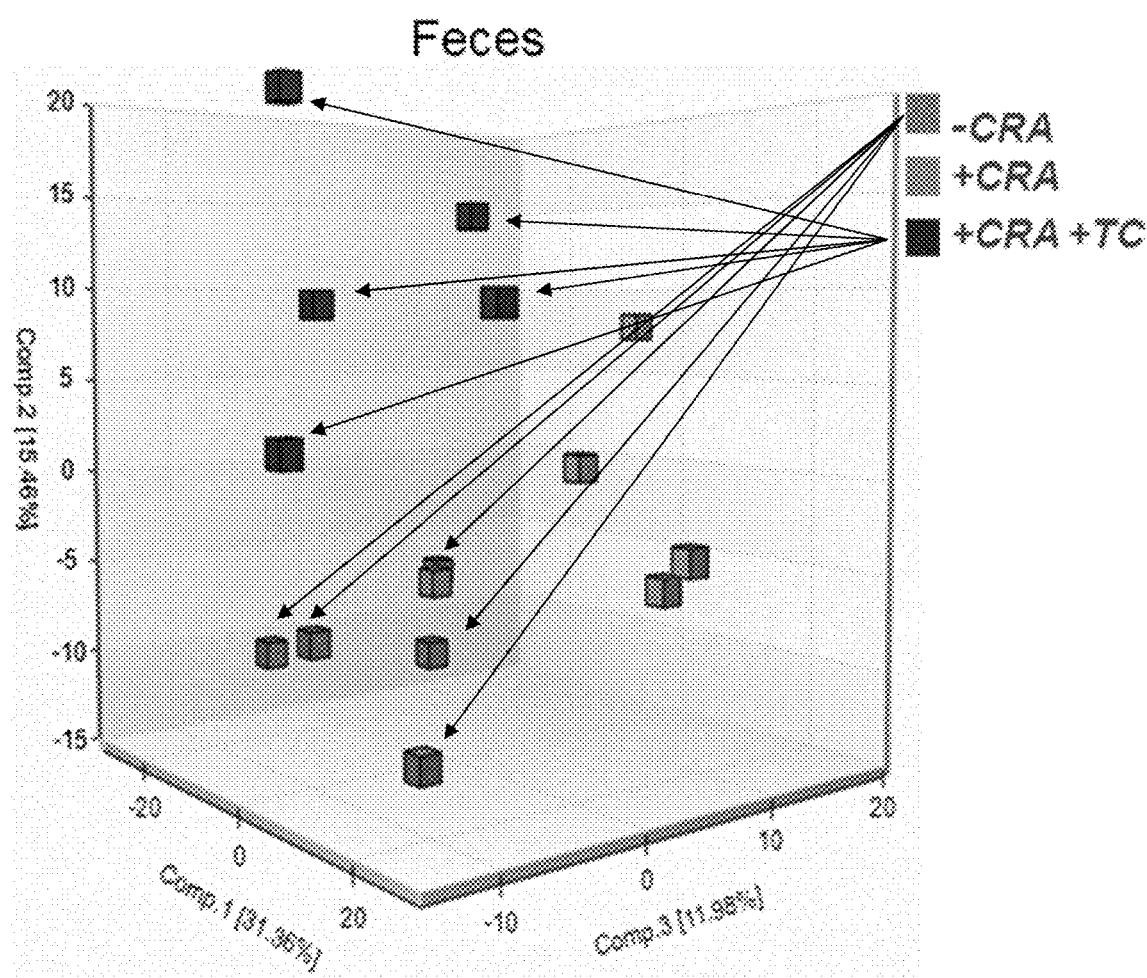
Figure 12B:
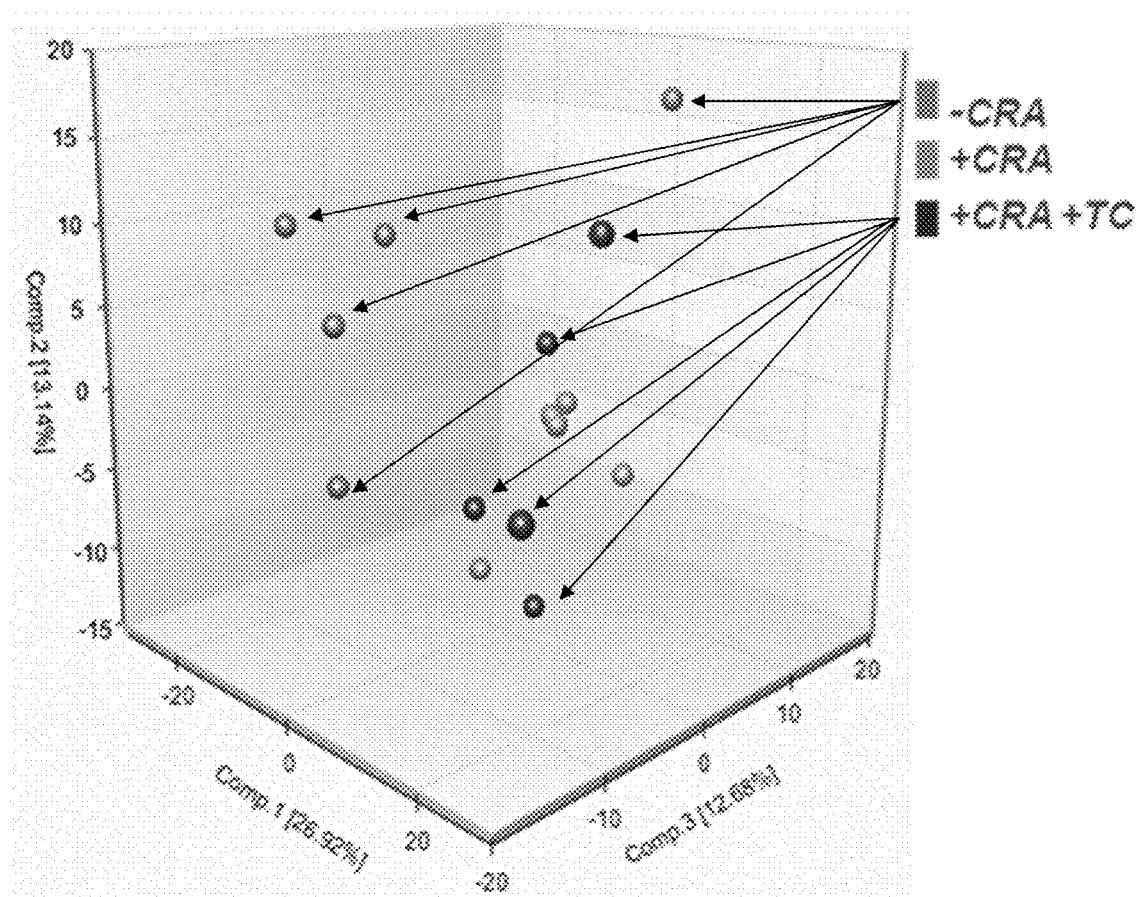

FIGS. 12A-12B. Oral supplementation of mice with the TC promotes metabolic reprogramming in both the gut lumen and periphery and includes significant increases in circulating itaconate, which is associated with a repair macrophage effector phenotype. FIG. 12A: Principle components analysis of the dominant luminal metabolites using un-targeted liquid chromatography mass spectrometry revealed distinct metabolic profiles between the three groups (Canberra Distance Matrices; PERMANOVA, $R^2=0.29$, p=0.005). FIG. 12B: Principle components analysis of the circulating metabolites identified in the serum using the same strategy also revealed significant differences (Canberra Distance Matrices; PERMANOVA, $R^2=0.29$, p=0.002 between the groups examined. Untargeted LC GC Mass spectrometry was used to identify and determine the relative concentrations of several hundred metabolites in the feces (FIG. 12A) and serum (FIG. 12B) of mice supplemented with the TC or PBS prior to cockroach (CRA) antigen challenge. Significant spatial separation of TC-supplemented versus PBS supplemented animals on a PcoA plot indicates that the profile of metabolites in the feces and serum of these animals is significantly different.

Figure 13A:
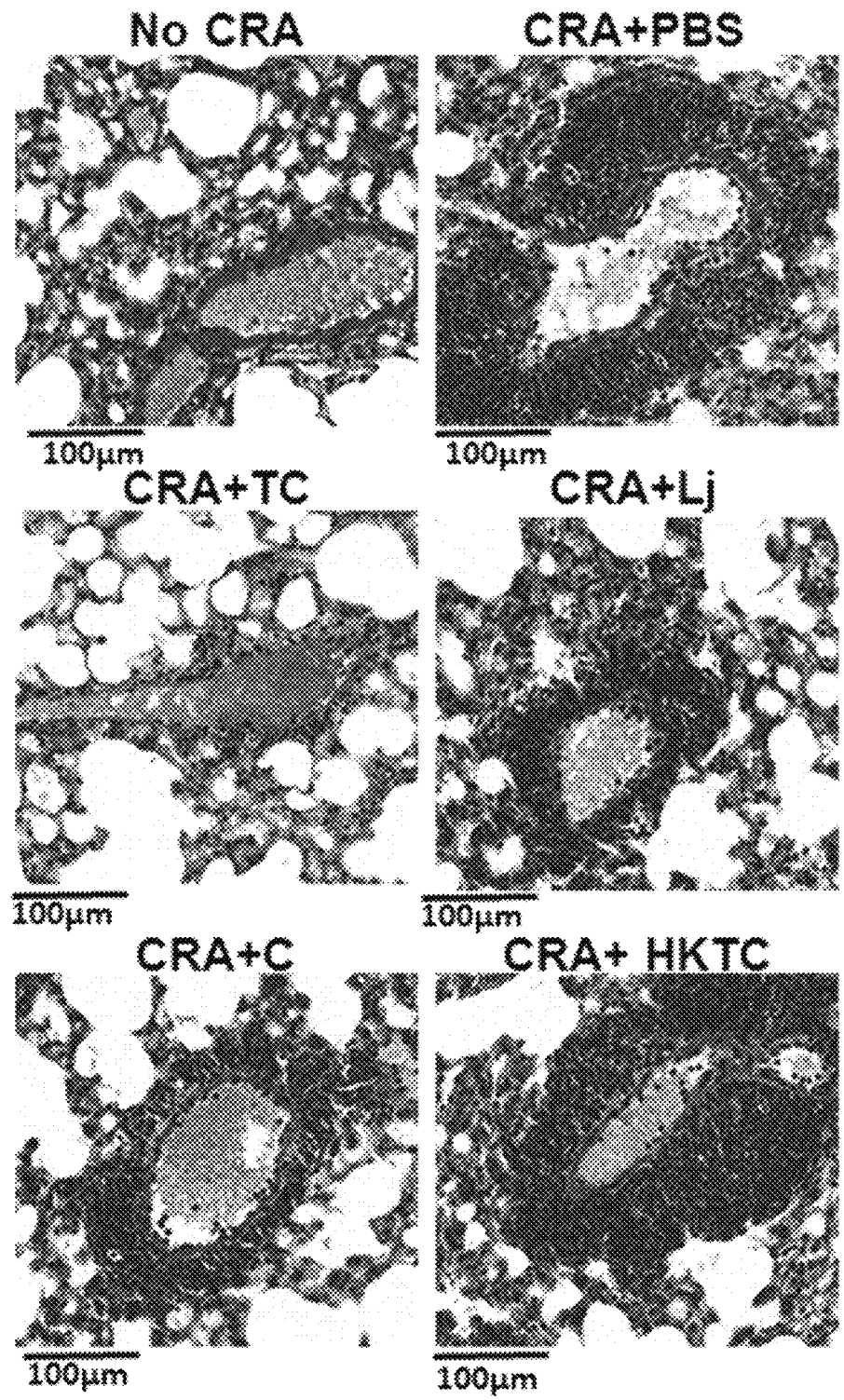
Figure 13B:
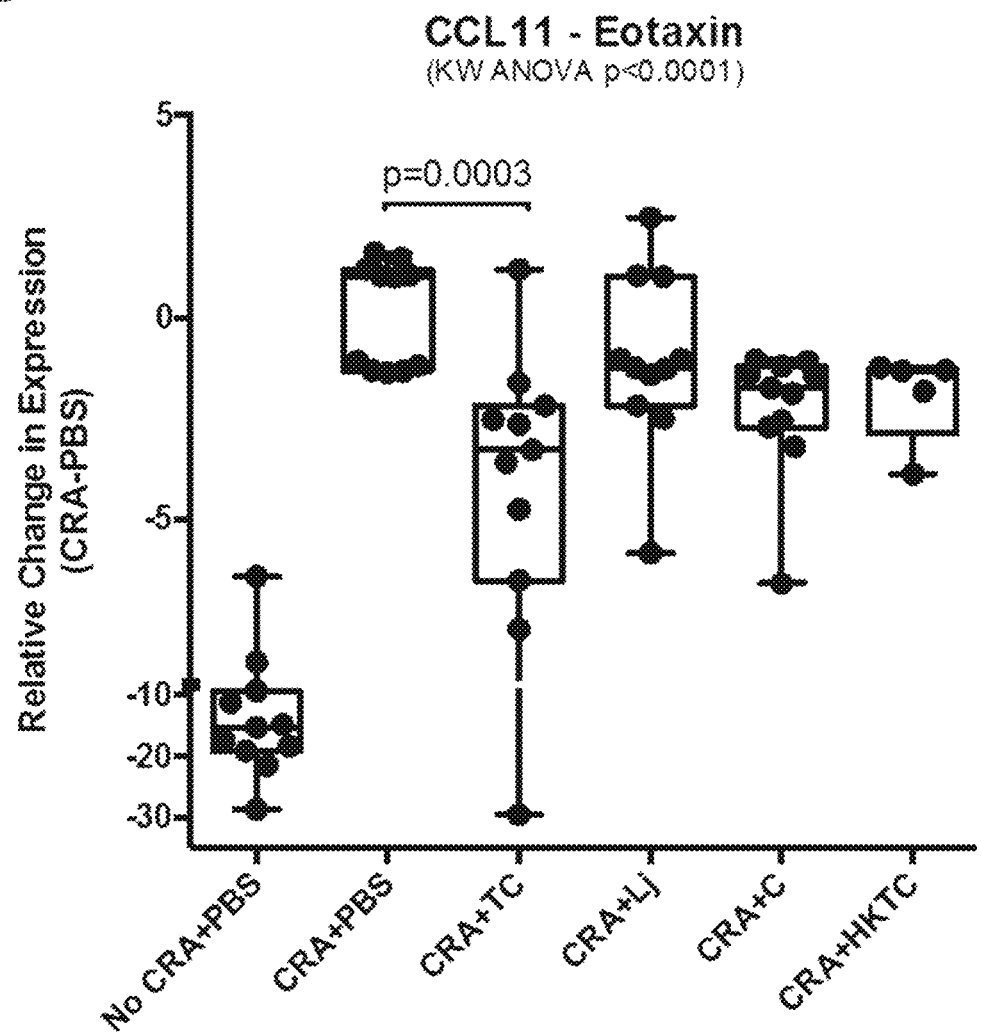

FIGS. 13A-13B. FIG. 13A: Histological sections of the murine airway (lung) indicate that oral supplementation of mice with the metabolically active therapeutic consortium (CRA+TC) significantly reduces inflammatory influx [Hemotoxylin and Eosin (H&E) Staining; dark stained nucleated cells] in a murine model of airway allergic sensitization. *L. johnsonii* alone does not confer protection (CRA+Lj), nor does supplementation of animals with four of the TC (omitting *L. johnsonii*; CRA+C), indicating that *L. johnsonii* acts in synergy with the other four members of the TC to effect protection at the airway mucosal surface. A heat-killed, metabolically inactive TC also does not confer protection indicating that only the metabolically active TC protects. FIG. 13B: Gene expression analyses of CCL-11 expression, a marker of eosinophils, confirm that the CRA+TC group exhibits significantly reduced eosinophil presence in the lungs following allergic sensitization.

Figure 14A:
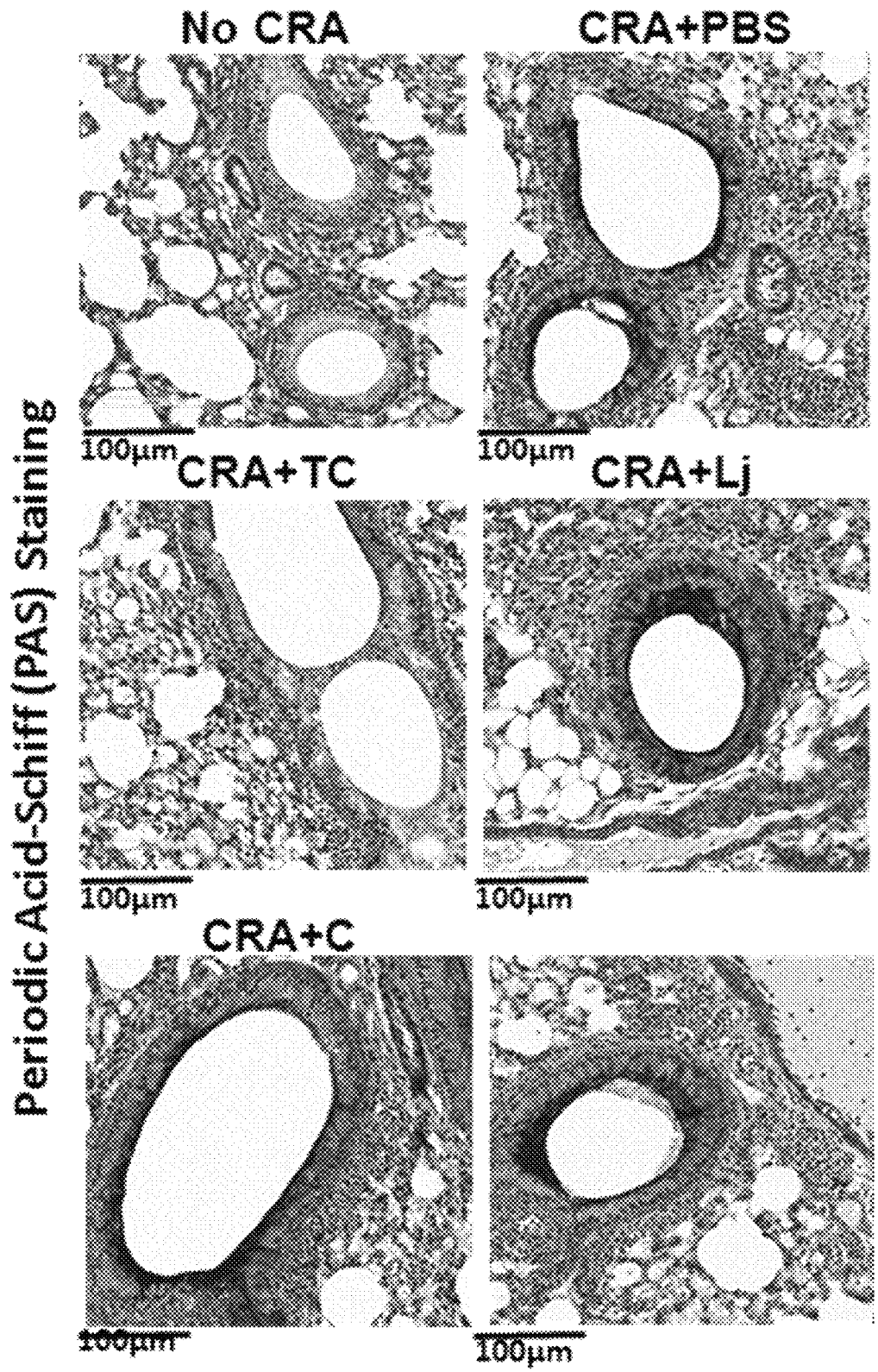
Figure 14B:
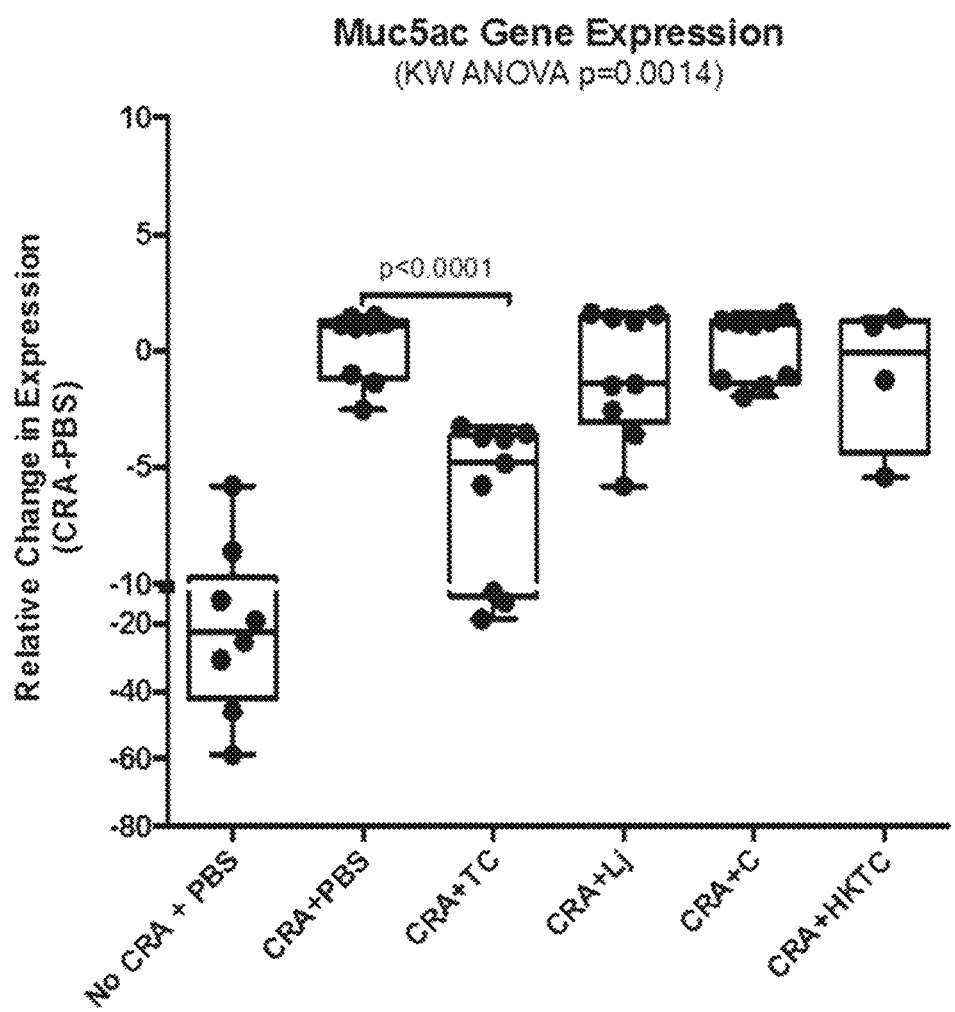

FIG. 14A-14B. FIG. 14A: Histological sections of the murine airway (lung) indicate that oral supplementation of mice with the metabolically active therapeutic consortium (CRA+TC) significantly reduces mucin hyper-secretion (Periodic Acid-Schiff (PAS) Staining: dark staining) in a murine model of airway allergic sensitization. *L. johnsonii* alone does not reduce mucin secretion (CRA+Lj), nor does supplementation of animals with four of the TC (omitting *L. johnsonii*; CRA+C), indicating that *L. johnsonii* acts in synergy with the other four members of the TC to suppress mucin secretion at the airway mucosal surface. A heat-killed, metabolically inactive TC also does not reduce mucin secretion indicating that only the metabolically active TC protects. FIG. 14B: Gene expression analyses of Muc5AC expression, the primary gene responsible for mucin secretion in the airways, confirm that the CRA+TC group exhibits significantly reduced mucin gene expression the lungs, compared to the other treatment groups.

Figure 15A:
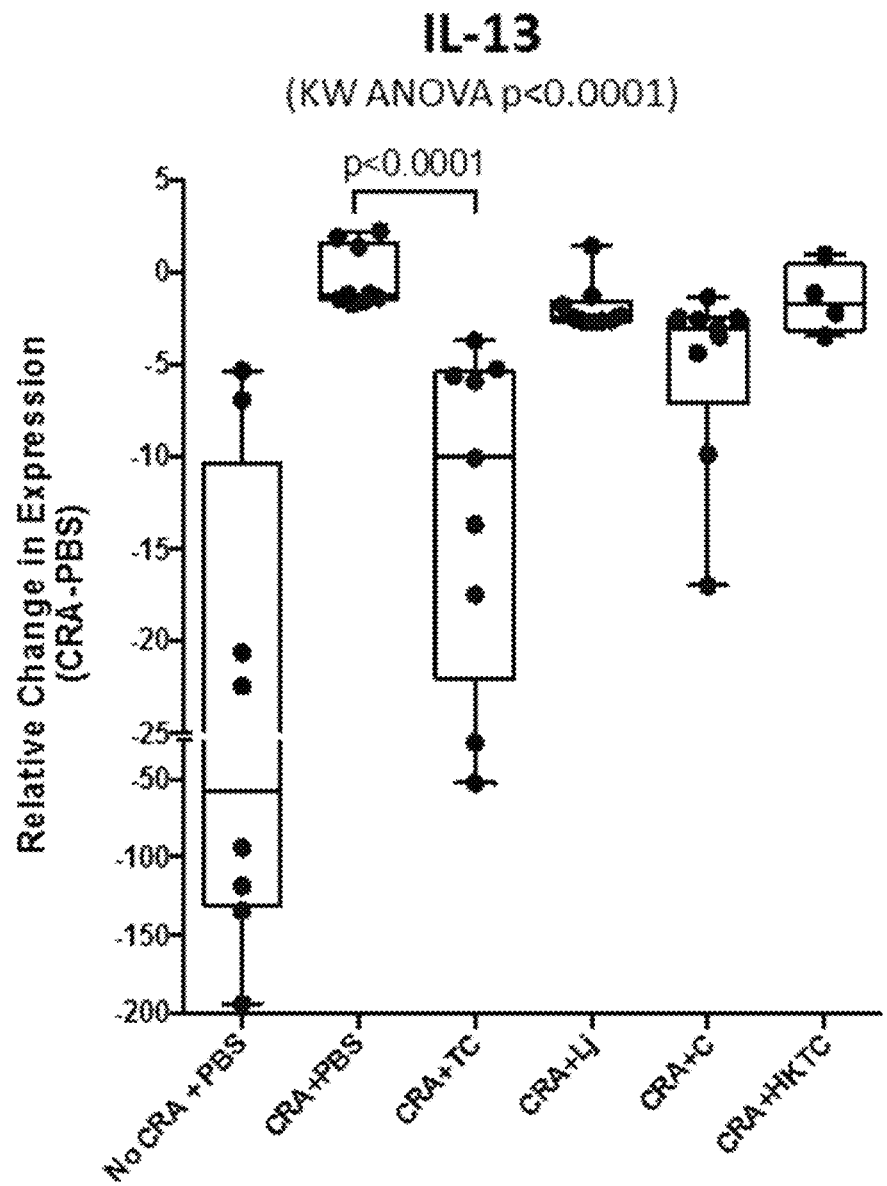
Figure 15B:
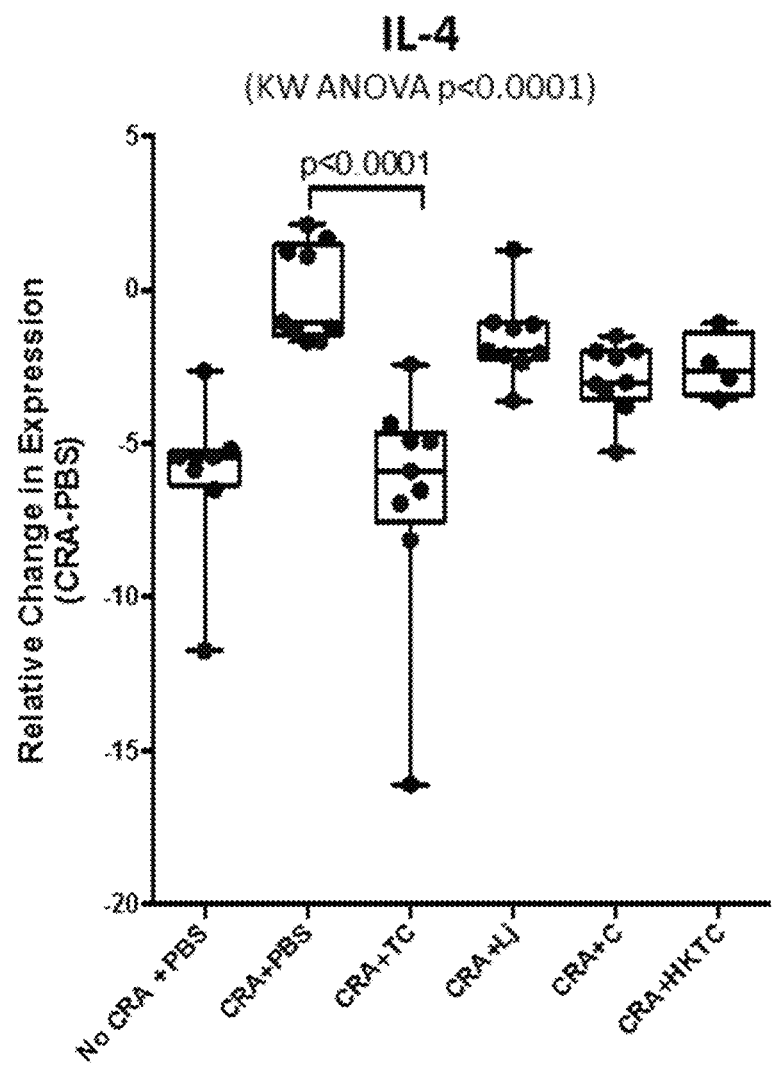
Figure 15C:
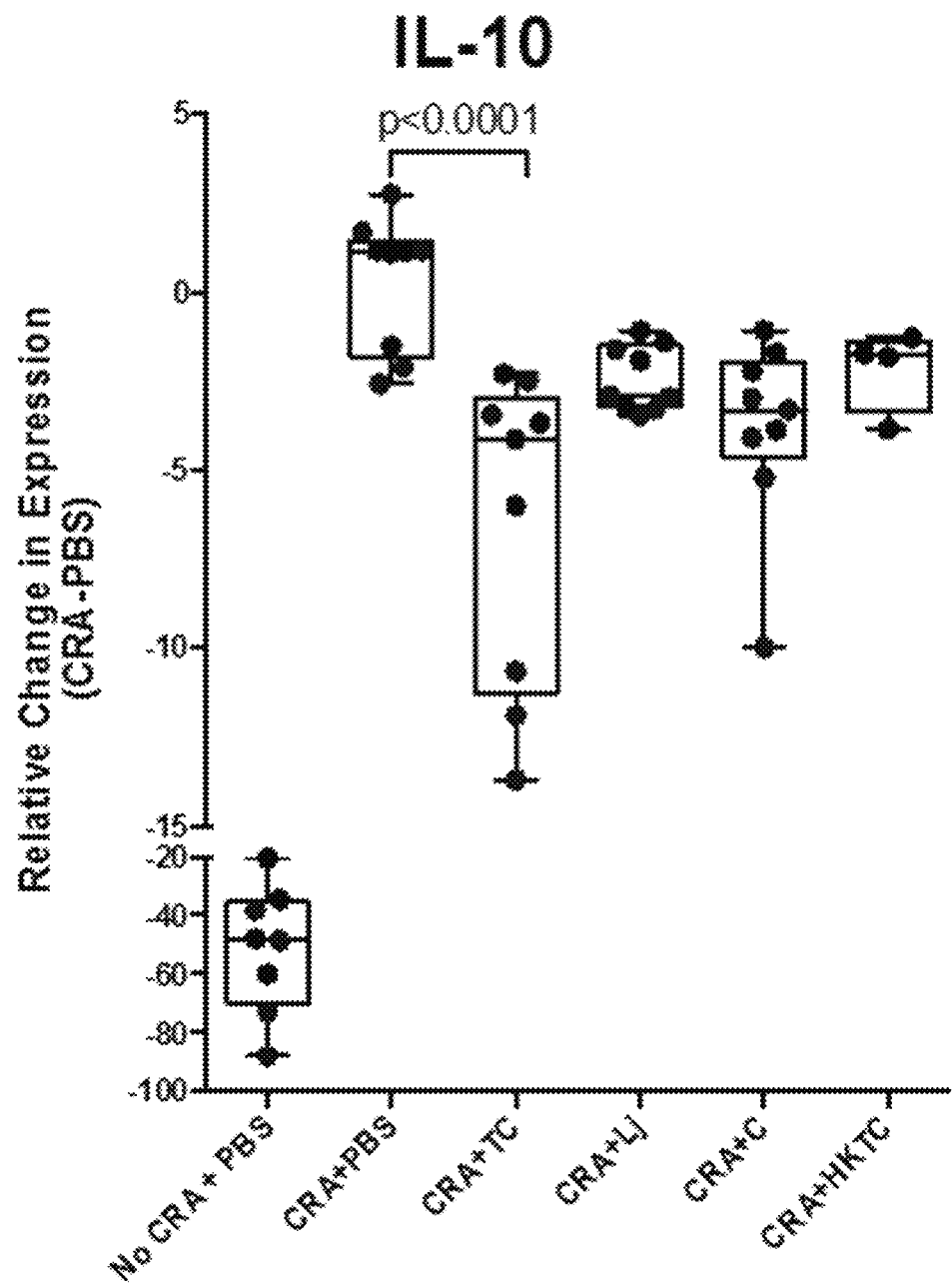

FIGS. 15A-15C. Oral supplementation of mice with the metabolically active TC significantly reduces cytokine expression associated with allergic inflammation in a murine model of airway allergic sensitization. FIG. 15A: Boxplot demonstrating a significant decrease in relative change in expression of IL-13 in animals treated with TC and CRA challenged compared with PBS treatment and CRA challenged. FIG. 15B: Boxplot demonstrating a significant decrease in relative change in expression of IL-4 in animals treated with TC and CRA challenged compared with PBS treatment and CRA challenge. FIG. 15C: Boxplot demonstrating a significant decrease in relative change in expression of IL-10 in animals treated with TC and CRA challenged compared with PBS treatment and CRA challenge.

Figure 16A:
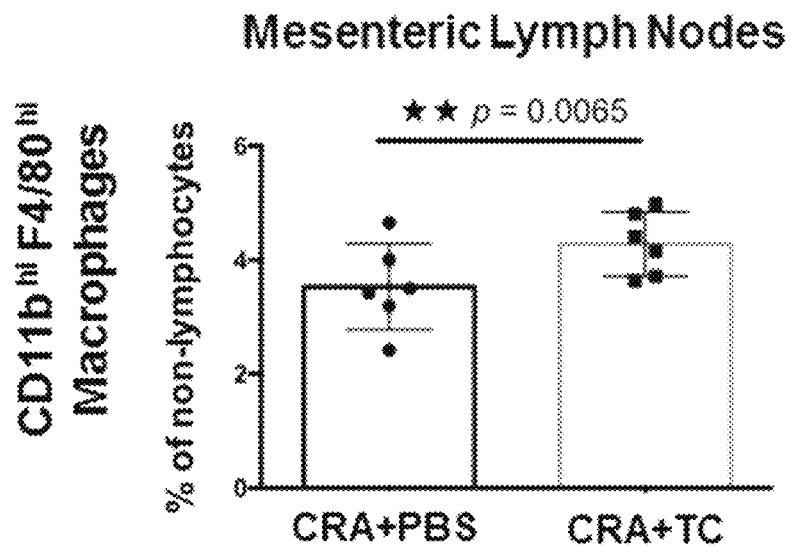
Figure 16B:
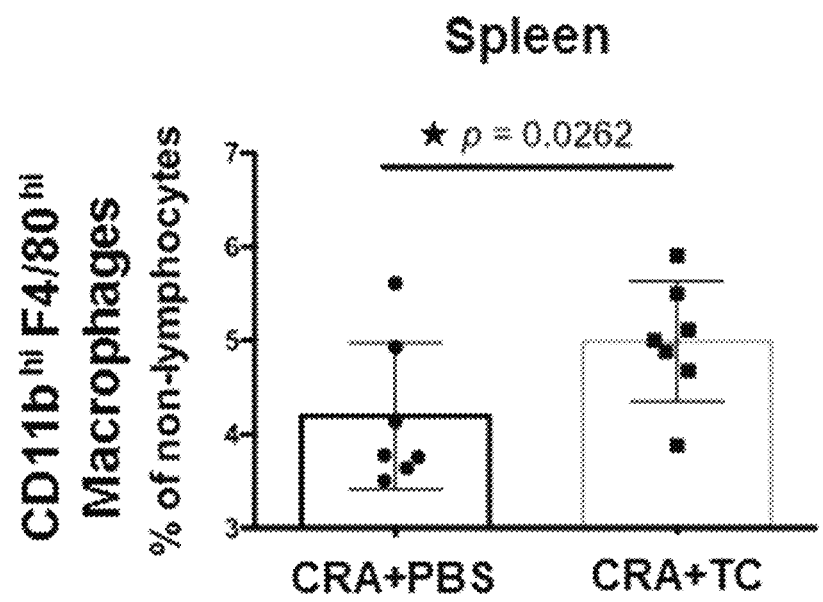
Figure 16C:
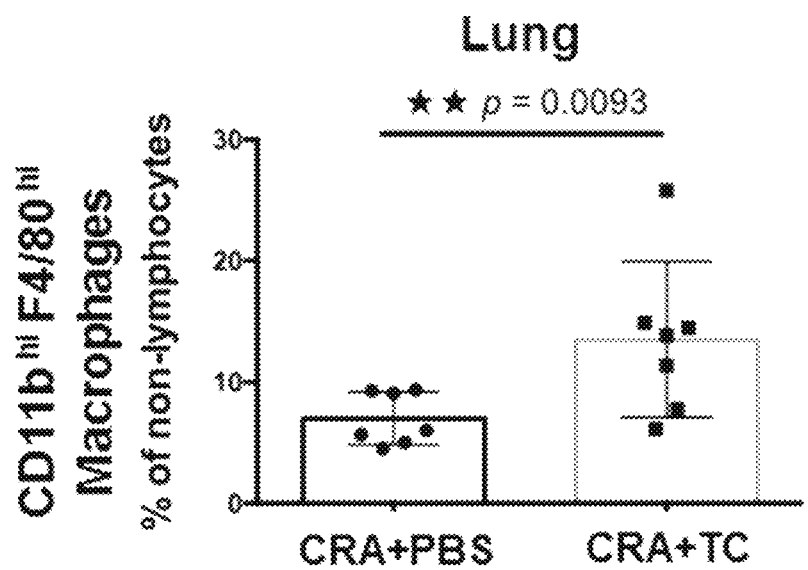
Figure 16D:
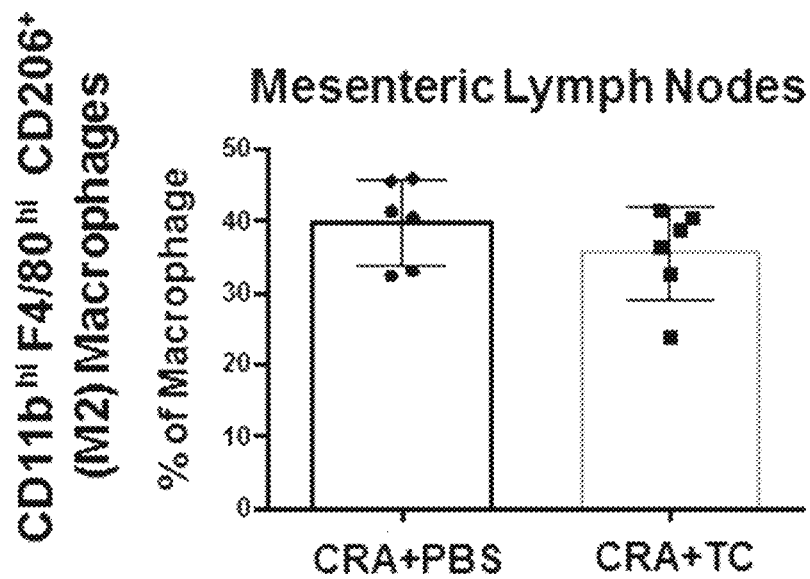
Figure 16E:
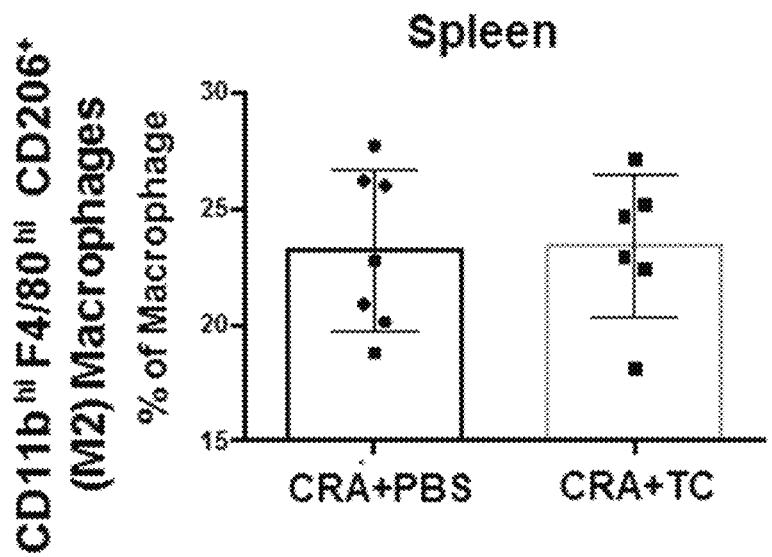
Figure 16F:
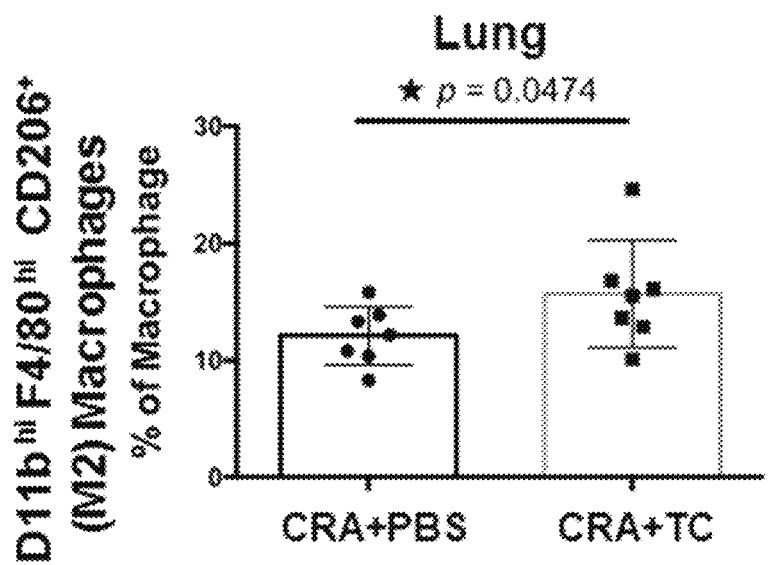

FIGS. 16A-16F. Oral supplementation of mice with the TC results in a repair macrophage effector phenotype in a murine model of airway allergic sensitization. In CRA+TC treated mice, $CD11b^{hi}F4/80^{hi}$ macrophages form a larger percentage of the non-lymphocyte population in (FIG. 16A) mesenteric lymph nodes, (FIG. 16B) spleen, and (FIG. 16C) lung compared to CRA+PBS treated animals. CRA+TC and CRA+PBS treated animals show similar percentages of $CD11b^{hi}F4/80^{hi}$ $CD206^+$ (M2) macrophages in the non-lymphocyte population in both (FIG. 16D) mesenteric lymph nodes and (FIG. 16E) spleen. FIG. 16F: In lung, CRA+TC treated animals show an increased percentage of $CD11b^{hi}F4/80^{hi}$ $CD206^+$ (M2) macrophages in the non-lymphocyte population compared to CRA+PBS treated mice.

FIG. 17. Table showing treatment groups utilized in murine model of airway allergic sensitization study.

Figure 18A:
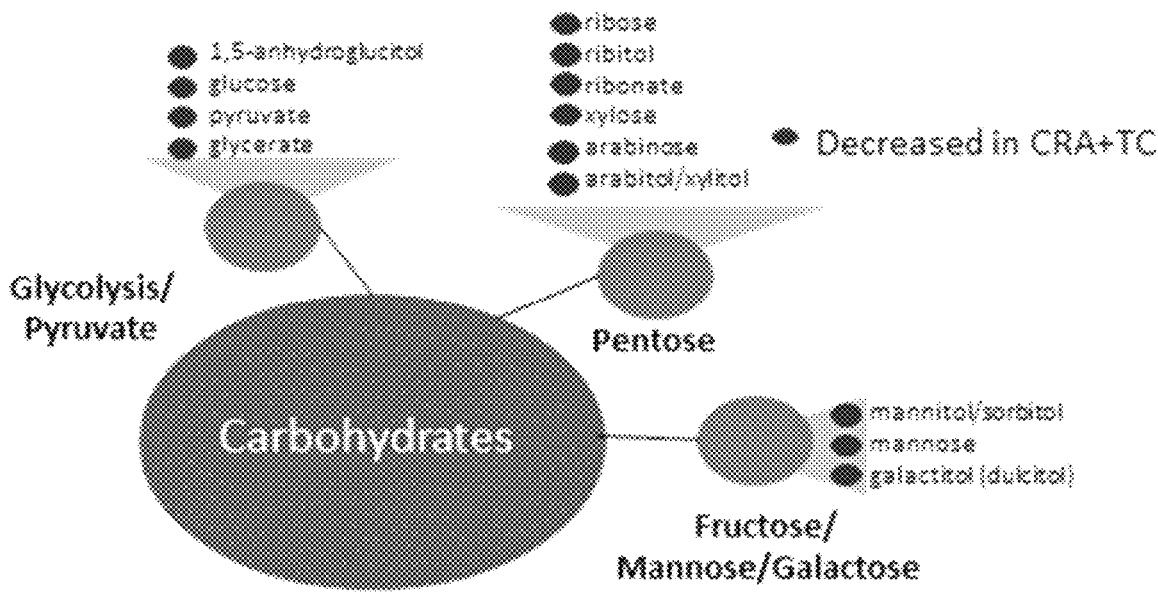
Figure 18B:
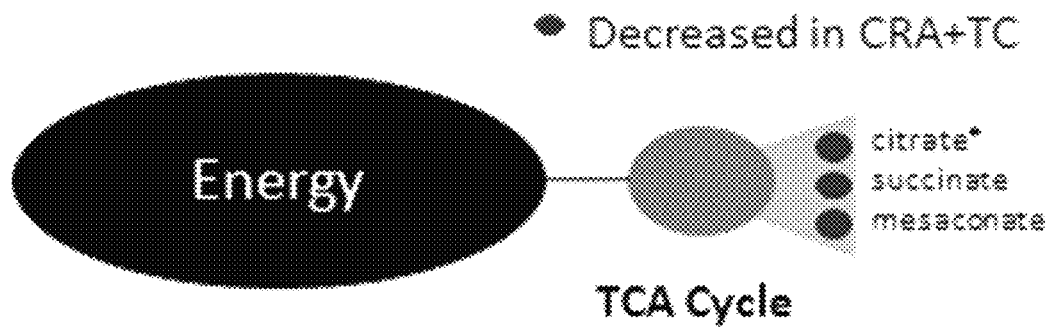
Figure 18C:
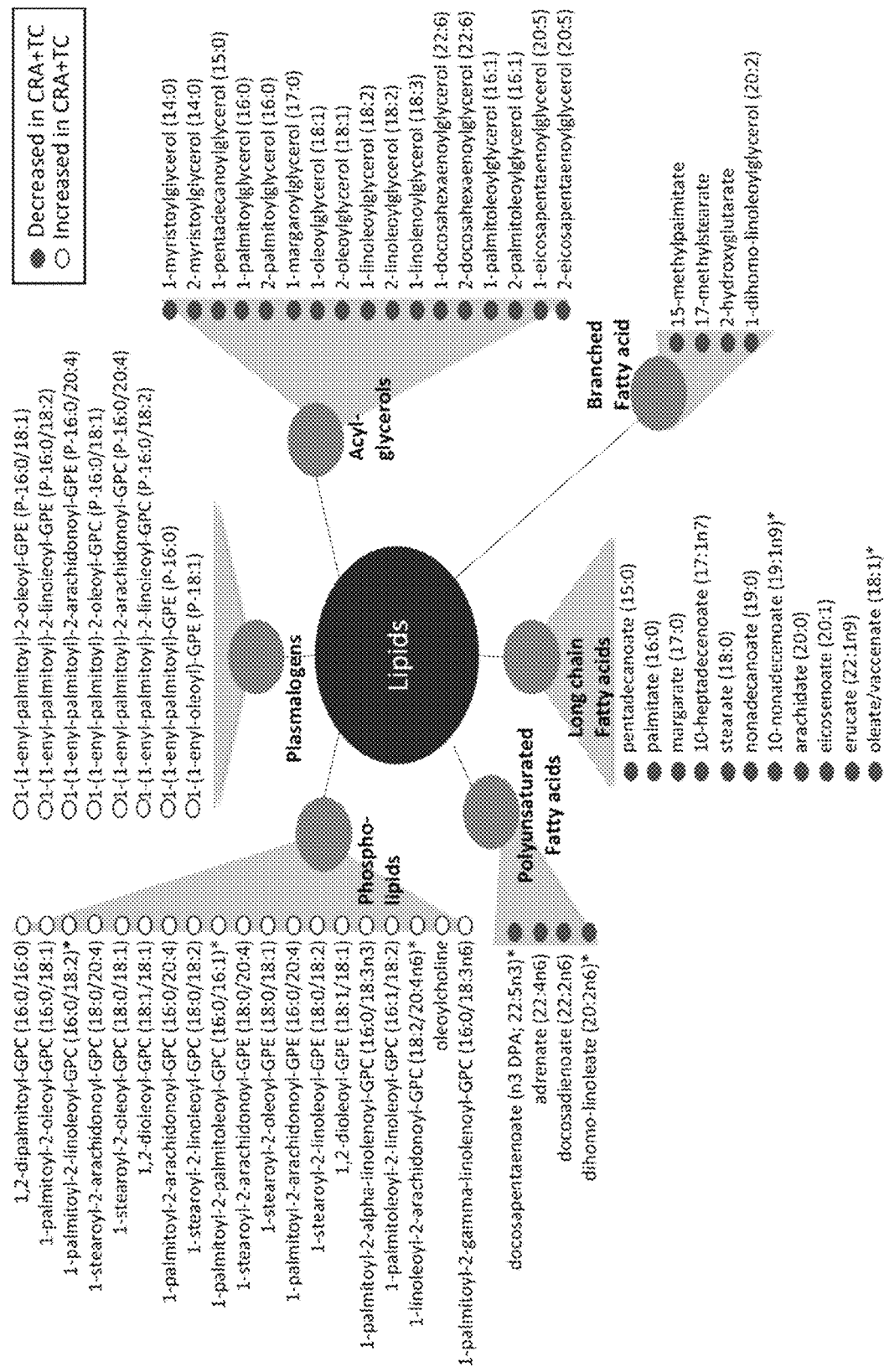

FIGS. 18A-18C. Metabolic reprogramming in gut lumen following oral supplementation of mice with the therapeutic consortium (TC) promotes increased concentrations of specialized lipids, plasmalogens, which are enriched in poly-unsaturated fatty acids (PUFAs). PUFAs are increased in the feces of neonates at low risk for allergies and asthma in childhood. FIG. 18A: Carbohydrate compounds decreased in concentration following treatment with the TC. FIG. 18B: Energy compounds decreased in concentration following treatment with the TC. FIG. 18C: Lipid compounds decreased in concentration (PUFAs, Long chain fatty acids, acyl-glycerols, and branched fatty acids) and increased (phospholipids and plasmalogens) following treatment with the TC.

Figure 19:
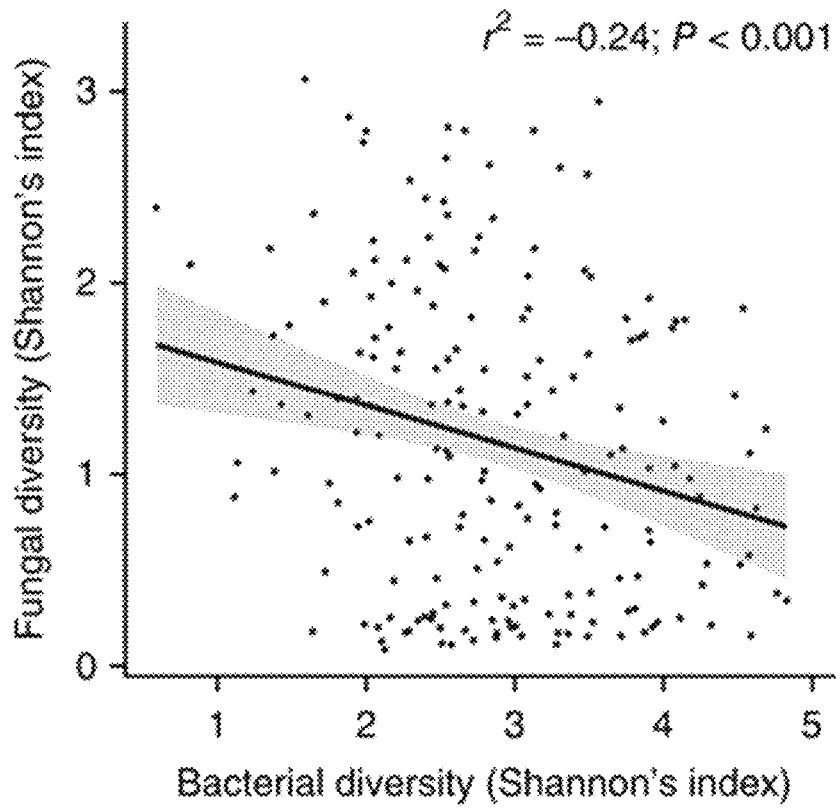

FIG. 19. Bacterial and fungal α- and β-diversity are related to participant age at the time of fecal-sample collection. Bacterial and fungal α-diversities are inversely correlated (Shannon's index; n=188; Pearson's correlation, $r^2$=−0.24; P<0.001).

Figure 20A:
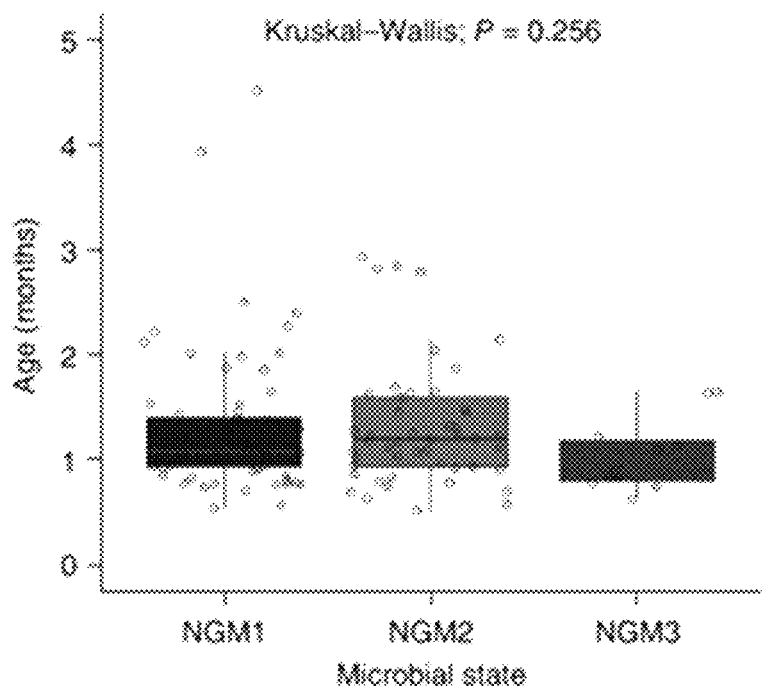
Figure 20B:
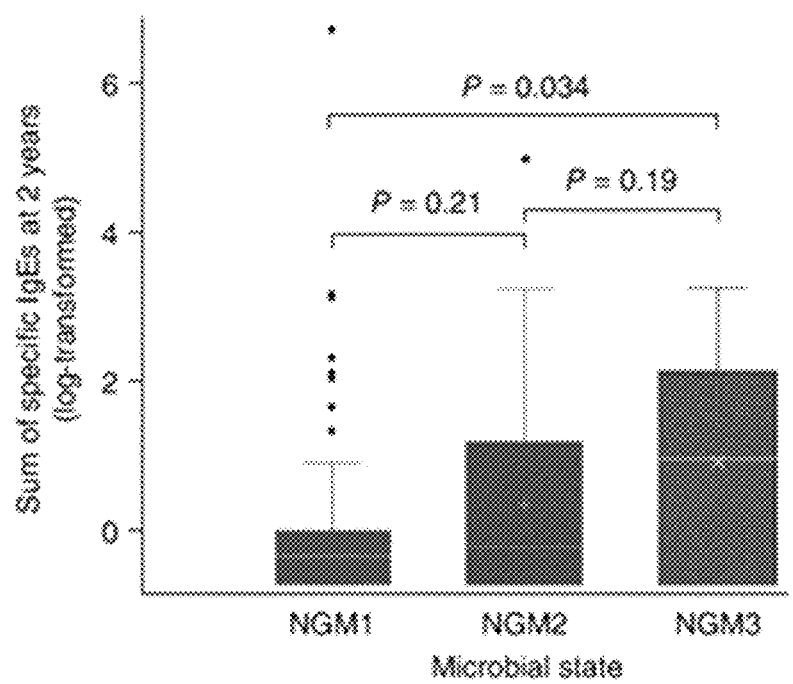

FIGS. 20A-20B. Compositionally distinct, age-independent NGM states exist in neonates, exhibit significant differences in fungal taxonomy and are related to the RR of atopy at the age of 2 years. FIG. 20A: NGM participants do not differ significantly in age (n=130; Kruskal-Wallis; P=0.256). Box plots are defined by the $25^{th}$ and $75^{th}$ percentiles. Center line represents the median ($50^{th}$ percentile). Whiskers are defined as 1.5 times the interquartile range (IQR, $75^{th}$-$25^{th}$ percentile), plus or minus the $75^{th}$ and $25^{th}$ percentiles, respectively. FIG. 20B: The sum of allergen-specific serum IgE concentrations measured at 2 years of age (n=130) is significantly higher for NGM3 compared with NGM1 participants (Welch's t test; P=0.034). Box plots are constructed as defined in FIG. 20A.

FIG. 21. NGMs exhibit significantly different RRs of PM atopy development at age 2 years and of parental report of doctor-diagnosed asthma at age 4 years. Significance of risk ratios between microbiota states was calculated on the basis of log-binomial regression.

Figure 22A:
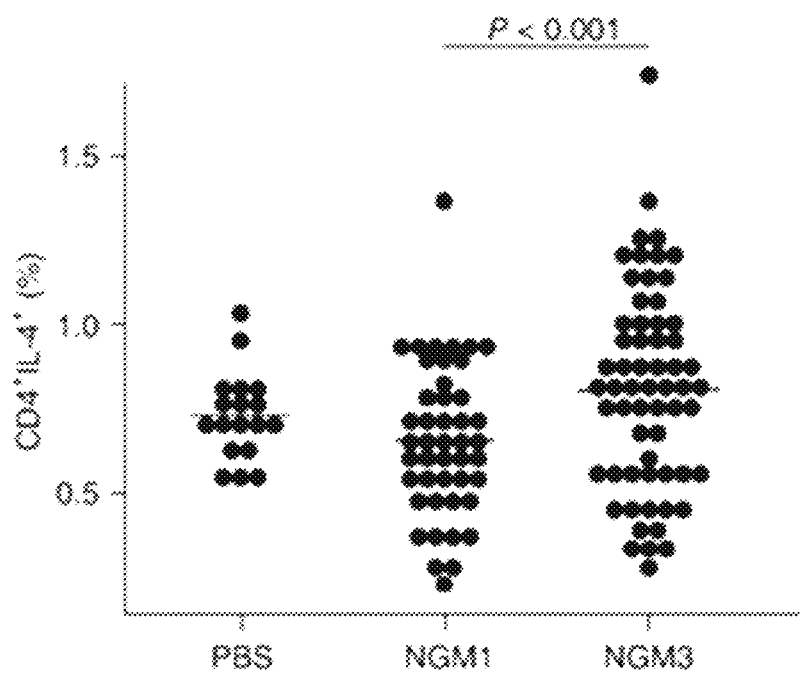
Figure 22B:
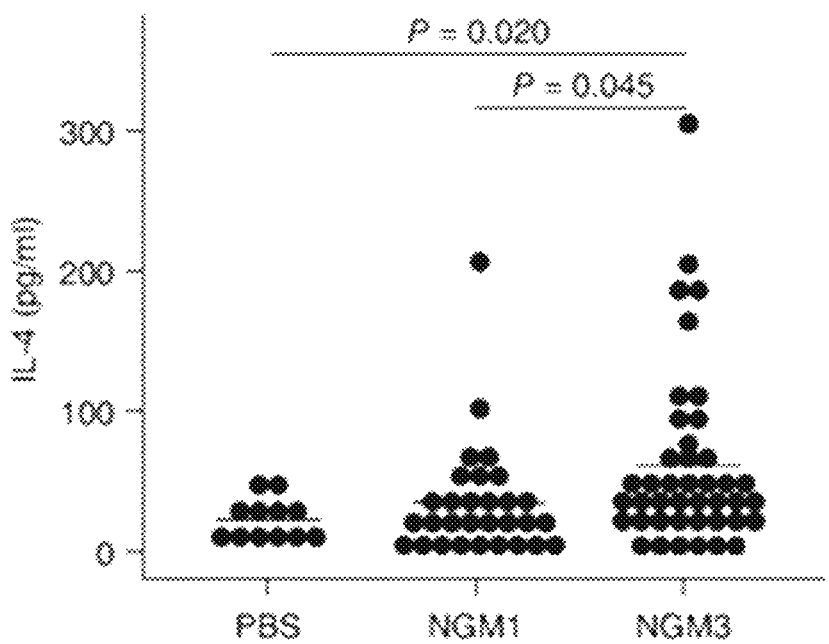
Figure 22C:
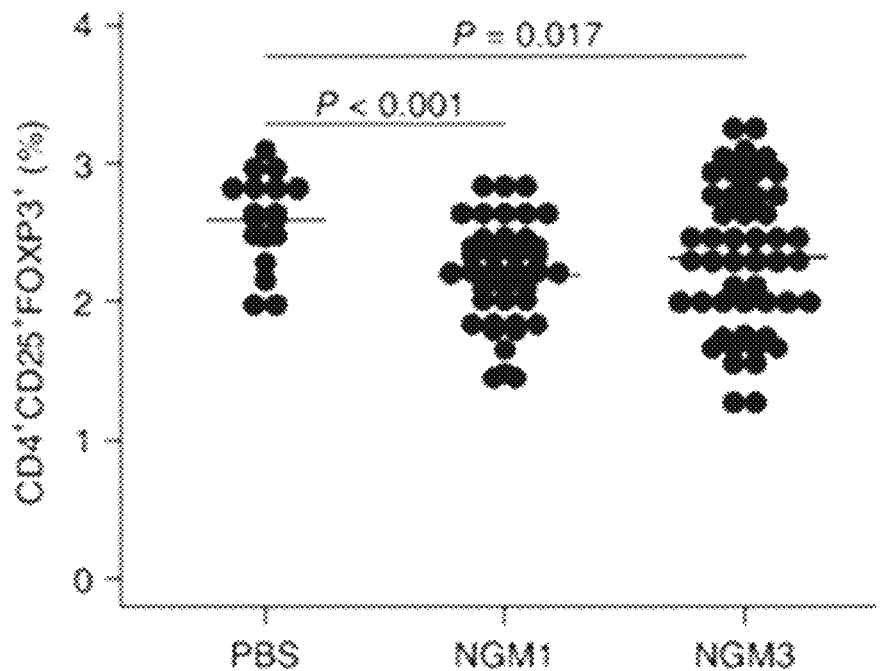
Figure 22D:
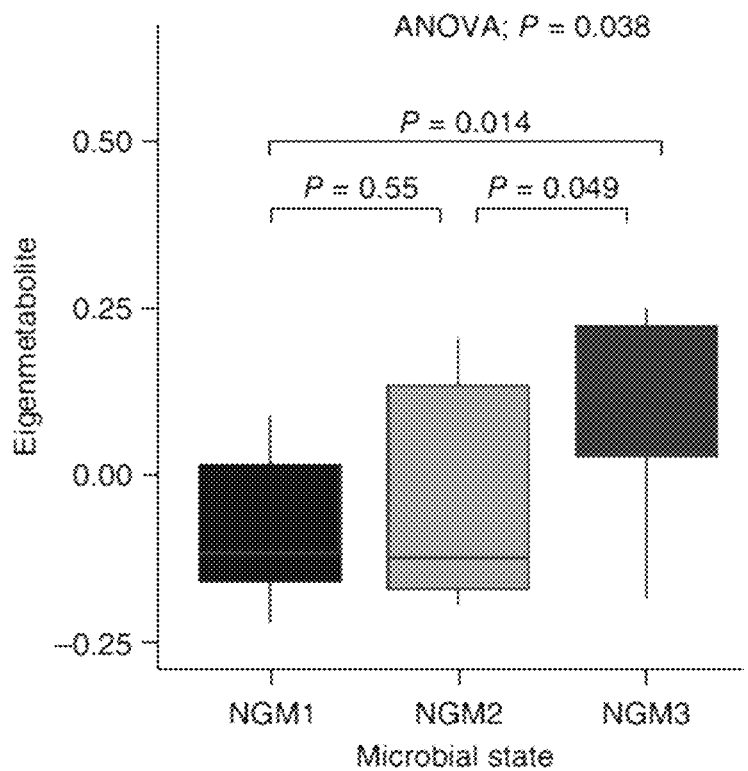
Figure 22E:
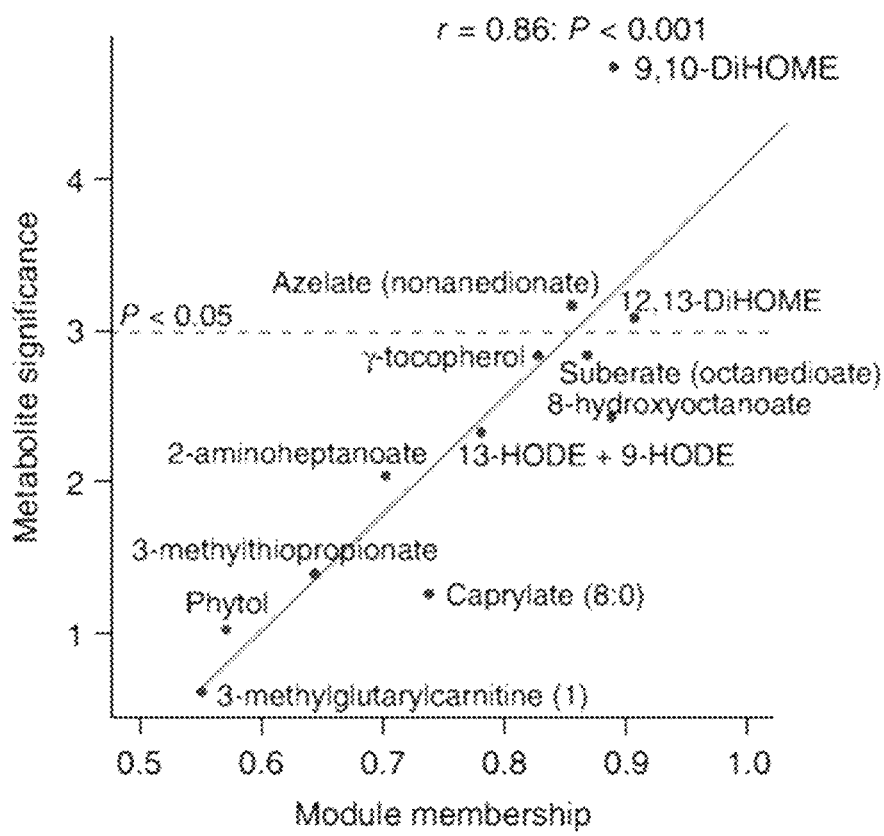
Figure 22F:
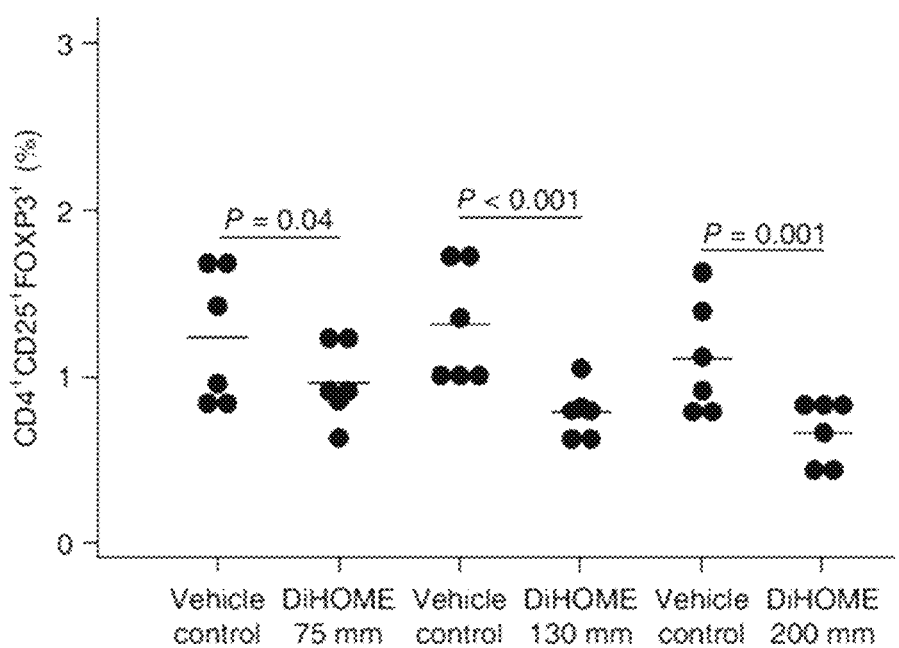

FIGS. 22A-22F. Sterile fecal water from NGM3 participants induces $CD4^+$ cell population dysfunction associated with atopic asthma. Dendritic cells and autologously purified naïve $CD4^+$ cells from the serum of two healthy adult donors (biological replicates) were incubated with sterile fecal water from NGM1 (n=7; three biological replicates per sample) or NGM3 (n=5; three biological replicates per sample) participants. FIGS. 22A and 22B: Fecal water from NGM3 participants induced significantly increased proportions of $CD4^+IL-4^+$ cells (LME, P<0.001; center line represents mean) (FIG. 22A) and expression of IL-4 (LME; P=0.045) (FIG. 22B). FIG. 22C: Fecal water from both NGM1 and NGM3 participants induced significantly increased proportions of $CD4^+CD25^+FOXP3^+$ cells (LME; P<0.001 for NGM1 and P=0.017 for NGM3), compared with control. FIG. 22D: Weighted correlation network analysis identified a metabolic module that differentiates NGM3 from NGM2 and NGM1 participants (n=28; ANOVA; P=0.038). Box plots define the $25^{th}$ and $75^{th}$ percentiles; the median is represented by the center line. IQR ($75^{th}$-$25^{th}$ percentile) is represented by whiskers. FIG. 22E: Scatterplot of metabolite significance versus module membership (MM) of the 12 metabolites in the NGM3-discriminating metabolic module. Metabolites with a higher metabolite significance value discriminate NGM3 from other NGMs. Metabolites plotted above the dashed line (representing the overall p-value for between-NGM differences) are significantly associated with NGM differentiation (P<0.05), and were detected in higher concentrations in NGM3 compared to the other NGMs. MM values indicate the degree of interconnectedness of a specific metabolite to other metabolites in the module (higher MM value indicates greater interconnectedness). FIG. 22F: When the same ex vivo assay that was performed in FIGS. 22A-22C was used, 12,13-DiHOME significantly reduced the proportion of $CD4^+CD25^+FOXP3^+$ cells at three different concentrations compared to vehicle control (LME; P=0.04, P<0.001, P=0.001 for concentrations of 75, 130 and 200 μM, respectively; center line represents mean proportion of cells).

Figure 23:
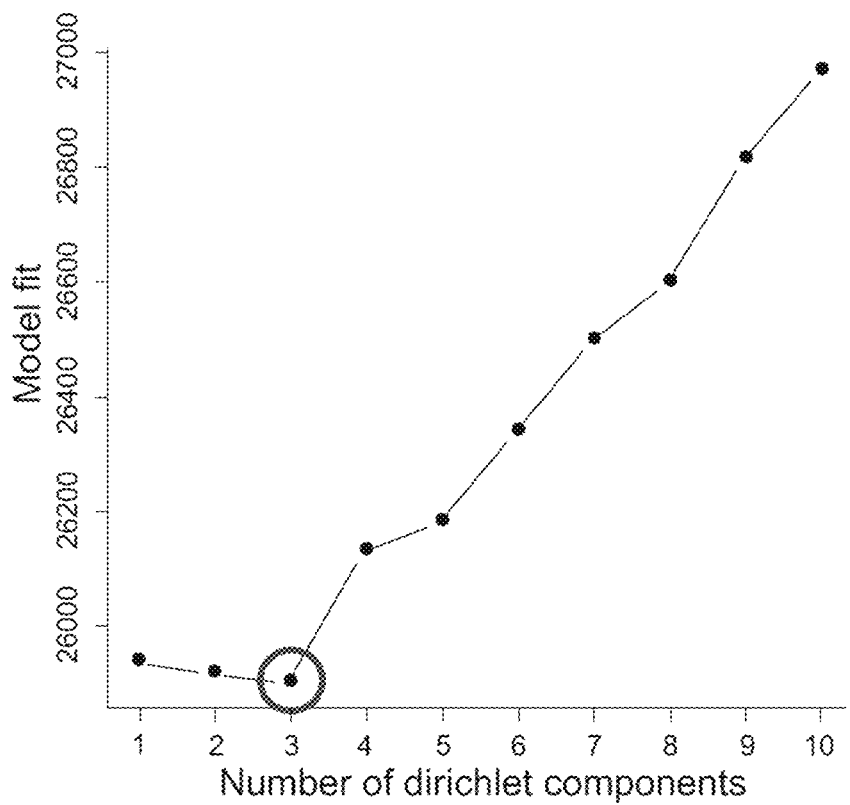

FIG. 23. Dirichlet multinomial mixture model identifies three compositionally distinct bacterial NGMs as the best model fit. Model fit was based on the Laplace approximation to the negative log model where a lower value indicates a better model fit.

Figure 24:
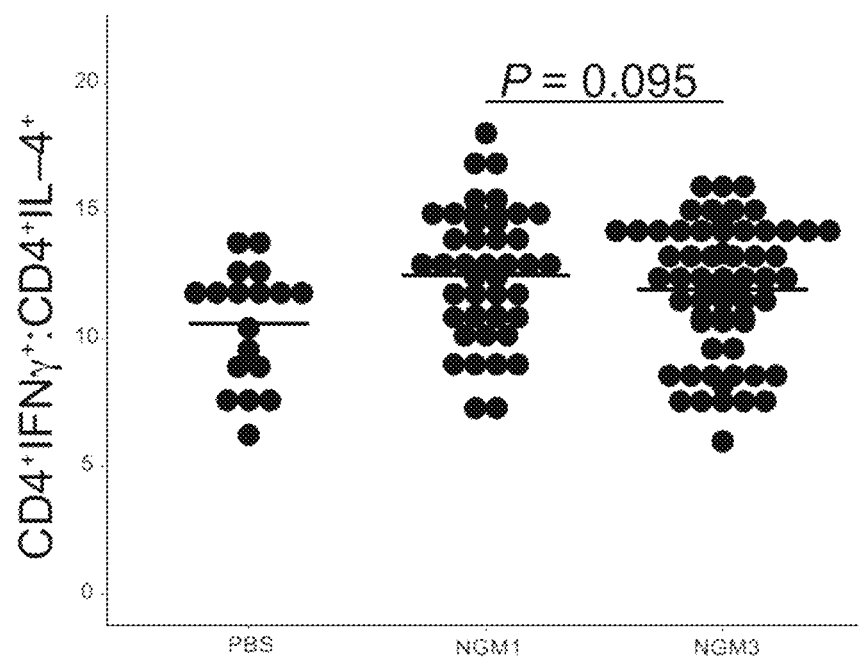

FIG. 24. Sterile fecal water from NGM3 participants induces a $CD4^+IL-4^+$ cell skew. Dendritic cells from serum of two healthy adult donors (biological replicates), were incubated with sterile fecal water from NGM1 (n=7; three biological replicates per sample) or NGM3 (n=5; three biological replicates per sample) participants, prior to co-incubation with autologously purified naïve $CD4^+$ cells. NGM3 fecal water induces a trend toward a $CD4^+IL-4^+$ cell skew compared with NGM1 (LME; P=0.095).

Figures 25, 26:
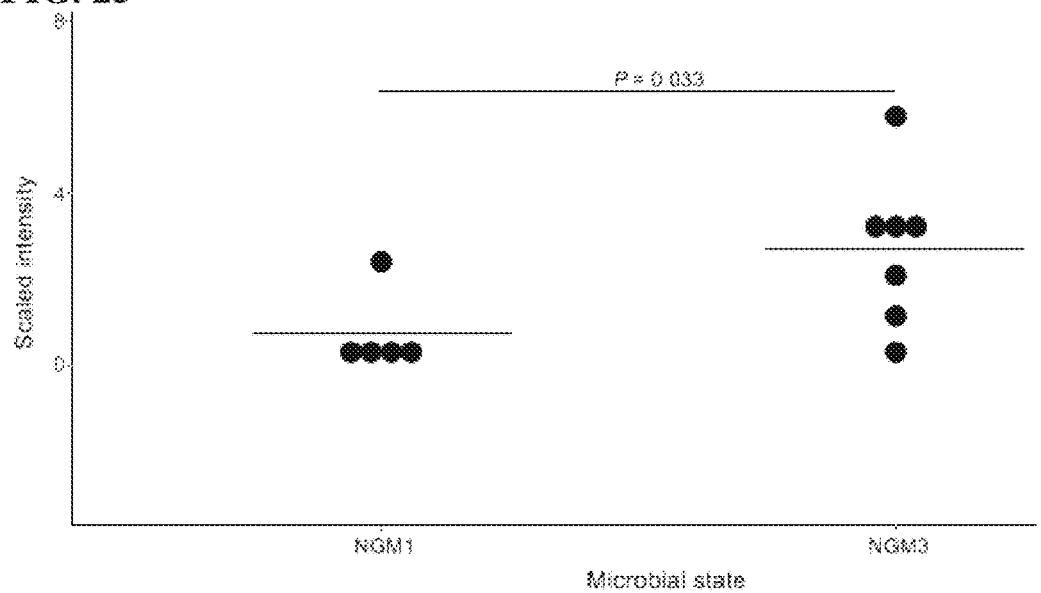

FIG. 25. Confirmation that the concentration of the dihydroxy fatty acid 12, 13 DiHOME, is significantly increased in the NGM3 sample subset used for ex vivo assays. Using the subset of samples employed in the ex vivo DC-T-cell assay and based on metabolite scaled intensity data, 12, 13 DiHOME is significantly increased in relative concentration in NGM3 (n=7) compared to NGM1 (n=5) samples (Welch's-test; P=0.033).

FIG. 26. Allergens used to determine PM atopy status of participants in this study. Mean and median of allergen-specific IgE (IU ml$^{-1}$) is provided for each.

FIG. 27. Risk ratio of IGMs (infants>6 months old) for developing atopy or having parental report of doctor's diagnosis of asthma. Risk ratios were calculated based on log-binomial regression.

FIG. 28. Fungal taxa exhibiting significantly increased relative abundance in lower-risk NGM1 versus higher-risk NGM3 neonatal gut microbiota. Significant difference in relative abundance was determined using a zero-inflated negative binomial regression model (q<0.20). White background indicates taxa enriched in NGM1 (compared with NGM3), gray background indicates taxa enriched in NGM3 (compared with NGM1). Findings are ranked by difference in relative abundance (NGM1-NGM3).

FIG. 29. Fungal taxa exhibiting significantly increased relative abundance in lower-risk NGM2 versus higher-risk NGM3 neonatal gut microbiota. Significant difference in relative abundance was determined using zero-inflated negative binomial regression model (q<0.20). White background indicates taxa enriched in NGM2 (compared with NGM3), gray background indicates taxa enriched in NGM3 (compared with NGM2). Findings are ranked by difference in relative abundance (NGM2-NGM3).

Figures 30, 31A:
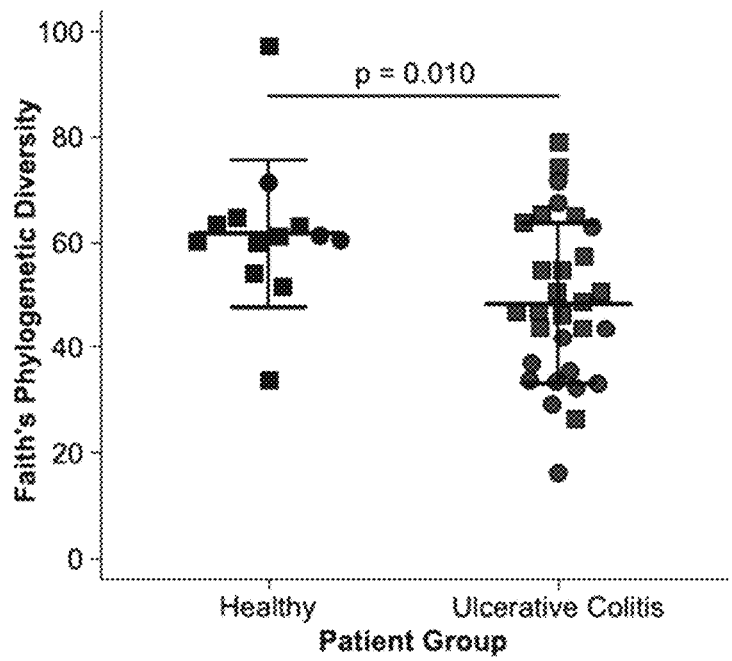

FIG. 30. Procrustes analyses of 16S rRNA-based β-diversity, PICRUSt and metabolomic datasets. Results from Procrustes analyses indicate that bacterial β-diversity, PICRUSt and metabolomic data is highly and significantly correlated.

Figure 31B:
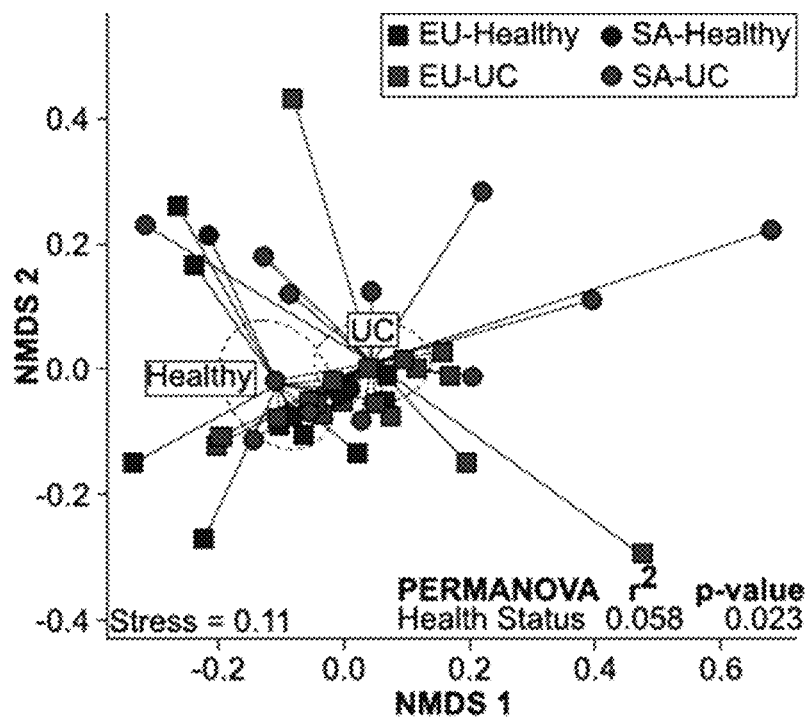
Figure 31C:
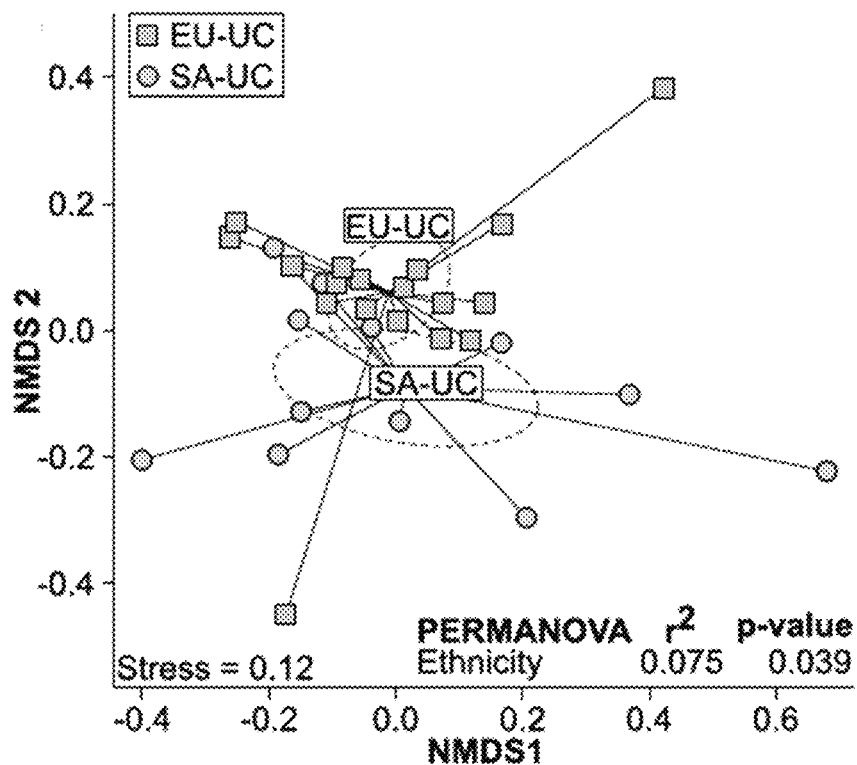

FIGS. 31A-31C. Comparison of healthy (n=13) and UC-associated (n=30) fecal microbiotas. FIG. 31A: Bacterial diversity. Horizontal bars represent means±standard deviations. P values were obtained by two-tailed Student t test. FIG. 31B: Bacterial community composition represented by nonmetric multidimensional scaling (NMDS) of pairwise weighted UniFrac distances. FIG. 31C: Bacterial community composition of UC patients stratified by ethnicity (18 EU UC, 12 SA UC) represented by NMDS of pairwise weighted UniFrac distances. In FIG. 31B and FIG. 31C, each dashed ellipse represents the 95% confidence interval for the centroid of each stratification group as calculated by ordiellipse.

Figure 32A:
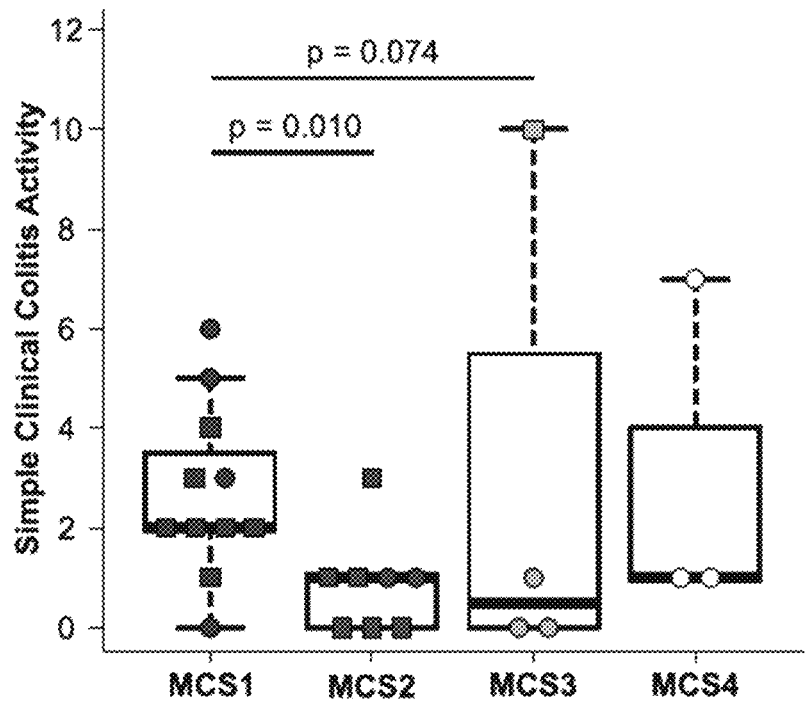
Figure 32B:
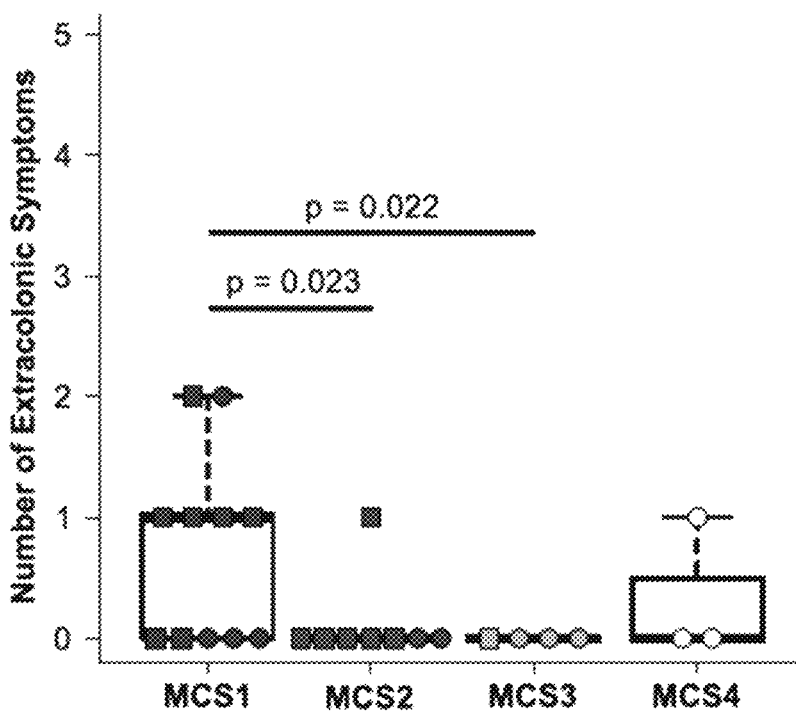
Figure 32C:
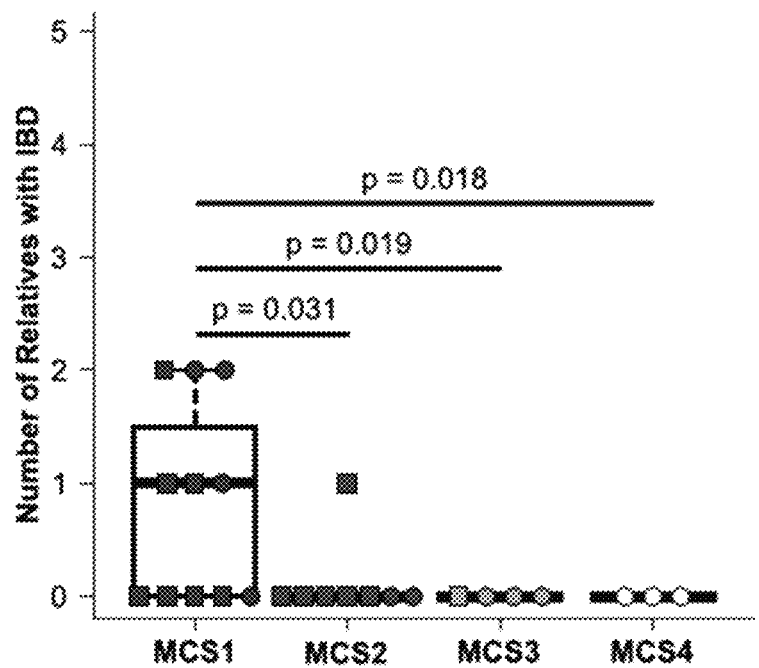
Figure 32D:
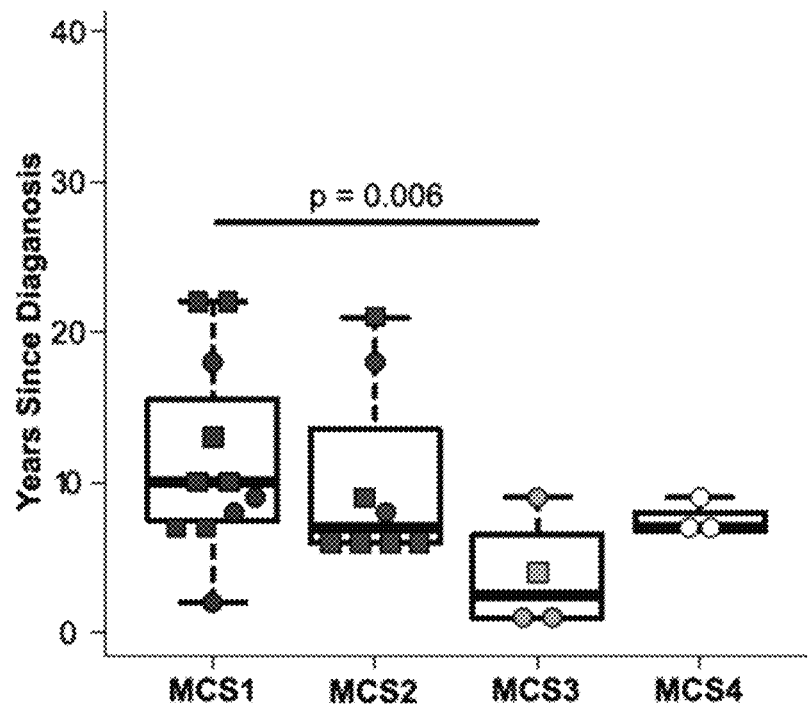

FIGS. 32A-32D. Clinical measurements of UC severity among UC MCSs (11 for MCS1, 8 for MCS2, 4 for MCS3, 3 for MCS4). FIG. 32A: Simple clinical *colitis* activity. FIG. 32B: Number of extracolonic symptoms. FIG. 32C: Number of family members diagnosed with IBD. FIG. 32D: Duration of disease. All pairwise comparisons were done with a two-tailed Dunn test. Only P values of <0.1 are indicated. EU UC, squares; SA UC, circles.

Figure 33A:
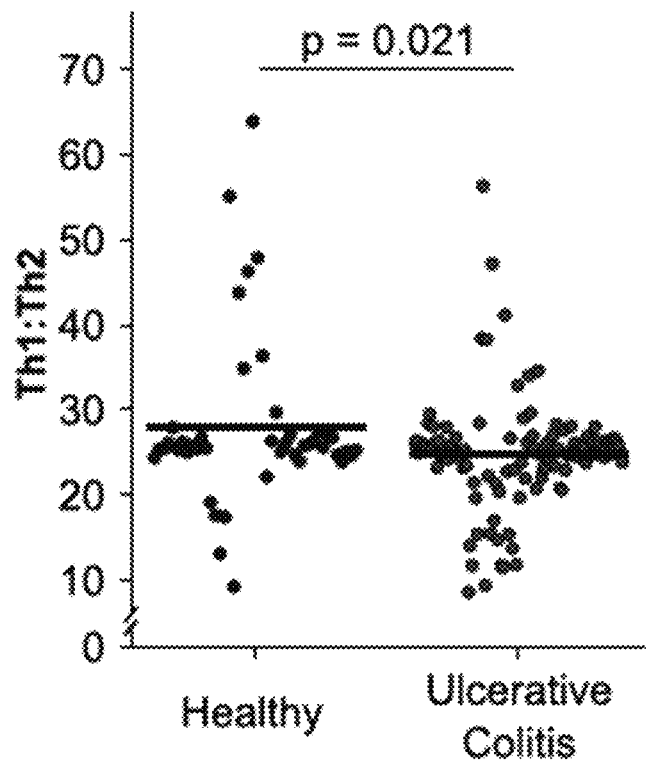
Figure 33B:
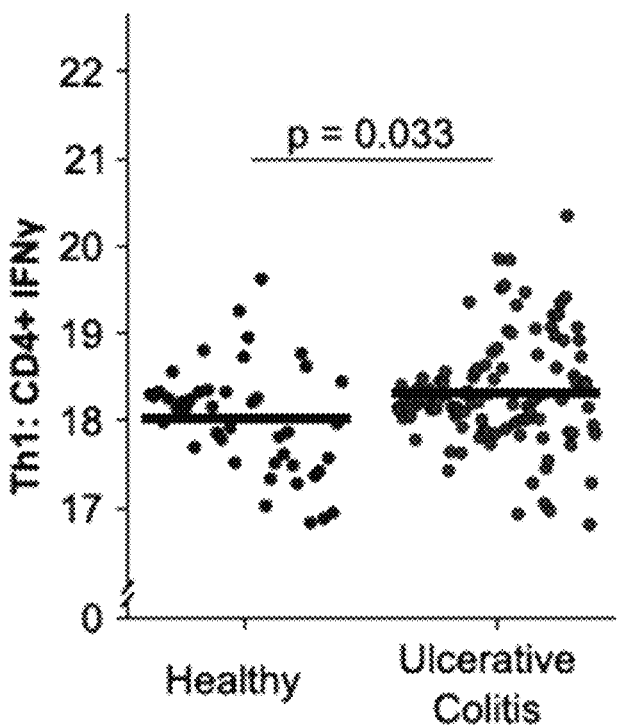
Figure 33C:
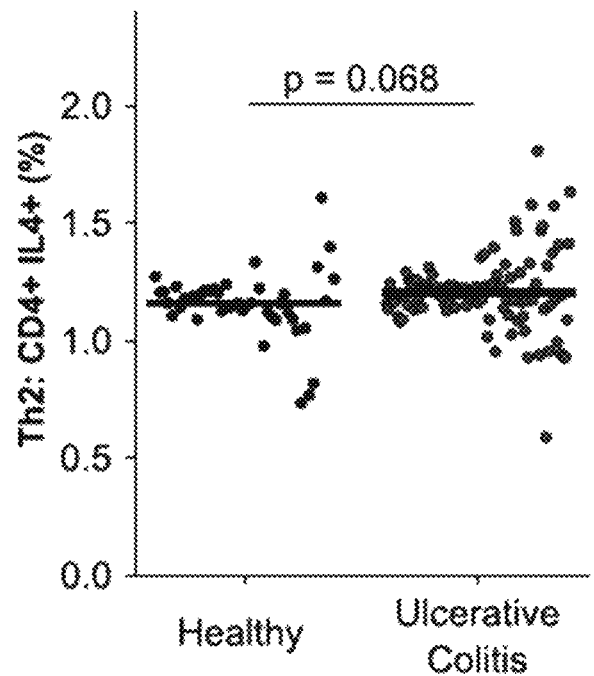
Figure 33D:
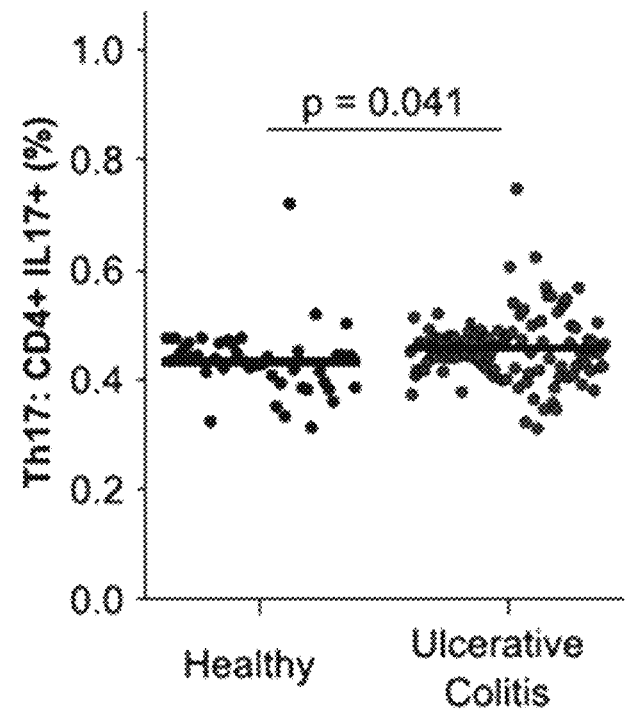
Figure 33E:
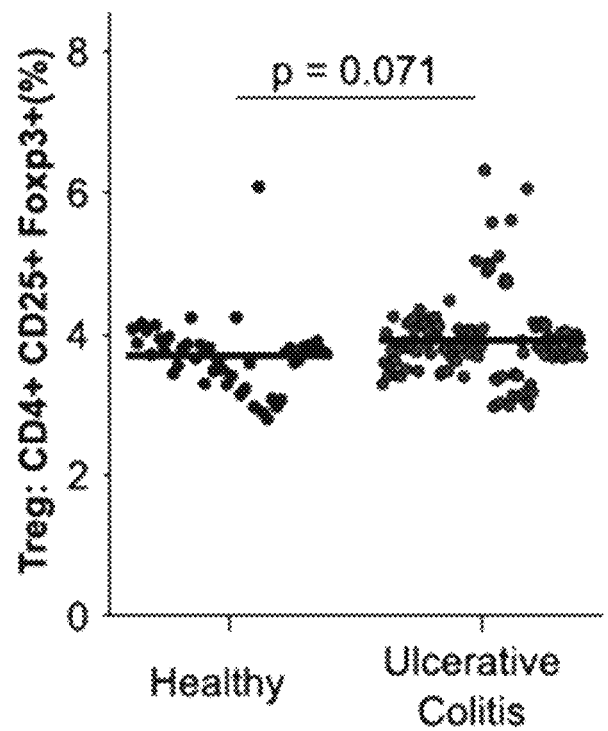

FIG. 33A-33K. In vitro human T-cell activity following coculture with autologous DCs coincubated with sterile fecal water. FIG. 33A: Th1-to-Th2 ratio; FIG. 33B: Th1 frequency; FIG. 33C: Th2 frequency; FIG. 33D: Th17 frequency; e, regulatory T-cell frequency (48 healthy, 116 UC). Comparisons of the Th1 frequencies (FIG. 33F), Th2 frequencies (FIG. 33G), and Th1-to-Th2 ratios (FIG. 33H) of healthy and UC MCSs are shown (48 for healthy, 48 for MCS1, 40 for MCS2, 16 for MCS3, and 8 for MCS4). Concentrations of IL-4 (FIG. 33I), IL-5 (FIG. 33J), and IL-13 (FIG. 33K) in cell supernatant following coculture of human T cells with autologous DCs challenged with sterilized fecal water from healthy participants and MCS1 and MCS2 patients are shown (48 for healthy participants, 48 for MCS1 patients, and 40 for MCS2 patients). Data were generated from four (FIGS. 33A-33H) or two (FIG. 33I-33K) replicate experiments with DCs/T cells obtained from two anonymous PBMC donors. Horizontal bars (mean fitted values for each group) and P values were determined by linear mixed-effect modeling (see Materials and Methods). P values of <0.1 are indicated.

Figure 34A:
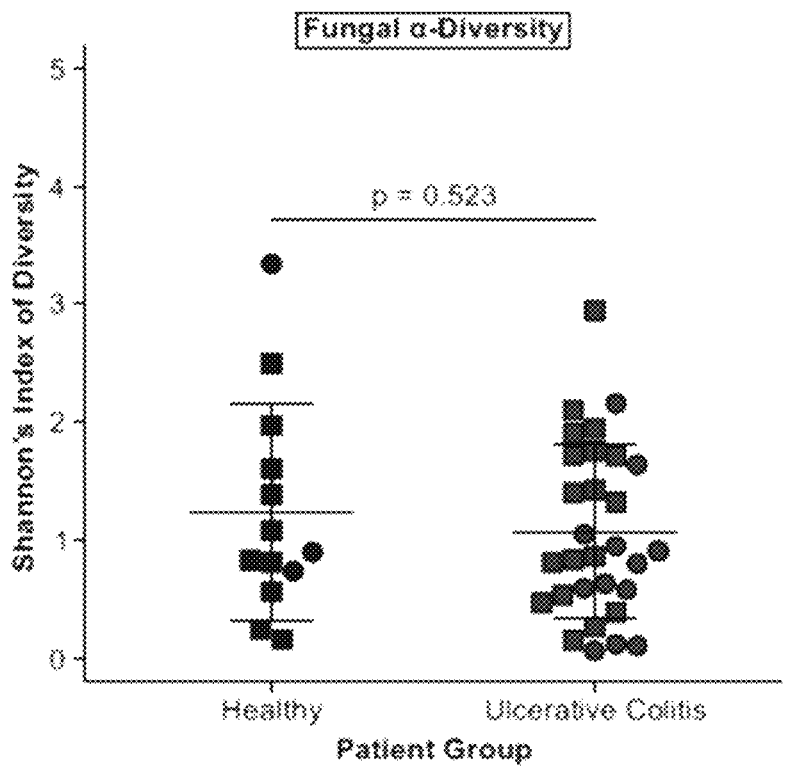
Figure 34B:
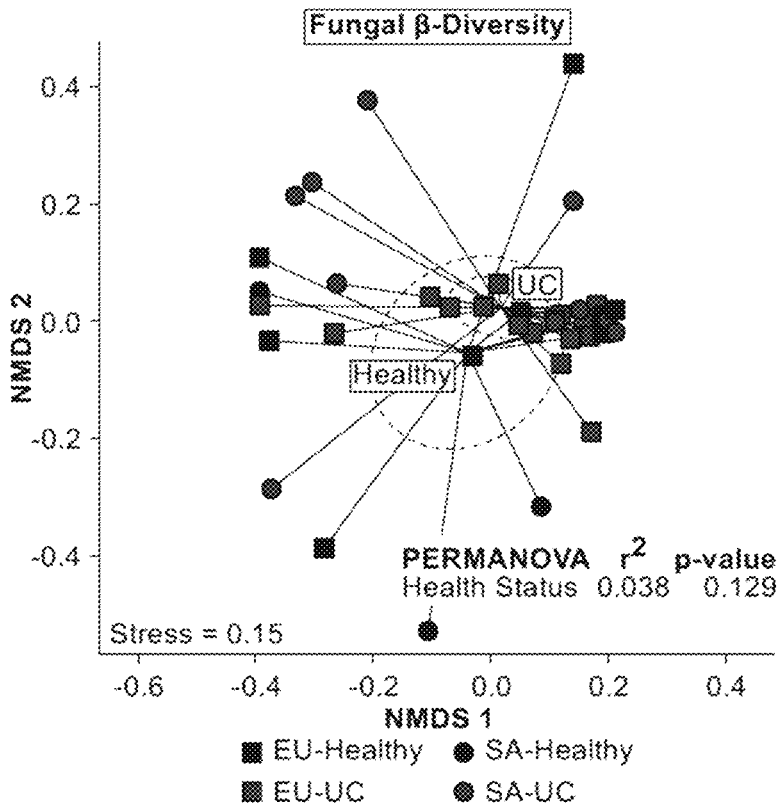
Figure 34C:
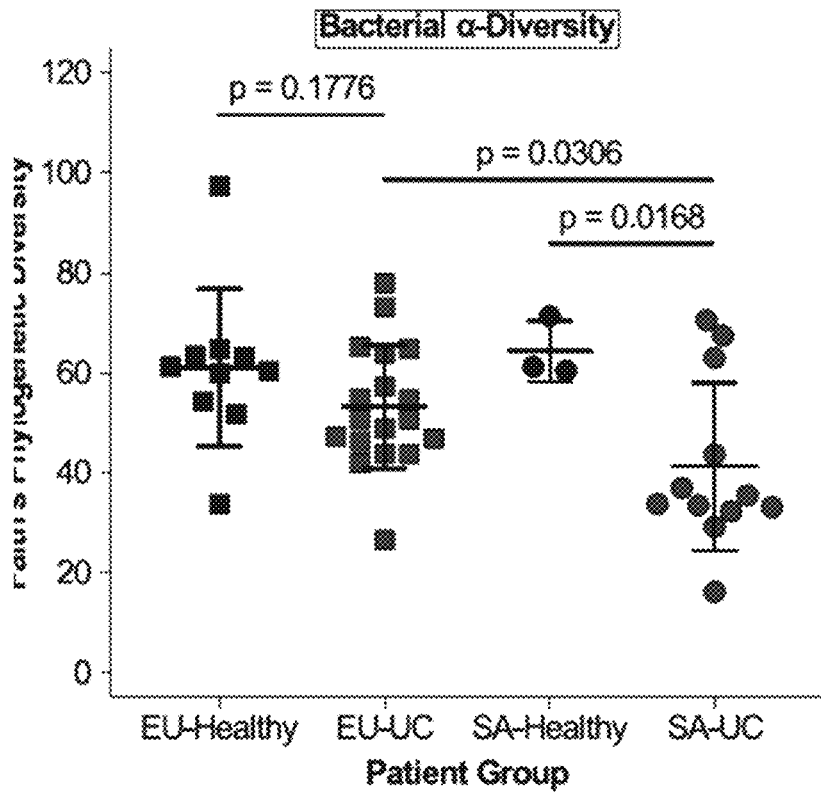
Figure 34D:
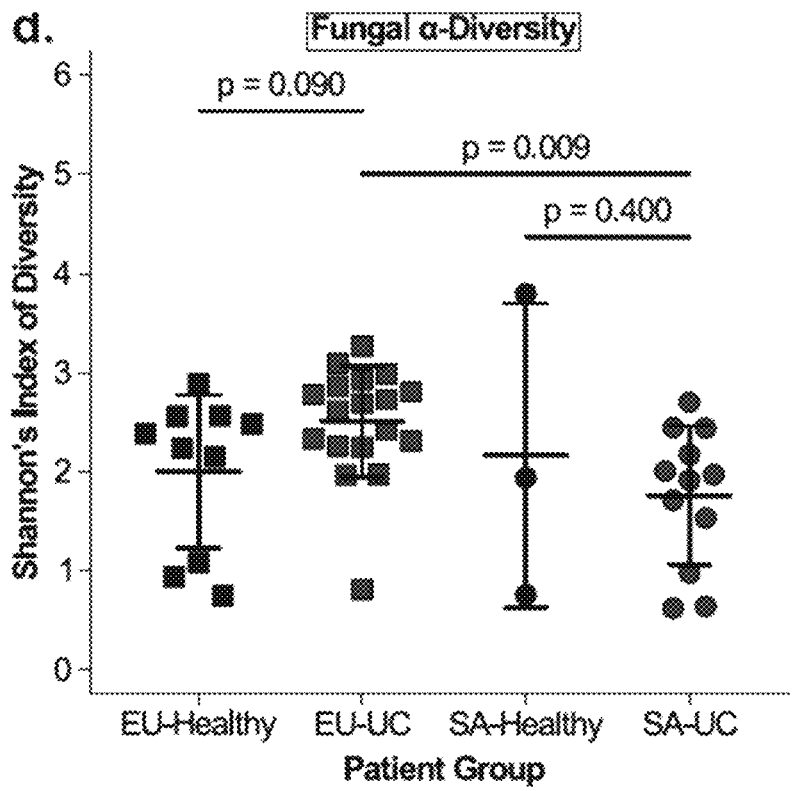
Figure 34E:
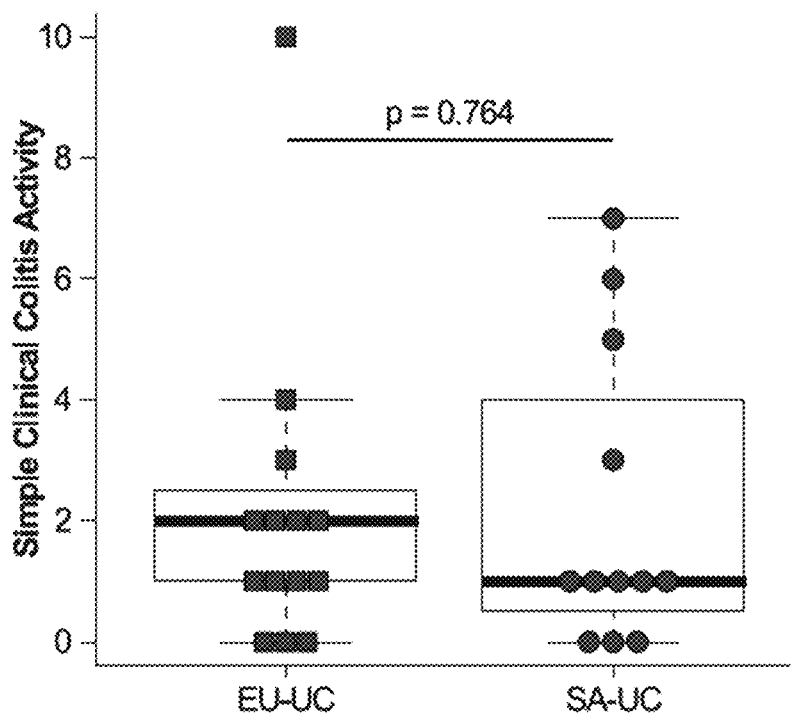
Figure 34F:
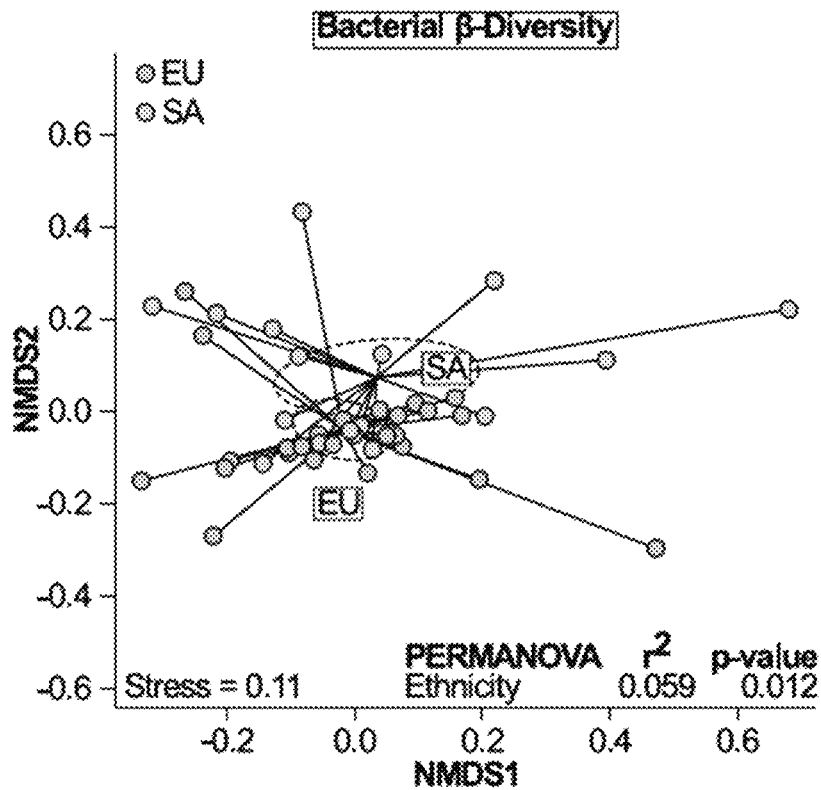
Figure 34G:
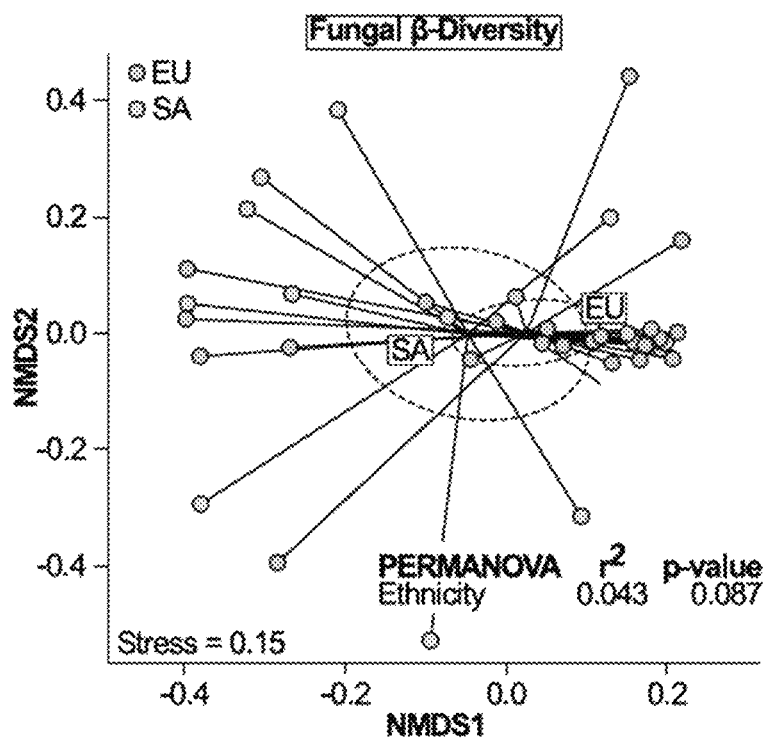
Figure 34H:
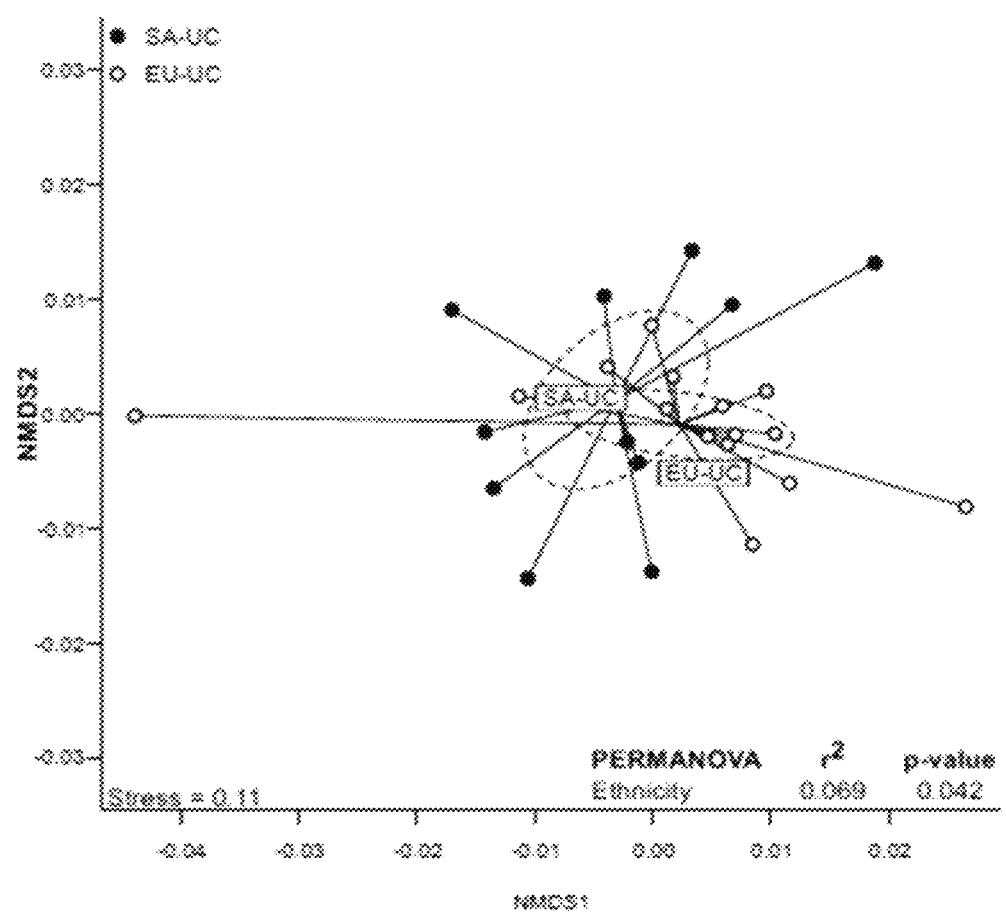

FIGS. 34A-34H. Comparison of healthy (n=13) and UC-associated (n=30) fecal fungal microbiotas. FIG. 34A: Fungal α diversity stratified by healthy status. FIG. 34B: Fungal community composition represented by NMDS of pairwise Bray-Curtis distances. Participants are colored by health status. Bacterial α diversity FIG. 34C and fungal α diversity FIG. 34D were stratified by health status and ethnicity (10 healthy EU, 3 healthy SA, 18 UC EU, 12 UC SA). FIG. 34E: Simple clinical *colitis* activity of UC patients stratified by ethnicity (14 EU UC, 12 SA UC). P values were obtained by two-tailed rank sum test. FIG. 34F Bacterial community composition of all participants stratified by ethnicity (28 EU, 15 SA) represented by NMDS of pairwise weighted UniFrac distances. FIG. 34G: Fungal community composition of all participants stratified by ethnicity (28 EU, 15 SA) represented by NMDS of pairwise Bray-Curtis distances. FIG. 34H: PhyloChip-profiled bacterial community composition of UC patients stratified by ethnicity (15 EU UC, 11 SA UC) represented by NMDS of pairwise Canberra distances. In panels a, c, and d, horizontal bars represent means±standard deviations. P values were obtained by two-tailed t test. In FIG. 34B and FIGS. 34F-34H, each dashed ellipse represents the 95% confidence interval for the centroid of each participant stratification group as calculated by ordiellipse. Each dot/square represents a single fecal sample obtained from a single donor.

Figure 35A:
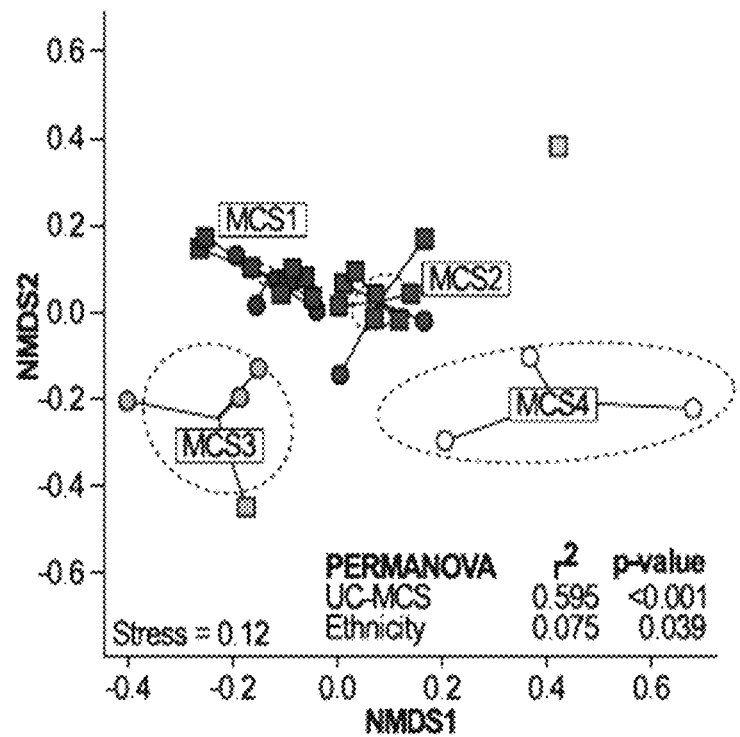
Figure 35B:
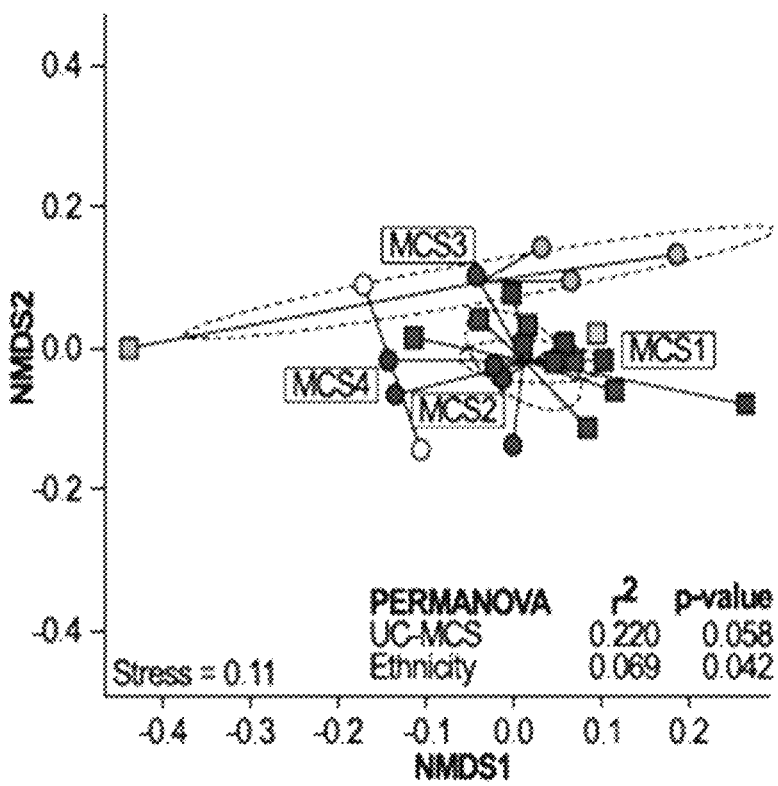

FIGS. 35A-35B. Bacterial community compositions of UC patients stratified by UC MCS. FIG. 35A: NMDS of pairwise weighted UniFrac distances for 16S rRNA profiles obtained via Illumina MiSeq (12 MCS1, 10 MCS2, 4 MCS3, 3 MCS4, 1 other). FIG. 35B: NMDS of pairwise Canberra distances for 16S rRNA profiles obtained via PhyloChip (10 MCS1, 8 MCS2, 4 MCS3, 2 MCS4, 1 other). Each dashed ellipse represents the 95% confidence interval for the centroid of each participant stratification group as calculated by ordiellipse. Each dot/square represents a single fecal sample obtained from a single donor.

Figures 36, 37:
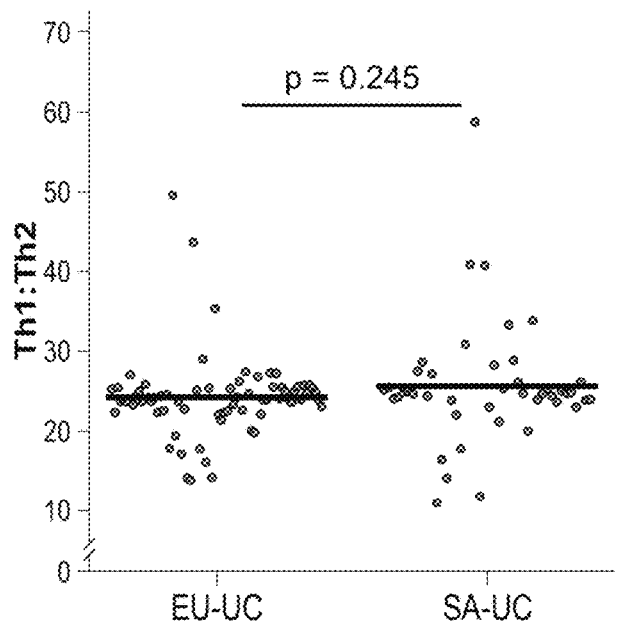

FIG. 36. In vitro human T-cell activity following coculture with autologous DCs coincubated with sterile fecal water. Induced Th1-to-Th2 ratios of EU UC (n=) and SA UC patients are compared. Data were generated from four replicate experiments with DCs/T cells obtained from two anonymous PBMC donors. Horizontal bars (mean fitted values for each group) and P values were determined by linear mixed-effect modeling.

FIG. 37. Breakdown of Study Participant Cohort. Note: one SA-UC participant failed to report their sex.

FIG. 38. Description of Metabolon QC Samples.

FIG. 39. Metabolon QC Standards.

DETAILED DESCRIPTION

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "isolated", when applied to a bacterium, refers to a bacterium that has been (1) separated from at least some of the components with which it was associated when initially produced (whether in nature or in an experimental setting), and/or (2) produced, prepared, purified, and/or manufactured by the hand of man, e.g. using artificial culture conditions such as (but not limited to) culturing on a plate and/or in a fermenter. Isolated bacteria include those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In embodiments, isolated bacteria are more than about 80%, about 85%, about 90%, about 91%, about 92%, about 93%, about 94%, about 95%, about 96%, about 97%, about 98%, about 99%6, or more than about 99% pure. In embodiments, a bacterial population provided herein comprises isolated bacteria. In embodiments, a composition provided herein comprises isolated bacteria. In embodiments, the bacteria that are administered are isolated bacteria.

As used herein, a substance is "pure" if it is substantially free of other components. The terms "purify," "purifying" and "purified", when applied to a bacterium, refer to a bacterium that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, or by passage through culture, and a purified bacterium or bacterial population may contain other materials up to about 10%, about 20%, about 30%, about 40%, about 50%, about 60%, about 70%, about 80%, about 90%, or above about 90% and still be considered "isolated." In some embodiments, purified bacteria and bacterial populations are more than about 80%, about 85%, about 90%0, about 91%, about 92%, about 93%, about 94%, about 95%, about 96%, about 97%, about 98%, about 99%, or more than about 99% pure. In the instance of microbial compositions provided herein, the one or more bacterial types (species or strains) present in the composition can be independently purified from one or more other bacteria produced and/or present in the material or environment containing the bacterial type. Microbial compositions and the bacterial components thereof are generally purified from residual habitat products.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A "label" or a "detectable moiety" is a composition detectable by spectroscopic, photochemical, biochemical, immunochemical, chemical, or other physical means. For example, useful labels include 32P, fluorescent dyes (e.g. cyanine), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. chemical compounds including biomolecules and/or cells such as bacterial cells) to become sufficiently proximal to react, interact or physically touch. It should be appreciated; however, a resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, an antibody domain as described herein and an antibody-binding domain. In embodiments contacting includes, for example, allowing an antibody domain as described herein to interact with an antibody-binding domain.

"Patient" or "subject in need thereof" refers to a living member of the animal kingdom suffering from or that may suffer from the indicated disorder. In embodiments, the subject is a member of a species comprising individuals who naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human. In embodiments, the subject is a non-mammalian animal such as a turkey, a duck, or a chicken. In embodiments, a subject is a living organism suffering from or prone to a disease or condition that can be treated by administration of a composition or pharmaceutical composition as provided herein.

The terms "disease" or "condition" refer to a state of being or health status of a patient or subject capable of being treated with a compound, pharmaceutical composition, or method provided herein. In embodiments, the disease is an inflammatory disease (e.g. asthma, ulcerative *colitis*, irritable bowel syndrome, arthritis, uveitis, pyoderma gangrenosum, erythema nodosum, or any other inflammatory disease mentioned herein). As used herein, a "symptom" of a disease includes any clinical or laboratory manifestation associated with the disease, and is not limited to what a subject can feel or observe.

As used herein, the term "inflammatory disease" refers to a disease or condition characterized by aberrant inflammation (e.g., an increased level of inflammation compared to a control such as a healthy person not suffering from a disease). Non-limiting examples of inflammatory diseases include allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous colitis, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

As used herein the term "dysbiosis" means a difference in the gastrointestinal microbiota compared to a healthy or general population. In embodiments, dysbiosis comprises a difference in gastrointestinal microbiota commensal species diversity compared to a healthy or general population. In an embodiment, dysbiosis comprises a decrease of beneficial microorganisms and/or increase of pathobionts (pathogenic or potentially pathogenic microorganisms) and/or decrease of overall microbiota species diversity. Many factors can harm the beneficial members of the intestinal microbiota leading to dysbiosis, including (but not limited to) antibiotic use, psychological and physical stress, radiation, and dietary changes. In an embodiment, dysbiosis comprises or promotes the overgrowth of a bacterial opportunistic pathogen such as *Enterococcus faecalis, Enterococcus faecium*, or *Clostridium difficile*. In an embodiment, the dysbiosis comprises a reduced amount (absolute number or proportion of the total microbial population) of bacterial or fungal cells of a species or genus (e.g., 5%, 10%, 15%, 20%$^1$, 25%, 30%, 35%, 40%, 45%/O, 50%, 55%, 600, 65%, 70%, 75%, 80%, 85%, 90%, 95% or more lower) compared to a healthy subject (e.g., a corresponding subject who does not have an inflammatory disease, an infection, and who has not been administered an antibiotic within about 1, 2, 3, 4, 5, or 6 months, and/or compared to a healthy or general population). In an embodiment, the dysbiosis comprises an increased amount (absolute number or proportion of the total microbial population) of bacterial or fungal cells within a species or genus (e.g., 5%, 10%, 15%, 20%, 25%, 30%, 35%, 40%, 45%, 50%, 55%, 60%, 65%, 70%, 75%, 80%, 85%, 90%, 95%/O or more higher) compared to a healthy subject (e.g., a corresponding subject who does not have an inflammatory disease, an infection, and who has not been administered an antibiotic within about 1, 2, 3, 4, 5, or 6 months, and/or compared to a healthy or general population). In an embodiment, a subject who comprises a gastrointestinal infection, gastrointestinal inflammation, diarrhea, *colitis*, or who has received an antibiotic within about 1, 2, 3, 4, 5, 6, 7, 8, 9, or 10 weeks is deemed to comprise dysbiosis. In an embodiment, the impaired microbiota comprises small intestinal bacterial or fungal overgrowth. Antibiotic administration (e.g., systemically, such as by intravenous injection or orally) is a common and significant cause of major alterations in the normal microbiota. Thus, as used herein, the term "antibiotic-induced dysbiosis" refers to dysbiosis caused by or following the administration of an antibiotic.

Non-limiting examples of dysbiosis are described in the examples provided herein. Non-limiting examples of dysbiosis in the context of neonates are also described in Fujimura et al. (2016) "Neonatal gut microbiota associates with childhood multisensitized atopy and T cell differentiation" *Nature Medicine* 22(10): 1187-1191 (hereinafter "Fujimura et al. 2016"), the entire content of which (including all supplemental information and data) is incorporated herein by reference. In some embodiments, a subject with dysbiosis has the NGM3 microbiome profile as set forth in Fujimura et al. 2016. Non-limiting examples of dysbiosis in the context of ulcerative *colitis* are described in Mar et al. (2016) "Disease Severity and Immune Activity Relate to Distinct Interkingdom Gut Microbiome States in Ethnically Distinct Ulcerative Colitis Patients" *mBio* 7(4):e01072-16 (herein after "Mar et al. 2016"), the entire content of which (including all supplemental information and data) is incorporated herein by reference. In some embodiments, a subject with dysbiosis has the MCS4 microbiome profile as set forth in Mar et al. 2016. In some embodiments, a subject with dysbiosis has the MCS 3 microbiome profile as set forth in Mar et al. 2016. In some embodiments, a subject with dysbiosis has the MCS2 microbiome profile as set forth in Mar et al. 2016. In some embodiments, a subject with dysbiosis has the MCS1 microbiome profile as set forth in Mar et al. 2016.

The term "associated" or "associated with" in the context of a substance or substance activity or function associated with a disease (e.g., an allergy, asthma, ulcerative *colitis*, irritable bowel syndrome, arthritis, uveitis, pyoderma gangrenosum, or erythema nodosum) means that the disease is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

A "control" or "standard control" refers to a sample, measurement, or value that serves as a reference, usually a known reference, for comparison to a test sample, measurement, or value. For example, a test sample can be taken from a patient suspected of having a given disease (e.g. dysbiosis, an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. microbiome, RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The term "diagnosis" refers to a relative probability that a disease (e.g. an autoimmune, inflammatory autoimmune, cancer, infectious, immune, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. an autoimmune, inflammatory autoimmune, cancer, infectious, immune, or other disease), or the likely severity of the disease (e.g., duration of disease). The terms are not intended to be absolute, as will be appreciated by any one of skill in the field of medical diagnostics.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), feces and feces fractions or products (e.g., fecal water, such as but not limited to fecal water separated from other fecal components and solids by methods such as centrifugation and filtration) sputum, tissue, cultured cells (e.g., primary cultures, explants, and transformed cells), stool, urine, synovial fluid, joint tissue, synovial tissue, synoviocytes, fibroblast-like synoviocytes, macrophage-like synoviocytes, immune cells, hematopoietic cells, fibroblasts, macrophages, dendritic cells, T-cells, etc. In embodiments, a sample is obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality comprising more than 2) species within an indicated genus or indicated genera. In embodiments, 1, 2, 3, 4, 5, or more or all or the indicated species is or are isolated. In embodiments, the indicated species are administered together. In embodiments, each of the indicated species is present in a single composition that comprises each of the species. In embodiments, each of the species is administered concurrently, e.g., within about 1, 2, 3, 4, 5, 6, 7, 8, 9, 10, 30, or 60, 1-5, 1-10, 1-30, 1-60, or 5-15 seconds or minutes of each other.

In this disclosure, "comprises," "comprising," "containing," and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. By contrast, the transitional phrase "consisting of" excludes any element, step, or ingredient not specified.

As used herein, the term "about" in the context of a numerical value or range means±10% of the numerical value or range recited or claimed, unless the context requires a more limited range.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

II. Bacterial Populations and Microbial Compositions

In an aspect, a composition comprising a bacterial population that comprises, consists essentially of, or consists of, 1, 2, 3, 4, 5, 6, 7, or 8 (or at least 1, 2, 3, 4, 5, 6, 7, or 8) bacterial species. In embodiments, the bacterial population comprises, consists essentially of, or consists of any 1, 2, 3, 4, 5, 6, 7, or 8 of *Lactobacillus* sp., *Faecalibacterium* sp., *Akkermansia* sp., *Myxococcus* sp., *Cystobacter* sp., *Pediococcus* sp., *Bifidobacterium* sp., and *Clostridium* sp. In embodiments, the bacterial population comprises *Lactobacillus* sp. and *Faecalibacterium prausnitzii*. In embodiments, the bacterial population comprises *Lactobacillus* sp. and *Akkermansia muciniphila*. In embodiments, the bacterial population comprises *Lactobacillus* sp., and *Myxococcus xanthus*. In embodiments, the bacterial population comprises *Lactobacillus* sp. and *Cystobacter fuscus*. In embodiments, the bacterial population comprises *Lactobacillus* sp. and *Pediococcus pentosaceus*, *Pediococcus acidilactici*, *Pediococcus damnosus*, *Pediococcus ethanolidurans*, or *Pediococcus parvulus*. In embodiments, the bacterial population comprises *Lactobacillus* sp. and *Bifidobacterium bifidum*, *Bifidobacterium pseudolongum*, *Bifidobacterium saeculare*, or *Bifidobacterium subtile*. In embodiments, the bacterial population comprises *Lactobacillus* sp. and *Clostridium hiranonis*. In embodiments, the *Lactobacillus* sp. is *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*. In embodiments, the *Lactobacillus* sp. is *Lactobacillus johnsonii*. In embodiments, the bacterial population comprises at least 1, 2, 3, 4, 5, 6, 7, 8, 9, or 10, or from 1-5, 1-10, 1-5, or 1-20 of any combination of the following: *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, *Lactococcus lactis*, *Faecalibacterium prausnitzii*, *Akkermansia muciniphila*, *Myxococcus xanthus*, *Cystobacter fuscus*, *Pediococcus pentosaceus*, *Pediococcus acidilactici*, *Pediococcus damnosus*, *Pediococcus ethanolidurans*, and *Pediococcus parvulus*. In embodiments, the bacterial population includes *Lactobacillus johnsonii*, *Faecalibacterium prausnitzii*, *Akkermansia muciniphila*, *Myxococcus xanthus*, and/or *Pediococcus pentosaceus*. In embodiments, the bacteria are isolated bacteria.

In an aspect, a composition including *Lactobacillus* sp., *Faecalibacterium* sp., *Akkermansia* sp., *Myxococcus* sp., and/or *Pediococcus* sp is provided. In embodiments, (i) the *Lactobacillus* sp. is *Lactobacillus johnsonii*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; and (v) the *Pediococcus* sp. is *Pediococcus pentosaceus*.

In an aspect, a composition including *Lactobacillus* sp., *Faecalibacterium* sp., *Akkermansia* sp., *Cystobacter* sp., and *Pediococcus* sp is provided. In embodiments, (i) the *Lactobacillus* sp. is *Lactobacillus johnsonii*; (ii) the *Faecalibacterium* sp., is *Faecalibacterium prausnitzii*; (iii) the *Akkermansia* sp. is *Akkermansia muciniphila*; (iv) the *Cystobacter* sp. is *Cystobacter fuscus*; and (v) the *Pediococcus* sp. is *Pediococcus pentosaceus*.

In embodiments, the bacterial population further comprises *Bifidobacterium* sp. or *Clostridium* sp. In embodiments, the *Bifidobacterium* sp. is *Bifidobacterium bifidum*, *Bifidobacterium pseudolongum*, *Bifidobacterium saeculare*, or *Bifidobacterium subtile*. In embodiments, the *Clostridium* sp. is *Clostridium hiranonis*.

In an aspect, a microbial composition is provided. The composition includes *Lactobacillus johnsonii*, *Faecalibacterium prausnitzii*, *Akkermansia muciniphila*, *Myxococcus xanthus*, *Pediococcus pentosaceus* and a biological carrier suitable for administration to the gut.

In an aspect, a microbial composition is provided. The composition includes *Lactobacillus johnsonii*, *Faecalibacterium prausnitzii*, *Akkermansia muciniphila*, *Myxococcus xanthus* or *Pediococcus pentosaceus* and a biological carrier suitable for administration to the gut.

In embodiments, the biological carrier is suitable for oral or rectal administration. In embodiments, the biological carrier is suitable for colonization of the gut. A "biologically acceptable" (or "pharmacologically acceptable") carrier as referred to herein refers to molecular entities and compositions as described herein that do not produce an adverse, allergic or other untoward reaction when administered to an animal or a human.

In embodiments, the composition includes less than about 20, 19, 18, 17, 16, 15, 14, 13, 12, 11, 10, 9, 8, 7, 6, 5, 4, 3, or 2 different species of bacteria. In embodiments, the composition includes less than about 20 different species of bacteria. In embodiments, the composition includes less than 20 different species of bacteria. In embodiments, the composition includes less than about 15 different species of bacteria. In embodiments, the composition includes less than 15 different species of bacteria. In embodiments, the composition includes less than about 10 different species of bacteria. In embodiments, the composition includes less than 10 different species of bacteria. In embodiments, the composition includes less than about 9 different species of bacteria. In embodiments, the composition includes less than 9 different species of bacteria. In embodiments, the composition includes less than about 8 different species of bacteria. In embodiments, the composition includes less than 8 different species of bacteria. In embodiments, the composition includes less than about 7 different species of bacteria. In embodiments, the composition includes less than 7 different species of bacteria. In embodiments, the composition includes less than about 6 different species of bacteria. In embodiments, the composition includes less than 6 different species of bacteria. In embodiments, the composition includes less than about 5 different species of bacteria. In embodiments, the composition includes less than 5 different species of bacteria. In embodiments, the composition includes less than about 4 different species of bacteria. In embodiments, the composition includes less than 4 different species of bacteria. In embodiments, the composition includes less than about 3 different species of bacteria. In embodiments, the composition includes less than 3 different species of bacteria. In embodiments, the composition includes less than about 2 different species of bacteria. In embodiments, the composition includes less than 2 different species of bacteria.

In embodiments, the composition is not a fecal transplant. In embodiments, the composition further includes a pharmaceutically acceptable excipient. In embodiments, the composition is a capsule, a tablet, a suspension, a suppository, a powder, a cream, an oil, an oil-in-water emulsion, a water-in-oil emulsion, or an aqueous solution. In embodiments, the composition is in the form of a powder, a solid, a semi-solid, or a liquid. In embodiments, the composition is a food or a beverage.

In embodiments, the *Lactobacillus* sp., the *Faecalibacterium* sp., the *Akkermansia* sp., the *Myxococcus* sp., and/or the *Pediococcus* sp. is in the form of a powder. In embodiments, the *Lactobacillus* sp., the *Faecalibacterium* sp., the *Akkermansia* sp., the *Myxococcus* sp., and/or the *Pediococcus* sp. has been lyophilized.

In embodiments, the *Myxococcus* sp. is in the form of spores, vegetative bacteria, or a mixture of spores and vegetative bacteria. In embodiments, the *Myxococcus* sp. is in the form of a powder comprising spores. In embodiments, the *Clostridium* sp. is in the form of spores, vegetative bacteria, or a mixture of spores and vegetative bacteria. In embodiments, the *Clostridium* sp. is in the form of a powder comprising spores.

In embodiments, the bacterial composition has a water activity ($a_w$) less than about 0.9, 0.8, 0.7, 0.6, 0.5, 0.4, 0.3, 0.2, or 0.1 at 20° C. In embodiments, the bacterial composition has an $a_w$ less than about 0.9 at 20° C. In embodiments, the bacterial composition has an $a_w$ less than 0.9 at 20° C. In embodiments, the bacterial composition has an $a_w$ less than about 0.8 at 20° C. In embodiments, the bacterial composition has an $a_w$ less than 0.8 at 20° C. In embodiments, the bacterial composition has an $a_w$ less than about 0.7 at 20° C. In embodiments, the bacterial composition has an $a_w$ less than 0.7 at 20° C. In embodiments, the bacterial composition has an $a_w$ less than about 0.6 at 20° C. In embodiments, the bacterial composition has an $a_w$ less than 0.6 at 20° C. In embodiments, the bacterial composition has an $a_w$ less than about 0.5 at 20° C. In embodiments, the bacterial composition has an $a_w$ less than 0.5 at 20° C. In embodiments, the bacterial composition has an $a_w$ less than about 0.4 at 20° C. In embodiments, the bacterial composition has an $a_w$ less than 0.4 at 20° C. In embodiments, the bacterial composition has an $a_w$ less than about 0.3 at 20° C. In embodiments, the bacterial composition has an $a_w$ less than 0.3 at 20° C. In embodiments, the bacterial composition has an $a_w$ less than about 0.2 at 20° C. In embodiments, the bacterial composition has an $a_w$ less than 0.2 at 20° C. In embodiments, the bacterial composition has an $a_w$ less than about 0.1 at 20° C. In embodiments, the bacterial composition has an $a_w$ less than 0.1 at 20° C.

A "microbial composition" as provided herein refers to a composition including a bacterial population that comprises, consists essentially of, or consists of any 1, 2, 3, 4, 5, 6, 7, or 8 of *Lactobacillus* sp., *Faecalibacterium* sp., *Akkermansia* sp., *Myxococcus* sp., *Cystobacter* sp., *Pediococcus* sp., *Bifidobacterium* sp., and *Clostridium* sp. In embodiments, the bacterial population comprises *Lactobacillus* sp. and *Faecalibacterium prausnitzii*. In embodiments, the bacterial population comprises *Lactobacillus* sp. and *Akkermansia muciniphila*. In embodiments, the bacterial population comprises *Lactobacillus* sp., and *Myxococcus xanthus*. In embodiments, the bacterial population comprises *Lactobacillus* sp. and *Cystobacter fuscus*. In embodiments, the bacterial population comprises *Lactobacillus* sp. and *Pediococcus pentosaceus*, *Pediococcus acidilactici*, *Pediococcus damnosus*, *Pediococcus ethanolidurans*, or *Pediococcus parvulus*. In embodiments, the bacterial population comprises *Lactobacillus* sp. and *Bifidobacterium bifidum*, *Bifidobacterium pseudolongum*, *Bifidobacterium saeculare*, or *Bifidobacterium subtile*. In embodiments, the bacterial population comprises *Lactobacillus* sp. and *Clostridium hiranonis*. In embodiments, the *Lactobacillus* sp. is *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus dioliovorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*. In embodiments, the *Lactobacillus* sp. is *Lactobacillus johnsonii*. In embodiments, the bacterial population comprises at least 1, 2, 3, 4, 5, 6, 7, 8, 9, or 10, or from 1-5, 1-10, 1-5, or 1-20 of any combination of the following: *Lactobacillus johnsonii*. *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus dioliovorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*. *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, *Lactococcus lactis*, *Faecalibacterium prausnitzii*, *Akkermansia muciniphila*, *Myxococcus xanthus*, *Cystobacter fuscus*, *Pediococcus pentosaceus*, *Pediococcus acidilactici*, *Pediococcus damnosus*, *Pediococcus ethanolidurans*, and *Pediococcus parvulus*. In embodiments, the bacterial population includes *Lactobacillus johnsonii*, *Faecalibacterium prausnitzii*, *Akkermansia muciniphila*, *Myxococcus xanthus*, and/or *Pediococcus pentosaceus*. In some embodiments, a microbial composition comprises one or more bacterial cells of the bacterial type *Lactobacillus johnsonii*, *Faecalibacterium prausnitzii*, *Akkermansia muciniphila*, *Myxococcus xanthus* or *Pediococcus pentosaceus*. In embodiments, the composition includes *Lactobacillus johnsonii*, *Faecalibacterium praus-*

*nitzii, Akkermansia muciniphila, Myxococcus xanthus* and *Pediococcus pentosaceus*. In embodiments, the composition includes *Lactobacillus johnsonii, Faecalibacterium prausnitzii, Akkermansia muciniphila, Myxococcus xanthus* or *Pediococcus pentosaceus*. In embodiments, the bacteria are isolated. As used herein, a "type" or more than one "types" of bacteria may be differentiated at the genus level, the species, level, the sub-species level, the strain level or by any other taxonomic method described herein and otherwise known in the art.

In embodiments, the composition includes an effective amount of *Lactobacillus johnsonii, Faecalibacterium prausnitzii, Akkermansia muciniphila, Myxococcus xanthus* and *Pediococcus pentosaceus*. In embodiments, the composition includes an effective amount of *Lactobacillus johnsonii, Faecalibacterium prausnitzii, Akkermansia muciniphila, Myxococcus xanthus* or *Pediococcus pentosaceus*. In embodiments, the composition consists essentially of an effective amount of *Lactobacillus johnsonii, Faecalibacterium prausnitzii, Akkermansia muciniphila, Myxococcus xanthus* and *Pediococcus pentosaceus*. In embodiments, the composition consists of an effective amount of *Lactobacillus johnsonii, Faecalibacterium prausnitzii, Akkermansia muciniphila, Myxococcus xanthus* and *Pediococcus pentosaceus*. Where a microbial composition "consists essentially of" *Lactobacillus johnsonii, Faecalibacterium prausnitzii, Akkermansia muciniphila, Myxococcus xanthus* and *Pediococcus pentosaceus*, other agents may be included that do not interfere with the operation or basic and novel characteristics of the microbial composition.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." Thus, an "effective amount" or "therapeutically effective amount" as provided herein refers to the amount of a bacterial population (e.g., a bacterial population comprising one or more species or strains of bacteria, such as a bacterial population comprising *Lactobacillus johnsonii, Faecalibacterium prausnitzii, Akkermansia muciniphila, Myxococcus xanthus*, and/or *Pediococcus pentosaceus*) required to ameliorate or prevent the symptoms of a disease (e.g., dysbiosis, an infection, or an inflammatory disease) relative to an untreated patient. In embodiments, the microbial composition does not include *Lactobacillus rhamnosus*.

A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of a disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 50%, 100%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

In embodiments, a composition provided herein may be administered orally and include live microorganisms from $10^3$ to $10^{15}$ colony forming units (cfu)/g. In embodiments, the composition includes $10^4$ to $10^{15}$ cfu/g. In embodiments, the composition includes $10^5$ to $10^{15}$ cfu/g. In embodiments, the composition includes $10^6$ to $10^{15}$ cfu/g. In embodiments, the composition includes $10^7$ to $10^{15}$ cfu/g. In embodiments, the composition includes $10^8$ to $10^{15}$ cfu/g. In embodiments, the composition includes $10^9$ to $10^{15}$ cfu/g. In embodiments, the composition includes $10^{10}$ to $10^{15}$ cfu/g. In embodiments, the composition includes $10^8$ to $10^{15}$ cfu/g. In embodiments, the composition includes $10^{12}$ to $10^{15}$ cfu/g. In embodiments, the composition includes $10^{13}$ to $10^{15}$ cfu/g. In embodiments, the composition includes $10^{14}$ to $10^{15}$ cfu/g. In embodiments, the composition includes from $10^3$ to $10^{15}$ cfu. In embodiments, the composition includes $10^4$ to $10^{15}$ cfu. In embodiments, the composition includes $10^5$ to $10^{15}$ cfu. In embodiments, the composition includes $10^6$ to $10^{15}$ cfu. In embodiments, the composition includes $10^7$ to $10^{15}$ cfu. In embodiments, the composition includes 01 to $10^{15}$ cfu. In embodiments, the composition includes $10^9$ to $10^{15}$ cfu. In embodiments, the composition includes $10^{10}$ to $10^{15}$ cfu. In embodiments, the composition includes $10^{11}$ to $10^{15}$ cfu. In embodiments, the composition includes $10^{12}$ to $10^{15}$ cfu. In embodiments, the composition includes $10^{13}$ to $10^{15}$ cfu. In embodiments, the composition includes $10^{14}$ to $10^{15}$ cfu.

In embodiments, a composition provided herein may be administered orally and include live microorganisms from $10^3$ to $10^{14}$ colony forming units (cfu)/g. In embodiments, the composition includes $10^4$ to $10^{14}$ cfu/g. In embodiments, the composition includes $10^5$ to $10^{14}$ cfu/g. In embodiments, the composition includes $10^6$ to $10^{14}$ cfu/g. In embodiments, the composition includes $10^7$ to $10^{14}$ cfu/g. In embodiments, the composition includes $10^8$ to $10^{14}$ cfu/g. In embodiments, the composition includes $10^9$ to $10^{14}$ cfu/g. In embodiments, the composition includes $10^{10}$ to $10^{14}$ cfu/g. In embodiments, the composition includes $10^{11}$ to $10^{14}$ cfu/g. In embodiments, the composition includes $10^{12}$ to $10^{14}$ cfu/lg. In embodiments, the composition includes $10^{13}$ to $10^{14}$ cfu/g. In embodiments, the composition includes from $10^3$ to $10^{14}$ cfu. In embodiments, the composition includes $10^4$ to $10^{14}$ cfu. In embodiments, the composition includes $10^5$ to $10^{14}$ cfu. In embodiments, the composition includes $10^6$ to $10^{14}$ cfu. In embodiments, the composition includes $10^7$ to $10^{14}$ cfu. In embodiments, the composition includes $10^8$ to $10^{14}$ cfu. In embodiments, the composition includes $10^9$ to $10^{14}$ cfu. In embodiments, the composition includes $10^{10}$ to $10^{14}$ cfu. In embodiments, the composition includes $10^{11}$ to $10^{14}$ cfu. In embodiments, the composition includes $10^{12}$ to $10^{14}$ cfu. In embodiments, the composition includes $10^{13}$ to $10^{14}$ cfu.

In embodiments, a composition provided herein may be administered orally and include live microorganisms from $10^3$ to $10^{13}$ colony forming units (cfu)/g. In embodiments, the composition includes $10^4$ to $10^{13}$ cfu/g. In embodiments, the composition includes $10^5$ to $10^{13}$ cfu/g. In embodiments, the composition includes $10^6$ to $10^{13}$ cfu/g. In embodiments, the composition includes $10^7$ to $10^{13}$ cfu/g. In embodiments, the composition includes $10^8$ to $10^{13}$ cfu/g. In embodiments, the composition includes $10^9$ to $10^{13}$ cfu/g. In embodiments, the composition includes $10^{10}$ to $10^{13}$ cfu/g. In embodiments, the composition includes $10^{11}$ to $10^{13}$ cfu/g. In embodiments, the composition includes $10^{12}$ to $10^{13}$ cfu/g. In embodiments, the composition includes from $10^3$ to $10^{13}$ cfu. In embodiments, the composition includes $10^4$ to $10^{13}$ cfu. In embodiments, the composition includes $10^5$ to $10^{13}$ cfu. In embodiments, the composition includes $10^6$ to $10^{13}$ cfu. In embodiments, the composition includes $10^7$ to $10^{13}$ cfu. In embodiments, the composition includes $10^8$ to $10^{13}$ cfu. In embodiments, the composition includes $10^9$ to $10^{13}$ cfu. In embodiments, the composition includes $10^{10}$ to $10^{13}$ cfu. In embodiments, the composition includes $10^{11}$ to $10^{13}$ cfu. In embodiments, the composition includes $10^{12}$ to $10^{13}$ cfu.

In embodiments, a composition provided herein may be administered orally and include live microorganisms from $10^3$ to $10^{12}$ colony forming units (cfu)/g. In embodiments, the composition includes $10^4$ to $10^{12}$ cfu/g. In embodiments, the composition includes $10^5$ to $10^{12}$ cfu/g. In embodiments, the composition includes $10^6$ to $10^{12}$ cfu/g. In embodiments, the composition includes $10^7$ to $10^{12}$ cfu/g. In embodiments, the composition includes $10^8$ to $10^{12}$ cfu/g. In embodiments, the composition includes $10^9$ to $10^{12}$ cfu/g. In embodiments, the composition includes $10^{10}$ to $10^{12}$ cfu/g. In embodiments, the composition includes $10^{11}$ to $10^{12}$ cfu/g. In embodiments, the composition includes from $10^3$ to $10^{12}$ cfu. In embodiments, the composition includes $10^4$ to $10^{12}$ cfu/g. In embodiments, the composition includes $10^5$ to $10^{12}$ cfu. In embodiments, the composition includes $10^6$ to $10^{12}$ cfu. In embodiments, the composition includes $10^7$ to $10^{12}$ cfu. In embodiments, the composition includes $10^8$ to $10^{12}$ cfu. In embodiments, the composition includes $10^9$ to $10^{12}$ cfu. In embodiments, the composition includes $10^{10}$ to $10^{12}$ cfu. In embodiments, the composition includes $10^{11}$ to $10^{12}$ cfu.

In embodiments, a composition provided herein may be administered orally and include live microorganisms from $10^3$ to $10^{11}$ colony forming units (cfu)/g. In embodiments, the composition includes $10^4$ to $10^{11}$ cfu/g. In embodiments, the composition includes $10^5$ to $10^{11}$ cfu/g. In embodiments, the composition includes $10^6$ to $10^{11}$ cfu/g. In embodiments, the composition includes $10^7$ to $10^{11}$ cfu/g. In embodiments, the composition includes $10^8$ to $10^{11}$ cfu/g. In embodiments, the composition includes $10^9$ to $10^{11}$ cfu/g. In embodiments, the composition includes from $10^3$ to $10^{11}$ cfu. In embodiments, the composition includes $10^4$ to $10^{11}$ cfu. In embodiments, the composition includes $10^5$ to $10^{11}$ cfu. In embodiments, the composition includes $10^6$ to $10^{11}$ cfu. In embodiments, the composition includes $10^7$ to $10^{11}$ cfu. In embodiments, the composition includes 10 to $10^{11}$ cfu. In embodiments, the composition includes $10^9$ to $10^{11}$ cfu.

In embodiments, a composition provided herein may be administered orally and include live microorganisms from $10^3$ to $10^{10}$ colony forming units (cfu)/g. In embodiments, the composition includes $10^4$ to $10^{10}$ cfu/g. In embodiments, the composition includes $10^5$ to $10^{10}$ cfu/g. In embodiments, the composition includes $10^6$ to $10^{10}$ cfu/lg. In embodiments, the composition includes $10^7$ to $10^{10}$ cfu/g. In embodiments, the composition includes $10^8$ to $10^{10}$ cfu/g. In embodiments, the composition includes $10^9$ to $10^{10}$ cfu/g. In embodiments, the composition includes from $10^3$ to $10^{10}$ cfu. In embodiments, the composition includes $10^4$ to $10^{10}$ cfu. In embodiments, the composition includes $10^5$ to $10^{10}$ cfu. In embodiments, the composition includes $10^6$ to $10^{10}$ cfu. In embodiments, the composition includes $10^7$ to $10^{10}$ cfu. In embodiments, the composition includes $10^8$ to $10^{10}$ cfu. In embodiments, the composition includes $10^9$ to $10^{10}$ cfu.

In embodiments, a composition provided herein may be administered orally and include live microorganisms from $10^3$ to $10^9$ colony forming units (cfu)/g. In embodiments, the composition includes $10^4$ to $10^9$ cfu/g. In embodiments, the composition includes $10^5$ to $10^9$ cfu/g. In embodiments, the composition includes $10^6$ to $10^9$ cfu/g. In embodiments, the composition includes $10^7$ to $10^9$ cfu/g. In embodiments, the composition includes $10^8$ to $10^9$ cfu/g. In embodiments, the composition comprises from $10^3$ to $10^9$ cfu. In embodiments, the composition includes $10^4$ to $10^9$ cfu. In embodiments, the composition includes $10^5$ to $10^9$ cfu. In embodiments, the composition includes $10^6$ to $10^9$ cfu. In embodiments, the composition includes $10^7$ to $10^9$ cfu. In embodiments, the composition includes $10^8$ to $10^9$ cfu.

In embodiments, a composition provided herein may be administered orally and include live microorganisms from $10^3$ to $10^8$ colony forming units (cfu)/g. In embodiments, the composition includes $10^4$ to 10 cfu/g. In embodiments, the composition includes $10^5$ to $10^8$ cfu/g. In embodiments, the composition includes $10^6$ to $10^8$ cfu/lg. In embodiments, the composition includes $10^7$ to $10^8$ cfu/g. In embodiments, the composition includes from $10^3$ to $10^8$ cfu. In embodiments, the composition includes $10^4$ to $10^8$ cfu. In embodiments, the composition includes $10^5$ to $10^8$ cfu. In embodiments, the composition includes $10^6$ to $10^8$ cfu. In embodiments, the composition includes $10^7$ to $10^8$ cfu.

In embodiments, a composition provided herein may be administered orally and include live microorganisms from $10^3$ to $10^7$ colony forming units (cfu)/g. In embodiments, the composition includes $10^4$ to $10^7$ cfu/g. In embodiments, the composition includes $10^5$ to $10^7$ cfu/g. In embodiments, the composition includes $10^6$ to $10^7$ cfu/g. In embodiments, the composition includes from $10^3$ to $10^7$ cfu. In embodiments, the composition includes $10^4$ to $10^7$ cfu. In embodiments, the composition includes $10^5$ to $10^7$ cfu. In embodiments, the composition includes $10^6$ to $10^7$ cfu.

It is understood that the amount of colony forming units (cfu)/g and cfu as provided herein may refer to the amount of each bacterial species strain administered (individually) or the total cfu/g or cfu for a bacterial population.

The proportion or concentration of the compositions of the invention in a pharmaceutical composition can vary depending upon a number of factors including dosage, chemical characteristics (e.g., hydrophobicity), and the route of administration. For example, the defined microbial composition can be provided in a capsule containing from about 0.005 mg to about 1000 mg for oral administration. Alternatively or in addition, the dosage can be expressed as cfu or cfu/g of bacteria (e.g., of dry weight when expressed as cfu/g) as described above. In embodiments, the dosage may vary, but can range from the equivalent of about $10^2$ to about $10^{15}$ cfu/g, e.g., $1\times10^2$ cfu/g, $5\times10^2$ cfu/g, $1\times10^3$ cfu/g, $5\times10^3$ cfu/g, $1\times10^4$ cfu/g, $5\times10^4$ cfu/g, $1\times10^5$ cfu/g, $5\times10^5$ cfu/g, $1\times10^6$ cfu/g, $5\times10^6$ cfu/g, $1\times10^7$ cfu/g, $5\times10^7$ cfu/g, $1\times10^8$ cfu/g, $5\times10^8$ cfu/g, $1\times10^9$ cfu/g, $5\times10^9$ cfu/g, $1\times10^{10}$ cfu/g, $5\times10^{10}$ cfu/g, $1\times10^{11}$ cfu/g, $5\times10^{11}$ cfu/g, or $1\times10^{12}$ cfu/g of dry weight. In embodiments, *Lactobacillus johnsonii*, *Faecalibacterium prausnitzii*, *Akkermansia muciniphila*, *Myxococcus xanthus* or *Pediococcus pentosaceus* are administered at any one of $10^3$, $10^4$, $10^5$, $10^6$, $10^7$, $10^8$, $10^9$, $10^{10}$, $10^{11}$, $10^{12}$, $10^{13}$, $10^{14}$, or $10^{15}$ colony forming units (cfu)/g of dry weight, or total cfu, individually or total. In embodiments, the composition includes *Lactobacillus johnsonii* at about $10^7$ colony forming units (cfu)/g or a total of $10^7$ cfu. In embodiments, the composition includes *Akkermansia muciniphila* at about $10^7$ colony forming units (cfu)/g or a total of $10^7$ cfu. In embodiments, the composition includes *Myxococcus xanthus* at about $10^7$ colony forming units (cfu)/g or a total of $10^7$ cfu. In embodiments, the composition includes *Pediococcus pentosaceus* at about $10^7$ colony forming units (cfu)/g or a total of $10^7$ cfu. In embodiments, the composition includes *Faecalibacterium prausnitzii* at about 10 colony forming units (cfu)/g or a total of 10 cfu. In embodiments, the composition includes live microorganisms (e.g., *Lactobacillus johnsonii*, *Faecalibacterium prausnitzii*, *Akkermansia muciniphila*, *Myxococcus xanthus* or *Pediococcus pentosaceus*) per gram of composition, or equivalent doses calculated for inactivated or dead microorganisms or for microorganism fractions or for produced metabolites.

In embodiments, *Lactobacillus johnsonii* as provided herein refers to one or more isolated bacterial cells of a strain cultured from murine intestines using *Lactobacillus* isolation media (deMan, Rogose and Sharpe agar). Non-limiting examples of *Lactobacillus johnsonii* include strains deposited with ATCC under Accession Nos. 11506 and 53672.

In embodiments, *Lactobacillus rhamnosus* as provided herein refers to one or more isolated bacterial cells of a bacterial strain having all the identifying characteristics of a strain deposited with ATCC as Accession No. 53103; variants of the strain deposited with ATCC as Accession No. 53103 having all the identifying characteristics of the ATCC No. 53103 strain; and mutants of the strain deposited with ATCC as Accession No. 53103 having all the identifying characteristics of the ATCC No. 53103 strain.

In embodiments, *Faecalibacterium prausnitzii* as provided herein refers to one or more isolated bacterial cells of a bacterial strain having all the identifying characteristics of a strain deposited with ATCC as Accession No. 27766; variants of the strain deposited with ATCC as Accession No. 27766 having all the identifying characteristics of the ATCC No. 27766 strain; and mutants of the strain deposited with ATCC as Accession No. 27766 having all the identifying characteristics of the ATCC No. 27766 strain.

In embodiments, *Akkermansia muciniphila* as provided herein refers to one or more isolated bacterial cells of a bacterial strain having all the identifying characteristics of a strain deposited with ATCC as Accession No. BAA-835; variants of the strain deposited with ATCC as Accession No. BAA-835 having all the identifying characteristics of the ATCC No. BAA-835 strain; and mutants of the strain deposited with ATCC as Accession No. BAA-835 having all the identifying characteristics of the ATCC No. BAA-835 strain.

In embodiments, *Myxococcus xanthus* as provided herein refers to one or more isolated bacterial cells of a bacterial strain having all the identifying characteristics of a strain deposited with ATCC as Accession No. 25232; variants of the strain deposited with ATCC as Accession No. 25232 having all the identifying characteristics of the ATCC No. 25232 strain; and mutants of the strain deposited with ATCC as Accession No. 25232 having all the identifying characteristics of the ATCC No. 25232 strain.

In embodiments, *Pediococcus pentosaceus* as provided herein refers to one or more isolated bacterial cells of a bacterial strain having all the identifying characteristics of a strain deposited with ATCC as Accession No. 25744; variants of the strain deposited with ATCC as Accession No. 25744 having all the identifying characteristics of the ATCC No. 25744 strain; and mutants of the strain deposited with ATCC as Accession No. 25744 having all the identifying characteristics of the ATCC No. 25744 strain.

In embodiments, the composition is effective to increase an anti-inflammatory metabolite. In embodiments, the *Lactobacillus johnsonii* is effective to increase an anti-inflammatory metabolite. In embodiments, the *Faecalibacterium prausnitzii* is effective to increase an anti-inflammatory metabolite. In embodiments, the *Akkermansia muciniphila* is effective to increase an anti-inflammatory metabolite. In embodiments, the *Myxococcus xanthus* is effective to increase an anti-inflammatory metabolite. In embodiments, the *Pediococcus pentosaceus* is effective to increase an anti-inflammatory metabolite. A "metabolite" as provided herein refers to intermediates and products of the metabolism of a bacterial cell, wherein the bacterial cell resides within the gut of a mammal. The term metabolite also includes intermediates and products formed by a mammalian cell. Non-limiting examples of metabolites include amino acids, alcohols, vitamins, polyols, organic acids, nucleotides (e.g. inosine-5'-monophosphate and guanosine-5'-monophosphate), lipids, carbohydrates, peptides and proteins. An "anti-inflammatory metabolite" as provided herein refers to a metabolite produced by a cell (e.g., bacterial cell, mammalian cell) and capable of inhibiting inflammation. As defined herein, the term "inhibition", "inhibit", "inhibiting" and the like in reference to a protein-anti-inflammatory metabolite interaction means negatively affecting (e.g., decreasing) the activity or function of the protein (e.g., decreasing the activity of an inflammatory metabolite) relative to the activity or function of the protein in the absence of the inhibitor (e.g., anti-inflammatory metabolite). The term "inhibiting" includes, at least in part, partially or totally blocking stimulation, decreasing, preventing, or delaying activation, or inactivating, desensitizing, or down-regulating signal transduction, gene expression, enzymatic activity or protein expression (e.g., inflammatory metabolite) necessary for inflammation. In some embodiments inhibition refers to reduction of a disease or symptoms of disease (e.g., inflammation). Similarly an "inhibitor" is a compound (e.g., metabolite) that inhibits inflammation, e.g., by binding, partially or totally blocking, decreasing, preventing, delaying, inactivating, desensitizing, or down-regulating inflammatory metabolite activity. A metabolite capable of inhibiting or decreasing inflammation as provided herein refers to a substance that results in a detectably lower activity level of inflammation of as compared to a control. The decreased activity can be 10%, 20%, 30%, 40%, 50%, 60%, 70%, 80%, 90% or less than that in a control. In certain instances, the decrease is 1.5-fold, 2-fold, 3-fold, 4-fold, 5-fold, 10-fold, or less in comparison to a control.

In embodiments, the anti-inflammatory metabolite is a microbial lipid or a microbial carbohydrate. In embodiments, the anti-inflammatory metabolite is a microbial lipid. In embodiments, the anti-inflammatory metabolite is a phospholipid. In embodiments, the anti-inflammatory metabolite is a poly-unsaturated fatty acid. In embodiments, the anti-inflammatory metabolite is microbial carbohydrate. In embodiments, the anti-inflammatory metabolite is itoconate. In embodiments, the anti-inflammatory metabolite is n-acetylglucosamine. In embodiments, the anti-inflammatory metabolite is n-acetylgalactosamine. In embodiments, the anti-inflammatory metabolite is fucosyllactose. In embodiments, the anti-inflammatory metabolite is an amino acid. In embodiments, the anti-inflammatory metabolite is tryptophan.

In embodiments, the composition is effective to decrease a pro-inflammatory metabolite. In embodiments, the composition is effective to decrease pro-inflammatory metabolite. In embodiments, the *Lactobacillus johnsonii* is effective to decrease a pro-inflammatory metabolite. In embodiments, the *Faecalibacterium prausnitzii* is effective to decrease a pro-inflammatory metabolite. In embodiments, the *Akkermansia muciniphila* is effective to decrease a pro-inflammatory metabolite. In embodiments, the *Myxococcus xanthus* is effective to decrease pro-inflammatory metabolite. In embodiments, the *Pediococcus pentosaceus* is effective to decrease pro-inflammatory metabolite. A "pro-inflammatory metabolite" as provided herein refers to a metabolite produced by a cell (e.g., bacterial cell, mammalian cell) and capable of increasing inflammation. A metabolite capable of increasing inflammation as provided herein refers to a substance that results in a detectably higher level of inflammation as compared to a control. The increased activity can be 10%, 20%, 30%, 40%, 50%, 60%, 70%, 80%, 900/or more than that in a control. In certain instances, the increase is 1.5-fold, 2-fold, 3-fold, 4-fold, 5-fold, 10-fold, or more in comparison to a control.

In embodiments, the pro-inflammatory metabolite is a microbial lipid, a microbial carbohydrate or a microbial amino acid. In embodiments, the pro-inflammatory metabolite is a microbial lipid. In embodiments, the pro-inflammatory metabolite is dihydroxyoctadec-12-enoic acid, cholate or methylmalonate. In embodiments, the pro-inflammatory metabolite is a microbial carbohydrate. In embodiments, the pro-inflammatory metabolite is n-acetylmuramate, lactobionate or maltotriose. In embodiments, the pro-inflammatory metabolite is a microbial amino acid. In embodiments, the pro-inflammatory metabolite is ornithine or taurine.

The compositions provided herein may include metabolically active bacteria or metabolically inactive bacteria or fractions thereof. In embodiments, the *Lactobacillus johnsonii*, *Faecalibacterium prausnitzii*, the *Akkermansia muciniphila*, the *Myxococcus xanthus* and the *Pediococcus pentosaceus* are metabolically active. In embodiments, the said *Lactobacillus johnsonii*, *Faecalibacterium prausnitzii*, *Akkermansia muciniphila*, *Myxococcus xanthus* and *Pediococcus pentosaceus* are metabolically inactive. Metabolically active bacteria are capable of dividing and produce metabolites such as carbohydrates, lipids or amino acids. In contrast metabolically inactive bacteria do not divide or produce metabolites.

III. Pharmaceutical Compositions

As described herein, the microbial compositions provided herein may include a bacterial population that comprises, consists essentially of, or consists of any 1, 2, 3, 4, 5, 6, 7, or 8 of *Lactobacillus* sp., *Faecalibacterium* sp., *Akkermansia* sp., *Myxococcus* sp., *Cystobacter* sp., *Pediococcus* sp., *Bifidobacterium* sp., and *Clostridium* sp. In embodiments, the bacterial population comprises *Lactobacillus* sp. and *Faecalibacterium prausnitzii*. In embodiments, the bacterial population comprises *Lactobacillus* sp. and *Akkermansia muciniphila*. In embodiments, the bacterial population comprises *Lactobacillus* sp., and *Myxococcus xanthus*. In embodiments, the bacterial population comprises *Lactobacillus* sp. and *Cystobacter fuscus*. In embodiments, the bacterial population comprises *Lactobacillus* sp. and *Pediococcus pentosaceus*, *Pediococcus acidilactici*, *Pediococcus damnosus*, *Pediococcus ethanolidurans*, or *Pediococcus parvulus*. In embodiments, the bacterial population comprises *Lactobacillus* sp. and *Bifidobacterium bifidum*, *Bifidobacterium pseudolongum*, *Bifidobacterium saeculare*, or *Bifidobacterium subtile*. In embodiments, the bacterial population comprises *Lactobacillus* sp. and *Clostridium hiranonis*. In embodiments, the *Lactobacillus* sp. is *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*. In embodiments, the *Lactobacillus* sp. is *Lactobacillus johnsonii*. In embodiments, the bacterial population comprises at least 1, 2, 3, 4, 5, 6, 7, 8, 9, or 10, or from 1-5, 1-10, 1-5, or 1-20 of any combination of the following: *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, *Lactococcus lactis*, *Faecalibacterium prausnitzii*, *Akkermansia muciniphila*, *Myxococcus xanthus*, *Cystobacter fuscus*, *Pediococcus pentosaceus*, *Pediococcus acidilactici*, *Pediococcus damnosus*, *Pediococcus ethanolidurans*, and *Pediococcus parvulus*. In embodiments, the bacterial population includes *Lactobacillus johnsonii*, *Faecalibacterium prausnitzii*, *Akkermansia muciniphila*, *Myxococcus xanthus*, and/or *Pediococcus pentosaceus*. In some embodiments, a microbial composition comprises one or more bacterial cells of the bacterial type *Lactobacillus johnsonii*. *Faecalibacterium prausnitzii*, *Akkermansia muciniphila*, *Myxococcus xanthus* or *Pedio-* coccus pentosaceus. In embodiments, the composition includes *Lactobacillus johnsonii, Faecalibacterium prausnitzii, Akkermansia muciniphila, Myxococcus xanthus* and *Pediococcus pentosaceus*. In embodiments, the composition includes *Lactobacillus johnsonii, Faecalibacterium prausnitzii, Akkermansia muciniphila, Myxococcus xanthus* or *Pediococcus pentosaceus*. In embodiments, the bacteria are isolated bacteria.

In embodiments, the microbial composition includes a therapeutically effective amount of *Lactobacillus johnsonii, Faecalibacterium prausnitzii. Akkermansia muciniphila, Myxococcus xanthus* and/or *Pediococcus pentosaceus*.

In embodiments, the microbial composition further includes a pharmaceutically acceptable excipient. Thus, in one aspect a pharmaceutical composition including a therapeutically effective amount of *Lactobacillus johnsonii, Faecalibacterium prausnitzii, Akkermansia muciniphila, Myxococcus xanthus*, and *Pediococcus pentosaceus* and a pharmaceutically acceptable excipient are provided.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The microbial compositions provided herein including embodiments thereof may be adminstered orally, gastrointestinally, or rectally. Administration can be in the form of a single bolus dose, or may be, for example, by a continuous perfusion pump. In embodiments, the microbial consortium provided herein is combined with one or more excipients, for example, a disintegrant, a filler, a glidant, or a preservative. In embodiments, the microbial consortium provided herein forms part of a capsule. Suitable capsules include both hard shell capsules or soft-shelled capsules. Any lipid-based or polymer-based colloid may be used to form the capsule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment.

The microbial compositions can be formulated in a unit dosage form, each dosage containing, for example, from about 0.005 mg to about 2000 mg of a defined microbial consortium having minimal urease activity per dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the microbial composition provided herein.

The microbial compositions can be formulated in a unit dosage form, each dosage containing, for example, from about 0.1 mg to about 50 mg, from about 0.1 mg to about 40 mg, from about 0.1 mg to about 20 mg from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of *Lactobacillus* sp. (e.g., *Lactobacillus johnsonii*), *Faecalibacterium* sp. (*Faecalibacterium prausnitzii*), *Akkermansia* sp. (e.g., *Akkermansia muciniphila*), *Myxococcus* sp. (e.g., *Myxococcus xanthus*) and/or *Pediococcus* sp. (e.g., *Pediococcus pentosaceus*) individually or combined.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

IV. Methods of Treatment

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation, infection, or dysbiosis). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

For prophylactic use, a therapeutically effective amount of the microbial composition described herein are administered to a subject prior to or during early onset (e.g., upon initial signs and symptoms of an autoimmune disease). Therapeutic treatment involves administering to a subject a therapeutically effective amount of the agents described herein after diagnosis or development of disease. Thus, in another aspect, a method of treating a disease (e.g., an inflammatory disease, an infection, or dysbiosis) in a subject in need thereof is provided.

The terms "subject," "patient," "individual," etc. are not intended to be limiting and can be generally interchanged. That is, an individual described as a "patient" does not necessarily have a given disease, but may be merely seeking medical advice.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 200, 30%, 40%, 50%, 60%, 70%, 80%, 90%, or 100% reduction in the severity of an established disease, condition, or symptom of the disease or condition (e.g., inflammation, infection, or dysbiosis). For example, a method for treating a disease is considered to be a treatment if there is a 10% reduction in one or more symptoms of the disease in a subject as compared to a control. Thus the reduction can be a 10%, 20%, 30%, 40%, 50°, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Compositions comprising a defined microbial compositions can be administered to the gastrointestinal tract of a subject by nasoduodenal catheter, by enema, or by endoscopy, enteroscopy, or colonoscopy or orally in a consumable capsule or pill. In certain embodiments, the defined microbial compositions are diluted in a suitable excipient (e.g., saline solution). In a preferred embodiment, the bacteria are delivered in lyophilized form.

Regardless of how the compositions are formulated, the dosage required will depend on the route of administration, the nature of the formulation, the nature of the subject's condition, e.g., immaturity of the immune system or a gastrointestinal disorder, the subject's size, weight, surface area, age, and sex, other drugs being administered, and the judgment of the attending clinicians. In embodiments, suitable dosages are in the range of 0.01-1,000 mg/kg. Some typical dose ranges are from about 1 µg/kg to about 1 g/kg of body weight per day. In embodiments, the dose range is from about 0.01 mg/kg to about 100 mg/kg of body weight per day. In embodiments, the dose can be, for example, 1 mg/kg, 2 mg/kg, 5 mg kg, 10 mg/kg, 20 mg/kg, 50 mg/kg or 100 mg/kg. Alternatively or in addition, the dosage can be expressed as cfu or as cfu/g of dry weight. In embodiments, the dosage may vary, but can range from the equivalent of about $10^2$ to about $10^{12}$ cfu/g, e.g., $1 \times 10^2$ cfu/g, $5 \times 10^2$ cfu/g, $1 \times 10^3$ cfu/g, $5 \times 10^3$ cfu/g, $1 \times 10^4$ cfu/g, $5 \times 10^4$ cfu/g, $1 \times 10^5$ cfu/g, $5 \times 10^5$ cfu/g, $1 \times 10^6$ cfu/g, $5 \times 10^6$ cfu/g, $1 \times 10^7$ cfu/g, $5 \times 10^7$ cfu/g, $1 \times 10^8$ cfu/g, $5 \times 10^8$ cfu/g, $1 \times 10^9$ cfu/g, $5 \times 10^9$ cfu/g, $1 \times 10^{10}$ cfu/g, $5 \times 10^{10}$ cfu/g, $1 \times 10^{11}$ cfu/g, $5 \times 10^{11}$ cfu/g, or $1 \times 10^{12}$ cfu/g of dry weight of any one of the administered bacteria (individually) or of the total population of bacteria. In embodiments, the dosage can range from about $10^2$ to about $10^{12}$ cfu, e.g., $1 \times 10^2$ cfu, $5 \times 10^2$ cfu, $1 \times 10^3$ cfu, $5 \times 10^3$ cfu, $1 \times 10^4$ cfu, $5 \times 10^4$ cfu, $1 \times 10^5$ cfu, $5 \times 10^5$ cfu, $1 \times 10^6$ cfu, $5 \times 10^6$ cfu, $1 \times 10^7$ cfu, $5 \times 10^7$ cfu, $1 \times 10^8$ cfu, $5 \times 10^8$ cfu, $1 \times 10^9$ cfu, $5 \times 10^9$ cfu, $1 \times 10^{10}$ cfu, $5 \times 10^{10}$ cfu, $1 \times 10^{11}$ cfu, $5 \times 10^{11}$ cfu, or $1 \times 10^{12}$ cfu of any one of the administered bacteria (individually) or of the total population of bacteria.

Administrations can be single or multiple (e.g., 2- or 3-, 4-, 6-, 8-, 10-, 20-, 50-, 100-, 150-, or more fold). The duration of treatment with any composition provided herein can be any length of time from as short as one day to as long as the life span of the host (e.g., many years). For example, a composition can be administered 1, 2, 3, 4, 5, 6, or 7 times a week (for, for example, 4 weeks to many months or years); once a month (for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

The compositions may also be administered in conjunction with other therapeutic agents. Other therapeutic agents will vary according to the particular disorder, but can include, for example, dietary modification, hemodialysis, therapeutic agents such as sodium benzoate, phenylacetate, arginine, or surgical remedies. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Provided herein are methods of treating and preventing inflammatory diseases, infections (such as respiratory or gastrointestinal infections) and dysbiosis comprising administering the bacterial populations or microbial compositions described herein including embodiments thereof.

In an aspect, a method of treating or preventing dysbiosis, an inflammatory disease, or a viral respiratory infection, in a subject in need thereof is provided.

In an aspect, a method of increasing the level of an anti-inflammatory compound and/or decreasing the level of a pro-inflammatory compound in a subject in need thereof is provided.

In an aspect, a method of altering the metabolism of a subject in need thereof is provided.

In embodiments, the method includes administering to the subject an effective amount of a bacterial population that comprises, consists essentially of, or consists of, 1, 2, 3, 4, 5, 6, 7, or 8 (or at least 1, 2, 3, 4, 5, 6, 7, or 8) bacterial species. In embodiments, the bacterial population comprises, consists essentially of, or consists of any 1, 2, 3, 4, 5, 6, 7, or 8 of *Lactobacillus* sp., *Faecalibacterium* sp., *Akkermansia* sp., *Myxococcus* sp., *Cystobacter* sp., *Pediococcus* sp., *Bifidobacterium* sp., and *Clostridium* sp. In embodiments, the bacterial population comprises *Lactobacillus* sp. and *Faecalibacterium prausnitzii*. In embodiments, the bacterial population comprises *Lactobacillus* sp. and *Akkermansia muciniphila*. In embodiments, the bacterial population comprises *Lactobacillus* sp., and *Myxococcus xanthus*. In embodiments, the bacterial population comprises *Lactobacillus* sp. and *Cystobacter fuscus*. In embodiments, the bacterial population comprises *Lactobacillus* sp. and *Pediococcus pentosaceus*, *Pediococcus acidilactici*, *Pediococcus damnosus*, *Pediococcus ethanolidurans*, or *Pediococcus parvulus*. In embodiments, the bacterial population comprises *Lactobacillus* sp. and *Bifidobacterium bifidum*, *Bifidobacterium pseudolongum*, *Bifidobacterium saeculare*, or *Bifidobacterium subtile*. In embodiments, the bacterial population comprises *Lactobacillus* sp. and *Clostridium hiranonis*. In embodiments, the *Lactobacillus* sp. is *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus dioliovorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*. In embodiments, the *Lactobacillus* sp. is *Lactobacillus johnsonii*. In embodiments, the bacterial population comprises at least 1, 2, 3, 4, 5, 6, 7, 8, 9, or 10, or from 1-5, 1-10, 1-5, or 1-20 of any combination of the following: *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus dioliovorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, *Lactococcus lactis*, *Faecalibacterium prausnitzii*, *Akkermansia muciniphila*, *Myxococcus xanthus*, *Cystobacter fuscus*, *Pediococcus pentosaceus*, *Pediococcus acidilactici*, *Pediococcus damnosus*, *Pediococcus ethanolidurans*, and *Pediococcus parvulus*. In embodiments, the bacterial population includes *Lactobacillus johnsonii*, *Faecalibacterium prausnitzii*, *Akkermansia muciniphila*, *Myxococcus xanthus*, and/or *Pediococcus pentosaceus*. In embodiments, the bacteria are isolated bacteria.

In embodiments, the method includes administering to the subject an effective amount of a bacterial population including *Lactobacillus* sp., *Faecalibacterium* sp., *Akkermansia* sp., *Myxococcus* sp., and *Pediococcus* sp. In embodiments, (i) the *Lactobacillus* sp. is *Lactobacillus johnsonii*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; and (v) the *Pediococcus* sp. is *Pediococcus pentosaceus*. In embodiments, (i) the *Lactobacillus* sp. is *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus dioliovorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae, or Lactococcus lactis; (ii) the Faecalibacterium sp., is Faecalibacterium prausnitzii; (iii) the Akkermansia sp. is Akkermansia muciniphila; (iv) the Myxococcus sp. is Myxococcus xanthus; and (v) the Pediococcus sp. is Pediococcus pentosaceus, Pediococcus acidilactici, Pediococcus damnosus, Pediococcus ethanolidurans, or Pediococcus parvulus.

In embodiments, the Myxococcus sp. is in the form of spores, vegetative bacteria, or a mixture of spores and vegetative bacteria. In embodiments, the Myxococcus sp. is in the form of a powder comprising spores. In embodiments, the Clostridium sp. is in the form of spores, vegetative bacteria, or a mixture of spores and vegetative bacteria. In embodiments, the Clostridium sp. is in the form of a powder comprising spores.

In embodiments, less than about 20, 15, 10, 9, 8, 7, or 6 different species of bacteria are administered to the subject. In embodiments, less than about 20 different species of bacteria are administered to the subject. In embodiments, less than 20 different species of bacteria are administered to the subject. In embodiments, less than about 15 different species of bacteria are administered to the subject. In embodiments, less than 15 different species of bacteria are administered to the subject. In embodiments, less than about 10 different species of bacteria are administered to the subject. In embodiments, less than 10 different species of bacteria are administered to the subject. In embodiments, less than about 9 different species of bacteria are administered to the subject. In embodiments, less than 9 different species of bacteria are administered to the subject. In embodiments, less than about 8 different species of bacteria are administered to the subject. In embodiments, less than 8 different species of bacteria are administered to the subject. In embodiments, less than about 7 different species of bacteria are administered to the subject. In embodiments, less than 7 different species of bacteria are administered to the subject. In embodiments, less than about 6 different species of bacteria are administered to the subject. In embodiments, less than 6 different species of bacteria are administered to the subject.

In embodiments, the bacterial population forms part of a bacterial composition. In embodiments, the bacterial composition includes less than about 20, 15, 10, 9, 8, 7, or 6 species of bacteria. In embodiments, the bacterial composition includes less than about 20 species of bacteria. In embodiments, the bacterial composition includes less than 20 species of bacteria. In embodiments, the bacterial composition includes less than about 15 species of bacteria. In embodiments, the bacterial composition includes less than 15 species of bacteria. In embodiments, the bacterial composition includes less than about 10 species of bacteria. In embodiments, the bacterial composition includes less than 10 species of bacteria. In embodiments, the bacterial composition includes less than about 9 species of bacteria. In embodiments, the bacterial composition includes less than 9 species of bacteria. In embodiments, the bacterial composition includes less than about 8 species of bacteria. In embodiments, the bacterial composition includes less than 8 species of bacteria. In embodiments, the bacterial composition includes less than about 7 species of bacteria. In embodiments, the bacterial composition includes less than 7 species of bacteria. In embodiments, the bacterial composition includes less than about 6 species of bacteria. In embodiments, the bacterial composition includes less than 6 species of bacteria.

In embodiments, the bacterial composition further includes a pharmaceutically acceptable excipient. In embodiments, the bacterial composition is not a fecal transplant. In embodiments, the bacterial composition is a capsule, a tablet, a suspension, a suppository, a powder, a cream, an oil, an oil-in-water emulsion, a water-in-oil emulsion, or an aqueous solution. In embodiments, the bacterial composition is in the form of a powder, a solid, a semi-solid, or a liquid.

In embodiments, the bacterial composition has a water activity ($a_w$) less than about 0.9, 0.8, 0.7, 0.6, 0.5, 0.4, 0.3, 0.2, or 0.1 at 20° C. In embodiments, the bacterial composition has an $a_w$ less than about 0.9 at 20° C. In embodiments, the bacterial composition has an $a_w$ less than 0.9 at 20° C. In embodiments, the bacterial composition has an $a_w$ less than about 0.8 at 20° C. In embodiments, the bacterial composition has an $a_w$ less than 0.8 at 20° C. In embodiments, the bacterial composition has an $a_w$ less than about 0.7 at 20° C. In embodiments, the bacterial composition has an $a_w$ less than 0.7 at 20° C. In embodiments, the bacterial composition has an $a_w$ less than about 0.6 at 20° C. In embodiments, the bacterial composition has an $a_w$ less than 0.6 at 20° C. In embodiments, the bacterial composition has an $a_w$ less than about 0.5 at 20° C. In embodiments, the bacterial composition has an $a_w$ less than 0.5 at 20° C. In embodiments, the bacterial composition has an $a_w$ less than about 0.4 at 20° C. In embodiments, the bacterial composition has an $a_w$ less than 0.4 at 20° C. In embodiments, the bacterial composition has an $a_w$ less than about 0.3 at 20° C. In embodiments, the bacterial composition has an $a_w$ less than 0.3 at 20° C. In embodiments, the bacterial composition has an $a_w$ less than about 0.2 at 20° C. In embodiments, the bacterial composition has an $a_w$ less than 0.2 at 20° C. In embodiments, the bacterial composition has an $a_w$ less than about 0.1 at 20° C. In embodiments, the bacterial composition has an $a_w$ less than 0.1 at 20° C.

In embodiments, the bacterial composition is a food or a beverage.

In embodiments, the bacterial composition is administered orally or rectally.

In embodiments, the Lactobacillus sp., the Faecalibacterium sp., the Akkermansia sp., the Myxococcus sp., and/or the Pediococcus sp. is in the form of a powder. In embodiments, the Lactobacillus sp., the Faecalibacterium sp., the Akkermansia sp., the Myxococcus sp., and/or the Pediococcus sp. has been lyophilized.

In embodiments, the subject is a human. In embodiments, the subject suffers from or resides with someone who suffers from a bacterial, viral, or fungal gastrointestinal infection.

In embodiments, the subject has an inflammatory disease. In embodiments, the subject is at risk of suffering from an inflammatory disease. In embodiments, the subject has at least 1, 2, 3, or 4 cousins, grandparents, parents, aunts, uncles, and/or siblings who have been diagnosed with an inflammatory disease. In embodiments, the subject has at least 4 cousins, grandparents, parents, aunts, uncles, and/or siblings who have been diagnosed with an inflammatory disease. In embodiments, the subject has at least 3 cousins, grandparents, parents, aunts, uncles, and/or siblings who have been diagnosed with an inflammatory disease. In embodiments, the subject has at least 2 cousins, grandparents, parents, aunts, uncles, and/or siblings who have been diagnosed with an inflammatory disease. In embodiments, the subject has at least 1 cousin, grandparent, parent, aunt, uncle, and/or sibling who has been diagnosed with an inflammatory disease.

In embodiments, the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, colitis, ulcerative colitis, collagenous colitis, lymphocytic colitis, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

In embodiments, the inflammatory disease is pediatric allergic asthma or inflammatory bowel disease. In embodiments, the subject suffers from constipation, diarrhea, bloating, urgency, and/or abdominal pain.

In embodiments, the subject has been administered an antibiotic within the last 1, 2, 3, or 4 months. In embodiments, the subject has been administered an antibiotic within the last 4 months.

In embodiments, the subject has been administered an antibiotic within the last 3 months. In embodiments, the subject has been administered an antibiotic within the last 2 months. In embodiments, the subject has been administered an antibiotic within the last 1 month.

In embodiments, the subject is a neonate. In embodiments, the subject is less than about 1, 2, 3, 4, 5, 6, 7, 8, 9, 12, 18, or 24 months old. In embodiments, the subject is less than about 1 month old. In embodiments, the subject is less than 1 month old. In embodiments, the subject is less than about 2 months old. In embodiments, the subject is less than 2 months old. In embodiments, the subject is less than about 3 months old. In embodiments, the subject is less than 3 months old. In embodiments, the subject is less than about 4 months old. In embodiments, the subject is less than 4 months old. In embodiments, the subject is less than about 5 months old. In embodiments, the subject is less than 5 months old. In embodiments, the subject is less than about 6 months old. In embodiments, the subject is less than 6 months old. In embodiments, the subject is less than about 7 months old. In embodiments, the subject is less than 7 months old. In embodiments, the subject is less than about 8 months old. In embodiments, the subject is less than 8 months old. In embodiments, the subject is less than about 9 months old. In embodiments, the subject is less than 9 months old. In embodiments, the subject is less than about 12 months old. In embodiments, the subject is less than 12 months old. In embodiments, the subject is less than about 18 months old. In embodiments, the subject is less than 18 months old. In embodiments, the subject is less than about 24 months old. In embodiments, the subject is less than 24 months old.

In embodiments, the subject is between about 2 and about 18 years old, or is at least about 18 years old. In embodiments, the subject is between 2 and 18 years old, or is at least 18 years old. In embodiments, the subject is between about 2 and about 18 years old, or is at least about 18 (e.g., 19, 20, 25, 30, 40, 50, 60, 70, 80, 90) years old. In embodiments, the subject is between about 2 and about 18 years old, or is about 19 years old. In embodiments, the subject is between about 2 and about 18 years old, or is 19 years old. In embodiments, the subject is between about 2 and about 18 years old, or is about 20 years old. In embodiments, the subject is between about 2 and about 18 years old, or is 20 years old. In embodiments, the subject is between about 2 and about 18 years old, or is about 25 years old. In embodiments, the subject is between about 2 and about 18 years old, or is 25 years old. In embodiments, the subject is between about 2 and about 18 years old, or is about 30 years old. In embodiments, the subject is between about 2 and about 18 years old, or is 30 years old. In embodiments, the subject is between about 2 and about 18 years old, or is about 40 years old. In embodiments, the subject is between about 2 and about 18 years old, or is 40 years old. In embodiments, the subject is between about 2 and about 18 years old, or is about 50 years old. In embodiments, the subject is between about 2 and about 18 years old, or is 50 years old. In embodiments, the subject is between about 2 and about 18 years old, or is about 60 years old. In embodiments, the subject is between about 2 and about 18 years old, or is 60 years old. In embodiments, the subject is between about 2 and about 18 years old, or is about 70 years old. In embodiments, the subject is between about 2 and about 18 years old, or is 70 years old. In embodiments, the subject is between about 2 and about 18 years old, or is about 80 years old. In embodiments, the subject is between about 2 and about 18 years old, or is 80 years old. In embodiments, the subject is between about 2 and about 18 years old, or is about 90 years old. In embodiments, the subject is between about 2 and about 18 years old, or is 90 years old.

In embodiments, the subject comprises a gastrointestinal microbiome that (a) has an increased proportion of Streptococcus spp., Bifidobacterium spp., and Enterococcus spp. compared to a healthy or general population; (b) has a reduced proportion of Alternaria alternata, Aspergillus flavus, Aspergillus cibarius, and Candida sojae compared to a healthy or general population; (c) has an increased proportion of Candida albicans and Debaryomyces spp. compared to a healthy or general population; (d) has a reduced proportion of Bifdobacteria spp., Lactobacillus spp., Faecalibacterium spp. and Akkermansia spp. compared to a healthy or general population; (e) has a reduced proportion of Malassezia spp. compared to a healthy or general population; (f) has an increased proportion of Bacterioides spp., Ruminococcus spp., Prevotella spp., or Bifidobacterium spp. compared to a healthy or general population; or (g) has an increased proportion of Enterococcus faecalis, Enterococcus faecium, or Clostridium difficile compared to a healthy or general population.

In embodiments, the effective amount is effective to (i) increase the level of a Bifidobacterium sp., Clostridia sp. belonging to Clade IV or XIV, a Lachnospira sp., and/or a Ruminococcus sp. in the subject; (ii) lower the pH in the feces of the subject; (iii) increase the level of lactic acid in the feces of the subject; (iv) increase the level of circulating itaconate in the subject; (v) treat, reduce, or prevent allergic inflammation in a subject; (vi) reduce an adaptive immune response in an airway of the subject; (vii) reduce dendritic cell activation in a gastrointestinal-associated mesenteric lymoph node; (viii) increase the level of repair macrophages in the lungs, blood, serum, or plasma of the subject; (ix) increase the level of an anti-inflammatory compound in the subject; (x) decrease the level of a pro-inflammatory compound in the subject; (xi) decrease the level of eotaxin expression and/or secretion in the subject; and/or (xii) decrease the level of mucin expression and/or secretion in the subject.

In embodiments, the effective amount is effective to decrease the level of mucin secretion and/or secretion in the lungs of the subject.

In embodiments, the anti-inflammatory compound is a cytokine, a microbial lipid, a microbial carbohydrate, or a microbial amino acid. In embodiments, the anti-inflammatory compound is IL-17. In embodiments, In embodiments, the pro-inflammatory compound is a cytokine, a microbial lipid, a microbial carbohydrate, or a microbial amino acid. In embodiments, the pro-inflammatory compound is IL-4, IL-10, IL-8, IL-13, TNF-α, or MUC5B.

In embodiments, the *Lactobacillus* sp., *Faecalibacterium* sp., *Akkermansia* sp., *Myxococcus* sp., and/or *Pediococcus* sp. is metabolically active. In embodiments, the *Lactobacillus* sp., *Faecalibacterium* sp., *Akkermansia* sp., *Myxococcus* sp., and/or *Pediococcus* sp. is metabolically inactive.

In embodiments, the method further includes administering (a) a *Bifidobacterium* sp., (b) *Cystobacter* sp., or (c) a fungal microorganism to the subject.

In embodiments, the effective amount is effective to alter the metabolism of the subject. In embodiments, altering the metabolism of the subject includes increasing the level of a lipid, a phospholipid, or a plasmalogen. In embodiments, altering the metabolism of the subject includes increasing the level of any compound listed in Table 3, or any combination of at least 2, 3, 4, 5, 6, 7, 8, 9, 10, 11, 12, 13, 14, 15, 16, 17, 18, 19, 20, 21, 22, 23, 24, or 25 compounds listed in Table 3, in the subject. In embodiments, altering the metabolism of the subject includes increasing the level of any compound listed in Table 3, or any combination of 2 compounds listed in Table 3, in the subject. In embodiments, altering the metabolism of the subject includes increasing the level of any compound listed in Table 3, or any combination of 3 compounds listed in Table 3, in the subject. In embodiments, altering the metabolism of the subject includes increasing the level of any compound listed in Table 3, or any combination of 4 compounds listed in Table 3, in the subject. In embodiments, altering the metabolism of the subject includes increasing the level of any compound listed in Table 3, or any combination of 5 compounds listed in Table 3, in the subject. In embodiments, altering the metabolism of the subject includes increasing the level of any compound listed in Table 3, or any combination of 6 compounds listed in Table 3, in the subject. In embodiments, altering the metabolism of the subject includes increasing the level of any compound listed in Table 3, or any combination of 7 compounds listed in Table 3, in the subject. In embodiments, altering the metabolism of the subject includes increasing the level of any compound listed in Table 3, or any combination of 8 compounds listed in Table 3, in the subject. In embodiments, altering the metabolism of the subject includes increasing the level of any compound listed in Table 3, or any combination of 9 compounds listed in Table 3, in the subject. In embodiments, altering the metabolism of the subject includes increasing the level of any compound listed in Table 3, or any combination of 10 compounds listed in Table 3, in the subject. In embodiments, altering the metabolism of the subject includes increasing the level of any compound listed in Table 3, or any combination of 11 compounds listed in Table 3, in the subject. In embodiments, altering the metabolism of the subject includes increasing the level of any compound listed in Table 3, or any combination of 12 compounds listed in Table 3, in the subject. In embodiments, altering the metabolism of the subject includes increasing the level of any compound listed in Table 3, or any combination of 13 compounds listed in Table 3, in the subject. In embodiments, altering the metabolism of the subject includes increasing the level of any compound listed in Table 3, or any combination of 14 compounds listed in Table 3, in the subject. In embodiments, altering the metabolism of the subject includes increasing the level of any compound listed in Table 3, or any combination of 15 compounds listed in Table 3, in the subject. In embodiments, altering the metabolism of the subject includes increasing the level of any compound listed in Table 3, or any combination of 16 compounds listed in Table 3, in the subject. In embodiments, altering the metabolism of the subject includes increasing the level of any compound listed in Table 3, or any combination of 17 compounds listed in Table 3, in the subject. In embodiments, altering the metabolism of the subject includes increasing the level of any compound listed in Table 3, or any combination of 18 compounds listed in Table 3, in the subject. In embodiments, altering the metabolism of the subject includes increasing the level of any compound listed in Table 3, or any combination of 19 compounds listed in Table 3, in the subject. In embodiments, altering the metabolism of the subject includes increasing the level of any compound listed in Table 3, or any combination of 20 compounds listed in Table 3, in the subject. In embodiments, altering the metabolism of the subject includes increasing the level of any compound listed in Table 3, or any combination of 21 compounds listed in Table 3, in the subject. In embodiments, altering the metabolism of the subject includes increasing the level of any compound listed in Table 3, or any combination of 22 compounds listed in Table 3, in the subject. In embodiments, altering the metabolism of the subject includes increasing the level of any compound listed in Table 3, or any combination of 23 compounds listed in Table 3, in the subject. In embodiments, altering the metabolism of the subject includes increasing the level of any compound listed in Table 3, or any combination of 24 compounds listed in Table 3, in the subject. In embodiments, altering the metabolism of the subject includes increasing the level of any compound listed in Table 3, or any combination of 25 compounds listed in Table 3, in the subject. In embodiments, the level is increased in the feces of the subject. In embodiments, the level is increased in a body fluid of the subject. In embodiments, altering the metabolism of the subject comprises decreasing the level of a carbohydrate, a lipid, or an energy compound in a subject. In embodiments, altering the metabolism of the subject comprises decreasing the level of any compound listed in Table 4, or any combination of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 compounds listed in Table 4, in the subject. In embodiments, altering the metabolism of the subject includes decreasing the level of any compound listed in Table 4, or any combination of 2 compounds listed in Table 4, in the subject. In embodiments, altering the metabolism of the subject includes decreasing the level of any compound listed in Table 4, or any combination of 3 compounds listed in Table 4, in the subject. In embodiments, altering the metabolism of the subject includes decreasing the level of any compound listed in Table 4, or any combination of 4 compounds listed in Table 4, in the subject. In embodiments, altering the metabolism of the subject includes decreasing the level of any compound listed in Table 4, or any combination of 5 compounds listed in Table 4, in the subject. In embodiments, altering the metabolism of the subject includes decreasing the level of any compound listed in Table 4, or any combination of 6 compounds listed in Table 4, in the subject. In embodiments, altering the metabolism of the subject includes decreasing the level of any compound listed in Table 4, or any combination of 7 compounds listed in Table 4, in the subject. In embodiments, altering the metabolism of the subject includes decreasing the level of any compound listed in Table 4, or any combination of 8 compounds listed in Table 4, in the subject. In embodiments, altering the metabolism of the subject includes decreasing the level of any compound listed in Table 4, or any combination of 9 compounds listed in Table 4, in the subject. In embodiments, altering the metabolism of the subject includes decreasing the level of any compound listed in Table 4, or any combination of 10 compounds listed in Table 4, in the subject. In embodiments, altering the metabolism of the subject includes decreasing the level of any compound listed in Table 4, or any combination of 11 compounds listed in Table 4, in the subject. In embodiments, altering the metabolism of the subject includes decreasing the level of any compound listed in Table 4, or any combination of 12 compounds listed in Table 4, in the subject. In embodiments, altering the metabolism of the subject includes decreasing the level of any compound listed in Table 4, or any combination of 13 compounds listed in Table 4, in the subject. In embodiments, altering the metabolism of the subject includes decreasing the level of any compound listed in Table 4, or any combination of 14 compounds listed in Table 4, in the subject. In embodiments, altering the metabolism of the subject includes decreasing the level of any compound listed in Table 4, or any combination of 15 compounds listed in Table 4, in the subject. In embodiments, altering the metabolism of the subject includes decreasing the level of any compound listed in Table 4, or any combination of 16 compounds listed in Table 4, in the subject. In embodiments, altering the metabolism of the subject includes decreasing the level of any compound listed in Table 4, or any combination of 17 compounds listed in Table 4, in the subject. In embodiments, altering the metabolism of the subject includes decreasing the level of any compound listed in Table 4, or any combination of 18 compounds listed in Table 4, in the subject. In embodiments, altering the metabolism of the subject includes decreasing the level of any compound listed in Table 4, or any combination of 19 compounds listed in Table 4, in the subject. In embodiments, altering the metabolism of the subject includes decreasing the level of any compound listed in Table 4, or any combination of 20 compounds listed in Table 4, in the subject. In embodiments, altering the metabolism of the subject includes decreasing the level of any compound listed in Table 4, or any combination of 21 compounds listed in Table 4, in the subject. In embodiments, altering the metabolism of the subject includes decreasing the level of any compound listed in Table 4, or any combination of 22 compounds listed in Table 4, in the subject. In embodiments, altering the metabolism of the subject includes decreasing the level of any compound listed in Table 4, or any combination of 23 compounds listed in Table 4, in the subject. In embodiments, altering the metabolism of the subject includes decreasing the level of any compound listed in Table 4, or any combination of 24 compounds listed in Table 4, in the subject. In embodiments, altering the metabolism of the subject includes decreasing the level of any compound listed in Table 4, or any combination of 25 compounds listed in Table 4, in the subject. In embodiments, altering the metabolism of the subject includes decreasing the level of any compound listed in Table 4, or any combination of 30 compounds listed in Table 4, in the subject. In embodiments, altering the metabolism of the subject includes decreasing the level of any compound listed in Table 4, or any combination of 35 compounds listed in Table 4, in the subject. In embodiments, altering the metabolism of the subject includes decreasing the level of any compound listed in Table 4, or any combination of 40 compounds listed in Table 4, in the subject. In embodiments, altering the metabolism of the subject includes decreasing the level of any compound listed in Table 4, or any combination of 45 compounds listed in Table 4, in the subject. In embodiments, altering the metabolism of the subject includes decreasing the level of any compound listed in Table 4, or any combination of 50 compounds listed in Table 4, in the subject. In embodiments, the level is decreased in the feces of the subject. In embodiments, the level is decreased in a body fluid of the subject.

In an aspect is provided a method of treating or preventing an inflammatory disease in a subject in need thereof. The method includes administering to the subject a therapeutically effective amount of *Lactobacillus johnsonii*. *Faecalibacterium prausnitzii*. *Akkermansia muciniphila*, *Myxococcus xanthus* and *Pediococcus pentosaceus*. In embodiments, the *Lactobacillus johnsonii*, *Faecalibacterium prausnitzii*, *Akkermansia muciniphila*, *Myxococcus xanthus* and *Pediococcus pentosaceus* form a microbial composition as provided herein. Where the *Lactobacillus johnsonii*, *Faecalibacterium prausnitzii*, *Akkermansia muciniphila*, *Myxococcus xanthus* and *Pediococcus pentosaceus* form a microbial composition, the bacteria form part of a composition including a pharmaceutically acceptable carrier for administration to and colonialization of the gut. Acceptable carriers include, but are not limited to inulin. In embodiments, the gut is of a healthy subject. In embodiments, the gut is of a subject in need of treatment or prevention of an inflammatory disease. In embodiments, the subject is a neonate. A "neonate" as provided herein refers to a newborn child or mammal. In embodiments, the neonate is less than about four weeks old.

In an aspect, a method of treating or preventing an inflammatory disease in a subject in need thereof is provided. The method including administering to the subject an effective amount of a bacterial population comprising *Lactobacillus* sp., *Faecalibacterium* sp., *Akkermansia* sp., *Myxococcus* sp., and *Pediococcus* sp.

In embodiments, the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous *colitis*, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

In embodiments, the *Lactobacillus johnsonii, Faecalibacterium prausnitzii, Akkermansia muciniphila, Myxococcus xanthus* and *Pediococcus pentosaceus* are metabolically active. "Metabolically active" as provided herein refer to cells (e.g., bacteria) capable of cell division. In embodiments the metabolically active cell is capable of substrate (e.g. glucose) consumption. In embodiments, the *Lactobacillus johnsonii, Faecalibacterium prausnitzii, Akkermansia muciniphila, Myxococcus xanthus* and *Pediococcus pentosaceus* are metabolically inactive. In embodiments, the microbial composition is effective for administration to the gut. In embodiments, the microbial composition does not include *Lactobacillus rhamnosus*.

In embodiments, the microbial composition is effective to increase an anti-inflammatory metabolite (e.g., microbial lipid, a microbial carbohydrate or a microbial amino acid). As described herein, the anti-inflammatory metabolite may be a microbial lipid (e.g., phospholipid, poly-unsaturated fatty acid). In embodiments, the anti-inflammatory metabolite is a phospholipid. In embodiments, the anti-inflammatory metabolite is poly-unsaturated fatty acid. In embodiments, the anti-inflammatory metabolite is a microbial carbohydrate (e.g., itoconate, n-acetylglucosamine, n-acetylgalactosamine, fucosyllactose). In embodiments, the anti-inflammatory metabolite is itoconate. In embodiments, the anti-inflammatory metabolite is n-acetylglucosamine. In embodiments, the anti-inflammatory metabolite is n-acetylgalactosamine. In embodiments, the anti-inflammatory metabolite is fucosyllactose. In embodiments, the anti-inflammatory metabolite is a microbial amino acid (e.g., tryptophan). In embodiments, the anti-inflammatory metabolite is tryptophan. A composition capable of increasing an anti-inflammatory metabolite as provided herein refers to a composition that results in a detectably higher level of an anti-inflammatory metabolite as compared to a control. The increased activity can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control. In embodiments, the microbial composition is effective to increase the number of IL-17-secreting T helper cells.

In embodiments, the microbial composition is effective to decrease a pro-inflammatory metabolite. As described herein, the pro-inflammatory metabolite may be a microbial lipid (e.g., dihydroxyoctadec-12-enoic acid, cholate or methylmalonate). In embodiments, the pro-inflammatory metabolite is dihydroxyoctadec-12-enoic acid. In embodiments, the pro-inflammatory metabolite is a cholate. In embodiments, the pro-inflammatory metabolite is methylmalonate. In embodiments, the pro-inflammatory metabolite is a microbial carbohydrate (e.g., n-acetylmuramate, lactobionate or maltotriose). In embodiments, the pro-inflammatory metabolite is n-acetylmuramate. In embodiments, the pro-inflammatory metabolite is lactobionate. In embodiments, the pro-inflammatory metabolite is maltotriose. In embodiments, the pro-inflammatory metabolite is a microbial amino acid (e.g., ornithine or taurine). In embodiments, the pro-inflammatory metabolite is ornithine. In embodiments, the pro-inflammatory metabolite is taurine. A composition capable of decreasing a pro-inflammatory metabolite as provided herein refers to a composition that results in a detectably lower level of a pro-inflammatory metabolite as compared to a control. The decreased activity can be 10%, 20%, 300, 40%, 50%, 60%, 70%, 80%, 90% or less than that in a control. In certain instances, the decrease is 1.5-fold, 2-fold, 3-fold, 4-fold, 5-fold, 10-fold, or less in comparison to a control.

In embodiments, the pro-inflammatory metabolite is IL-4, IL-10, IL-13 or MUC5B. In embodiments, the pro-inflammatory metabolite is IL-4. In embodiments, the pro-inflammatory metabolite is IL-10. In embodiments, the pro-inflammatory metabolite is IL-13. In embodiments, the pro-inflammatory metabolite MUC5B. In embodiments, the pro-inflammatory metabolite MUC5AC. In embodiments, the microbial composition is effective to decrease T helper cell type 2 cytokine expression.

The term "IL-4" as provided herein includes any of the recombinant or naturally-occurring forms of the interleukin 4 (IL-4) cytokine or variants or homologs thereof that maintain IL-4 protein activity (e.g. within at least 50%, 80%, 90%, 95%, 96%, 97%, 98%, 99% or 100% activity compared to IL-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-4 polypeptide. In embodiments, 1-4 is the protein as identified by the NCBI sequence reference GI:4504669 (Accession No. NP_000580.1; SEQ ID NO: 1), or an isoform, a homolog or functional fragment thereof.

The term "IL-10" as provided herein includes any of the recombinant or naturally-occurring forms of the interleukin 10 (IL-10) cytokine or variants or homologs thereof that maintain IL-10 protein activity (e.g. within at least 50%, 80%, 90%, 95%, 96%, 97%, 98%, 99% or 100% activity compared to IL-10). In some aspects, the variants or homologs have at least 90%, 95%, 96%, 97%, 98%, 99⁰% or 100% amino acid sequence identity across the whole sequence or a portion of the sequence (e.g. a 50, 100, 150 or 200 continuous amino acid portion) compared to a naturally occurring IL-10 polypeptide. In embodiments, IL-10 is the protein as identified by the NCBI sequence reference GI:10835141 (Accession No. NP_000563.1; SEQ ID NO:2), or an isoform, a homolog or functional fragment thereof.

The term "IL-13" as provided herein includes any of the recombinant or naturally-occurring forms of the interleukin 13 (IL-13) cytokine or variants or homologs thereof that maintain IL-13 protein activity (e.g. within at least 50%, 80%, 90%, 95%, 96° %, 97%, 98%, 99% or 100% activity compared to IL-13). In some aspects, the variants or homologs have at least 90° %, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-13 polypeptide. In embodiments, IL-13 is the protein as identified by the NCBI sequence reference GI:26787978 (Accession No. NP_002179.2; SEQ ID NO:3), or an isoform, a homolog or functional fragment thereof.

The term "IL-17" as provided herein includes any of the recombinant or naturally-occurring forms of the interleukin 17 (IL-17) cytokine or variants or homologs thereof that maintain IL-17 protein activity (e.g. within at least 50%, 80%, 90%, 95%, 96%, 97%, 98%, 99% or 100% activity compared to IL-17). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-17 polypeptide. In embodiments, IL-17 is the protein as identified by the UniProt sequence reference Q16552 (SEQ ID NO:4), or a homolog or functional fragment thereof. In embodiments, IL-17 is the protein as identified by the UniProt sequence reference Q9UHF5, or an isoform, a homolog or functional fragment thereof.

The term "MUC5AC" as provided herein includes any of the recombinant or naturally-occurring forms of the mucin 5AC (MUC5AC) protein or variants or homologs thereof that maintain MUC5AC protein activity (e.g. within at least 50%, 80%, 90%, 95%, 96%, 97%, 98%, 99% or 100% activity compared to MUC5AC). In some aspects, the variants or homologs have at least 90%, 95%, 96%, 97%, 98%, 99% or 100%0, amino acid sequence identity across the whole sequence or a portion of the sequence (e.g. a 50, 100, 150 or 200 continuous amino acid portion) compared to a naturally occurring MUC5AC polypeptide. In embodiments, MUC5AC is the protein as identified by the UniProt sequence reference P98088 (SEQ ID NO:5), or an isoform, a homolog or functional fragment thereof.

The term "MUC5B" as provided herein includes any of the recombinant or naturally-occurring forms of the mucin 5B (MUC5B) protein or variants or homologs thereof that maintain MUC5B protein activity (e.g. within at least 50%, 80%, 90%, 95%, 96%, 97%, 98%, 99% or 100%0/activity compared to MUC5B). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MUC5B polypeptide. In embodiments, MUC5B is the protein as identified by the UniProt sequence reference Q9HC84 (SEQ ID NO:6), or an isoform, a homolog or functional fragment thereof.

In embodiments, the method further includes administering a therapeutically effective amount of a fungus. In embodiments, the fungus is a *Malassezia* fungus. In embodiments, the microbial composition is effective to decrease a pathogenic fungal activity. A "pathogenic fungal activity" as referred to herein is a metabolic activity derived from a pathogenic fungus. In embodiments, the pathogenic fungus is *Candida albicans*. In embodiments, the pathogenic fungus forms a pro-inflammatory lipid.

In embodiments, the subject is a neonate. In embodiments, the neonate is less than about four weeks old. In embodiments, the neonate is treated for at least about one month. In embodiments, the neonate is treated for at least about two months. In embodiments, the neonate is treated for at least about three months. In embodiments, the neonate is treated for at least about four months. In embodiments, the neonate is treated for at least about five months. In embodiments, the neonate is treated for at least about six months.

In embodiments, the neonate is treated for about one month. In embodiments, the neonate is treated for about two months. In embodiments, the neonate is treated for about three months. In embodiments, the neonate is treated for about four months. In embodiments, the neonate is treated for about five months. In embodiments, the neonate is treated for about six months.

In embodiments, the neonate is treated for less than about one month. In embodiments, the neonate is treated for less than about two months. In embodiments, the neonate is treated for less than about three months. In embodiments, the neonate is treated for less than about four months. In embodiments, the neonate is treated for less than about five months. In embodiments, the neonate is treated for less than about six months.

In embodiments, the neonate is treated for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54, weeks.

In embodiments, the inflammatory disease is asthma, ulcerative *colitis*, irritable bowel syndrome, arthritis, uveitis, pyoderma gangrenosum or erythema nodosum. In embodiments, the inflammatory disease is asthma. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of increasing an anti-inflammatory metabolite in a subject in need thereof is provided. The method includes administering to the subject a therapeutically effective amount of *Lactobacillus johnsonii, Faecalibacterium prausnitzii, Akkermansia muciniphila, Myxococcus xanthus* and *Pediococcus pentosaceus*. In embodiments, the method further includes a pharmaceutically active excipient as provided herein. The *Lactobacillus johnsonii, Faecalibacterium prausnitzii, Akkermansia muciniphila, Myxococcus xanthus* and *Pediococcus pentosaceus* may form a microbial composition provided herein including embodiments thereof. Thus, in embodiments, the *Lactobacillus johnsonii, Faecalibacterium prausnitzii, Akkermansia muciniphila, Myxococcus xanthus* and *Pediococcus pentosaceus* form a microbial composition.

The anti-inflammatory metabolite may be a microbial lipid (e.g., a phospholipid, a poly unsaturated fatty acid), a microbial carbohydrate (e.g., itoconate, n-acetylglucosamine, n-acetylgalactosamine, fucosyllactose) or a microbial amino acid (e.g., tryptophan) as provided herein. In embodiments, the anti-inflammatory metabolite is a microbial lipid. In embodiments, the anti-inflammatory metabolite is a microbial carbohydrate. In embodiments, the anti-inflammatory metabolite is a microbial amino acid.

In an aspect is provided a method of decreasing a pro-inflammatory metabolite in a subject in need thereof. The method includes administering to the subject a therapeutically effective amount of *Lactobacillus johnsonii, Faecalibacterium prausnitzii, Akkermansia muciniphila, Myxococcus xanthus* and *Pediococcus pentosaceus*. In embodiments, the method further includes a pharmaceutically active excipient as provided herein. The *Lactobacillus johnsonii, Faecalibacterium prausnitzii, Akkermansia muciniphila, Myxococcus xanthus* and *Pediococcus pentosaceus* may form a microbial composition provided herein including embodiments thereof. Thus, in embodiments, the *Lactobacillus johnsonii, Faecalibacterium prausnitzii, Akkermansia muciniphila, Myxococcus xanthus* and *Pediococcus pentosaceus* form a microbial composition.

As described herein, the pro-inflammatory metabolite may be a microbial lipid (e.g., dihydroxyoctadec-12-enoic acid, cholate or methylmalonate). In embodiments, the pro-inflammatory metabolite is dihydroxyoctadec-12-enoic acid. In embodiments, the pro-inflammatory metabolite is a cholate. In embodiments, the pro-inflammatory metabolite is methylmalonate. In embodiments, the pro-inflammatory metabolite is a microbial carbohydrate (e.g., n-acetylmuramate, lactobionate or maltotriose). In embodiments, the pro-inflammatory metabolite is n-acetylmuramate. In embodiments, the pro-inflammatory metabolite is lactobionate. In embodiments, the pro-inflammatory metabolite is maltotriose. In embodiments, the pro-inflammatory metabolite is a microbial amino acid (e.g., ornithine or taurine). In embodiments, the pro-inflammatory metabolite is ornithine. In embodiments, the pro-inflammatory metabolite is taurine.

In an aspect, a method of increasing the level of an anti-inflammatory compound and/or decreasing the level of a pro-inflammatory compound in a subject in need thereof is provided. In embodiments, the method includes administering to the subject an effective amount of a bacterial population comprising *Lactobacillus* sp., *Faecalibacterium* sp., *Akkermansia* sp., *Myxococcus* sp., and *Pediococcus* sp.

In embodiments, the method for increasing the level of the anti-inflammatory compound increases and/or decreases the level of the pro-inflammatory compound in the feces, blood, plasma, serum, broncheoalveolar lavage fluid, sweat, saliva, sputum, lymph, spinal fluid, urine, tears, bile, aqueous humour, vitreous humour, aminiotic fluid, breast milk, cerebrospinal fluid, cerumen, nasal mucus, phlegm, or sebum of the subject.

In embodiments, the anti-inflammatory compound is a microbial lipid, a microbial carbohydrate, or a microbial amino acid.

In embodiments, the subject suffers from dysbiosis or an inflammatory disease.

In embodiments, the inflammatory disease is a disease as described herein. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of treating or preventing a viral respiratory infection in a subject in need thereof is provided. The method including administering to the subject an effective amount of a bacterial population comprising *Lactobacillus* sp., *Faecalibacterium* sp., *Akkermansia* sp., *Myxococcus* sp., and *Pediococcus* sp.

In embodiments, wherein the viral respiratory infection is caused by a respiratory syncytial virus, an influenza virus, a parainfluenza virus, an adenovirus, a coronavirus, or a rhinovirus. In embodiments, the viral respiratory infection is bronchiolitis, a cold, croup, or pneumonia.

In aspects is provided a method of treating or preventing an allergy in a subject in need thereof. The method including administering to the subject an effective amount of a bacteria population comprising *Lactobacillus* sp., *Faecalibacterium* sp., *Akkermansia* sp., *Myxococcus* sp., and *Pediococcus* sp.

In embodiments, the allergy is an allergy to milk, eggs, fish, shellfish, a tree nut, peanuts, wheat, dander from a cat, dog, or rodent, an insect sting, pollen, latex, dust mites, or soybeans. In embodiments, the allergy is pediatric allergic asthma, hay fever, or allergic airway sensitization.

V. Methods of Detection

In an aspect a method of detecting an anti-inflammatory metabolite in a subject that has or is at risk for developing an inflammatory disease is provided. The method includes (i) obtaining a biological sample from the subject; and (ii) determining an expression level of an anti-inflammatory metabolite in the biological sample. The anti-inflammatory metabolite may be a microbial lipid (e.g., a phospholipid, a poly unsaturated fatty acid), a microbial carbohydrate (e.g., itoconate, n-acetylglucosamine, n-acetylgalactosamine, fucosyllactose) or a microbial amino acid (e.g., tryptophan) as provided herein. Thus, in embodiments, the anti-inflammatory metabolite is a microbial lipid or a microbial carbohydrate as described herein. In embodiments, the anti-inflammatory metabolite is a microbial lipid. In embodiments, the anti-inflammatory metabolite is a microbial carbohydrate.

In embodiments, the expression level of a compound (e.g., a metabolite) is the amount (e.g., weight) of the compound. In embodiments, the expression level of a compound (e.g., a protein such as a cytokine) is the level of mRNA expression.

In an aspect a method of detecting a pro-inflammatory metabolite in a subject that has or is at risk for developing an inflammatory disease is provided. The method includes (i) obtaining a biological sample from the subject; and (ii) determining an expression level of a pro-inflammatory metabolite in the biological sample. The pro-inflammatory metabolite may be a microbial lipid (e.g., dihydroxyoctadec-12-enoic acid, cholate or methylmalonate), a microbial carbohydrate (e.g., n-acetylymuramate, lactobionate or maltotriose syllactose) or a microbial amino acid (e.g., ornithine or taurine) as provided herein.

In an aspect, a method of detecting a pro-inflammatory compound in a subject in need thereof is provided. In embodiments, the method includes (i) obtaining a biological sample from the subject; and (ii) detecting the pro-inflammatory compound in the biological sample.

In an aspect, a method of monitoring the effect of treatment for dysbiosis or an inflammatory disease is provided. In embodiments, the method includes (i) obtaining a biological sample from the subject; and (ii) detecting whether the biological sample is pro-inflammatory.

In an aspect, a method of determining an inflammatory disease activity in a subject is provided. In embodiments, the method includes (i) obtaining a biological sample from the subject; and (ii) detecting whether the biological sample is pro-inflammatory.

In an aspect, a method of detecting an anti-inflammatory metabolite in a subject that has or is at risk for developing an inflammatory disease is provided. In embodiments, the method includes (i) obtaining a biological sample from the subject; and (ii) determining an expression level of an anti-inflammatory metabolite in the biological sample.

In embodiments, the subject has or is at risk for developing dysbiosis. In embodiments, the subject has an inflammatory disease. In embodiments, the subject is at risk of suffering from an inflammatory disease.

In embodiments, the subject (i) has at least 1, 2, 3, or 4 cousins, grandparents, parents, aunts, uncles, and/or siblings who have been diagnosed with an inflammatory disease; (ii) suffers from constipation, diarrhea, bloating, urgency, and/or abdominal pain; and/or (iii) has been administered an antibiotic within the last 1, 2, or 4 months.

In embodiments, the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous *colitis*, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

In embodiments, the subject is less than about 1, 2, 3, 4, 5, 6, 7, 8, 9, 12, 18, or 24 months old. In embodiments, the subject is less than about 1 month old. In embodiments, the subject is less than 1 month old. In embodiments, the subject is less than about 2 months old. In embodiments, the subject is less than 2 months old. In embodiments, the subject is less than about 3 months old. In embodiments, the subject is less than 3 months old. In embodiments, the subject is less than about 4 months old. In embodiments, the subject is less than 4 months old. In embodiments, the subject is less than about 5 months old. In embodiments, the subject is less than 5 months old. In embodiments, the subject is less than about 6 months old. In embodiments, the subject is less than 6 months old. In embodiments, the subject is less than about 7 months old. In embodiments, the subject is less than 7 months old. In embodiments, the subject is less than about 8 months old. In embodiments, the subject is less than 8 months old. In embodiments, the subject is less than about 9 months old. In embodiments, the subject is less than 9 months old. In embodiments, the subject is less than about 12 months old. In embodiments, the subject is less than 12 months old. In embodiments, the subject is less than about 18 months old. In embodiments, the subject is less than 18 months old. In embodiments, the subject is less than about 24 months old. In embodiments, the subject is less than 24 months old.

In embodiments, the subject is between about 2 and about 18 years old, or is at least about 18 years old. In embodiments, the subject is between 2 and 18 years old, or is at least 18 years old. In embodiments, the subject is between about 2 and about 18 years old, or is at least about 18 (e.g., 19, 20, 25, 30, 40, 50, 60, 70, 80, 90) years old. In embodiments, the subject is between about 2 and about 18 years old, or is about 19 years old. In embodiments, the subject is between about 2 and about 18 years old, or is 19 years old. In embodiments, the subject is between about 2 and about 18 years old, or is about 20 years old. In embodiments, the subject is between about 2 and about 18 years old, or is 20 years old. In embodiments, the subject is between about 2 and about 18 years old, or is about 25 years old. In embodiments, the subject is between about 2 and about 18 years old, or is 25 years old. In embodiments, the subject is between about 2 and about 18 years old, or is about 30 years old. In embodiments, the subject is between about 2 and about 18 years old, or is 30 years old. In embodiments, the subject is between about 2 and about 18 years old, or is about 40 years old. In embodiments, the subject is between about 2 and about 18 years old, or is 40 years old. In embodiments, the subject is between about 2 and about 18 years old, or is about 50 years old. In embodiments, the subject is between about 2 and about 18 years old, or is 50 years old. In embodiments, the subject is between about 2 and about 18 years old, or is about 60 years old. In embodiments, the subject is between about 2 and about 18 years old, or is 60 years old. In embodiments, the subject is between about 2 and about 18 years old, or is about 70 years old. In embodiments, the subject is between about 2 and about 18 years old, or is 70 years old. In embodiments, the subject is between about 2 and about 18 years old, or is about 80 years old. In embodiments, the subject is between about 2 and about 18 years old, or is 80 years old. In embodiments, the subject is between about 2 and about 18 years old, or is about 90 years old. In embodiments, the subject is between about 2 and about 18 years old, or is 90 years old.

In embodiments, the subject comprises a gastrointestinal microbiome that (a) has an increased proportion of *Streptococcus* spp., *Bifidobacterium* spp., and *Enterococcus* spp. compared to a healthy or general population; (b) has a reduced proportion of *Alternaria alternata, Aspergillus flavus, Aspergillus cibarius*, and *Candida sojae* compared to a healthy or general population; (c) has an increased proportion of *Candida albicans* and *Debaryomyces* spp. compared to a healthy or general population; (d) has a reduced proportion of *Bifidobacteria* spp., *Lactobacillus* spp., *Faecalibacterium* spp. and *Akkermansia* spp. compared to a healthy or general population; (e) has a reduced proportion of *Malassezia* spp. compared to a healthy or general population; (f) has an increased proportion of *Bacterioides* spp., *Ruminococcus* spp., *Prevotella* spp., or *Bifidobacterium* spp. compared to a healthy or general population; or (g) has an increased proportion of *Enterococcus faecalis, Enterococcus faecium*, or *Clostridium difficile* compared to a healthy or general population.

In embodiments, the biological sample is a bodily fluid. In embodiments, wherein the bodily fluid is blood, plasma, serum, fecal water, or a brancheoaleolar lavage. In embodiments, the bodily fluid is fecal water.

In embodiments, detecting the pro-inflammatory compound includes contacting an antigen presenting cell with the biological sample. In embodiments, the antigen presenting cell is a dendritic cell. In embodiments, the dendritic cell has been isolated from blood. In embodiments, the dendritic cell has been isolated from the blood of a healthy subject (e.g., a subject who does not have an inflammatory disease, an infection, and who has not been administered an antibiotic within about 1, 2, 3, 4, 5, or 6 months). In embodiments, the dendritic cell has been obtained (e.g., isolated, selected, or enriched) from peripheral blood mononuclear cells. In embodiments, the dendritic cell is part of a primary culture of dendritic cells. In embodiments, the dendritic cell is part of a culture of dendritic cells that has been passaged less than about 1, 2, 3, 4, 5, 6, 7, 8, 9, or 10 times. In embodiments, the dendritic cell is not immortalized. In embodiments, the dendritic cell is an immortalized dendritic cell.

In embodiments, detecting the pro-inflammatory compound further includes contacting a naïve T cell with the antigen presenting cell to produce a contacted T cell. In embodiments, the method further includes detecting a cytokine produced by the contacted T cell and/or the progeny of the contacted T cell. In embodiments, the T cell has been isolated from blood. In embodiments, the T cell has been isolated from the blood of a healthy subject (e.g., a subject who does not have an inflammatory disease, an infection, and who has not been administered an antibiotic within about 1, 2, 3, 4, 5, or 6 months). In embodiments, the T cell has been obtained (e.g., isolated, selected, or enriched) from peripheral blood mononuclear cells. In embodiments, the T cell is part of a primary culture of T cells. In embodiments, the T cell is part of a culture of T cells that has been passaged less than about 1, 2, 3, 4, 5, 6, 7, 8, 9, or 10 times. In embodiments, the T cell is not immortalized. In embodiments, the T cell is an immortalized T cell.

In embodiments, the pro-inflammatory compound is detected if (i) the proportion of T-helper (TH)-2 cells is increased in the progeny of the contacted T cell compared to a control; (ii) the proportion of TH-1, TH-17, and/or TH22 cells is increased in the progeny of the contacted T cell compared to a control; (iii) the ratio of TH-1 cells to TH-2 cells is decreased in the progeny of the contacted T cell compared to a control; (iv) the proportion of IL-17 producing CD8+ T cells is increased in the progeny of the contacted T cell compared to a control; and/or (v) the amount of IL-4, IL-10, and/or IL-13 produced by the progeny of the contacted T cell and/or the progeny thereof is increased compared to a control.

In embodiments, the control is (i) the corresponding proportion, ratio, and/or amount of a corresponding T cell that has been contacted with sterile culture medium and/or the progeny thereof; (ii) the corresponding proportion, ratio, and/or amount of a corresponding T cell that has been contacted with an antigen presenting cell that has been contacted with a biological sample from a subject who does not have dysbiosis, an inflammatory disease, or a gastrointestinal infection, and/or the progeny thereof; and/or (iii) a reference value corresponding to the proportion, ratio, and/or amount in the general population or a population of subjects who do not have dysbiosis, an inflammatory disease, or a gastrointestinal infection.

In embodiments, the method further includes directing the subject to receive treatment or further testing or monitoring for dysbiosis or an inflammatory disease if the pro-inflammatory compound is detected in the subject.

In embodiments, the method further includes administering the composition as described herein including embodiments thereof to the subject if the pro-inflammatory compound is detected in the subject.

In embodiments, the method further includes diagnosing the subject as having or at risk of developing dysbiosis or an inflammatory disease if the pro-inflammatory compound is detected in the subject.

In embodiments, a method of determining whether a subject has or is at risk of developing dysbiosis or an inflammatory disease is provided. In embodiments, the method includes (i) obtaining a biological sample from the subject; and (ii) detecting a pro-inflammatory compound according to a method described herein including embodiments thereof.

In some examples of the disclosed methods, when the expression level of an anti-inflammatory metabolite or pro-inflammatory metabolite is assessed, the level is compared with a control expression level of the anti-inflammatory metabolite or pro-inflammatory metabolite. By control level is meant the expression level of a particular an anti-inflammatory metabolite or pro-inflammatory metabolite from a sample or subject lacking a disease (e.g. an inflammatory disease), at a selected stage of a disease or disease state, or in the absence of a particular variable such as a therapeutic agent. Alternatively, the control level comprises a known amount of anti-inflammatory metabolite or pro-inflammatory metabolite. Such a known amount correlates with an average level of subjects lacking a disease, at a selected stage of a disease or disease state, or in the absence of a particular variable such as a therapeutic agent. A control level also includes the expression level of one or more anti-inflammatory metabolites or pro-inflammatory metabolites from one or more selected samples or subjects as described herein. For example, a control level includes an assessment of the expression level of one or more anti-inflammatory metabolites or pro-inflammatory metabolites in a sample from a subject that does not have a disease (e.g. an inflammatory disease), is at a selected stage of progression of a disease (e.g. inflammatory disease), or has not received treatment for a disease. Another exemplary control level includes an assessment of the expression level of one or more anti-inflammatory metabolites or pro-inflammatory metabolite in samples taken from multiple subjects that do not have a disease, are at a selected stage of progression of a disease, or have not received treatment for a disease.

When the control level includes the expression level of one or more anti-inflammatory metabolites or pro-inflammatory metabolites in a sample or subject in the absence of a therapeutic agent (e.g., the microbial composition provided herein including embodiments thereof), the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

In embodiments, the biological sample is a bodily fluid. In embodiments, the bodily fluid is serum, fecal water or brancheoaleolar lavage. In embodiments, the bodily fluid is serum. In embodiments, the bodily fluid is fecal water. In embodiments, the bodily fluid is brancheoaleolar lavage. In embodiments, the biological sample is a tissue. In embodiments, the tissue is lung, spleen, or ileum tissue. In embodiments, the biological sample is a cell. In embodiments, the biological sample is a lung cell. In embodiments, the biological sample is a spleen cell. In embodiments, the biological sample is an ileum cell. In embodiments, the sample includes one or more bacterial cells.

In embodiments, a biological sample is a bodily fluid obtained by filtration and/or centrifugation. For example, the biological sample may be a filtrate of e.g., blood or feces or the supernatant of centrifuged blood or feces. In embodiments, a filtrate is centrifuged. In embodiments a supernatant is filtered. In embodiments, centrifugation is used to increase the passage of a fluid through a filter. Non-limiting examples of filters include filters that restrict any molecule greater than, e.g., 50, 100, 200, 300, 400, 500, 50-500, 50-100, 100-500 nm in diameter (or average diameter), or greater than 0.5, 1, 1.5, 2, 2.5, 5, 10, 15, 25, 50, 100, or 200 microns in diameter (e.g., average diameter). In embodiments, a filter has pores of about 50, 100, 200, 300, 400, 500, 50-500, 50-100, 100-500 nm in diameter or about 0.5, 1, 1.5, 2, 2.5, 5, 10, 15, 25, 50, 100, or 200 microns in diameter.

In embodiments, detecting a compound (e.g., a metabolite) and/or the expression level thereof comprises High performance liquid chromatography (HPLC), gas chromatography, liquid chromatography, Mass spectrometry (MS), inductively coupled plasma-mass spectrometry (ICP-MS), accelerator mass spectrometry (AMS), thermal ionization-mass spectrometry (TIMS) and spark source mass spectrometry (SSMS), matrix-assisted laser desorption/ionization (MALDI), and/or MALDI-TOF.

In embodiments, detecting the expression level of a compound comprises lysing a cell. In embodiments, detecting the expression level of a compound comprises a polymerase chain reaction (e.g., reverse transcriptase polymerase chain reaction), microarray analysis, immunohistochemistry, or flow cytometry.

In embodiments, the determining includes: (a) contacting in vitro the anti-inflammatory metabolite with an antigen presenting cell, thereby forming a metabolite-antigen presenting cell; (b) contacting the metabolite-antigen presenting cell with a T cell, thereby forming a contacted T cell; and (c) detecting a cytokine produced by the contacted T cell. In embodiments, the cytokine is produced by an activated or differentiating T cell.

In embodiments, the determining includes: (a) contacting in vitro the pro-inflammatory metabolite with an antigen presenting cell, thereby forming a metabolite-antigen presenting cell; (b) contacting the metabolite-antigen presenting cell with a T cell, thereby forming a contacted T cell; (c) detecting a cytokine produced by the contacted T cell.

In embodiments, the inflammatory disease is asthma, ulcerative *colitis*, irritable bowel syndrome, arthritis, uveitis, pyoderma gangrenosum, or erythema nodosum. In embodiments, the inflammatory disease is asthma. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of determining whether a subject has or is at risk of developing an inflammatory disease is provided. The method includes (i) detecting an expression level of one or more anti-inflammatory metabolites or pro-inflammatory metabolites in a subject; (ii) determining whether the expression level is increased or decreased relative to a standard control, wherein an elevated expression level of an pro-inflammatory metabolite or a decreased expression level of an anti-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In an aspect, a method of determining whether a subject has or is at risk of developing an inflammatory disease is provided. The method includes (i) detecting an expression level of one or more pro-inflammatory metabolites in a subject; (ii) determining whether the expression level is increased or decreased relative to a standard control, wherein an increased expression level of an pro-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In another aspect, a method of determining whether a subject has or is at risk of developing an inflammatory disease is provided. The method includes (i) detecting an expression level of one or more anti-inflammatory metabolites in a subject; (ii) determining whether the expression level is increased or decreased relative to a standard control, wherein a decreased expression level of an anti-inflammatory metabolite relative to the standard control indicates that the subject has or is at risk of developing an inflammatory disease; and (iii) based at least in part on the expression level in step (ii), determining whether the subject has or is at risk for developing an inflammatory disease.

In embodiments, the anti-inflammatory metabolite is a microbial lipid, a microbial carbohydrate or a microbial amino acid as provided herein. The anti-inflammatory metabolite may be a microbial lipid (e.g., a phospholipid, a poly unsaturated fatty acid), a microbial carbohydrate (e.g., itoconate, n-acetylglucosamine, n-acetylgalactosamine, fucosyllactose) or a microbial amino acid (e.g., tryptophan) as provided herein. In embodiments, the anti-inflammatory metabolite is a microbial lipid. In embodiments, the anti-inflammatory metabolite is a microbial carbohydrate. In embodiments, the anti-inflammatory metabolite is a microbial amino acid.

In embodiments, the pro-inflammatory metabolite is a microbial lipid, a microbial carbohydrate or a microbial amino acid as provided herein. The pro-inflammatory metabolite may be a microbial lipid (e.g., dihydroxyoctadec-12-enoic acid, cholate or methylmalonate), a microbial carbohydrate (e.g., n-acetylymuramate, lactobionate or maltotriose syllactose) or a microbial amino acid (e.g., ornithine or taurine) as provided herein.

In embodiments, the inflammatory disease is asthma, ulcerative *colitis*, irritable bowel syndrome, arthritis, uveitis, pyoderma gangrenosum, or erythema nodosum. In embodiments, the inflammatory disease is asthma. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of monitoring the effect of treatment for an inflammatory disease in a subject undergoing inflammatory disease therapy or a patient that has received inflammatory disease therapy is provided. The method includes (i) determining a first expression level of an anti-inflammatory metabolite in the subject at a first time point; (ii) determining a second expression level of an anti-inflammatory metabolite in the subject at a second time point; and (iii) comparing the second expression level of an anti-inflammatory metabolite to the first expression level of an anti-inflammatory metabolite, thereby determining the effect of treatment for an inflammatory disease in the subject.

In embodiments, the anti-inflammatory metabolite is a microbial lipid, a microbial carbohydrate or a microbial amino acid as provided herein. In embodiments, the anti-inflammatory metabolite is a microbial lipid. In embodiments, the anti-inflammatory metabolite is a microbial carbohydrate. In embodiments, the anti-inflammatory metabolite is a microbial amino acid.

In an aspect, a method of monitoring the effect of treatment for an inflammatory disease in a subject undergoing inflammatory disease therapy or a patient that has received inflammatory disease therapy is provided. The method includes (i) determining a first expression level of a pro-inflammatory metabolite in the subject at a first time point; (ii) determining a second expression level of a pro-inflammatory metabolite in the subject at a second time point; and (iii) comparing the second expression level of a pro-inflammatory metabolite to the first expression level of a pro-inflammatory metabolite, thereby determining the effect of treatment for an inflammatory disease in the subject.

In embodiments, the pro-inflammatory metabolite is a microbial lipid, a microbial carbohydrate or a microbial amino acid as provided herein. In embodiments, the pro-inflammatory metabolite is a microbial lipid. In embodiments, the pro-inflammatory metabolite is a microbial carbohydrate. In embodiments, the pro-inflammatory metabolite is a microbial amino acid.

In embodiments, the inflammatory disease is asthma, ulcerative *colitis*, irritable bowel syndrome, arthritis, uveitis, pyoderma gangrenosum, or erythema nodosum. In embodiments, the inflammatory disease is asthma. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of determining whether a subject has or is at risk of developing dysbiosis or an inflammatory disease is provided. The method including: (i) obtaining a biological sample from the subject; and (ii) detecting whether the biological sample is pro-inflammatory.

In embodiments, the subject suffers from or resides with someone who suffers from a bacterial, viral, or fungal gastrointestinal infection.

In embodiments, the subject (i) has at least 1, 2, 3, or 4 cousins, grandparents, parents, aunts, uncles, and/or siblings who have been diagnosed with an inflammatory disease; (ii) suffers from constipation, diarrhea, bloating, urgency, and/or abdominal pain; and/or (iii) has been administered an antibiotic within the last 1, 2, or 4 months.

In embodiments, the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, colitis, ulcerative colitis, collagenous colitis, lymphocytic colitis, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

In embodiments, the subject is less than about 1, 2, 3, 4, 5, 6, 7, 8, 9, 12, 18, or 24 months old. In embodiments, the subject is less than about 1 month old. In embodiments, the subject is less than 1 month old. In embodiments, the subject is less than about 2 months old. In embodiments, the subject is less than 2 months old. In embodiments, the subject is less than about 3 months old. In embodiments, the subject is less than 3 months old. In embodiments, the subject is less than about 4 months old. In embodiments, the subject is less than 4 months old. In embodiments, the subject is less than about 5 months old. In embodiments, the subject is less than 5 months old. In embodiments, the subject is less than about 6 months old. In embodiments, the subject is less than 6 months old. In embodiments, the subject is less than about 7 months old. In embodiments, the subject is less than 7 months old. In embodiments, the subject is less than about 8 months old. In embodiments, the subject is less than 8 months old. In embodiments, the subject is less than about 9 months old. In embodiments, the subject is less than 9 months old. In embodiments, the subject is less than about 12 months old. In embodiments, the subject is less than 12 months old. In embodiments, the subject is less than about 18 months old. In embodiments, the subject is less than 18 months old. In embodiments, the subject is less than about 24 months old. In embodiments, the subject is less than 24 months old.

In embodiments, the subject is between about 2 and about 18 years old, or is at least about 18 years old. In embodiments, the subject is between 2 and 18 years old, or is at least 18 years old. In embodiments, the subject is between about 2 and about 18 years old, or is at least about 18 (e.g., 19, 20, 25, 30, 40, 50, 60, 70, 80, 90) years old. In embodiments, the subject is between about 2 and about 18 years old, or is about 19 years old. In embodiments, the subject is between about 2 and about 18 years old, or is 19 years old. In embodiments, the subject is between about 2 and about 18 years old, or is about 20 years old. In embodiments, the subject is between about 2 and about 18 years old, or is 20 years old. In embodiments, the subject is between about 2 and about 18 years old, or is about 25 years old. In embodiments, the subject is between about 2 and about 18 years old, or is 25 years old. In embodiments, the subject is between about 2 and about 18 years old, or is about 30 years old. In embodiments, the subject is between about 2 and about 18 years old, or is 30 years old. In embodiments, the subject is between about 2 and about 18 years old, or is about 40 years old. In embodiments, the subject is between about 2 and about 18 years old, or is 40 years old. In embodiments, the subject is between about 2 and about 18 years old, or is about 50 years old. In embodiments, the subject is between about 2 and about 18 years old, or is 50 years old. In embodiments, the subject is between about 2 and about 18 years old, or is about 60 years old. In embodiments, the subject is between about 2 and about 18 years old, or is 60 years old. In embodiments, the subject is between about 2 and about 18 years old, or is about 70 years old. In embodiments, the subject is between about 2 and about 18 years old, or is 70 years old. In embodiments, the subject is between about 2 and about 18 years old, or is about 80 years old. In embodiments, the subject is between about 2 and about 18 years old, or is 80 years old. In embodiments, the subject is between about 2 and about 18 years old, or is about 90 years old. In embodiments, the subject is between about 2 and about 18 years old, or is 90 years old.

In embodiments, the subject comprises a gastrointestinal microbiome that (a) has an increased proportion of Streptococcus spp., Bifidobacterium spp., and Enterococcus spp. compared to a healthy or general population; (b) has a reduced proportion of Alternaria alternata, Aspergillus flavus, Aspergillus cibarius, and Candida sojae compared to a healthy or general population; (c) has an increased proportion of Candida albicans and Debaryomyces spp. compared to a healthy or general population; (d) has a reduced proportion of Bifidobacteria spp., Lactobacillus spp., Faecalibacterium spp. and Akkermansia spp. compared to a healthy or general population; (e) has a reduced proportion of Malassezia spp. compared to a healthy or general population; (f) has an increased proportion of Bacterioides spp., Ruminococcus spp., Prevotella spp., or Bifidobacterium spp. compared to a healthy or general population; or (g) has an increased proportion of Enterococcus faecalis, Enterococcus faecium, or Clostridium difficile compared to a healthy or general population.

In embodiments, the biological sample is a bodily fluid. In embodiments, the bodily fluid is blood, plasma, serum, fecal water, or a brancheoaleolar lavage. In embodiments, the bodily fluid is fecal water.

In embodiments, detecting whether the biological sample is pro-inflammatory includes contacting an antigen presenting cell with the biological sample. In embodiments, the antigen presenting cell is a dendritic cell.

In embodiments, detecting whether the biological sample is pro-inflammatory further includes contacting a naïve T cell with the antigen presenting cell to produce a contacted T cell.

In embodiments, the method further includes detecting a cytokine produced by the contacted T cell and/or the progeny of the contacted T cell.

In embodiments, the biological sample is detected to be pro-inflammatory if (i) the proportion of T-helper (TH)-2 cells is increased in the progeny of the contacted T cell compared to a control; (ii) the proportion of TH-1, TH-17, and/or TH22 cells is increased in the progeny of the contacted T cell compared to a control; (iii) the ratio of TH-1 cells to TH-2 cells is decreased in the progeny of the contacted T cell compared to a control; (iv) the proportion of IL-17 producing CD8+ T cells is increased in the progeny of the contacted T cell compared to a control; and/or (v) the amount of IL-4, IL-10, and/or IL-13 produced by the progeny of the contacted T cell and/or the progeny thereof is increased compared to a control.

In embodiments, the control is (i) the corresponding proportion, ratio, and/or amount of a corresponding T cell that has been contacted with sterile culture medium and/or the progeny thereof; (ii) the corresponding proportion, ratio, and/or amount of a corresponding T cell that has been contacted with an antigen presenting cell that has been contacted with a biological sample from a subject who does not have dysbiosis, an inflammatory disease, or a gastrointestinal infection, and/or the progeny thereof, and/or (iii) a reference value corresponding to the proportion, ratio, and/or amount in the general population or a population of subjects who do not have dysbiosis, an inflammatory disease, or a gastrointestinal infection.

In embodiments, the method further includes directing the subject to receive treatment or further testing or monitoring for dysbiosis or an inflammatory disease if the biological sample is detected to be pro-inflammatory.

In embodiments, the method further includes administering a bacterial population or composition as described herein including embodiments thereof to the subject if the biological sample is detected to be pro-inflammatory.

In embodiments, the subject includes a gastrointestinal microbiome that (a) has an increased proportion of *Streptococcus* spp., *Bifidobacterium* spp., and *Enterococcus* spp. compared to a healthy or general population; (b) has a reduced proportion of *Alternaria alternata, Aspergillus flavus, Aspergillus cibarius*, and *Candida sojae* compared to a healthy or general population; (c) has an increased proportion of *Candida albicans* and *Debaryomyces* spp. compared to a healthy or general population; (d) has a reduced proportion of *Bifidobacteria* spp., *Lactobacillus* spp., *Faecalibacterium* spp. and *Akkermansia* spp. compared to a healthy or general population; (e) has a reduced proportion of *Malassezia* spp. compared to a healthy or general population; (f) has an increased proportion of *Bacterioides* spp., *Ruminococcus* spp., *Prevotella* spp., or *Bifidobacterium* spp. compared to a healthy or general population; or (g) has an increased proportion of *Enterococcus faecalis, Enterococcus faecium*, or *Clostridium difficile* compared to a healthy or general population.

In embodiments, the method further includes determining whether the subject has a gastrointestinal microbiome that (a) has an increased proportion of *Streptococcus* spp., *Bifidobacterium* spp., and *Enterococcus* spp. compared to a healthy or general population; (b) has a reduced proportion of *Alternaria alternata, Aspergillus flavus, Aspergillus cibarius*, and *Candida sojae* compared to a healthy or general population; (c) has an increased proportion of *Candida albicans* and *Debaryomyces* spp. compared to a healthy or general population; (d) has a reduced proportion of *Bifidobacteria* spp., *Lactobacillus* spp., *Faecalibacterium* spp. and *Akkermansia* spp. compared to a healthy or general population; (e) has a reduced proportion of *Malassezia* spp. compared to a healthy or general population; (f) has an increased proportion of *Bacterioides* spp., *Ruminococcus* spp., *Prevotella* spp., or *Bifidobacterium* spp. compared to a healthy or general population; or (g) has an increased proportion of *Enterococcus faecalis, Enterococcus faecium*, or *Clostridium difficile* compared to a healthy or general population.

In embodiments, a method of treating or preventing dysbiosis, a viral respiratory infection, or an inflammatory disease in a subject determined to have or be at risk of developing dysbiosis, a viral respiratory infection, or an inflammatory disease according to a method described herein including embodiments thereof. In embodiments, the method includes administering a bacterial population disclosed herein to the subject.

In another aspect, a method of determining an inflammatory disease activity in a subject is provided. The method includes (i) detecting an expression level of one or more anti-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

In embodiments, the anti-inflammatory metabolite is a microbial lipid, a microbial carbohydrate or a microbial amino acid as provided herein. In embodiments, the anti-inflammatory metabolite is a microbial lipid. In embodiments, the anti-inflammatory metabolite is a microbial carbohydrate. In embodiments, the anti-inflammatory metabolite is a microbial amino acid.

In another aspect, a method of determining an inflammatory disease activity in a subject is provided. The method includes (i) detecting an expression level of one or more pro-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

In embodiments, the pro-inflammatory metabolite is a microbial lipid, a microbial carbohydrate or a microbial amino acid as provided herein. In embodiments, the anti-inflammatory metabolite is a microbial lipid. In embodiments, the anti-inflammatory metabolite is a microbial carbohydrate. In embodiments, the anti-inflammatory metabolite is a microbial amino acid.

In embodiments, the inflammatory disease is asthma, ulcerative *colitis*, irritable bowel syndrome, arthritis, uveitis, pyoderma gangrenosum, or erythema nodosum. In embodiments, the inflammatory disease is asthma. In embodiments, the inflammatory disease is ulcerative *colitis*. In embodiments, the inflammatory disease is irritable bowel syndrome. In embodiments, the inflammatory disease is arthritis. In embodiments, the inflammatory disease is uveitis. In embodiments, the inflammatory disease is pyoderma gangrenosum. In embodiments, the inflammatory disease is erythema nodosum.

In an aspect, a method of determining whether a subject has or is at risk of developing dysbiosis or an inflammatory disease is provided. The method including: (i) detecting an expression level of one or more anti-inflammatory metabolites or pro-inflammatory metabolites in a subject; (ii) determining whether the expression level is increased or decreased relative to a standard control, wherein an elevated expression level of an pro-inflammatory metabolite or a decreased expression level of an anti-inflammatory metabolite relative to the standard control indicates that the subject has or is at risk of developing an inflammatory disease, and (iii) based at least in part on the expression level in step (ii), determining whether the subject has or is at risk for developing an inflammatory disease.

In an aspect, a method of monitoring the effect of treatment for an inflammatory disease in a subject undergoing inflammatory disease therapy or a patient that has received inflammatory disease therapy including: (i) determining a first expression level of an anti-inflammatory or pro-inflammatory metabolite in the subject at a first time point; (ii) determining a second expression level of an anti-inflammatory or pro-inflammatory metabolite in the subject at a second time point; and (iii) comparing the second expression level of an anti-inflammatory or pro-inflammatory metabolite to the first expression level of an anti-inflammatory or pro-inflammatory metabolite, thereby determining the effect of treatment for an inflammatory disease in the subject is provided.

In an aspect, a method of determining an inflammatory disease activity in a subject is provided. The method including: (i) detecting an expression level of one or more anti-inflammatory or pro-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

TABLE 1

Non-limiting examples of *Lactobacillus* sp., *Faecalibacterium* sp., *Akkermansia* sp., *Myxococcus* sp., *Cystobacter* sp., and *Pediococcus* sp. that can be used singly, or in any combination in bacterial populations of methods and compositions provided herein.

| Phylum | Class | Order | Family | Genus | Species |
|---|---|---|---|---|---|
| Verrucomicrobia | Verrucomicrobiae | Verrucomicrobiales | Verrucomicrobiaceae | *Akkermansia* | *Akkermansia muciniphila* |
| Firmicutes | Clostridia | Clostridiales | Ruminococcaceae | *Faecalibacterium* | *Faecalibacterium prausnitzii* |
| Proteobacteria | Deltaproteobacteria | Myxococcales | unclassified | sfA | unclassified |
| Proteobacteria | Deltaproteobacteria | Myxococcales | Cystobacteraceae | *Cystobacter* | *Cystobacter fuscus* |
| Proteobacteria | Deltaproteobacteria | Myxococcales | Myxococcaceae | *Myxococcus* | *Myxococcus xanthus* |
| Firmicutes | Bacilli | Lactobacillales | Lactobacillaceae | *Lactobacillus* | *Lactobacillus zeae* (*Lactobacillus rhamnosus*) |
| Firmicutes | Bacilli | Lactobacillales | Lactobacillaceae | *Lactobacillus* | *Lactobacillus acidipiscis* |
| Firmicutes | Bacilli | Lactobacillales | Lactobacillaceae | *Lactobacillus* | *Lactobacillus acidophilus* |
| Firmicutes | Bacilli | Lactobacillales | Lactobacillaceae | *Lactobacillus* | *Lactobacillus agilis* |
| Firmicutes | Bacilli | Lactobacillales | Lactobacillaceae | *Lactobacillus* | *Lactobacillus aviarius* |
| Firmicutes | Bacilli | Lactobacillales | Lactobacillaceae | *Lactobacillus* | *Lactobacillus brevis* |
| Firmicutes | Bacilli | Lactobacillales | Lactobacillaceae | *Lactobacillus* | *Lactobacillus coleohominis* |
| Firmicutes | Bacilli | Lactobacillales | Lactobacillaceae | *Lactobacillus* | *Lactobacillus crispatus* |
| Firmicutes | Bacilli | Lactobacillales | Lactobacillaceae | *Lactobacillus* | *Lactobacillus crustorum* |
| Firmicutes | Bacilli | Lactobacillales | Lactobacillaceae | *Lactobacillus* | *Lactobacillus curvatus* |
| Firmicutes | Bacilli | Lactobacillales | Lactobacillaceae | *Lactobacillus* | *Lactobacillus dioliovorans* |
| Firmicutes | Bacilli | Lactobacillales | Lactobacillaceae | *Lactobacillus* | *Lactobacillus farraginis* |
| Firmicutes | Bacilli | Lactobacillales | Lactobacillaceae | *Lactobacillus* | *Lactobacillus fermentum* |
| Firmicutes | Bacilli | Lactobacillales | Lactobacillaceae | *Lactobacillus* | *Lactobacillus fuchuensis* |
| Firmicutes | Bacilli | Lactobacillales | Lactobacillaceae | *Lactobacillus* | *Lactobacillus harbinensis* |
| Firmicutes | Bacilli | Lactobacillales | Lactobacillaceae | *Lactobacillus* | *Lactobacillus helveticus* |
| Firmicutes | Bacilli | Lactobacillales | Lactobacillaceae | *Lactobacillus* | *Lactobacillus hilgardii* |
| Firmicutes | Bacilli | Lactobacillales | Lactobacillaceae | *Lactobacillus* | *Lactobacillus intestinalis* |

TABLE 1-continued

Non-limiting examples of *Lactobacillus* sp., *Faecalibacterium* sp., *Akkermansia* sp., *Myxococcus* sp., *Cystobacter* sp., and *Pediococcus* sp. that can be used singly, or in any combination in bacterial populations of methods and compositions provided herein.

| Phylum | Class | Order | Family | Genus | Species |
|---|---|---|---|---|---|
| Firmicutes | Bacilli | Lactobacillales | Lactobacillaceae | *Lactobacillus* | *Lactobacillus jensenii* |
| Firmicutes | Bacilli | Lactobacillales | Lactobacillaceae | *Lactobacillus* | *Lactobacillus johnsonii* |
| Firmicutes | Bacilli | Lactobacillales | Lactobacillaceae | *Lactobacillus* | *Lactobacillus kefiranofaciens* |
| Firmicutes | Bacilli | Lactobacillales | Lactobacillaceae | *Lactobacillus* | *Lactobacillus kefiri* |
| Firmicutes | Bacilli | Lactobacillales | Lactobacillaceae | *Lactobacillus* | *Lactobacillus lindneri* |
| Firmicutes | Bacilli | Lactobacillales | Lactobacillaceae | *Lactobacillus* | *Lactobacillus mali* |
| Firmicutes | Bacilli | Lactobacillales | Lactobacillaceae | *Lactobacillus* | *Lactobacillus manihotivorans* |
| Firmicutes | Bacilli | Lactobacillales | Lactobacillaceae | *Lactobacillus* | *Lactobacillus mucosae* |
| Firmicutes | Bacilli | Lactobacillales | Lactobacillaceae | *Lactobacillus* | *Lactobacillus oeni* |
| Firmicutes | Bacilli | Lactobacillales | Lactobacillaceae | *Lactobacillus* | *Lactobacillus oligofermentans* |
| Firmicutes | Bacilli | Lactobacillales | Lactobacillaceae | *Lactobacillus* | *Lactobacillus panis* |
| Firmicutes | Bacilli | Lactobacillales | Lactobacillaceae | *Lactobacillus* | *Lactobacillus pantheris* |
| Firmicutes | Bacilli | Lactobacillales | Lactobacillaceae | *Lactobacillus* | *Lactobacillus parabrevis* |
| Firmicutes | Bacilli | Lactobacillales | Lactobacillaceae | *Lactobacillus* | *Lactobacillus paracollinoides* |
| Firmicutes | Bacilli | Lactobacillales | Lactobacillaceae | *Lactobacillus* | *Lactobacillus parakefiri* |
| Firmicutes | Bacilli | Lactobacillales | Lactobacillaceae | *Lactobacillus* | *Lactobacillus paraplantarum* |
| Firmicutes | Bacilli | Lactobacillales | Lactobacillaceae | *Lactobacillus* | *Lactobacillus pentosus* |
| Firmicutes | Bacilli | Lactobacillales | Lactobacillaceae | *Lactobacillus* | *Lactobacillus pontis* |
| Firmicutes | Bacilli | Lactobacillales | Lactobacillaceae | *Lactobacillus* | *Lactobacillus reuteri* |
| Firmicutes | Bacilli | Lactobacillales | Lactobacillaceae | *Lactobacillus* | *Lactobacillus rossiae* |
| Firmicutes | Bacilli | Lactobacillales | Lactobacillaceae | *Lactobacillus* | *Lactobacillus salivarius* |
| Firmicutes | Bacilli | Lactobacillales | Lactobacillaceae | *Lactobacillus* | *Lactobacillus siliginis* |
| Firmicutes | Bacilli | Lactobacillales | Lactobacillaceae | *Lactobacillus* | *Lactobacillus sucicola* |
| Firmicutes | Bacilli | Lactobacillales | Lactobacillaceae | *Lactobacillus* | *Lactobacillus vaccinostercus* |
| Firmicutes | Bacilli | Lactobacillales | Lactobacillaceae | *Lactobacillus* | *Lactobacillus vaginalis* |
| Firmicutes | Bacilli | Lactobacillales | Lactobacillaceae | *Lactobacillus* | *Lactobacillus vini* |
| Firmicutes | Bacilli | Lactobacillales | Lactobacillaceae | *Lactobacillus* | *Lactococcus garvieae* |
| Firmicutes | Bacilli | Lactobacillales | Lactobacillaceae | *Lactobacillus* | *Lactococcus lactis* |
| Firmicutes | Bacilli | Lactobacillales | Lactobacillaceae | *Pediococcus* | *Pediococcus pentosaceus* |
| Firmicutes | Bacilli | Lactobacillales | Lactobacillaceae | *Pediococcus* | *Pediococcus acidilactici* |
| Firmicutes | Bacilli | Lactobacillales | Lactobacillaceae | *Pediococcus* | *Pediococcus damnosus* |
| Firmicutes | Bacilli | Lactobacillales | Lactobacillaceae | *Pediococcus* | *Pediococcus ethanolidurans* |
| Firmicutes | Bacilli | Lactobacillales | Lactobacillaceae | *Pediococcus* | *Pediococcus parvulus* |
| Actinobacteria | Actinobacteria | Bifidobacteriales | Bifidobacteriaceae | *Bifidobacterium* | *Bifidobacterium bifidum* |
| Actinobacteria | Actinobacteria | Bifidobacteriales | Bifidobacteriaceae | *Bifidobacterium* | *Bifidobacterium pseudolongum* |
| Actinobacteria | Actinobacteria | Bifidobacteriales | Bifidobacteriaceae | *Bifidobacterium* | *Bifidobacterium saeculare* |
| Actinobacteria | Actinobacteria | Bifidobacteriales | Bifidobacteriaceae | *Bifidobacterium* | *Bifidobacterium subtile* |

TABLE 1-continued

Non-limiting examples of *Lactobacillus* sp., *Faecalibacterium* sp., *Akkermansia* sp., *Myxococcus* sp., *Cystobacter* sp., and *Pediococcus* sp. that can be used singly, or in any combination in bacterial populations of methods and compositions provided herein.

| Phylum | Class | Order | Family | Genus | Species |
|---|---|---|---|---|---|
| Firmicutes | Clostridia | Clostridiales | Clostridiaceae | *Clostridium* | *Clostridium hiranonis* |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiments include P1 to P34 following.

Embodiment P1

A method of treating or preventing an inflammatory disease in a subject in need thereof, said method comprising administering to said subject a therapeutically effective amount of *Lactobacillus johnsonii, Faecalibacterium prausnitzii, Akkermansia muciniphila, Myxococcus xanthus* and *Pediococcus pentosaceus*.

Embodiment P2

The method of embodiment 1, further comprising a pharmaceutically active excipient.

Embodiment P3

The method of embodiment 1 or 2, wherein said *Lactobacillus johnsonii. Faecalibacterium prausnitzii, Akkermansia muciniphila. Myxococcus xanthus* and *Pediococcus pentosaceus* form a microbial composition.

Embodiment P4

The method of embodiment 3, wherein said microbial composition is effective for administration to the gut.

Embodiment P5

The method of embodiment 3, wherein said microbial composition is effective to increase an anti-inflammatory metabolite.

Embodiment P6

The method of embodiment 3, wherein said microbial composition is effective to decrease a pro-inflammatory metabolite.

Embodiment P7

The method of embodiment 5, wherein said anti-inflammatory metabolite is a microbial lipid, a microbial carbohydrate or a microbial amino acid.

Embodiment P8

The method of embodiment 6, wherein said pro-inflammatory metabolite is a microbial lipid, a microbial carbohydrate or a microbial amino acid.

Embodiment P9

The method of embodiment 8, wherein said pro-inflammatory metabolite is IL-4. IL-10, IL-13 or MUC5B.

Embodiment P10

The method of one of embodiments 1 or 9, wherein said *Lactobacillus johnsonii, Faecalibacterium prausnitzii, Akkermansia muciniphila, Myxococcus xanthus* and *Pediococcus pentosaceus* are metabolically active.

Embodiment P11

The method of one of embodiment 1 or 9, wherein said *Lactobacillus johnsonii, Faecalibacterium prausnitzii, Akkermansia muciniphila, Myxococcus xanthus* and *Pediococcus pentosaceus* are metabolically inactive.

Embodiment P12

The method of one of embodiments 1-11, further comprising administering a therapeutically effective amount of a fungus.

Embodiment P13

The method of one of embodiments 1-12, wherein said subject is a neonate.

Embodiment P14

The method of one of embodiments 1-13, wherein said inflammatory disease is asthma, ulcerative *colitis*, irritable bowel syndrome, arthritis, uveitis, pyoderma gangrenosum, or erythema nodosum.

Embodiment P15

A method of increasing an anti-inflammatory metabolite in a subject in need thereof, the method comprising administering to said subject a therapeutically effective amount of *Lactobacillus johnsonii, Faecalibacterium prausnitzii, Akkermansia muciniphila, Myxococcus xanthus* and *Pediococcus pentosaceus*.

Embodiment P16

The method of embodiment 15, further comprising a pharmaceutically active excipient.

Embodiment P17

The method of embodiment 15 or 16, wherein said *Lactobacillus johnsonii, Faecalibacterium prausnitzii, Akkermansia muciniphila, Myxococcus xanthus* and *Pediococcus pentosaceus* form a microbial composition.

Embodiment P18

The method of one of embodiments 15-17, wherein said anti-inflammatory metabolite is a microbial lipid, a microbial carbohydrate or a microbial amino acid.

Embodiment P19

The method of one of embodiments 15-18, wherein said inflammatory disease is asthma, ulcerative *colitis*, irritable bowel syndrome, arthritis, uveitis, pyoderma gangrenosum, or erythema nodosum.

Embodiment P20

A method of detecting an anti-inflammatory metabolite in a subject that has or is at risk for developing an inflammatory disease, said method comprising: (i) obtaining a biological sample from said subject; and (ii) determining an expression level of an anti-inflammatory metabolite in said biological sample.

Embodiment P21

The method of embodiment 20, wherein said anti-inflammatory metabolite is a microbial lipid or a microbial carbohydrate.

Embodiment P22

The method of embodiment 20 or 21, wherein said biological sample is a bodily fluid.

Embodiment P23

The method of embodiment 22, wherein said bodily fluid is serum, fecal water or brancheoaleolar lavage.

Embodiment P24

The method of one of embodiments 20-23, wherein said determining comprises: (a) contacting in vitro said anti-inflammatory metabolite with an antigen presenting cell, thereby forming a metabolite-antigen presenting cell; (b) contacting said metabolite-antigen presenting cell with a T cell, thereby forming a contacted T cell; and (c) detecting a cytokine produced by said contacted T cell.

Embodiment P25

The method of one of embodiments 20-24, wherein said inflammatory disease is asthma, ulcerative *colitis*, irritable bowel syndrome, arthritis, uveitis, pyoderma gangrenosum, or erythema nodosum.

Embodiment P26

A method of determining whether a subject has or is at risk of developing an inflammatory disease, said method comprising: (i) detecting an expression level of one or more anti-inflammatory metabolites or pro-inflammatory metabolites in a subject; (ii) determining whether said expression level is increased or decreased relative to a standard control, wherein an elevated expression level of an pro-inflammatory metabolite or a decreased expression level of an anti-inflammatory metabolite relative to said standard control indicates that said subject has or is at risk of developing an inflammatory disease; and (iii) based at least in part on said expression level in step (ii), determining whether said subject has or is at risk for developing an inflammatory disease.

Embodiment P27

The method of embodiment 26, wherein said inflammatory disease is asthma, ulcerative *colitis*, irritable bowel syndrome, arthritis, uveitis, pyoderma gangrenosum, or erythema nodosum.

Embodiment P28

The method of embodiment 26, wherein said anti-inflammatory metabolite is a microbial lipid, a microbial carbohydrate or a microbial amino acid.

Embodiment P29

A method of monitoring the effect of treatment for an inflammatory disease in a subject undergoing inflammatory disease therapy or a patient that has received inflammatory disease therapy comprising: (i) determining a first expression level of an anti-inflammatory metabolite in the subject at a first time point; (ii) determining a second expression level of an anti-inflammatory metabolite in the subject at a second time point; and (iii) comparing the second expression level of an anti-inflammatory metabolite to the first expression level of an anti-inflammatory metabolite, thereby determining the effect of treatment for an inflammatory disease in the subject.

Embodiment P30

The method of embodiment 29, wherein said inflammatory disease is asthma, ulcerative *colitis*, irritable bowel syndrome, arthritis, uveitis, pyoderma gangrenosum, or erythema nodosum.

Embodiment P31

The method of embodiment 29, wherein said anti-inflammatory metabolite is a microbial lipid, a microbial carbohydrate or a microbial amino acid.

Embodiment P32

A method of determining an inflammatory disease activity in a subject, said method comprising: (i) detecting an expression level of one or more anti-inflammatory metabolites in a subject; (ii) determining whether said expression level is modulated relative to a standard control, thereby determining an inflammatory disease activity in said subject; and (iii) based at least in part on said expression level in step (ii), determining said inflammatory disease activity in said subject.

Embodiment P33

The method of embodiment 32, wherein said inflammatory disease is asthma, ulcerative *colitis*, irritable bowel syndrome, arthritis, uveitis, pyoderma gangrenosum, or erythema nodosum.

Embodiment P34

The method of embodiment 32, wherein said anti-inflammatory metabolite is a microbial lipid, a microbial carbohydrate or a microbial amino acid.

Further embodiments include embodiments 1 to 111 following.

Embodiment 1

A method of treating or preventing dysbiosis in a subject in need thereof, the method comprising administering to the subject an effective amount of a bacterial population comprising *Lactobacillus* sp., *Faecalibacterium* sp., *Akkermansia* sp., *Myxococcus* sp., and *Pediococcus* sp.

Embodiment 2

The method of embodiment 1, wherein (i) the *Lactobacillus* sp. is *Lactobacillus johnsonii*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; and (v) the *Pediococcus* sp. is *Pediococcus pentosaceus*.

Embodiment 3

The method of embodiment 1 or 2, wherein (i) the *Lactobacillus* sp. is *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus diolivorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae,* or *Lactococcus lactis*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; and (v) the *Pediococcus* sp. is *Pediococcus pentosaceus, Pediococcus acidilactici, Pediococcus damnosus, Pediococcus ethanolidurans,* or *Pediococcus parvulus*.

Embodiment 4

The method of any one of embodiments 1 to 3, wherein the *Myxococcus* sp. is in the form of spores, vegetative bacteria, or a mixture of spores and vegetative bacteria.

Embodiment 5

The method of embodiment 4, wherein the *Myxococcus* sp. is in the form of a powder comprising spores.

Embodiment 6

The method of any one of embodiments 1 to 5, wherein less than about 20, 15, 10, 9, 8, 7, or 6 different species of bacteria are administered to the subject.

Embodiment 7

The method of embodiment 1, wherein the bacterial population forms part of a bacterial composition.

Embodiment 8

The method of embodiment 7, wherein the bacterial composition comprises less than about 20, 15, 10, 9, 8, 7, or 6 species of bacteria.

Embodiment 9

The method of embodiment 7 or 8, wherein the bacterial composition is not a fecal transplant.

Embodiment 10

The method of any one of embodiments 7 to 9, wherein the bacterial composition further comprises a pharmaceutically acceptable excipient.

Embodiment 11

The method of any one of embodiments 7 to 10, wherein the bacterial composition is a capsule, a tablet, a suspension, a suppository, a powder, a cream, an oil, an oil-in-water emulsion, a water-in-oil emulsion, or an aqueous solution.

Embodiment 12

The method of any one of embodiments 7 to 10, wherein the bacterial composition is in the form of a powder, a solid, a semi-solid, or a liquid.

Embodiment 13

The method of any one of embodiments 7 to 12, wherein the bacterial composition has a water activity ($a_w$) less than about 0.9, 0.8, 0.7, 0.6, 0.5, 0.4, 0.3, 0.2, or 0.1 at 20° C.

Embodiment 14

The method of any one of embodiments 7 to 13, wherein the bacterial composition is a food or a beverage.

Embodiment 15

The method of any one of embodiments 7 to 14, wherein the bacterial composition is administered orally or rectally.

Embodiment 16

The method of any one of embodiments 1 to 15, wherein the *Lactobacillus* sp., the *Faecalibacterium* sp., the *Akkermansia* sp., the *Myxococcus* sp., and/or the *Pediococcus* sp. is in the form of a powder.

Embodiment 17

The method of any one of embodiments 1 to 16, wherein the *Lactobacillus* sp., the *Faecalibacterium* sp., the *Akkermansia* sp., the *Myxococcus* sp., and/or the *Pediococcus* sp. has been lyophilized.

Embodiment 18

The method of any one of embodiments 1 to 17, wherein the subject is a human.

Embodiment 19

The method of any one of embodiments 1 to 18, wherein the subject suffers from or resides with someone who suffers from a bacterial, viral, or fungal gastrointestinal infection.

Embodiment 20

The method of any one of embodiments 1 to 19, wherein the subject has an inflammatory disease.

Embodiment 21

The method of any one of embodiments 1 to 20, wherein the subject is at risk of suffering from an inflammatory disease.

Embodiment 22

The method of any one of embodiments 1 to 21, wherein the subject has at least 1, 2, 3, or 4 cousins, grandparents, parents, aunts, uncles, and/or siblings who have been diagnosed with an inflammatory disease.

Embodiment 23

The method of any one of embodiments 20 to 22, wherein the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous *colitis*, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

Embodiment 24

The method of embodiment 23, wherein the inflammatory disease is pediatric allergic asthma or inflammatory bowel disease.

Embodiment 25

The method of any one of embodiments 1 to 24, wherein the subject suffers from constipation, diarrhea, bloating, urgency, and/or abdominal pain.

Embodiment 26

The method of any one of embodiments 1 to 25, wherein the subject has been administered an antibiotic within the last 1, 2, 3, or 4 months.

Embodiment 27

The method of any one of embodiments 1 to 26, wherein the subject is a neonate.

Embodiment 28

The method of any one of embodiments 1 to 26, wherein the subject is less than about 1, 2, 3, 4, 5, 6, 7, 8, 9, 12, 18, or 24 months old.

Embodiment 29

The method of any one of embodiments 1 to 26, wherein the subject is between about 2 and about 18 years old, or is at least about 18 years old.

Embodiment 30

The method of any one of embodiments 1 to 29, wherein the subject comprises a gastrointestinal microbiome that
   (a) has an increased proportion of *Streptococcus* spp., *Bifidobacterium* spp., and *Enterococcus* spp. compared to a healthy or general population;
   (b) has a reduced proportion of *Alternaria alternata*, *Aspergillus flavus*, *Aspergillus cibarius*, and *Candida sojae* compared to a healthy or general population;
   (c) has an increased proportion of *Candida albicans* and *Debaryomyces* spp. compared to a healthy or general population;
   (d) has a reduced proportion of *Bifidobacteria* spp., *Lactobacillus* spp., *Faecalibacterium* spp. and *Akkermansia* spp. compared to a healthy or general population;
   (e) has a reduced proportion of *Malassezia* spp. compared to a healthy or general population;
   (f) has an increased proportion of *Bacterioides* spp., *Ruminococcus* spp., *Prevotella* spp., or *Bifidobacterium* spp. compared to a healthy or general population; or
   (g) has an increased proportion of *Enterococcus faecalis*, *Enterococcus faecium*, or *Clostridium difficile* compared to a healthy or general population.

Embodiment 31

The method of any one of embodiments 1 to 30, wherein the effective amount is effective to (i) increase the level of a *Bifidobacterium* sp., *Clostridia* sp. belonging to Clade IV or XIV, a *Lachnospira* sp., and/or a *Ruminococcus* sp. in the subject;
(ii) lower the pH in the feces of the subject;
(iii) increase the level of lactic acid in the feces of the subject;
(iv) increase the level of circulating itaconate in the subject;
(v) treat, reduce, or prevent allergic inflammation in a subject;
(vi) reduce an adaptive immune response in an airway of the subject;
(vii) reduce dendritic cell activation in a gastrointestinal-associated mesenteric lymoph node;
(viii) increase the level of repair macrophages in the lungs, blood, serum, or plasma of the subject;
(ix) increase the level of an anti-inflammatory compound in the subject;
(x) decrease the level of a pro-inflammatory compound in the subject;
(xi) decrease the level of eotaxin expression and/or secretion in the subject; and/or decrease the level of mucin expression and/or secretion in the subject.

Embodiment 32

The method of embodiment 31, wherein the effective amount is effective to decrease the level of mucin secretion and/or secretion in the lungs of the subject.

Embodiment 33

The method of embodiment 31 or 32, wherein the anti-inflammatory compound is a cytokine, a microbial lipid, a microbial carbohydrate, or a microbial amino acid.

Embodiment 34

The method of embodiment 33, wherein the anti-inflammatory compound is IL-17.

Embodiment 35

The method of any one of embodiments 31 to 34, wherein the pro-inflammatory compound is a cytokine, a microbial lipid, a microbial carbohydrate, or a microbial amino acid.

Embodiment 36

The method of embodiment 35, wherein the pro-inflammatory compound is IL-4, IL-10, IL-8, IL-13, TNF-α, or MUC5B.

Embodiment 37

The method of one of embodiments 1 or 36, wherein the *Lactobacillus* sp., *Faecalibacterium* sp., *Akkermansia* sp., *Myxococcus* sp., and/or *Pediococcus* sp. is metabolically active.

Embodiment 38

The method of one of embodiments 1 or 36, wherein the *Lactobacillus* sp., *Faecalibacterium* sp., *Akkermansia* sp., *Myxococcus* sp., and/or *Pediococcus* sp. is metabolically inactive.

Embodiment 39

The method of any one of embodiments 1 to 38, further comprising administering (a) a *Bifidobacterium* sp., (b) *Cystobacter* sp., or (c) a fungal microorganism to the subject.

Embodiment 40

A method of treating or preventing an inflammatory disease in a subject in need thereof, the method comprising administering to the subject an effective amount of a bacterial population comprising *Lactobacillus* sp., *Faecalibacterium* sp., *Akkermansia* sp., *Myxococcus* sp., and *Pediococcus* sp.

Embodiment 41

The method of embodiment 40, wherein the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous *colitis*, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

Embodiment 42

A method of treating or preventing a viral respiratory infection in a subject in need thereof, the method comprising administering to the subject an effective amount of a bacterial population comprising *Lactobacillus* sp., *Faecalibacterium* sp., *Akkermansia* sp., *Myxococcus* sp., and *Pediococcus* sp.

Embodiment 43

The method of embodiment 42, wherein the viral respiratory infection is caused by a respiratory syncytial virus, an influenza virus, a parainfluenza virus, an adenovirus, a coronavirus, or a rhinovirus.

Embodiment 44

The method of embodiment 42 or 43, wherein the viral respiratory infection is bronchiolitis, a cold, croup, or pneumonia.

Embodiment 45

A method of treating or preventing an allergy in a subject in need thereof, the method comprising administering to the subject an effective amount of a bacteria population comprising *Lactobacillus* sp., *Faecalibacterium* sp., *Akkermansia* sp., *Myxococcus* sp., and *Pediococcus* sp.

Embodiment 46

The method of embodiment 45, wherein the allergy is an allergy to milk, eggs, fish, shellfish, a tree nut, peanuts, wheat, dander from a cat, dog, or rodent, an insect sting, pollen, latex, dust mites, or soybeans.

Embodiment 47

The method of embodiment 45 or 46, wherein the allergy is pediatric allergic asthma, hay fever, or allergic airway sensitization.

Embodiment 48

A method of increasing the level of an anti-inflammatory compound and/or decreasing the level of a pro-inflammatory compound in a subject in need thereof, comprising administering to the subject an effective amount of a bacterial population comprising *Lactobacillus* sp., *Faecalibacterium* sp., *Akkermansia* sp., *Myxococcus* sp., and *Pediococcus* sp.

Embodiment 49

The method of embodiment 48, for increasing the level of the anti-inflammatory compound increases and/or decreases the level of the pro-inflammatory compound in the feces, blood, plasma, serum, broncheoalveolar lavage fluid, sweat, saliva, sputum, lymph, spinal fluid, urine, tears, bile, aqueous humour, vitreous humour, aminiotic fluid, breast milk, cerebrospinal fluid, cerumen, nasal mucus, phlegm, or sebum of the subject.

Embodiment 50

The method of one of embodiments 48 or 49, wherein the anti-inflammatory compound is a microbial lipid, a microbial carbohydrate, or a microbial amino acid.

Embodiment 51

The method of any one of embodiments 48 to 50, wherein subject suffers from dysbiosis or an inflammatory disease.

Embodiment 52

A composition comprising *Lactobacillus* sp., *Faecalibacterium* sp., *Akkermansia* sp., *Myxococcus* sp., and *Pediococcus* sp.

Embodiment 53

The composition of embodiment 52, wherein (i) the *Lactobacillus* sp. is *Lactobacillus johnsonii*, (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; and (v) the *Pediococcus* sp. is *Pediococcus pentosaceus*.

Embodiment 54

The composition of embodiment 52 or 53, wherein the composition comprises less than about 20, 15, 10, 9, 8, 7, or 6 different species of bacteria.

Embodiment 55

The composition of any one of embodiments 52 to 54, wherein the composition is not a fecal transplant.

Embodiment 56

The composition of any one of embodiments 52 to 55, further comprising a pharmaceutically acceptable excipient.

Embodiment 57

The composition of any one of embodiments 52 to 56, which is a capsule, a tablet, a suspension, a suppository, a powder, a cream, an oil, an oil-in-water emulsion, a water-in-oil emulsion, or an aqueous solution.

Embodiment 58

The composition of any one of embodiments 52 to 57, which is in the form of a powder, a solid, a semi-solid, or a liquid.

Embodiment 59

The composition of any one of embodiments 52 to 58, which has a water activity ($a_w$) less than about 0.9, 0.8, 0.7, 0.6, 0.5, 0.4, 0.3, 0.2, or 0.1 at 20° C.

Embodiment 60

The composition of any one of embodiments 52 to 59, which is a food or a beverage.

Embodiment 61

The composition of any one of embodiments 52 to 60, wherein the *Lactobacillus* sp., the *Faecalibacterium* sp., the *Akkermansia* sp., the *Myxococcus* sp., and/or the *Pediococcus* sp. is in the form of a powder.

Embodiment 62

The composition of any one of embodiments 52 to 61, wherein the *Lactobacillus* sp., the *Faecalibacterium* sp., the *Akkermansia* sp., the *Myxococcus* sp., and/or the *Pediococcus* sp. has been lyophilized.

Embodiment 63

A method of detecting a pro-inflammatory compound in a subject in need thereof, comprising: (i) obtaining a biological sample from the subject; and (ii) detecting the pro-inflammatory compound in the biological sample.

Embodiment 64

The method of embodiment 63, wherein the subject has or is at risk for developing dysbiosis.

Embodiment 65

The method of embodiments 63 or 64, wherein the subject has an inflammatory disease.

Embodiment 66

The method of any one of embodiments 63 to 65, wherein the subject is at risk of suffering from an inflammatory disease.

Embodiment 67

The method of any one of embodiments 63 to 66, wherein the subject
(i) has at least 1, 2, 3, or 4 cousins, grandparents, parents, aunts, uncles, and/or siblings who have been diagnosed with an inflammatory disease;
(ii) suffers from constipation, diarrhea, bloating, urgency, and/or abdominal pain; and/or
(iii) has been administered an antibiotic within the last 1, 2, or 4 months.

Embodiment 68

The method any one of embodiments 63 to 67, wherein the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, colitis, ulcerative colitis, collagenous colitis, lymphocytic colitis, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

Embodiment 69

The method of any one of embodiments 63 to 69, wherein the subject is less than about 1, 2, 3, 4, 5, 6, 7, 8, 9, 12, 18, or 24 months old.

Embodiment 70

The method of any one of embodiments 63 to 69, wherein the subject is between about 2 and about 18 years old, or is at least about 18 years old.

Embodiment 71

The method of any one of embodiments 63 to 70, wherein the subject comprises a gastrointestinal microbiome that (a) has an increased proportion of *Streptococcus* spp., *Bifidobacterium* spp., and *Enterococcus* spp. compared to a healthy or general population;
(b) has a reduced proportion of *Alternaria alternata*, *Aspergillus flavus*, *Aspergillus cibarius*, and *Candida sojae* compared to a healthy or general population;
(c) has an increased proportion of *Candida albicans* and *Debaryomyces* spp. compared to a healthy or general population;
(d) has a reduced proportion of *Bifidobacteria* spp., *Lactobacillus* spp., *Faecalibacterium* spp. and *Akkermansia* spp. compared to a healthy or general population;
(e) has a reduced proportion of *Malassezia* spp. compared to a healthy or general population
(f) has an increased proportion of *Bacterioides* spp., *Ruminococcus* spp., *Prevotella* spp., or *Bifidobacterium* spp. compared to a healthy or general population; or
(g) has an increased proportion of *Enterococcus faecalis*, *Enterococcus faecium*, or *Clostridium difficile* compared to a healthy or general population.

Embodiment 72

The method of any one of embodiments 63 to 71, wherein the biological sample is a bodily fluid.

Embodiment 73

The method of embodiment 72, wherein the bodily fluid is blood, plasma, serum, fecal water, or a brancheoaleolar lavage.

Embodiment 74

The method of embodiment 72 or 73, wherein the bodily fluid is fecal water.

Embodiment 75

The method of any one of embodiments 63 to 74, wherein detecting the pro-inflammatory compound comprises contacting an antigen presenting cell with the biological sample.

Embodiment 76

The method of embodiment 75, wherein the antigen presenting cell is a dendritic cell.

Embodiment 77

The method of any one of embodiments 63 to 74, wherein detecting the pro-inflammatory compound further comprises contacting a naïve T cell with the antigen presenting cell to produce a contacted T cell.

Embodiment 78

The method of embodiment 77, further comprising detecting a cytokine produced by the contacted T cell and/or the progeny of the contacted T cell.

Embodiment 79

The method of any one of embodiments 77 or 78, wherein the pro-inflammatory compound is detected if (i) the proportion of T-helper (TH)-2 cells is increased in the progeny of the contacted T cell compared to a control;
(ii) the proportion of TH-1, TH-17, and/or TH22 cells is increased in the progeny of the contacted T cell compared to a control;
(iii) the ratio of TH-1 cells to TH-2 cells is decreased in the progeny of the contacted T cell compared to a control;
(iv) the proportion of IL-17 producing CD8+ T cells is increased in the progeny of the contacted T cell compared to a control; and/or
(v) the amount of IL-4, IL-10, and/or IL-13 produced by the progeny of the contacted T cell and/or the progeny thereof is increased compared to a control.

Embodiment 80

The method of embodiment 79, wherein the control is (i) the corresponding proportion, ratio, and/or amount of a corresponding T cell that has been contacted with sterile culture medium and/or the progeny thereof; (ii) the corresponding proportion, ratio, and/or amount of a corresponding T cell that has been contacted with an antigen presenting cell that has been contacted with a biological sample from a subject who does not have dysbiosis, an inflammatory disease, or a gastrointestinal infection, and/or the progeny thereof; and/or (iii) a reference value corresponding to the proportion, ratio, and/or amount in the general population or a population of subjects who do not have dysbiosis, an inflammatory disease, or a gastrointestinal infection.

Embodiment 81

The method of any one of embodiments 63 to 80, further comprising directing the subject to receive treatment or further testing or monitoring for dysbiosis or an inflammatory disease if the pro-inflammatory compound is detected in the subject.

Embodiment 82

The method of any one of embodiments 63 to 81, further comprising administering the composition of any one of embodiments 52 to 62 to the subject if the pro-inflammatory compound is detected in the subject.

Embodiment 83

The method of any one of embodiments 63 to 82, further comprising diagnosing the subject as having or at risk of developing dysbiosis or an inflammatory disease if the pro-inflammatory compound is detected in the subject.

Embodiment 84

A method of determining whether a subject has or is at risk of developing dysbiosis or an inflammatory disease, the method comprising: (i) obtaining a biological sample from the subject; and (ii) detecting a pro-inflammatory compound according to the method of any one of embodiments 63 to 80.

Embodiment 85

A method of determining whether a subject has or is at risk of developing dysbiosis or an inflammatory disease, the method comprising: (i) obtaining a biological sample from the subject; and (ii) detecting whether the biological sample is pro-inflammatory.

Embodiment 86

The method of embodiment 85, wherein the subject suffers from or resides with someone who suffers from a bacterial, viral, or fungal gastrointestinal infection.

Embodiment 87

The method of embodiment 85 or 86, wherein the subject
(i) has at least 1, 2, 3, or 4 cousins, grandparents, parents, aunts, uncles, and/or siblings who have been diagnosed with an inflammatory disease;
(ii) suffers from constipation, diarrhea, bloating, urgency, and/or abdominal pain; and/or
(iii) has been administered an antibiotic within the last 1, 2, or 4 months.

Embodiment 88

The method any one of embodiments 85 to 87, wherein the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, *colitis*, ulcerative *colitis*, collagenous *colitis*, lymphocytic *colitis*, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behçet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, and atopic dermatitis.

Embodiment 89

The method of any one of embodiments 85 to 88, wherein the subject is less than about 1, 2, 3, 4, 5, 6, 7, 8, 9, 12, 18, or 24 months old.

Embodiment 90

The method of any one of embodiments 85 to 88, wherein the subject is between about 2 and about 18 years old, or is at least about 18 years old.

Embodiment 91

The method of any one of embodiments 85 to 90, wherein the subject comprises a gastrointestinal microbiome that (a) has an increased proportion of *Streptococcus* spp., *Bifidobacterium* spp., and *Enterococcus* spp. compared to a healthy or general population;
(b) has a reduced proportion of *Alternaria alternata, Aspergillus, flavus, Aspergillus cibarius*, and *Candida sojae* compared to a healthy or general population;
(c) has an increased proportion of *Candida albicans* and *Debaryomyces* spp. compared to a healthy or general population;
(d) has a reduced proportion of *Bifidobacteria* spp., *Lactobacillus* spp., *Faecalibacterium* spp. and *Akkermansia* spp. compared to a healthy or general population;
(e) has a reduced proportion of *Malassezia* spp. compared to a healthy or general population
(f) has an increased proportion of *Bacterioides* spp., *Ruminococcus* spp., *Prevotella* spp., or *Bifidobacterium* spp. compared to a healthy or general population; or
(g) has an increased proportion of *Enterococcus faecalis, Enterococcus faecium*, or *Clostridium difficile* compared to a healthy or general population.

Embodiment 92

The method of any one of embodiments 85 to 91, wherein the biological sample is a bodily fluid.

Embodiment 93

The method of embodiment 92, wherein the bodily fluid is blood, plasma, serum, fecal water, or a brancheoaleolar lavage.

Embodiment 94

The method of embodiment 92 or 93, wherein the bodily fluid is fecal water.

Embodiment 95

The method of any one of embodiments 93 to 94, wherein detecting whether the biological sample is pro-inflammatory comprises contacting an antigen presenting cell with the biological sample.

Embodiment 96

The method of embodiment 95, wherein the antigen presenting cell is a dendritic cell.

Embodiment 97

The method of embodiment 95 or 96, wherein detecting whether the biological sample is pro-inflammatory further comprises contacting a naïve T cell with the antigen presenting cell to produce a contacted T cell.

Embodiment 98

The method of embodiment 97, further comprising detecting a cytokine produced by the contacted T cell and/or the progeny of the contacted T cell.

Embodiment 99

The method of embodiments 97 or 98, wherein biological sample is detected to be pro-inflammatory if (i) the proportion of T-helper (TH)-2 cells is increased in the progeny of the contacted T cell compared to a control;
(ii) the proportion of TH-1, TH-17, and/or TH22 cells is increased in the progeny of the contacted T cell compared to a control;
(iii) the ratio of TH-1 cells to TH-2 cells is decreased in the progeny of the contacted T cell compared to a control;
(iv) the proportion of IL-17 producing CD8+ T cells is increased in the progeny of the contacted T cell compared to a control; and/or
(v) the amount of IL-4, IL-10, and/or IL-13 produced by the progeny of the contacted T cell and/or the progeny thereof is increased compared to a control.

Embodiment 100

The method of embodiment 99, wherein the control is (i) the corresponding proportion, ratio, and/or amount of a corresponding T cell that has been contacted with sterile culture medium and/or the progeny thereof; (ii) the corresponding proportion, ratio, and/or amount of a corresponding T cell that has been contacted with an antigen presenting cell that has been contacted with a biological sample from a subject who does not have dysbiosis, an inflammatory disease, or a gastrointestinal infection, and/or the progeny thereof; and/or (iii) a reference value corresponding to the proportion, ratio, and/or amount in the general population or a population of subjects who do not have dysbiosis, an inflammatory disease, or a gastrointestinal infection.

Embodiment 101

The method of any one of embodiments 85 to 100, further comprising directing the subject to receive treatment or further testing or monitoring for dysbiosis or an inflammatory disease if the biological sample is detected to be pro-inflammatory.

Embodiment 102

The method of any one of embodiments 85 to 101, further comprising administering the composition of any one of embodiments 52 to 62 to the subject if the biological sample is detected to be pro-inflammatory.

Embodiment 103

The method of any one of embodiments 95 to 102, wherein the subject comprises a gastrointestinal microbiome that
(a) has an increased proportion of *Streptococcus* spp., *Bifidobacterium* spp., and *Enterococcus* spp. compared to a healthy or general population;
(b) has a reduced proportion of *Alternaria alternata, Aspergillus flavus, Aspergillus cibarius*, and *Candida sojae* compared to a healthy or general population;
(c) has an increased proportion of *Candida albicans* and *Debaryomyces* spp. compared to a healthy or general population;
(d) has a reduced proportion of *Bifidobacteria* spp., *Lactobacillus* spp., *Faecalibacterium* spp. and *Akkermansia* spp. compared to a healthy or general population;
(e) has a reduced proportion of *Malassezia* spp. compared to a healthy or general population (f) has an increased proportion of *Bacterioides* spp., *Ruminococcus* spp., *Prevotella* spp., or *Bifidobacterium* spp. compared to a healthy or general population; or (g) has an increased proportion of *Enterococcus faecalis*, *Enterococcus faecium*, or *Clostridium difficile* compared to a healthy or general population.

Embodiment 104

The method of any one of embodiments 63 to 103, further comprising determining whether the subject has a gastrointestinal microbiome that (a) has an increased proportion of *Streptococcus* spp., *Bifidobacterium* spp., and *Enterococcus* spp. compared to a healthy or general population;

(b) has a reduced proportion of *Alternaria alternata*, *Aspergillus flavus*, *Aspergillus cibarius*, and *Candida sojae* compared to a healthy or general population;

(c) has an increased proportion of *Candida albicans* and *Debaryomyces* spp. compared to a healthy or general population;

(d) has a reduced proportion of *Bifidobacteria* spp., *Lactobacillus* spp., *Faecalibacterium* spp. and *Akkermansia* spp. compared to a healthy or general population;

(e) has a reduced proportion of *Malassezia* spp. compared to a healthy or general population (f) has an increased proportion of *Bacterioides* spp., *Ruminococcus* spp., *Prevotella* spp., or *Bifidobacterium* spp. compared to a healthy or general population; or (g) has an increased proportion of *Enterococcus faecalis*, *Enterococcus faecium*, or *Clostridium difficile* compared to a healthy or general population.

Embodiment 105

A method of treating or preventing dysbiosis or an inflammatory disease in a subject determined to have or be at risk of developing dysbiosis or an inflammatory disease according to the method of any one of embodiments 85 to 103, comprising administering a treatment for dysbiosis or the inflammatory disease to the subject.

Embodiment 106

A method of monitoring the effect of treatment for dysbiosis or an inflammatory disease, the method comprising: (i) obtaining a biological sample from the subject; and (ii) detecting whether the biological sample is pro-inflammatory.

Embodiment 107

A method of determining an inflammatory disease activity in a subject, the method comprising: (i) obtaining a biological sample from the subject; and (ii) detecting whether the biological sample is pro-inflammatory.

Embodiment 108

A method of detecting an anti-inflammatory metabolite in a subject that has or is at risk for developing an inflammatory disease, said method comprising: (i) obtaining a biological sample from said subject; and (ii) determining an expression level of an anti-inflammatory metabolite in said biological sample.

Embodiment 109

A method of determining whether a subject has or is at risk of developing dysbiosis or an inflammatory disease, the method comprising: (i) detecting an expression level of one or more anti-inflammatory metabolites or pro-inflammatory metabolites in a subject; (ii) determining whether the expression level is increased or decreased relative to a standard control, wherein an elevated expression level of an pro-inflammatory metabolite or a decreased expression level of an anti-inflammatory metabolite relative to the standard control indicates that the subject has or is at risk of developing an inflammatory disease; and (iii) based at least in part on the expression level in step (ii), determining whether the subject has or is at risk for developing an inflammatory disease.

Embodiment 110

A method of monitoring the effect of treatment for an inflammatory disease in a subject undergoing inflammatory disease therapy or a patient that has received inflammatory disease therapy comprising: (i) determining a first expression level of an anti-inflammatory or pro-inflammatory metabolite in the subject at a first time point; (ii) determining a second expression level of an anti-inflammatory or pro-inflammatory metabolite in the subject at a second time point; and (iii) comparing the second expression level of an anti-inflammatory or pro-inflammatory metabolite to the first expression level of an anti-inflammatory or pro-inflammatory metabolite, thereby determining the effect of treatment for an inflammatory disease in the subject.

Embodiment 111

A method of determining an inflammatory disease activity in a subject, the method comprising: (i) detecting an expression level of one or more anti-inflammatory or pro-inflammatory metabolites in a subject; (ii) determining whether the expression level is modulated relative to a standard control, thereby determining an inflammatory disease activity in the subject; and (iii) based at least in part on the expression level in step (ii), determining the inflammatory disease activity in the subject.

EXAMPLES

The following examples are offered to illustrate, but not to limit the claimed invention.

Example 1. Rationally Designed Microbial Consortium for Gastrointestinal Microbiome Restitution Without being bound by any scientific theory, *Lactobacillus johnsonii* shifts the composition of the gut microbiome and increases specific anti-inflammatory fatty acids and carbohydrate metabolites in the gastrointestinal tract. Although some beneficial metabolites are predicted to be microbially produced (e.g., by *L. johnsonii* and the bacterial species it co-enriches within the gut microbiome), it is also likely that others are host derived in response to an altered gut microbiome. In a study of neonates supplemented daily for the first six months of age with *Lactobacillus rhamnosus* GG, an altered gut microbiome associated with similar metabolic enrichments persisted for up to 12 months after the cessation of supplementation with *Lactobacillus*.

Surprisingly, a bacterial population comprising a consortium of bacterial species may be used to prevent or treat chronic inflammatory disease by introducing or restoring the metabolic capacity to regulate inflammatory responses. The consortium of bacterial species (the "consortium") achieves this by altering microbial colonization patterns in the gastrointestinal tract, and, most importantly, introducing or restoring the capacity to produce a suite of anti-inflammatory metabolites necessary for down-regulation of pro-inflammatory responses. Much of the risk of childhood disease is associated with early life events in microbiological development and this consortium offers the opportunity to treat high-risk neonates and infants.

The consortium may be used as a therapeutic grade formulation or over-the-counter supplement to, e.g., direct appropriate neonatal gut microbiome development and immune maturation. The consortium may also be used as a replacement for fecal transplantation for chronic inflammatory diseases in which member of the consortium are characteristically depleted or as a supplement to direct gut microbiome re-development following perturbation (e.g., peri- or post-antibiotic or anti-microbial administration).

Without being bound by any scientific theory, the species in the exemplary consortium work together with the main anchor probiotic species, *L. johnsonii*, in a symbiotic manner, with each providing other members of this bacterial guild with nutrients and co-factors for their survival and modulation of host immunity. Intervention using a regimen of microbial consortium (*Lactobacillus johnsonii. Akkermansia muciniphila, Faecalibacterium prausnitzii* and *Myxococcus xanthus*), provides improved protection against allergic sensitization due to an effect that is greater than the sum of the effects of the individual consortium members when administered alone. Using a similar mouse model to that previously published (Fujimura et al., (2014). *Proc. Natl. Acul. Sci.* 111(2) 805-810), an allergic challenge was combined with supplementation of the exemplary microbial consortium. Set forth herein, the host immune response and allergic response was evaluated using histology, qRT-PCR, and flow cytometry.

Cockroach Allergen (CRA) Murine Model.

To investigate the protective effects of supplementation, C57BL/6 mice (7-8 weeks old) were intratracheally sensitized (Day 1-3) and subsequently challenged once a week with cockroach allergen (CRA) for a total of three weeks. The mice were concurrently supplemented with phosphate buffered saline (PBS, negative vehicle control), *L. johnsonii* (Lj), the microbial consortium lacking *L. johnsonii* (C-Lj), a complete consortium (C+Lj), or a heat killed complete consortium (C+Lj Heat Killed, control for metabolically inactive consortium). In the first week supplementation was performed daily, followed by supplementation twice a week for the remaining two weeks. All supplementations were performed by oral gavage using bacteria resuspended in 100 µl of PBS. At the conclusion of the study, mice were euthanized, and various tissues (lung, spleen, ileum) were collected for downstream analyses.

Lung Histology.

Lung tissue was collected from each animal and immediately fixed in Carnoy's solution overnight and subsequently dehydrated in 70% ethanol. Three samples from each group were randomly chosen for embedding in paraffin and staining with hematoxylin and eosin (H&E) or Periodic acid-Schiff (PAS). Images for each stained sample were captured using an Aperio Scanscope XT (Leica Biosystems) at 20× magnification. ImageJ was also used to quantify the amount of mucin staining represented in each PAS-stained slide using set threshold parameters in the RGB stack based on the green channel. The percentage of the image that fell within the threshold values was measured and represented the percentage of positive staining within each image analyzed.

qRT-PCR for Gene Expression.

The mRNA from mouse lung was extracted using an AllPrep DNA/RNA Mini Kit (Qiagen). Prior to RNA isolation, lung samples were placed in Lysing Matrix A tubes (MP Bio) with 600 µl of Buffer RLT. Samples were bead-beaten using MPBio FastPrep-24 homogenizer at 5.5 m/s for 30 s. Manufacturer's instructions were followed for the remainder of the RNA isolation procedure. A total of 1.0 µg of RNA per sample was DNase treated and reverse-transcribed using the RT2 First Strand Kit (Qiagen) per the manufacturer's instructions. Quantitative PCR for allergy associated gene expression was performed using the Custom RT Profiler PCR Array (Qiagen) on a QuantStudio 6 Flex System. Reaction conditions were as follows: 95° C. for 10 min, followed by 40 cycles of 95° C. for 15 s and 60° C. for 1 min. Gene expression of cytokines was normalized to GAPDH and expressed as fold change compared to gene expression in CRA-challenged PBS-vehicle gavaged mice. Statistical analysis of cytokine expression levels was performed using Prism 6 software. Gene expression between experimental groups was compared using a Mann-Whitney U test, with p-values≤0.05 considered significant.

$CD4^+$ T Cell Isolation and Flow Cytometry Analysis.

Mouse spleens were removed and placed in ice-cold R10 media (RPMI 1640 supplemented with 10% heat-inactivated FCS, 2 mM L-glutamine, and 100 U/ml penicillin-streptomycin) (Life Technologies, Carlsbad, Calif.). Tissues were mechanically homogenized using sterile scalpels, followed by collagenase digestion (C6885, Sigma, 1 mg/ml) at 37° C. for 30 minutes in 1:1 R10-PBS solution. The single cell suspensions were obtained by passing digests 10× through a 16-gauge, blunt-end cannula followed by filtrations through a 40 µm filter. Cell suspensions were washed twice with ice cold PBS (2% FCS, 2 mM EDTA) and centrifuged at 1,200 rpm, 4° C., for 10 min to pellet, and resuspended in R10-EDTA media (R10 with 2 mM EDTA) on ice. One million cells were dispensed into each tube for subsequent antibody staining and analysis. Single-cell suspensions of splenocytes from each mouse were aliquoted (1 million cells per well) and subsequently stained with antibodies CD4 (RM4-5, BD Biosciences, Franklin Lakes, N.J.), CD8a(53-6.7, BD), CXCR5(SPRCL5, eBioscience, San Diego, Calif.), PD-1(RMP1-30, BioLegend, San Diego, Calif.), CD25(PC61, BD), and live/dead aqua stain (Life Technologies). Following surface staining, cells were permeabilized using BD Cytofix/Cytoperm and incubated with CD3e (500A2, BD), IFNγ(XMG1.2, BD), IL-4(11B11, BD), IL-17 DEC(eBiol7B7, eBioscience), and FoxP3(FJK-16s, eBioscience) specific antibodies for internal staining. Stained cells were assayed via flow cytometry on a BD LSR II (BD Biosciences).

Statistical Analysis.

Statistical analyses were performed using GraphPad Prism 6 software. Experimental groups were compared by a Kruskal-Wallis test with a Dun's multiple comparison post-test to determine if there were any significant differences between sample groups. In addition, Mann-Whitney tests were used in some cases to directly compare two groups of values. P-values≤0.05 were considered significant.

Results.

Figure 1A:
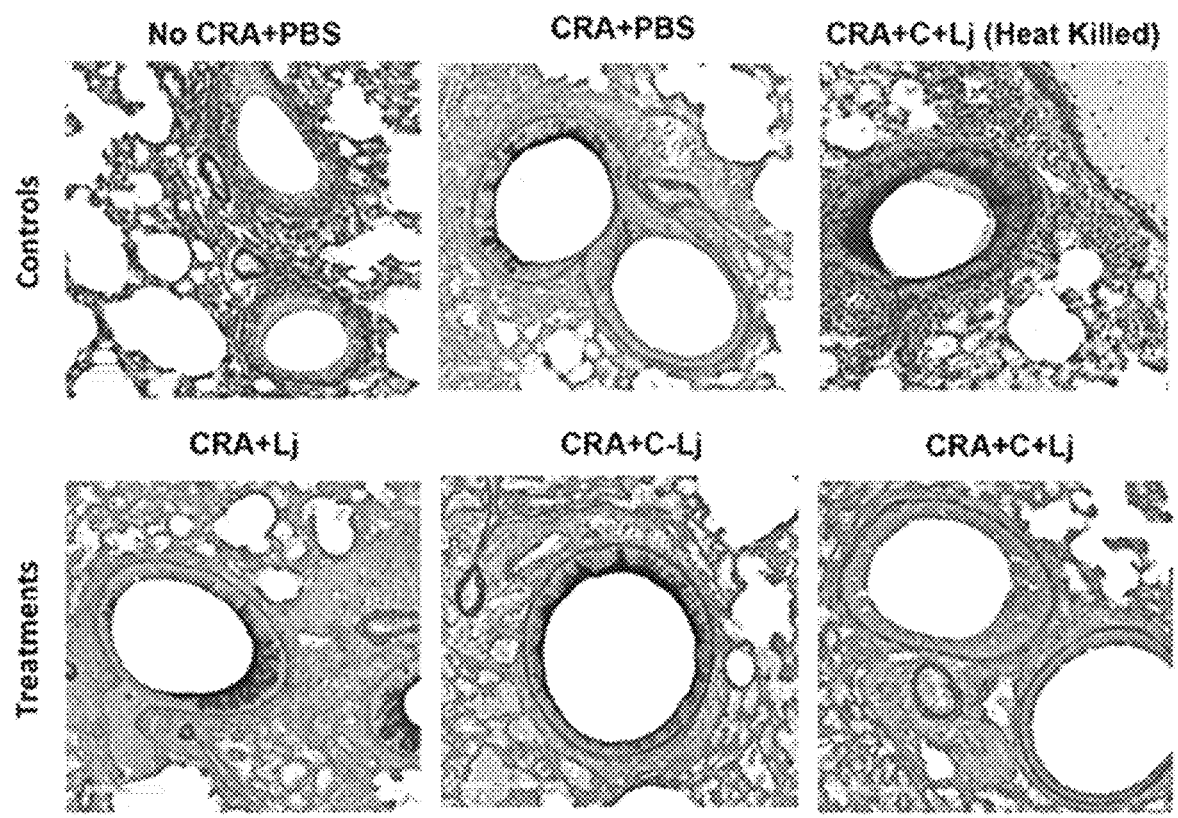
FIG. 1A-1B. Significantly improved lung histology and decreased goblet cell hyperplasia is evident only in mice supplemented with C+Lj. Histological samples from three mice in each of the six experimental groups were stained to visualize goblet cell hyperplasia in duplicate studies.
Figure 1B:
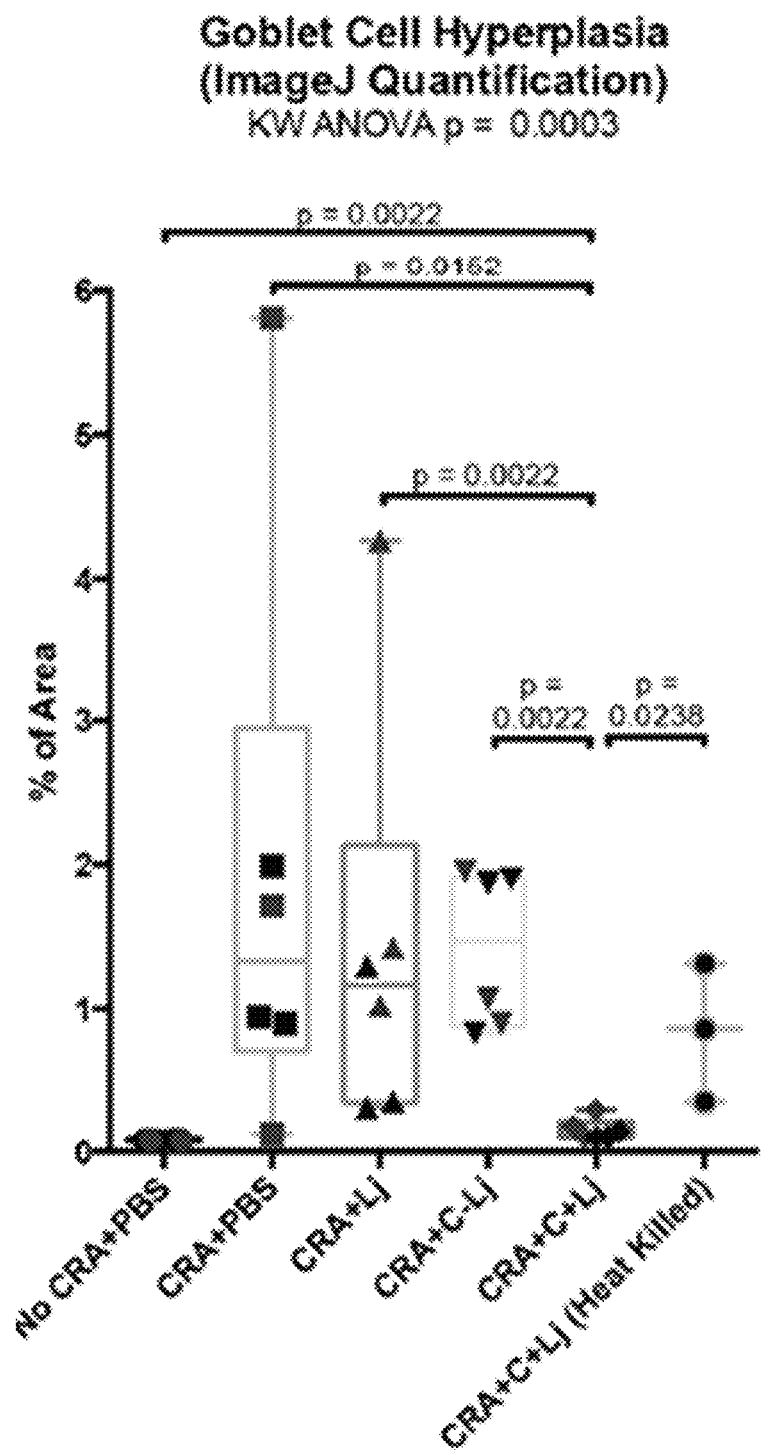
Figure 2:
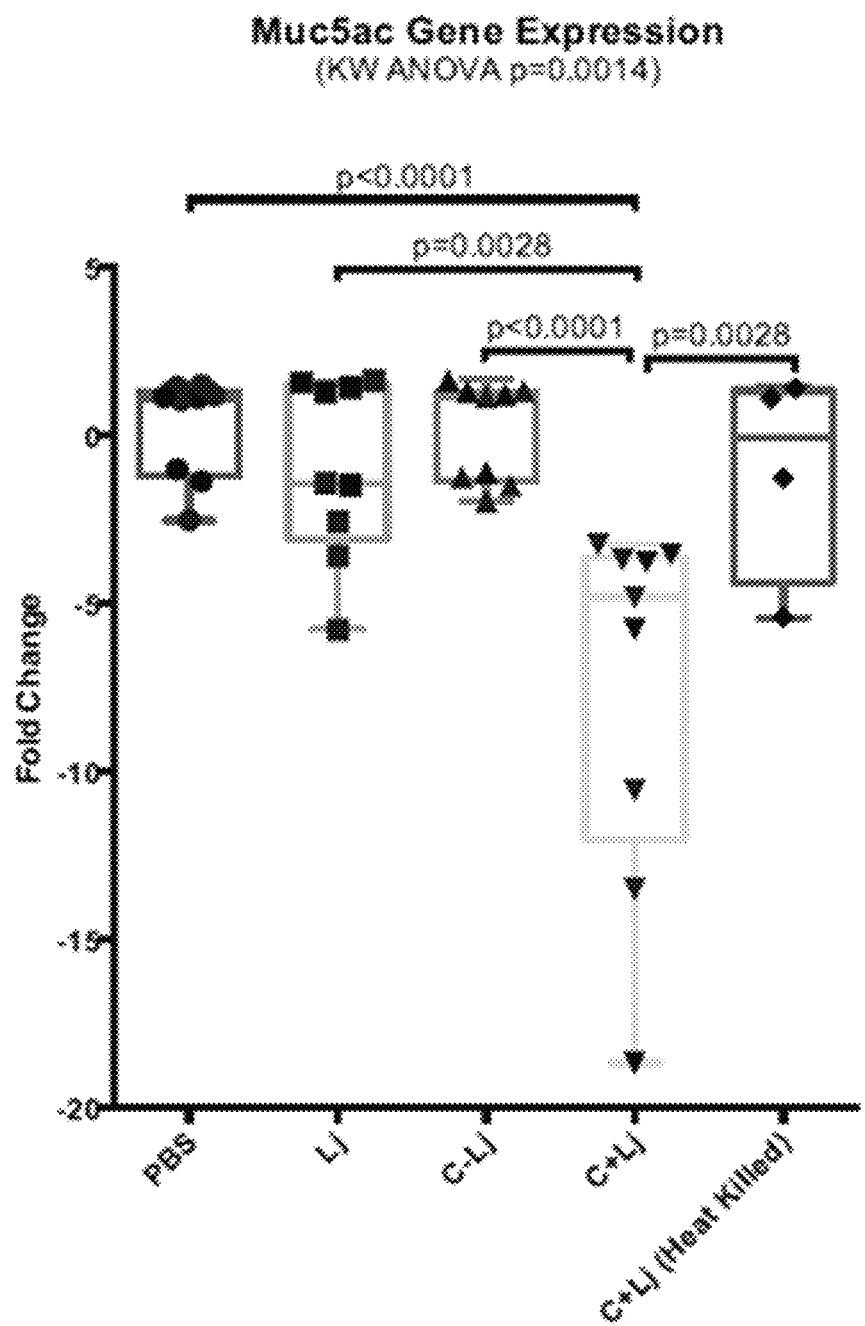
FIG. 2. Significantly decreased expression of MUC5AC in mice supplemented with C+Lj supports histological findings. RNA extracted from the lung of each animal was used to examine the gene expression level of MUC5AC, a gene involved in mucin production by goblet cells. Data from two independent murine studies is presented. Statistical analyses of this data show significant reductions in the percentage of Muc5ac gene expression associated with C+Lj supplemented mice compared to all other CRA treated groups.
Figure 3A:
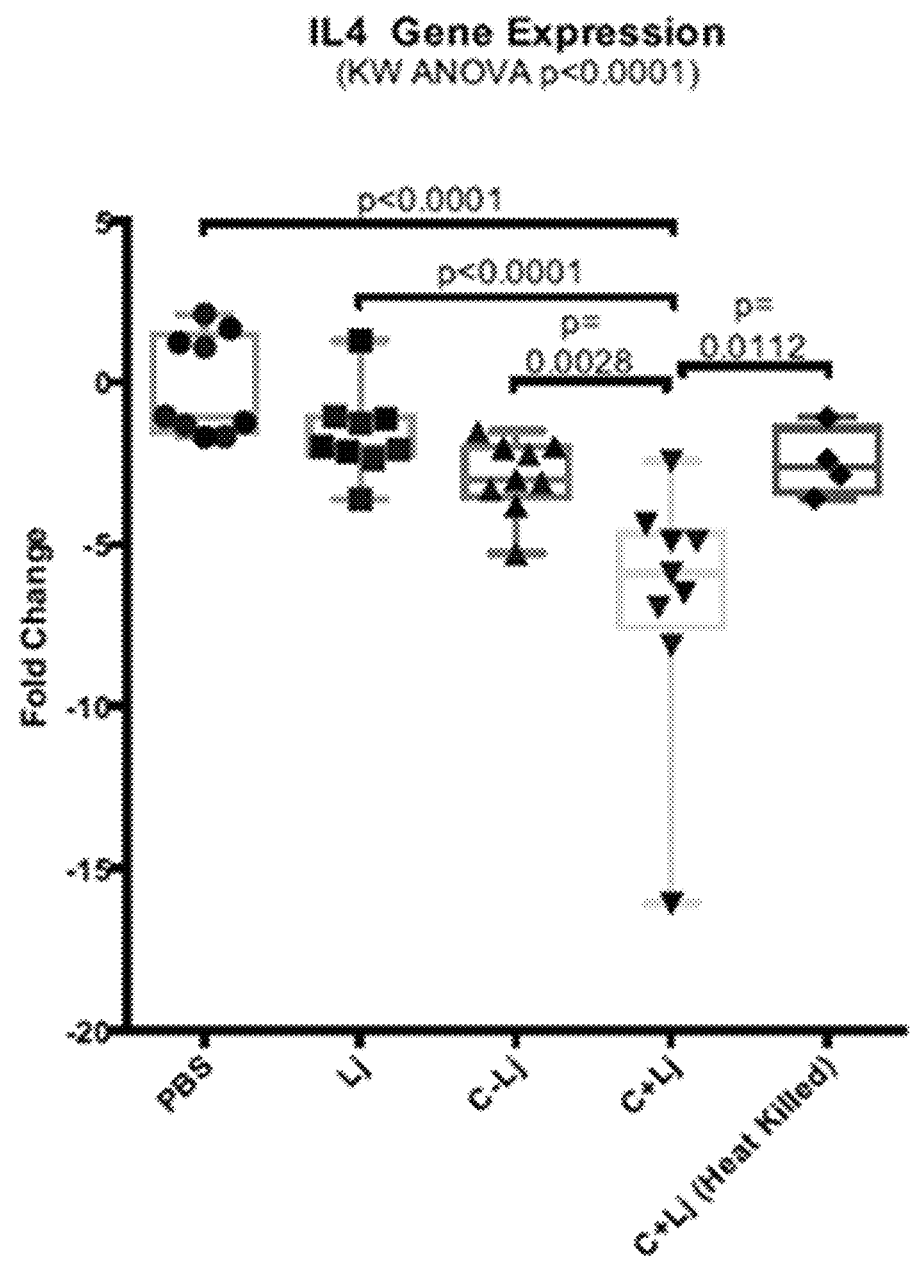
FIGS. 3A-3C. Supplementation with C+Lj resulted in decreased airway expression of cytokines associated with allergic response. RNA extracted from the lung of each animal was also used to examine the gene expression level of multiple cytokines associated with allergic responses, including IL-4 (FIG. 3A), IL-13 (FIG. 3B), IL-10 (FIG. 3C)
Figure 3B:
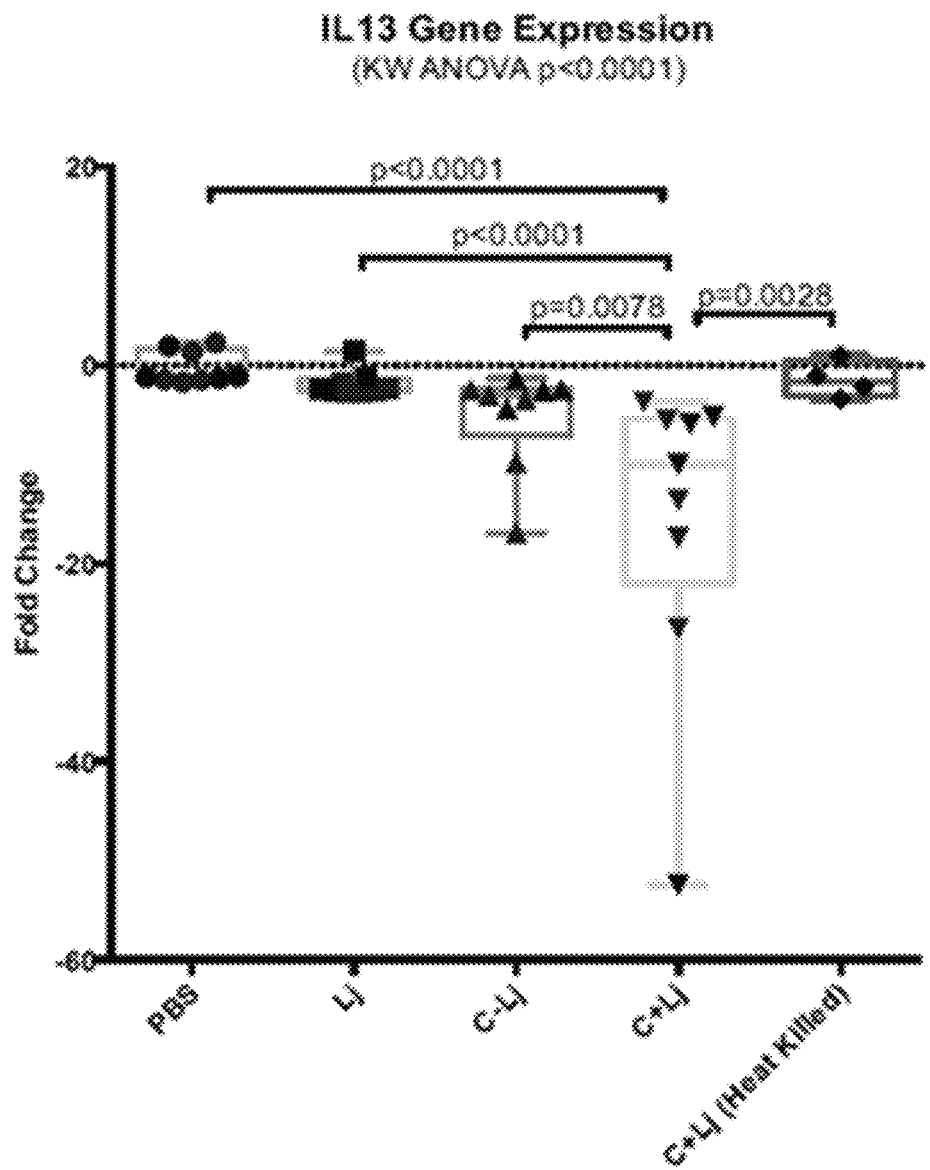
Figure 3C:
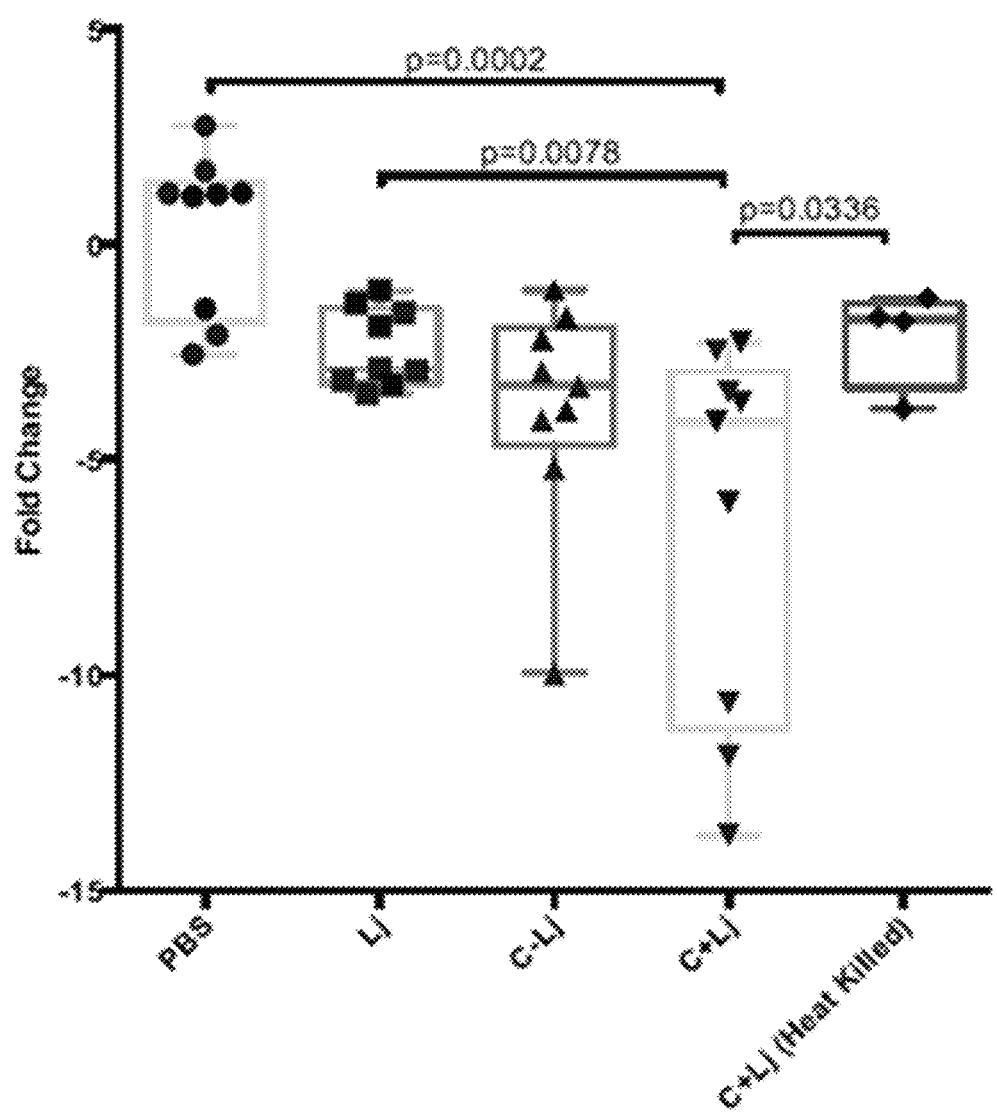

Supplementation with the complete consortium (C+Lj) provides the most robust protection against allergic sensitization. Protection is associated with significant decreases in lung mucin secretion (FIGS. 1A-1B), Muc5 gene expression (FIG. 2), and in Th2 cytokine expression (FIGS. 3A-3C). Protection against allergic sensitization by C+Lj is correlated with systemic increases in IL-17 secreting T helper cells (FIG. 4). *L. johnsonii* is more effective than *L. rhamnosus* GG and necessary for the attenuation of allergic sensitization associated Muc5ac expression in the lung of CRA challenged C57BL/6 mice (FIG. 5A-5B). The gut microbiota forms a complex functional network that influences both individual microbial members and host immune responses. Rationally designed microbial gastrointestinal consortium provide greater attenuation of allergic airway sensitization than an individual probiotic species.

Example 2. Effects of Consortium Supplementation on a Murine Model of Airway Allergic Sensitization Without being bound by any scientific theory, the therapeutic consortium (TC) represents a seed microbial guild that aids in the development of a healthy human gut microbiome. A study in C57BL/6 mice was designed, which have a distinct gut microbiome from BALB/c animals and are not protected against allergic airway sensitization following supplementation with *L. johnsonii* alone, to determine the effects of TC supplementation on allergic airway sensitization.

To investigate the protective effects of TC supplementation C57BL/6 mice were intratracheally sensitized (days 0-2) and subsequently challenged with cockroach allergen (CRA) on days 14 and 20 over the course of a three week period (FIG. 10). The mice were supplemented with either phosphate buffered saline (PBS, negative vehicle control) or the TC on days 0-5, 8, 12, 16, and 19 via oral gavage (FIG. 10). Table 2 and FIG. 17 show treatment groups utilized in this study.

Applicants examined the microbial community composition in the feces of animals in different treatment groups using 16S rRNA sequencing. The community present in that of the TC-supplemented animals was significantly compositionally distinct from that of the control groups (FIG. 11A). Importantly, the TC-supplemented group was enriched for species with the potential for immunomodulatory activity. For example, *Bifidobacterium* and specific *Clostridia* species belonging to Clade IV and XIV have been shown to induce T-regulatory cells. In addition, *Lachnospira* species have been identified as protective against allergic sensitization disease development. Expansion of *Bacteroides* was characteristic of allergic sensitization in control animals. In conclusion, oral supplementation of mice with the TC promotes increased relative abundance of genera associated with induction of immune tolerance (e.g., *Bifidobacteria, Clostridia, Lachnospira* and *Ruminococcus*; FIGS. 11A and 11B).

Oral supplementation with the TC promoted metabolic reprogramming in both the gut lumen and periphery (FIGS. 12A-12B and FIGS. 18A-18C). Increased levels of itaconate, which is associated with a repair macrophage effector phenotype, were also identified in TC supplemented animals.

TC supplemented mice demonstrated significantly reduced allergic inflammation in response to CRA challenge compared with CRA challenged animals treated with PBS (FIGS. 13A-13B; FIGS. 14A-14B; FIGS. 15A-15C). Thus, TC supplementation significantly reduced allergic inflammation in a murine model of airway allergic sensitization.

Oral supplementation of mice with the TC resulted in a repair macrophage effector phenotype (FIGS. 16A-16F). Therefore, TC supplementation is capable of initiating a repair macrophage effector phenotype in a murine model of airway allergic sensitization.

Example 3. In Vitro Assay for Assessment of Immune Activation Status Using Human Fecal Water or Microbial Products One of the shortcomings of human microbiome studies is the lack of parallel objective immune status information. Provided herein are partner assays for human microbiome studies to determine the extent of immune activation associated with a variety of bodily fluids, such as fecal water or broncheoalveolar lavage fluid, or to assess the capacity of microbial species, or combinations of microbial species to induce immune activation or, conversely induce immune tolerance. The assays provided herein may be used as diagnostics for chronic inflammatory diseases, as well as for screening for bioactive microbial products that induce immune phenotypes associated with disease (and by extension identify target pathways for therapeutic intervention) or represent novel microbial biotherapeutics. No known assay to date has this capacity.

Fecal samples (250 mg) were added to warm PBS (250 µl, containing 20% FCS) at 1 g/1 ml, (w/v), followed with vigorous vortex for 1 minute. Fecal mixtures were incubated for 10 minutes in 37° C., prior to removal of cellular material by microcentrifugation at 14,000 rpm for 5 minutes. Resulting fecal water was sterilized through a 0.2 µm filter and used in DC co-incubations.

Peripheral blood mononuclear cells (PBMCs) were isolated from peripheral blood of healthy adult donors by Ficoll-Hypaque gradient centrifugation. DCs were first enriched from the PBMCs using the EasySep™ Human Pan-DC Pre-Enrichment Kit (STEMCELL Technologies, Vancouver, Canada). Enriched DCs ($0.5 \times 10^6$ cells/ml) were co-incubated for 48 hours with fecal water (25 µl) and cultured in 96-well plates, in R10 media (RPMI 1640 with 10% heat-inactivated FCS with 2 mM L-glutamine and 100 U/ml penicillin-streptomycin; Life Technologies, Carlsbad, Calif.) supplemented for the first 24 hours with 10 ng/ml GM-CSF and 20 ng/ml IL-4 for. A combination of DC growth factors (10 ng/ml TNF-α, 10 ng/ml IL-1β, 10 ng/ml IL-6, and 1 µM PGE2) were added to the culture for the subsequent 24 hours of incubation. At the end of 48 hour treatment, DCs were washed (once) in fresh media prior to co-culture with CD4+ lymphocytes.

Autologous CD4+ T lymphocytes were purified from PBMC's by negative selection using a CD4+ T-cell isolation kit (Miltenyi Biotec, Bergisch Gladbach, Germany). These isolated T cells were suspended in the TexMACS Medium (Miltenyi Biotec) prior to being added to fecal water exposed DCs at a ratio of 10:1 in the presence of soluble anti-CD28 and anti-CD49d (1 µg/ml). DC and T-cells were co-cultured for 120 hours and replenished with fresh TexMACS Medium every 48 hours. Cells were stimulated with Phorbol Myristate Acetate-Ionomycin (Sigma) and Golgi-Plug (BD Biosciences) for the final 16 hours of co-incubation. Cell-free media from these co-cultures were collected and evaluated by ELISA (BioLegend) for human cytokines IL-4, IL-10, and IL-13 concentrations.

Single-cell suspensions were stained using two separate panels (phenotype panel and cyctokine panel) of antibodies including BD Biosciences Abs anti-CD3 (SP34-2), anti-CD4 (SK3), anti-CD25 (M-A251), anti-IFNγ (B27), anti-CD8a (RPA-T8, BioLegend), Miltenyi Biotec Abs anti-IL-10 (JES3-9D7), anti-IL-4 (7A3-3), Affymatrix eBioscience Abs anti-IL-22 (22URTI), anti-IL-17A (64DEC17) and anti-FoxP3 (PCH101). Dead cells were identified using LIVE/DEAD® Aqua Dead Cell Stain (Life Technologies). Cells were permeablized by either Cytofix/Cytoperm™ (BD Bioscience) or Fixation/Permeabilization (Affymatrix eBioscience) to stain for intracellular markers, IFNγ, IL-4, IL17A, IL-22, IL-10, FoxP3. Upon flow analysis, live T cells were gated as CD3+CD4+ cells. Amongst the CD4+ T cell sub-populations, Th1 were IFNγ+, Th2 were IL-4+, Th17 cells were IL-17A+, Th22 were IL17A-negative and IL-22+, and T-regulatory cells were both $CD25^{hi}$ and $FoxP3^{hi}$. Stained cells were assayed via flow cytometer on a BD LSR II (BD Biosciences).

Fecal water from a non-atopic neonate significantly reduces CD4+ IL4 and IL13 expression in vitro. Atopy is associated with early-life gastrointestinal bacterial overgrowth and murine microbial metabolism, thus implicating the neonatal gut microbiome in allergic disease development. Microbiota analysis of 298 early-life stool samples from a birth cohort revealed the existence of three compositionally distinct Neonatal Gut Microbiotypes (NGM1, NGM2 and NGM3). NGM3 neonates exhibited significantly higher relative risk for predominantly multisensitized atopy at age two (p<0.03) compared with NGM1 (RR=2.94; 95% CI 1.42-6.09) or NGM 2 (RR=2.06; 95% CI 1.01-4.19), and were more likely to report doctor-diagnosed asthma (p<0.03). Lower-risk NGMs were significantly enriched for commensal bacteria, fungi and a range of luminal anti-inflammatory lipids and carbohydrates. NGM3 neonates exhibited commensal microbial depletion, fungal expansion and metabolic reprogramming manifest as increased pro-inflammatory lipids and host-derived sterols associated with fungal infection.

Findings from this study of neonatal and infant gut microbiomes indicated that neonatal metabolic reprogramming was associated with risk of atopy development at age two and that neonates that exhibited significant increases in anti-inflammatory carbohydrates and lipids in their luminal contents were at significantly decreased risk for allergic sensitization. Previous murine studies have indicated that microbial-derived short chain fatty acids afford protection against airway allergen challenge. Applicants rationalized that fecal water from low-risk neonates (NGM1) which was enriched for known anti-inflammatory lipids and carbohydrates would exhibit the capacity to reduce allergy-associated cytokine expression. Applicants therefore incubated filter-sterilized fecal water from an NGM1 neonate with peripheral blood mononuclear cell-derived dendritic cells isolated from two distinct healthy adult donors, prior to their co-incubation with autologously purified naïve T-cells followed by ionomycin stimulation. Flow cytometry and ELISA analyses, used to examine T-helper 2 (CD4+, IL4+) cells and cytokine production respectively, indicated that fecal water did not substantially influence the number of Th2 cells (FIG. 6A), but significantly and consistently suppressed pro-inflammatory IL4 and IL13 expression (p<0.01 for both; FIG. 6B and FIG. 6C) across both donors.

In vitro DC-T-cell activity assay permits identification of microbes with pro-inflammatory potential. In our studies of the neonatal gut microbiome and atopy, *Candida* enrichment and host responses to fungal infection (beta-sitosterol and stigmasterol), were amongst the features that characterized high-risk for atopy NGM3 participants. Murine studies employing antimicrobial ablation of the commensal gastrointestinal microbiome, followed by instillation of *Candida albicans* spores, have previously demonstrated enhanced allergic sensitization even in the absence of allergen exposure. Without wishing to be bound by any scientific theory, it was rationalized that *Candida* enrichment in the gut microbiome of NMG3 neonates may promote adaptive T-helper cell subsets associated with atopy. Using *Candida*-selective Sabouraud media, four distinct species were isolated from NGM3 neonatal stool samples and identified using full length ITS sequencing as *C. metapsilosis, C. parapsilosis, C. orthopsilosis*, and *C. tropicalis*. Filter-sterilized cell-free supernatant (CFS) from cultures of these four *Candida* species was used to stimulate peripheral blood mononuclear cell-derived dendritic cells prior to their co-incubation with naïve T-cells in the presence or absence of cockroach antigenic stimulation. Flow cytometry analysis was used to examine T-helper 2 (CD4+, IL4+) and T-regulatory (CD4+, IL10+) subsets. CFS from each of the gastrointestinal *Candida* species induced significant increases in Th-2 cell proliferation compared to the control (sterile culture medium) exposure, irrespective of cockroach allergen challenge (FIG. 7A). Significant increases were also observed for other pro-inflammatory cytokine producing T-helper cell subsets (TH1, TH17 and TH22). However T-regulatory subsets did not exhibit a consistent significant increase in numbers, indeed most species did not affect T-reg numbers, with one, *C. tropicalis*, inducing T-regs and another *C. metapsilosis* inducing a significant reduction in T-reg cell numbers, only in the presence of cockroach allergen stimulation (FIG. 7B). Hence these in vitro analyses corroborate previous animal studies and indicate that the secreted products of distinct *Candida* species enriched in the gut microbiome of neonates with significantly higher relative risk for atopy at age two have the capacity to drive Th-2 proliferation and cytokine secretion irrespective of antigen presentation by DCs.

In vitro DC/T-cell fecal water assay can be used to discriminate sub-sets of ulcerative *colitis* patients that exhibit distinct fecal microtypes and differ significantly in disease severity. Statistical analyses has permitted us to identify three sub-groups of UC patients based on microbiota composition (bacterial and fungal profiling), referred to MBT-1 to -3). The clinical relevance of gut microbiota-based stratification of our UC patients was assessed by an inter-microbiotype comparison of disease severity (Simple Clinical Colitis Activity (SCCA) index duration (number of years since UC diagnosis), extracolonic manifestations (arthritis, pyoderma gangrenosum, erythema nodosum, and uveitis) and number of first- and second-degree relatives with IBD. MBT-1 patients exhibited higher median SCCA score compared to MBT-2 and MBT-3 groups (FIG. 8A). These patients also exhibited more extracolonic manifestations, and trended towards longer disease duration and a greater number of first- and second-degree relatives diagnosed with IBD (FIGS. 8B-8D).

In an effort to determine the capacity of healthy and disease-associated microbiota to influence adaptive immune responses, we next developed an in vitro assay involving exposure of dendritic cells (DCs; obtained from healthy human donors) to filter-sterilized fecal water from participants in our study, prior to co-culture of exposed DCs with naïve T-cells obtained from the same donor. Flow cytometry was used assess resulting T-cell populations and phenotypes. Compared to healthy control subjects, UC patients were characterized by significant differences in the ratio of CD4+ Th1 and Th2 cells; patients exhibited significantly decreased Th1:Th2 ratio (FIG. 9A). Other CD4+ populations (Th17, Th22, and T-regulatory cell) abundances did not exhibit significant differences in relative numbers, nor did CD8+ cell numbers differentiate based on health status. While differences in the Th1:Th2 ratio existed across healthy subjects and UC patients, we postulated that UC-associated gut microbiotypes associated with significantly different disease severity scores would also exhibit concomitant differences in this ratio. We therefore examined cytokine production patterns based on UC-microbiotype. The MBT-1 group, which exhibited the highest disease severity scores exhibited a significantly reduced Th1:Th2 ratio (FIG. 9B), which was associated with an expansion of CD4+, IL4 expressing T-cells (FIG. 9C). Other CD4+ T-cell populations (Th17, Th22, and Treg) also trended towards expansion in MBT-1 group, compared to the MBT2 and MBT3 groups. Additionally, the MBT-1 group exhibited a significant increase in IL-17 producing CD8+ T-cells compared to either MBT-2 and MBT-3 patient samples (FIG. 9D). These in vitro data are consistent with clinical observations in that compared to healthy subjects, UC patients are significantly skewed towards a Th2-enriched population of CD4+ cells, and that UC-microbiotypes exhibit significant differences in both their degree of Th2 skewing and expansion of IL17 producing cytotoxic CD8+ cells. Hence microbiological stratification allows identification of immunologically distinct UC patient populations.

TABLE 2

Treatment groups utilized in murine model of airway allergic sensitization study.

| Cockroach Allergen (CRA) | Gavage Intervention | Group |
|---|---|---|
| −(PBS) | PBS Vehicle | No CRA |
| + | PBS Vehicle | CRA + PBS |
| + | Therapeutic Consortium (TC) | CRA + TC |
| + | L. johnsonii (Lj) | CRA + Lj |
| + | Consortium without Lj (C) | CRA + C |
| + | Heat-Killed TC (HKTC) | CRA + HKTC |

TABLE 3

Supplementation with Therapeutic Consortium results in metabolic reprogramming leading to an increase in specific lipid compounds.

| Compound Type | Compound Subtype | Compound |
|---|---|---|
| Lipids | Phospholipids | 1-palmitoyl-2gamma-linolenoyl-GPC (16:0/18:3n6) |
| Lipids | Phospholipids | Oleoylcholine |
| Lipids | Phospholipids | 1-linoleoyl-2-arachidonoyl-GPC (18:2/20:4n6) |
| Lipids | Phospholipids | 1-palmitoleoyl-2-linoleoyl-GPC (16:1/18:2) |
| Lipids | Phospholipids | 1-palmitoyl-2-alpha-linolenoyl-GPC (16:0/18:3n3) |
| Lipids | Phospholipids | 1,2-dioleoyl-GPE (18:1/18:1) |
| Lipids | Phospholipids | 1-stearoyl-2-linoleoyl-GPE (18:0/18:2) |
| Lipids | Phospholipids | 1-palmitoyl-2-arachidonoyl-GPE (16:0/20:4) |
| Lipids | Phospholipids | 1-stearoyl-2-oleoyl-GPE (18:0/18:1) |
| Lipids | Phospholipids | 1-stearoyl-2-arachidonoyl-GPE (18:0/20:4) |
| Lipids | Phospholipids | 1-palmitoyl-2-palmitoleoyl-GPC (16:0/16:1) |
| Lipids | Phospholipids | 1-stearoyl-2-linoleoyl-GPC (18:0/18:2) |
| Lipids | Phospholipids | 1-palmitoyl-2-arachidonoyl-GPC (16:0/20:4) |
| Lipids | Phospholipids | 1,2-dioleoyl-GPC (18:1/18:1) |
| Lipids | Phospholipids | 1-stearoyl-2-oleoyl-GPC (18:0/18:1) |
| Lipids | Phospholipids | 1-stearoyl-2-arachidonoyl-GPC (18:0/20:4) |
| Lipids | Phospholipids | 1-palmitoyl-2-linoleoyl-GPC (16:0/18:2) |
| Lipids | Phospholipids | 1-palmitoyl-2-oleoyl-GPC (16:0/18:1) |
| Lipids | Phospholipids | 1,2-dipalmitoyl-GPC (16:0/16:0) |
| Lipids | Plasmalogens | 1-(1-enyl-oleoyl)-GPE (P-18:1) |
| Lipids | Plasmalogens | 1-(1-enyl-palmitoyl)-GPE (P-16:0) |
| Lipids | Plasmalogens | 1-(1-enyl-palmitoyl)-2-linoleoyl-GPC (P-16:0/18:2) |
| Lipids | Plasmalogens | 1-(1-enyl-palmitoyl)-2-arachidonoyl-GPC (P-16:0/20:4) |
| Lipids | Plasmalogens | 1-(1-enyl-palmitoyl)-2-oleoyl-GPC (P-16:0/18:1) |
| Lipids | Plasmalogens | 1-(1-enyl-palmitoyl)-2-arachidonoyl-GPE (P-16:0/20:4) |
| Lipids | Plasmalogens | 1-(1-enyl-palmitoyl)-2-linoleoyl-GPE (P-16:0/18:2) |
| Lipids | Plasmalogens | 1-(1-enyl-palmitoyl)-2-oleoyl-GPE (P-16:0/18:1) |

TABLE 4

Supplementation with Therapeutic Consortium results in metabolic reprogramming leading to a decrease in specific carbohydrate, lipid, energy compounds.

| Compound Type | Compound Subtype | Compound |
|---|---|---|
| Carbohydrates | Glycolysis/Pyruvate | 1,5-anhydroglucitol |
| Carbohydrates | Glycolysis/Pyruvate | Glucose |
| Carbohydrates | Glycolysis/Pyruvate | Pyruvate |
| Carbohydrates | Glycolysis/Pyruvate | Glycerate |
| Carbohydrates | Pentose | Ribose |
| Carbohydrates | Pentose | Ribitol |
| Carbohydrates | Pentose | Ribonate |
| Carbohydrates | Pentose | Xylose |
| Carbohydrates | Pentose | Arabinose |
| Carbohydrates | Pentose | Arabitol/Xylitol |
| Carbohydrates | Fructose/Mannose/Galactose | Mannitol/Sorbitol |
| Carbohydrates | Fructose/Mannose/Galactose | Mannose |
| Carbohydrates | Fructose/Mannose/Galactose | Galactitol (dulcitol) |
| Lipids | Polyunsaturated Fatty Acids | Docosapentaenoate (n3 DPA; 22:5n3) |

TABLE 4-continued

Supplementation with Therapeutic Consortium results in metabolic reprogramming leading to a decrease in specific carbohydrate, lipid, energy compounds.

| Compound Type | Compound Subtype | Compound |
|---|---|---|
| Lipids | Polyunsaturated Fatty Acids | Adrenate (22:4n6) |
| Lipids | Polyunsaturated Fatty Acids | Docosadienoate (22:2n6) |
| Lipids | Polyunsaturated Fatty Acids | Dihomo-linoleate (20:2n6) |
| Lipids | Acyl-glycerols | 1-myristoylglycerol (14:0) |
| Lipids | Acyl-glycerols | 2-myristoylglycerol (14:0) |
| Lipids | Acyl-glycerols | 1-pentadecanoylglycerol (15:0) |
| Lipids | Acyl-glycerols | 1-palmitoylglycerol (16:0) |
| Lipids | Acyl-glycerols | 2-palmitoylglycerol (16:0) |
| Lipids | Acyl-glycerols | 1-margaroylglycerol (17:0) |
| Lipids | Acyl-glycerols | 1-oleoylglycerol (18:1) |
| Lipids | Acyl-glycerols | 2-oleoylglycerol (18:1) |
| Lipids | Acyl-glycerols | 1-linoleoylglycerol (18:2) |
| Lipids | Acyl-glycerols | 2-linoleoylglycerol (18:2) |
| Lipids | Acyl-glycerols | 1-linolenoylglycerol (18:3) |
| Lipids | Acyl-glycerols | 1-docosahexaenoylglycerol (22:6) |
| Lipids | Acyl-glycerols | 2-docosahexaenoylglycerol (22:6) |
| Lipids | Acyl-glycerols | 1-palmitoleoylglycerol (16:1) |
| Lipids | Acyl-glycerols | 2-palmitoleoylglycerol (16:1) |
| Lipids | Acyl-glycerols | 1-eicosapentaenoylglycerol (20:5) |
| Lipids | Acyl-glycerols | 2-eicosapentaenoylglycerol (20:5) |
| Lipids | Branched Fatty Acids | 15-methylpalmitate |
| Lipids | Branched Fatty Acids | 17-methylstearate |
| Lipids | Branched Fatty Acids | 2-hydroxyglutarate |
| Lipids | Branched Fatty Acids | 1-dihomo-linoleoylglycerol (20:2) |
| Lipids | Long Chain Fatty Acids | Pentadecanoate (15:0) |
| Lipids | Long Chain Fatty Acids | Palmitate (16:0) |
| Lipids | Long Chain Fatty Acids | Margarate (17:0) |
| Lipids | Long Chain Fatty Acids | 10-heptadecenoate (17:1n7) |
| Lipids | Long Chain Fatty Acids | Stearate (18:0) |
| Lipids | Long Chain Fatty Acids | Nonadecanoate (19:0) |
| Lipids | Long Chain Fatty Acids | 10-nonadecenoate (19:1n9)* |
| Lipids | Long Chain Fatty Acids | Arachidate (20:0) |
| Lipids | Long Chain Fatty Acids | Eicosenoate (20:1) |
| Lipids | Long Chain Fatty Acids | Erucate (22:1n9) |
| Lipids | Long Chain Fatty Acids | Oleate/Vaccenate (18:1) |
| Energy | TCA Cycle | Citrate |
| Energy | TCA Cycle | Succinate |
| Energy | TCA Cycle | Mesaconate |

Example 4. Neonatal Gut Microbiota Associates with Childhood Multisensitized Atopy and T Cell Differentiation Gut microbiota bacterial depletions and altered metabolic activity at 3 months are implicated in childhood atopy and asthma[1]. We hypothesized that compositionally distinct human neonatal gut microbiota (NGM) exist, and are differentially related to relative risk (RR) of childhood atopy and asthma. Using stool samples (n=298; aged 1-11 months) from a US birth cohort and 16S rRNA sequencing, neonates (median age, 35 d) were divisible into three microbiota composition states (NGM1-3). Each incurred a substantially different RR for multisensitized atopy at age 2 years and doctor-diagnosed asthma at age 4 years. The highest risk group, labeled NGM3, showed lower relative abundance of certain bacteria (for example, Bifidobacterium, Akkermansia and Faecalibacterium), higher relative abundance of particular fungi (Candida and Rhodotorula) and a distinct fecal metabolome enriched for pro-inflammatory metabolites. Ex vivo culture of human adult peripheral T cells with sterile fecal water from NGM3 subjects increased the proportion of $CD4^+$ cells producing interleukin (IL)-4 and reduced the relative abundance of $CD4^+$ $CD25^+FOXP3^+$ cells. 12,13-DiHOME, enriched in NGM3 versus lower-risk NGM states, recapitulated the effect of NGM3 fecal water on relative CD4CD25 forkhead box P3 (FOXP3)$^+$ cell abundance. These findings suggest that neonatal gut microbiome dysbiosis might promote $CD4^+$ T cell dysfunction associated with childhood atopy.

Atopy, the propensity to produce IgE antibodies in response to allergens, is one of the most common chronic health issues[2] and is considered to be a substantial risk factor for childhood asthma development[3]. Recently, the condition has been linked to bacterial taxonomic depletions in the human gut microbiota at 3 months, but not at 12 months, of age[1]. We therefore hypothesized that compositionally and functionally distinct neonatal (~1 month of age) gut microbiota states exist, and that their associated products idiosyncratically influence $CD4^+$ populations in a manner that relates to the RR of atopy and asthma development in childhood. We studied independent fecal samples collected during a study visit that targeted 1 month olds (median age 35 d; range 16-138 d; n=130; 'neonates') or 6 month olds (median age 201 d; range 170-322 d; n=168; 'infants') from participants in the racially and socioeconomically diverse Wayne County Health, Environment, Allergy and Asthma Longitudinal Study birth cohort[4]. Predominantly multisensitized atopy (PM atopy) at age 2 years was defined using latent-class analysis, an unsupervised statistical algorithm that clusters subjects according to their pattern of serum specific-IgE (sIgE) responses to a panel of ten food and aeroallergens[5] (FIG. 26).

At the population level (independently of atopy status), bacterial community α-diversity (taxon number and distribution) expanded with increasing age (Pearson's correlation, r=0.47, P<0.001). In parallel, fungal α-diversity contracted (Pearson's correlation, r=−0.23, P=0.0014), and a reciprocal relationship between these microbial kingdoms existed (Shannon's index; Pearson's correlation, r=−0.24, P<0.001; FIG. 19). Both bacterial and fungal β-diversity (interpersonal taxonomic composition) were related to participant age (PERMANOVA; $R^2$=0.056, P<0.001; and $R^2$=0.034, P<0.001, respectively. Neonatal fecal microbiota were typically dominated by Bifidobacteriaceae, Enterobacteriaceae, Malasseziales (Malassezia) and Saccharomycetales (Saccharomyces). Infant participants exhibited sustained presence, but diminished relative abundance, of Bifidobacteriaceae and Enterobacteriaceae, an expansion of Lachnospiraceae (Blautia and Ruminococcus) and fungal communities characteristically dominated by Saccharomycetales (Saccharomyces and Candida), the dominant fungal order in healthy adults[6]. These findings indicate an interkingdom gut microbial co-evolution along an age-associated developmental gradient over the first year of life.

To address our primary hypothesis, a Dirichlet multinomial mixture (DMM) model was used to group participants on the basis of bacterial-community composition[7]; three distinct NGM states (NGM1, 2 and 3) represented the best model fit (FIG. 23). PERMANOVA confirmed that NGM designation explained a small but nontrivial proportion of bacterial β-diversity (PERMANOVA; $R^2$=0.09, P<0.001), indicating that NGMs [which did not differ in age (Kruskal-Wallis; P=0.256; FIG. 20A)] may represent a gradient of microbiota configurations in early-life. NGMs trended toward having a significant relationship with fungal β-diversity (Bray-Curtis; PERMANOVA, $R^2$=0.037, P=0.068), signifying that each NGM co-associates with a mycobiota that varies primarily in the relative abundance of the dominant fungal taxa present. Infant samples were divisible into two compositionally distinct gut microbiota states, IGM1 (typically Bifidobacteriaceae dominated) and IGM2 (typically Lachnospiraceae dominated (unweighted UniFrac; PERMANOVA, $R^2$=0.032, P=0.001)), which differed in age (Wilcoxon rank-sum, P=0.0257); IGM1 participants were younger. IGM states were not related to fungal community β-diversity (Bray-Curtis; PERMANOVA, $R^2$=0.011, P=0.33), presumably because infant subjects were consistently enriched for Saccharomycetales.

According to the conventional definition of atopy (IgE>0.35 IU/ml), no significant difference in RR between NGM groups was observed (FIG. 21). However, when the asthma-predictive[5] PM atopy definition was used, NGM3 participants incurred a higher RR of atopy at age 2 years, as compared to either NGM1 (RR=2.94, 95% CI 1.42-6.09 P=0.004; FIG. 21) or NGM2 groups (RR=2.06; 95% CI 1.01-4.19, P=0.048; FIG. 21). Even larger effect sizes for NGM3 were observed for RR of parental-reported, doctor-diagnosed asthma at age 4 years (FIG. 21). NGM-associated RR of PM atopy was supported by the sum of specific IgE responses at age 2 years (FIG. 20B). IGM participants did not exhibit different RRs for PM atopy (RR=1.02; 95% CI 0.59-1.75, P=0.94; FIG. 27) or asthma (RR=0.51; 95% CI 0.22-1.17, P=0.11), possibly due to increased age range and microbial heterogeneity within this group. Using available early-life characteristics, we identified factors including season of birth, age at sample collection and breastfeeding to be substantially distinct across IGM states. Detectable dog allergen (Can f 1) concentrations (P=0.045) in the home during the neonatal study visit (lowest in the NGM3 group) and baby gender (NGM3 was almost entirely male) significantly differed across NGMs (P=0.038). Despite adjustment for these and other early-life factors commonly related to allergic disease, the relationship between NGM and atopy or asthma persisted. Only one other large pediatric gut-microbiota atopy study exists[1], the youngest participants of which were substantially older (~100 d) than the neonates in our cohort (median age, 35 d). The application of our DMM model parameters to this data set identified two compositionally distinct groups (Bifidobacteria-dominated NGM1 and Lachnospiraceae-dominated IGM2; indicating that examination of neonatal stool samples is necessary to identify distinct pioneer microbiota related to differential RR.

NGM3 participants were characteristically depleted of bacterial taxa, including Bifidobacteria (Bifidobacteriaceae), Lactobacillus (Lactobacillaceae), Faecalibacterium (Clostridiaceae) and Akkermansia (Verrucomicrobiaceae), when compared with the NGM1 group (zero-inflated negative binomial regression (ZINB), Benjamini-Hochberg, q<0.05). These observations were consistent when NGM3 was compared to NGM2 and also with previously described atopy-associated taxonomic depletions[1]. Mycologically, NGM3 subjects were consistently depleted of multiple Malassezia taxa (ZINB, Benjamini-Hochberg, q<0.20, FIG. 28 and FIG. 29)-striking, given our population-based observation that this genus is characteristically enriched in the neonatal gut microbiota. Fungal taxonomic enrichments in the NGM3 group were also consistent when compared to either of the lower-risk groups, and included Rhodotorula and Candida (FIG. 28 and FIG. 29). Hence, neonatal interkingdom microbiota dysbiosis is characteristic of PM atopy and asthma development in childhood.

NGM3-associated bacterial taxonomic alterations were predicted[8] to result in a deficiency in amino acid, lipid and xenobiotic metabolism pathways. Untargeted liquid chromatography mass spectrometry identified fecal metabolites present in a subset (n=28) of the representative subjects from each NGM (those with the highest posterior probability of NGM membership). Substantial correlations existed between the 16S rRNA profile, predicted metagenome and the metabolome of NGMs (Procrustes; FIG. 30), indicating a deterministic relationship between bacterial community composition and the metabolic microenvironment of the neonatal gut. Between-group comparisons identified specific metabolites enriched in each NGM (Welch's t test; P<0.05). As previously reported from analysis of the urine of subjects with atopy[1], NGM3 participants exhibited fecal enrichment of primary and secondary bile metabolites. However, more expansive metabolic dysfunction, involving lipid, amino acid, carbohydrate, peptide, xenobiotic, nucleotide, vitamin and energy metabolism pathways—essentially, the bacterial pathways predicted to be deficient in NGM3—was evident. Although the NGM1 and NGM2 groups exhibited distinct metabolic programs, a common subset of metabolites differentiated them from NGM3. These included anti-inflammatory polyunsaturated fatty acids, docosapentaenoate (n3 DPA; 22 n5) and dihomo-γ-linolenate[9,10] (DGLA; 20:3n3 or n6), succinate and the breast-milk oligosaccharides, 3-fucosyllactose and lacto-N-fucopentaose II, which are known to influence gut epithelial colonization[11,12]. By contrast, NGM3 participants were consistently enriched for 12,13-DiHOME, stigma- and sitosterols, 8-hydroxyoctanoate, α-CEHC and γ-tocopherol.

Sterile fecal water from NGM3 participants (compared to that from NGM1), decreased the ratio of $CD4^+IFN\gamma^+$:$CD4^+IL-4^+$ cells (linear mixed-effects model (LME), P=0.095; FIG. 24), increased the proportion of $CD4^+IL-4^+$ cells (LME, P<0.001; FIG. 22A) and the concentration of IL-4 released (LME, P=0.045; FIG. 22B) and reduced the percentage of CD4$^+$CD25$^+$FOXP3$^+$ cells (compared with control; LME, P<0.017; FIG. 22C) ex vivo, indicating that the NGM3 gut microenvironment promotes adaptive immune dysfunction associated with established atopic asthma. Weighted correlation network analysis identified 32 metabolic modules, one of which discriminated the three NGMs (ANOVA; P=0.038; FIG. 22D) and contained 12,13-DiHOME, which was identified both as a hub metabolite (highest module membership (MM) value=0.91; FIG. 22E) and most NGM-discriminatory (highest MM to metabolite significance correlation (r=0.86, P<0.001; FIG. 22E). An observation supported by its relative enrichment in NGM3 subjects compared to NGM1 and NGM2 (P<0.05 for both; FIG. 25). All concentrations of 12,13-DiHOME examined reduced the proportion of CD4$^+$CD25$^+$FOXP3$^+$ cells, compared with vehicle treatment (LME, P=0.04, P<0.001, P=0.001 respectively; FIG. 22F).

These findings indicate that neonatal gut microbiota influences susceptibility to childhood allergic asthma, potentially via alterations in the gut microenvironment that influence CD4$^+$ T cell populations and function. This suggests that very early-life interventions to manipulate the composition and function of the gut microbiome might offer a viable strategy for disease prevention.

Methods

Accession codes. All sequence data related to this study are available from the European Nucleotide Archive (ENA) under accession number PRJEB13896. Additional information is available in Fujimura et al. 2016.

Study Population. Pregnant women (n=1,258) between the ages of 21 and 49 were recruited from August 2003-November 2007 as part of the Wayne County Health, Environment, Allergy and Asthma Longitudinal Study (WHEALS). WHEALS is a prospective birth cohort from southeastern Michigan designed to investigate early-life risk factors for allergic diseases, as previously described[4]. Briefly, women were considered eligible if they lived in a predefined cluster of contiguous zip codes in and surrounding Detroit, Mich., had no intention of moving out of the area and provided informed written consent. Five follow-up interviews were conducted at 1, 6, 12, 24 and 48 months after the birth of their child, with the 24-month appointment being at a standardized study clinic so that the child could be evaluated by a board-certified allergist. Stool samples were collected from the child at the 1- and 6-month home visits. All aspects of this research were approved by the Henry Ford Hospital Institutional Review Board.

Sample criteria of WHEALS subjects for stool microbiome analyses. For this study, we selected children who had completed their 24-month clinic visit, which included a blood draw for IgE measurements, and had had dust samples collected from their homes at the same time as their stool-sample collection (in =308). Stool samples from children ranging from age 1-11 months were collected from field staff during home visits and stored at −80° C. Samples were randomized before being shipped to the University of California, San Francisco (UCSF), on dry ice, where they were also stored at −80° C. until processed.

PM-atopy and asthma definition. Blood drawn at the 2-year clinic visit was used to determine participants' levels of total and ten allergen-specific IgEs (sIgE): *Alternaria* (*Alternaria alternata*), German cockroach (*Blattella germanica* Bla g 2), dog (*Canis lupus familiaris* Can f 1), house dust mites (*Dermatophagoides farinae* Der f 1), hen's egg (egg), cat (*Felis domesticus* Fel d 1), cow's milk (milk), peanut (*Arachis hypogaea*), common ragweed (*Ambrosia artemisiifolia*) and Timothy grass (*Phleum pratense*). Specific IgEs were measured using the Pharmacia UniCAP system (ThermoFisher Scientific, Waltham, Mass., USA). Latent class analysis was used to group participants into four discrete atopic classes according to sensitization patterns of the ten allergen sIgEs, as with the entire WHEALS cohort[5]. Our subset was assigned to one of four latent classes: (i) Low or no sensitization (in =226); (ii) highly sensitized (both food and inhalant allergens; n=9); (iii) milk- and egg-dominated (n=50) sensitization or (iv) peanut- and inhalant(s)-dominated (n=13) sensitization. Because of the sample size, latent classes ii-iv were collapsed and considered to be "predominately multisensitized" (PM atopy; n=72); remaining subjects represented the "low or no sensitization" group. The conventional definition of atopy (at least one positive test (sIgE≥0.35 IU ml$^{-1}$) to any of the ten allergens) was also used for comparative purposes. Children were defined as having asthma according to parental-reported doctor diagnosis of asthma at the 4-year interview.

Bacterial- and fungal-community profiling, PICRUSt and metabolomic analyses. DNA extraction. Stool samples from 308 infants were extracted by using a modified cetyltrimethylammonium bromide (CTAB)-buffer-based protocol[13]. Briefly, 0.5 ml of modified CTAB extraction buffer were added to 25 mg of stool in a 2-ml Lysing Matrix E tube (MP Biomedicals, Santa Ana, Calif.) and then incubated (65° C., 15 min). Samples were bead-beaten (5.5 m s$^{-1}$, 30 s) in a Fastprep-24 (MP Biomedicals, Santa Ana, Calif.), which was followed by the addition of 0.5 ml of phenol:chloroform:isoamyl alcohol (25:24:1). After centrifugation (14, 000 rpm, 5 min), the supernatant was added to a heavy phase-lock gel tube (5 Prime, Gaithersburg, Md.), and chloroform (v:v) was added. Samples were centrifuged (14,000 rpm, 5 min), and the resulting supernatants were added to fresh tubes, which was followed by the addition of 1 µl of linear acrylamide before PEG-NaCl (2v:v). Samples were incubated (21° C., 2 h), washed with 70% EtOH and resuspended in 10 mM Tris-Cl, pH 8.5.

Sequencing preparation. The V4 region of the 16S rRNA gene was amplified, as designed by Caporaso et al.[14]. PCR reactions were performed in 25-µl reactions using 0.025 U Takara Hot Start ExTaq (Takara Mirus Bio Inc, Madison, Wis.), 1× Takara buffer with MgCl$_2$, 0.4 pmol/µl of F515 and R806 primers, 0.56 mg/ml of bovine serum albumin (BSA; Roche Applied Science, Indianapolis, Ind.), 200 µM of dNTPs and 10 ng of gDNA. Reactions were performed in triplicate with the following: initial denaturation (98° C., 2 min), 30 cycles of 98° C. (20 s), annealing at 50° C. (30 s), extension at 72° C. (45 s) and final extension at 72° C. (10 min). Amplicons were pooled and verified using a 2% TBE agarose e-gel (Life Technologies, Grand Island, N.Y.), before undergoing purification using AMPure SPRI beads (Beckman Coulter, Brea, Calif.), being quality checked with the Bioanalyzer DNA 1000 Kit (Agilent, Santa Clara, Calif.) and being quantified using the Qubit 2.0 Fluorometer and the dsDNA HS Assay Kit (Life Technologies, Grand Island, N.Y.). Samples were pooled and sequenced on the Illumina MiSeq platform, as previously described[15].

The internal transcribed spacer region 2 (ITS2) of the rRNA gene was amplified using the primer pair fITS7 (5'-GTGARTCATCGAATCTTTG-3') (SEQ ID NO:7) and ITS4 (5'-TCCTCCGCTTATTGATATGC-3') (SEQ ID NO:8) Primers were designed for the Illumina MiSeq platform, as described above. PCR reactions were performed in triplicate in a 25-µl reaction with 1× Takara buffer (Takara Mirus Bio), 200 nM of each primer, 200 µM dNTPs, 2.75 mM of MgCl$_2$, 0.56 mg ml$^{-1}$ of BSA (Roche Applied Science, Indianapolis, Ind.), 0.025 U Takara Hot Start ExTaq and 50 ng of gDNA.

Reactions were conducted under the following conditions: initial denaturation (94° C., 5 min), 30 cycles of 94° C. (30 s), annealing at 54° C. (30 s), extension at 72° C. (30 s) and a final extension at 72° C. (7 min). PCR verification and purification were performed as described above. Samples were quantified using KAPA SYBR (KAPA Biosystems, Wilmington, Mass.) qPCR, following the manufacturer's protocol. Samples were pooled in equal moles (50 ng), and prepped and denatured libraries with PhiX spike-in control, as described above, were loaded onto the Illumina MiSeq cartridge.

Sequencing-data processing and quality control. For bacterial sequences, paired-end sequences were assembled using FLASH[16] v.1.2.7 and de-multiplexed by barcode, and low-quality reads (Q score, <30) were discarded in QIIME[17] 1.8. If three consecutive bases were <Q30, then the read was truncated and the resulting read retained in the data set only if it was at least 75% of the original length. Sequences were checked for chimeras using UCHIME[18] and filtered from the data set before operational taxonomic unit (OTU) picking at 97% sequence identification using UCLUST[19] against the Greengenes database[20] version 13_5. In embodiments, closely related microorganisms are grouped together based on sequence similarity thresholds (e.g., 97%). OTUs represent a user defined cut off for 16S rRNA sequence identity e.g. 97% identity; all sequences that share at least 97% sequence identity across the sequenced region of the gene form a single OTU. Sequencing reads that failed to cluster with a reference sequence were clustered de novo. Sequences were aligned using PyNAST[21], and taxonomy was assigned using the RDP classifier and Greengenes reference database version[20] 13_5. To de-noise the OTU table, taxa with fewer than five total sequences across all samples were removed. A bacterial phylogenetic tree was built using FastTree[22] 2.1.3.

Fungal sequences were quality trimmed (Q score, <25) and adaptor sequences removed using cutadapt[23], after which paired-end reads were assembled with FLASH[16]. Sequences were demultiplexed by barcode and truncated to 150 bp before undergoing clustering using USEARCH vers. 7 pipeline, specifically the UPARSE[24] function, and being chimera-checked using UCHIME. Taxonomy was assigned using UNITE[25] vers. 6.

To normalize variation in read depth across samples, data were rarefied to the minimum read depth of 202,367 sequences per sample for bacteria (n=298) and 30,590 for fungi (n=188). To ensure that a truly representative community was used for analysis for each sample, sequence subsampling at these defined depths was rarefied 100 times. The representative community composition for each sample was defined as that which exhibited the minimum average Euclidean distance to all other OTU vectors generated from all subsamplings for that particular sample. Investigators at UCSF were blinded to sample identity until microbiota data sets underwent the aforementioned processing and were ready for statistical analyses.

Phylogenetic Reconstruction of Unobserved States (PICRUSt).

PICRUSt[8] was used to predict the pathways of those taxa significantly enriched in each NGM state, according to zero-inflated negative binomial regression and corrected for multiple testing using the Benjamini-Hochberg false-discovery rate[26](q<0.05). These taxa were used to generate a new OTU table normalized in PICRUSt, and discriminatory pathways were illustrated in a heat map constructed in R.

Metabolomic Profiling.

Stool samples (200 mg) from each of the three microbiota states, eight NGM3 subjects, and ten from each of NGM1 and NGM2 groups were provided to Metabolon (Durham, N.C.) for ultrahigh performance liquid chromatography-tandem mass spectrometry (UPLC-MS/MS) and gas chromatography-mass spectrometry (GC-MS) using their standard protocol (on the World Wide Web.metabolon.com/). These samples were chosen because they exhibited the highest posterior probability of belonging to a given NGM group and possessed sufficient sample volume for UPLC-MS/MS analysis. Compounds were compared to Metabolon's in-house library of purified standards, which includes more than 3,300 commercially available compounds.

Ex vivo dendritic cell challenge and T cell co-culture. Fecal samples from five of ten NGM1 and seven of eight NGM3 neonates that had undergone metabolic profiling were used (biological replicates). Excluded samples from these groups had insufficient volume for analyses. Fecal samples were homogenized 1 g ml$^{-1}$ (w:v) in pre-warmed phosphate-buffered saline (PBS) containing 20% FBS (FBS). Samples were vortexed, incubated (37° C., 10 min) and centrifuged (14,000 rpm, 30 min). Supernatant was filter-sterilized through a 0.2-μm filter before being used in the dendritic cell (DC) T cell assay described below. PBS was used as the negative control. Treatment conditions used for the DiHOME experiment included: 75 μM, 130 μM and 200 μM 12,13 DiHOME (Cayman Chemical, Ann Arbor, Mich.) solubilized in 0.4%, 0.15% and 0.05% DMSO, respectively. DiHOME solutions were added to R10 media (Roswell Park Memorial Institute media 1640 with 10% heat-inactivated FBS (antigen activator) and 2 mM 1-glutamine and 100 U ml$^{-1}$ penicillin-streptomycin added; Life Technologies) and exposed to DCs within 1 h of preparation. Controls included PBS and DMSO (delivered in R10 media) at corresponding percentages used to dissolve the different concentrations of DiHOME. Treatment group size was determined on the basis of preliminary assays that demonstrated the effect size for the suppression of CD4$^+$CD25$^+$ FOXP3$^+$ using 130 μM of 12,13 DiHOME was approximately seven, indicating that at least two samples per group were required to achieve a power of >0.80.

Peripheral blood mononuclear cells (PBMCs) were purified from plasma obtained from healthy, de-identified human donors (Blood Centers of the Pacific, San Francisco, Calif.) through the cell-sourcing program that ensures donor confidentiality. Donors signed an agreement acknowledging that their blood may be used for research. PBMCs were isolated using Ficoll-Hypaque gradient centrifugation, washed twice with R10 media and incubated for 18 h. Dendritic cells (DCs) were isolated from PBMCs using the EasySep Human Pan-DC Pre-Enrichment Kit (STEMCELL Technologies, Vancouver, BC). DCs (0.5×10$^6$ cells ml$^{-1}$) from two donors (biological replication) were treated in triplicate (treatment replicate) with either cell-free fecal water (0.22 μM filtered) or varying concentrations of DiHOME, and cultured in R10 media supplemented with 10 ng ml$^{-1}$ GM-CSF and 20 ng ml$^{-1}$ IL-4 at 37° C.[27] for 2 d, for the fecal-water assay, or 5 d, for the DiHOME experiment. For the DiHOME experiment, freshly prepared media containing DiHOME or control exposures was replaced every 48 h. For the fecal-water experiment, the assay was repeated twice on one donor (technical replicates) and once on donor B owing to insufficient numbers of cells recovered from the latter donor. Treatment replicates were also considered biological replicates because the human donor cells are not clonal.

Twenty-four hours before co-culture with CD4$^+$ T cells, DC maturation was stimulated by using DC growth mediators (10 ng ml$^{-1}$ tumor nuclear factor-α [(TNF-α), 10 ng ml$^{-1}$ IL-1b, 10 ng ml$^{-1}$ IL-6 and 1 mM prostaglandin E2 (PGE2)]. In preparation for co-culture, DCs were washed in fresh R10 media, counted via flow cytometry and plated in TexMACs Medium (Miltenyi Biotec, San Diego, Calif.) at 0.5×10$^6$ live CD45$^+$ cells per well.

Autologous T lymphocytes were purified from the PBMCs using a naïve CD4$^+$ T cell isolation kit (Miltenyi Biotec). After purification, naïve autologous CD4$^+$ T cells were suspended in the TexMACS Medium (Miltenyi Biotec) and added to the treated DCs at a ratio of 10:1 in the presence of soluble anti-CD28 and anti-CD49d (1 mg ml$^{-1}$). T and DC cells were co-cultured for 5 d at 37° C. and replenished with fresh TexMACS media every 48 h. To assess cytokine production, the co-cultures were mixed with Phorbol Myristate Acetate-Ionomycin (SIGSa, St. Louis, Mo.) and GolgiPlug (Gplug; BD Biosciences, San Jose, Calif.) for 16 h before flow cytometry. Cell-free media from the co-cultures was collected at 48 h and 5 d, before PMA-Gplug addition, to assess cytokine secretion. Cytokine secretion was evaluated by cytometric bead array, following the manufacturer's protocol (BD Biosciences).

For flow cytometry, single-cell suspensions were stained using a panel of antibodies, including anti-CD3 (SP34-2, 1:100), anti-CD4 (L200, 1:100), anti-CD25 (M-A251, 1:25), anti-IFN-γ (B27, 1:200; BD Biosciences); anti-CD8a (RPA-T8, 1:100; BioLegend, San Diego, Calif.); anti-IL4 (7A3-3, 1:20; Miltenyi Biotec); anti-IL-17A (64DEC17, 1:20) and anti-FOXP3 (PCH101, 1:20; Affymetrix eBioscience, Santa Clara, Calif.). Validation for each primary antibody is provided on the manufacturers' websites. Dead cells were stained positive with LIVE-DEAD Aqua Dead Cell Stain (Life Technologies). Permeabilization buffer (Affymetrix eBioscience) was used to permeabilize cells before staining for the intracellular markers IFN-γ, IL-4, IL-17A and FoxP3. For flow analysis, live T cells were gated as CD3$^+$CD4$^+$ cells, wells containing <50% live cells were excluded from analyses. Among CD4$^+$ T cell subpopulations, T helper 1 (Th1) were IFN-γ, T helper 2 (Th2) were IL-4$^+$; T helper 17 (Th17) were IL-17A$^+$, and T regulatory (T reg) cells were both CD25$^{hi}$ and FOXP3$^{hi}$. Stained cells were assayed via a flow cytometer on a BD LSR II (BD Biosciences).

Statistical analysis. Shannon's diversity index was calculated using QIIME. Pearson's correlation was used to test for a relationship between bacterial and fungal Shannon's diversity. Distance matrices (unweighted UniFrac[28] and Bray-Curtis) were calculated in QIIME to assess compositional dissimilarity between samples, and visualized using PCoA plots constructed in Emperor[29]. Permutational multivariate analysis of variance (PERMANOVA) was performed using Adonis in the R environment to determine factors that significantly (P<0.05) explained variation in microbiota β-diversity.

To identify clusters of subjects on the basis of bacterial-taxonomy, DMM models were used, which implement an unsupervised Bayesian approach that is based on a Dirichlet prior[7]. The best-fitting DMM model was determined using the Laplace approximation to the negative-log model evidence, testing up to ten underlying microbiota states. Each sample was assigned to a particular neonatal gut microbiota (NGM) state on the basis of the maximum posterior probability of NGM membership. Kruskal-Wallis was used to test whether age differentiated the microbiota states. Relative risk (RR) ratios and corresponding 95% confidence intervals were calculated using PROC GENMOD in SAS version 9.4 (Cary, N.C.). Unadjusted and adjusted RRs were calculated on the basis of log-binomial regression using maximum likelihood estimation or robust Poisson regression, when prevalence ratios were near one or when the log-binomial model did not converge. Two-tailed Welch's t test was used to test whether sIgE concentrations (log-transformed) were significantly different between the three NGM states.

To determine which OTUs differed in relative abundance between NGM groups, the zero-inflated negative binomial regression (pscl package) was used as a primary modeling strategy, appropriate for sequence-count data. In cases in which OTU distributions were not zero-inflated and the model failed to converge, the standard negative binomial was used as a secondary modeling strategy. These were corrected for multiple testing using the minimum positive false-discovery rate (q<0.05 for bacteria; q<0.20 for fungi) [26]. Results were natural-log transformed for illustration on phylogenetic trees using iTOL[30] v.3.0. When examining the association between early-life factors and NGMs, P values were calculated on the basis of covariate distribution by ANOVA (numerical, normally distributed), Kruskal-Wallis (numerical, skewed), chi-square (categorical) or Fisher's exact (sparse categorical). Log-binomial-regression model was used to test for confounding factors when assessing the RR of individuals with different microbiota states developing atopy or asthma (PROC GENMOD in SAS version 9.4). Fisher's exact two-tailed test was conducted to test whether breastfeeding was practiced significantly (P<0.05) more often in any particular NGM.

Metabolites exhibiting significantly (P<0.05) different concentrations (log-transformed) between lower-risk NGM states and NGM3 were identified using two-tailed Welch's t test. Shared and distinct super- and sub-pathway products among NGMs were illustrated using Cytoscape, vers. 3.2.1 (ref. 31). Co-occurrence networks of metabolites were constructed using weighted correlation network analysis (WGCNA) with the R package WGCNA to find modules of highly interconnected, mutually exclusive metabolites. Pearson correlations were used to determine intermetabolite relationships, wherein modules are composed of positively correlated metabolites. To avoid spurious modules, the minimum module size was set to five. Module 'eigenmetabolites' (referred to as eigengenes) were defined as the first principal component of a given module and considered as a representative measure of the joint metabolic profile of that module. Each eigenmetabolite was used to test (ANOVA) the association between its respective module and NGM, module membership was used to determine the interconnectedness of each metabolite to its assigned module and to identify 'hub' metabolites: this was defined as the correlation between each metabolite and the eigenmetabolite (strong positive values indicate high interconnectedness).

Procrustes was used to test for concurrence between communities described by 16S phylogeny, PICRUSt and metabolomics data sets.

To test for T cell and cytokine differences, a linear mixed-effects model (LME) was used (R package lmerTest) and adjusted for donors. Except where indicated, all analyses were conducted in the R statistical programming language.

AOP: Differences in the composition of the gut microbiota of infants associate with relative risk of atopy in childhood, and metabolites linked with these distinct microbial states alter T cell differentiation in vitro.

Issue: Differences in the composition of the gut microbiota of infants associate with relative risk of atopy in childhood, and metabolites linked with these distinct microbial states alter T cell differentiation in vitro.

Gut microbiota-state validation in an independent cohort. To assess the validity of our DMM modeling, the published 16S rRNA fecal data of Arrieta et al.[1] was used (n=319 independent fecal samples collected at approximately 3-12 months of age in the Canadian Healthy Infant Longitudinal Development (CHILD) Study). The specific age of each participant was unavailable and the youngest participants in this cohort were 3 months of age, substantially older than neonates in the WHEALS cohort. Hence the dataset could not be segregated into samples that were > or <6 months of age, as had been performed for our Wayne County Health, Environment, Allergy and Asthma Longitudinal Study (WHEALS) cohort. This limited our capacity to identify neonatal microbiota states associated with subsequent childhood atopy and asthma outcomes. Nonetheless, we used the cohort to determine whether any of the microbiota states identified in our study were replicated in the CHILD cohort. Because of the age range of the CHILD cohort, we applied both our NGM and IGM model parameters to the entire data set. A better model fit (i.e., smaller laplace approximation to the negative log model evidence) was obtained when the CHILD data was fit to the NGM model compared with the IGM model (model fit: 32,502 versus 174,610, respectively) and a two-group solution represented the best fit for the CHILD data. Group 1 (G1) included 221 (69%) participants and group 2 (G2) 98 (31%). The posterior probabilities were on average higher for G1 compared to G2 (0.98 vs. 0.95, respectively). Consistent with our findings, CHILD participants assigned to G1 were typically defined by high *Bifidobacteriaceae* relative abundance (average relative abundance (aRA): 75%). G2 participants were characterized by *Lachnospiraceae* (aRA: 39%), *Clostridiaceae* (aRA: 290%), and Ruminococcaceae (aRA: 12°%), more reflective of the IGM2 cluster identified in our cohort.

Code Availability.

The following script may be used to calculate a representative multiply rarefied OTU table from an unrarefied OTU table, an alterative to singly rarefied tables. This approach stabilizes the effect of random sampling and results in an OTU table that is more representative of community composition. Multiple single-rarefied OTU tables are calculated for each sample, and the distance between the subject-specific rarefied vectors calculated. The rarefied vector that is the minimum average (or median) distance from itself to all other rarefied vectors is considered the most representative for that subject and used to represent community composition for that sample in the resulting multiply-rarified OTU table.

```
library(vegan) library(GUNifFrac)
Parameters
# specify the raw OTU count table, with samples=rows,
taxa=columns # rawtab=otu_tab_t
# specify the depth you would like to rarefy your tables to
the default is to just use the minimum sequencing # depth
raredepth=min(rowSums(rawtab))
# specify the number of rarefied tables you would like to
generate to calculate your representative rarefied # table
from ntables=100
# specify the distance measure to use to calculate distance
between rarefied data sets, for each subject
# can be any of the methods available in the vegdist function
of vegan distmethod="euclidean"
# specify the method to summarize across distances if mean
distance, then summarymeasure=mean
# if median distance, then summarymeasure=median
# summarymeasure=mean
# specify the seed start for the rarefied tables
# for each subsequent table, 1 will be added that the previous
seed
# for reproducibility, always save your seedstart value (or
just use the default for simplicity).
# seedstart=500
# specify if you want progress updates to be printed #
verbose
=TRUE ## returns a representative rarefied OTU table of
class matrix.## functions
reprare<-function(rawtab=otu_tab_t, raredepth=min(row-
Sums(otu_tab_t)), ntables=100, distmethod="euclidean",
summarymeasure=mean, seedstart=500, verbose=TRUE) {
raretabs=list( )
for (z in 1:ntables) {
if (verbose==TRUE) {
print(paste("calculating rarefied table number", z, sep=" "))
}
set.seed(seedstart+z)
raretabs[[z]]=Rarefy(rawtab, depth=raredepth)[[1]]
}
raretabsa=array(unlist(raretabs), dim=c(nrow(raretabs[[z]]),
ncol(rawtab), ntables))
final_tab=c( )
for (y in 1:nrow(raretabs[[z]])) {
if (verbose==TRUE) {
print(paste("determining rep rarefied vector for subject
number", y, sep=" "))
}
distmat=as.matrix(vegdist(t(raretabsa[y,]),
method=distmethod)) # distance across reps for subject y
distsummary=apply(distmat, 2, summarymeasure)
whichbestrep=which(distsummary==min(distsummary))[1]
# the best rep is the one with the minimum average/median
distance to all other reps. (in case of ties, just select the first)
bestrep=raretabsa[y, whichbestrep] # select that rep only for
subject y
final_tab=rbind(final_tab, bestrep) # build that rep for sub-
ject y into final table
}
rownames(final_tab)=rownames(raretabs[[z]])
colnames(final_tab)=colnames(rawtab)
return(final_tab)
}
example runs of the function: ######
dummy data set for example ###
ntaxa=200
nsubj=50
set.seed(444)
dummyOTU<-matrix(sample(0:500, ntaxa*nsubj, prob=c
(0, 7, 0, 1, 0.1, rep(0.1/498, 498)),
replace=TRUE), ncol=ntaxa)
colnames(dummyOTU)=paste("OTU", 1:ntaxa, sep=" ")
rownames(dummyOTU)=paste("subj", 1:nsubj, sep=" ")
sort(rowSums(dummyOTU)) # sequencing depth is uneven
# specify the minimum depth
repraretable=reprare(rawtab=dummyOTU, raredepth=min
(rowSums(dummyOTU)),
ntables=100, distmethod="euclidean",
summarymeasure=mean, seedstart=500, verbose=TRUE)
dim(repraretable)
sort(rowSums(repraretable)) # sequencing depth is now
even
# specify a depth other than the minimum
repraretable=reprare(rawtab=dummyOTU, raredepth=3380,
ntables=100, distmethod="euclidean",
summarymeasure=mean, seedstart=500, verbose=TRUE)
``` dim(repraretable) # subjects with less than the minimum are no longer in the table
sort(rowSums(repraretable)) # sequencing depth is now even Example 5: Disease Severity and Immune Activity Relate to Distinct Interkingdom Gut Microbiome States in Ethnically Distinct Ulcerative Colitis Patients Significant gut microbiota heterogeneity exists among ulcerative *colitis* (UC) patients, though the clinical implications of this variance are unknown. We hypothesized that ethnically distinct UC patients exhibit discrete gut microbiotas with unique metabolic programming that differentially influence immune activity and clinical status. Using parallel 16S rRNA and internal transcribed spacer 2 sequencing of fecal samples (UC, 30; healthy, 13), we corroborated previous observations of UC-associated bacterial diversity depletion and demonstrated significant *Saccharomycetales* expansion as characteristic of UC gut dysbiosis. Furthermore, we identified four distinct microbial community states (MCSs) within our cohort, confirmed their existence in an independent UC cohort, and demonstrated their coassociation with both patient ethnicity and disease severity. Each MCS was uniquely enriched for specific amino acid, carbohydrate, and lipid metabolism pathways and exhibited significant luminal enrichment of the metabolic products of these pathways. Using a novel ex vivo human dendritic cell and T-cell coculture assay, we showed that exposure to fecal water from UC patients caused significant Th2 skewing in $CD4^+$ T-cell populations compared to that of healthy participants. In addition, fecal water from patients in whom their MCS was associated with the highest level of disease severity induced the most dramatic Th2 skewing. In embodiments identification of highly resolved UC subsets based on defined microbial gradients or discrete microbial features are exploited for effective therapies.

Despite years of research, the etiology of UC remains enigmatic. Diagnosis is difficult and the patient population heterogeneous, which represents a significant barrier to the development of more effective, tailored therapy. In this study, we demonstrate the clinical utility of the gut microbiome in stratifying UC patients by identifying the existence of four distinct interkingdom pathogenic microbiotas within the UC patient population that are compositionally and metabolically distinct, co-vary with clinical markers of disease severity, and drive discrete $CD4^+$ T-cell expansions ex vivo. These findings offer new insight into the potential value of the gut microbiome as a tool for subdividing UC patients, opening avenues to the development of more personalized treatment plans and targeted therapies.

Though murine and human studies support the involvement of the gut microbiota in the development and pathogenesis of ulcerative *colitis* (UC; a common form of inflammatory bowel disease [IBD]), a single causative microbial agent has not been identified and depletion of bacterial diversity remains the primary constant feature of UC gut microbiome dysbiosis (1). Increasingly, disease endotypes have been described among patients within clinically defined chronic inflammatory diseases (2), suggesting that, in the context of immune dysfunction, distinct pathogenic processes may converge upon a common clinical disorder. Since UC pathogenesis is related to gut microbiome composition, we rationalized that factors that dictate the composition and function of these communities may lead to the development of distinct gut microbiome states that function as discrete pathogenic units to deterministically influence immune activation status and disease severity.

Host genetics, diet, and environmental exposures, three factors encompassed by ethnicity, influence both the gut microbiome and UC pathology (3). Indeed, healthy subjects in the United States, Venezuela, and Malawi exhibit a significant relationship between ethnicity and both the composition and function of the fecal microbiota, with diet representing strong selective pressure on the gut microbial assemblage (4). Independently, Frank et al. demonstrated that in a U.S. cohort, IBD risk alleles ATG16L1 and NOD2 (associated with autophagy and the host response to microbes, respectively) are significantly associated with gut microbiome β diversity (5). However, a meta-analysis of genome-wide association studies indicated that such UC risk alleles characteristic of Caucasian populations do not confer a heightened risk on ethnically distinct north Indian subjects (6). In embodiments, distinct pathogenic microbiotas exist within UC patients that covary with both patient ethnicity and disease severity. In embodiments, these distinct pathogenic microbiotas exhibit a predictable program of luminal metabolism that induces significantly different degrees of Th2 activation.

Results. Interkingdom gut microbiota perturbations are characteristic of UC patients. Our study population consisted of a cohort of 43 subjects (30 UC patients and 13 healthy subjects) of self-reported European or South Asian (SA) ethnicity. Several studies have examined bacterial community composition in fecal samples from UC patients; however, to date, none have examined the mycobiome of adult UC patients. Using parallel, high-resolution bacterial (16S rRNA) and fungal (internal transcribed spacer 2 [ITS2]) biomarker gene profiles, we confirmed that our ethnically restricted UC population exhibited bacterial microbiota dysbiosis consistent with that previously described (1). Compared to healthy subjects, UC patients had significantly reduced a diversity (P=0.010; FIG. 31A) and were compositionally distinct (permutational multivariate analysis of variance [PERMANOVA]: weighted UniFrac, $R^2$=0.058, P=0.023) (FIG. 31B). Neither fungal α- or β-diversity differed between healthy and UC patients (P=0.523; see FIG. 34A) (PERMANOVA: Bray-Curtis, $R^2$=0.038, P=0.129; see FIG. 34B), indicating that while profound bacterial depletion is characteristic of the UC gut microbiota, more subtle changes in fungal taxonomy characterize these patients.

A total of 165 bacterial taxa were significantly differentially enriched in healthy participants and UC patients. Consistent with previous reports, specific *Bacteroides* and *Prevotella* species and a number of unclassified members of the families *Lachnospiraceae* and Ruminococcaceae were among the bacterial taxa most significantly depleted in UC gut microbiotas (8, 9). UC patients also exhibited enrichment of members of the *Streptococcus, Bifidobacterium*, and *Enterococcus* genera, which was validated by independent phylogenetic microarray profiling of these same samples and confirms previous reports (8, 9). Only a small number of fungal taxa (n=13) exhibited differential relative abundance. UC patients were depleted of *Alternaria alternata, Aspergillus flavus, Aspergillus cibarius*, and *Candida sojae* while being significantly enriched in *Candida albicans* and *Debaryomyces* species. Collectively, these data indicate that the UC-associated gut microbiota is characterized by an interkingdom dysbiosis, highlighted by significant expansion of putatively pathogenic bacterial and fungal species, in the context of depleted bacterial diversity.

UC fecal microbiotas segregate by ethnicity, dominant microbial features, and disease characteristics. We next addressed our hypothesis that ethnicity is associated with distinct interkingdom fecal microbiota in UC patients. Healthy EU and SA participants exhibited no significant difference in bacterial or fungal α diversity (see FIG. 34C and FIG. 34D). However, SA-UC patients consistently exhibited less bacterial diversity than either healthy ethnically matched controls or EU UC patients (see FIG. 34C). They also were significantly depleted of fungal diversity compared to the EU UC group (see FIG. 34D), indicating more severe interkingdom microbiome depletion in these patients, though no difference in clinical disease severity between EU and SA-UC patients was observed (see FIG. 34E). Ethnicity was also significantly associated with bacterial, but not fungal, β diversity when all of the participants were considered (see FIG. 34F and FIG. 34G). Because health status was significantly associated with gut microbial composition (FIG. 31B), it represented a potential confounding factor. We therefore repeated PERMANOVA with only UC patients and showed that, while fungal community composition does not exhibit a significant relationship with patient ethnicity (PERMANOVA: Bray-Curtis, $R^2=0.061$, P=0.107), bacterial β diversity does (PERMANOVA: weighted UniFrac, $R^2=0.075$, P=0.039; FIG. 31C), an observation validated by PhyloChip data (see FIG. 34H). Thus, these data indicate that, despite chronic colonic inflammatory disease, ethnicity remains associated with compositionally distinct bacterial communities in the UC gut, though it explains only a small proportion (7.5%) of the observed variation in β diversity across these patients.

Recent pediatric Crohn's disease studies have demonstrated that patients cluster into subgroups based on patterns of microbial coassociation (10, 11). We next asked whether such patterns exist in our adult UC cohort and relate to patient ethnicity and/or clinical correlates of disease severity. Using hierarchical cluster analysis and multiscale bootstrap resampling, we identified four subgroups of UC patients based on fecal bacterial community composition and termed these microbial community state 1 (MCS1) to MCS4. These distinct patient subgroups were confirmed by PERMANOVA with both 16S rRNA sequence and PhyloChip data (see FIG. 35A and FIG. 35B). MCS distribution differed significantly across ethnicities, with EU UC populations primarily composed of MCS1 and MCS2 while SA UC patients exhibited a relatively equal distribution of all four MCSs (Fisher exact test, P=0.042).

The clinical relevance of grouping patients on the basis of MCSs was assessed by using an intergroup comparison of clinical disease severity (simple clinical *colitis* activity [SCCA] index) (12), extracolonic manifestations (arthritis, pyoderma gangreno-sum, erythema nodosum, and uveitis), the number of first- and second-degree relatives diagnosed with IBD, and duration (years since UC diagnosis). MCS1 patients exhibited more severe disease with higher median SCCA scores, a significant increase in the number extracolonic manifestations, a greater number of first- and second-degree relatives diagnosed with IBD, and longer disease duration (FIG. 32). Though the number of patients in our study is small, these data provide the first indication that distinct pathogenic UC gut microbiotas exist and are associated with clinical features of disease severity.

UC MCSs exhibit distinct taxonomic enrichments, metagenomic capacity, and metabolic productivity. The distribution of microbial taxa across the four UC MCSs was assessed to identify specific bacterial and fungal enrichments characteristic of each. Each MCS typically exhibited a distinct dominant bacterial family (MCS1, Bacteroidaceae; MCS2, *Lachnospiraceae*, Ruminococcaceae; MCS3, Prevotellaceae; MCS4, *Bifidobacteriaceae*). These MCS-specific bacterial enrichments extended beyond the dominant family and were further emphasized when the highest disease severity group (MCS1) was compared to each of the other three groups (MCS2, -3, or -4). Specifically, a majority of the bacterial taxa enriched in MCS1 were members of the *Bacteroides* genus, while the other subgroups were enriched for *Blautia, Ruminococcus* (MCS2), *Prevotella* (MCS3), or *Bifidobacterium* (MCS4, generalized linear models, P<0.05) species. Using the dominant bacterial family as a classifier, we validated the existence of MCS1 and -2 (the two major MCSs in EU UC patients) in two publicly available UC microbiota data sets obtained from patients primarily of European descent (9, 11), indicating that these MCSs are not exclusive to our study but exist in UC patient populations nationwide. Mycologically, *C. albicans* and *Debaryomyces* species were most highly enriched in MCS1 patients compared to each of the other three MCSs (generalized linear models, P<0.05), indicating that interkingdom gut microbiome expansion of *Bacteroides* species, *C. albicans*, and *Debaryomyces* species is associated with more severe UC disease.

To identify microbiota-derived pathways and products characteristic of each MCS that may modulate the host immune response and contribute to clinical disease severity, we performed in silico metagenomic predictions in parallel with broad-spectrum gas and liquid chromatography mass spectrometry of fecal samples. Phylogenetic investigation of communities by reconstruction of unobserved states (PICRUSt; picrust.github.io/picrust/) (13) was used to predict bacterial functional capacity. Presently, this algorithm cannot be used to predict fungal community function. Predicted metabolic capacity varied significantly by MCS (PERMANOVA: Bray-Curtis, $R^2=0.384$, P=0.002). A total of 144 bacterial KEGG pathways discriminated MCS1 to -4, including those involved in amino acid and lipid biosynthesis and metabolism (Kruskal-Wallis test, q<0.0006). Specifically, differential enrichment of glycerolipid, fatty acid, inositol, and multiple amino acid metabolism pathways, including phenylalanine, tyrosine, tryptophan, glutamate, and glutamine, differentiated these groups. We also generated functional predictions for MCS1 and -2 stool samples from the studies of Morgan et al. and Gevers et al. (9, 11). A total of 121 KEGG pathways were differentially enriched between MCS1 and MCS2 in our study; of these, 74 (61.2%) also discriminated MCS1 from MCS2 in both the data sets of Gevers et al. and Morgan et al., indicating a high degree of conserved microbial function associated with MCS1 and -2 across multiple independent studies.

We hypothesized that the predicted functional differences across MCSs would be manifested as distinct programs of luminal metabolism, particularly since the majority of the pathways that differentiated these communities were involved in amino acid and lipid metabolism. Indeed, each MCS exhibited significantly distinct metabolic programs (PERMANOVA: Canberra, $R^2=0.209$, p=0.004) that were significantly related to both the fecal microbiota present (Mantel test, r=0.38, P<0.0001) and its predicted metagenome (Mantel test, r=0.21, P<0.008). We were particularly interested in those luminal metabolites that discriminated the more severe MCS1 from each of the remaining MCSs. Of the 805 metabolites detected across all of the samples, 207 exhibited significant inter-MCS differences in relative concentration (Welch's t test, P<0.05). Compared to MCS groups with lower disease severity, MCS1, as our in silico predictions suggested, was significantly enriched for ophthalmate (a biomarker of increased oxidative stress and depleted glutathione) (14), oxidative-stress-inducing putrescine (15), proinflammatory p-cresol sulfate (16), 9-hydroxyoctadecadienoic acid and (9-HODE) and 13-HODE (a proinflammatory, leukocyte-recruiting monohydroxy fatty acid) (17, 18), and 9,10-dihydroxyoctadecanoic acid (9,10-DiHOME; a neutrophil-recruiting, cytotoxic dihydroxy fatty acid) (19), as well as bioactive lysolipids involved in leukocyte activation (FIG. 33) (18, 20). In contrast, lower disease severity MCSs (MCS2, -3, and -4) were enriched for a range of potentially protective dipeptides (including anti-inflammatory alanyl-glutamine) (21, 22), γ-glutamyl dipeptides indicative of improved oxidative stress coping mechanisms (23), and antioxidant immunosuppressive myo-inositol (24, 25). These observed differences in gut luminal metabolic programming between MCSs associated with high and low UC severities indicate the existence of putative mechanisms to control inflammation in patients with less severe disease.

T-cell activity in vitro is related to MCS and health status. Recent studies have demonstrated that specific gut microbiome-derived metabolites influence Th2 responses (7) and, independently, that proinflammatory cytokine production by T-helper cell populations, including Th2 cells, is a characteristic of UC (26). We therefore hypothesized that the luminal milieus associated with distinct MCSs differentially influence CD4$^+$ T-cell activation in a manner consistent with disease severity. To assess this, we developed an ex vive assay involving coincubation of human dendritic cells (DCs; obtained from healthy donors) with filter-sterilized fecal water prepared from study participants' feces. DCs were then cocultured with autologous CD4$^+$ T cells prior to analyses of T-cell phenotypes and cytokine productivity. Compared to healthy participants, UC patients exhibited a significant reduction in the ratio of Th1 to Th2 cells, significantly increased numbers of both Th1 and Th17 cells, and trends toward increases in both T-regulatory and Th2 cell populations (linear mixed effects, P<0.05) (FIG. 33A-33E). CD8 T-cell subsets did not differ significantly between healthy participants and UC patients (data not shown). These findings suggest that luminal microbial products captured in sterile fecal water contribute to UC by inducing a Th2-skewed expansion of CD4$^+$ T-cell populations.

Figure 33F:
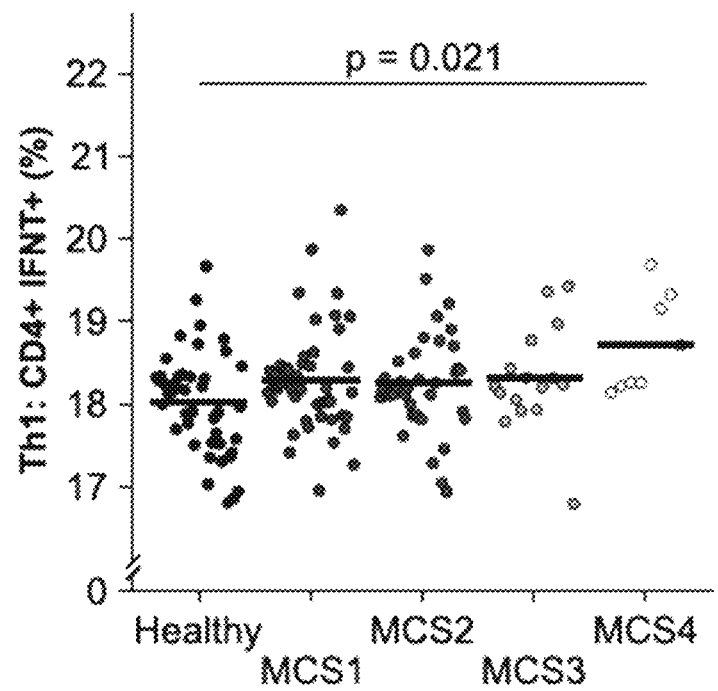
Figure 33G:
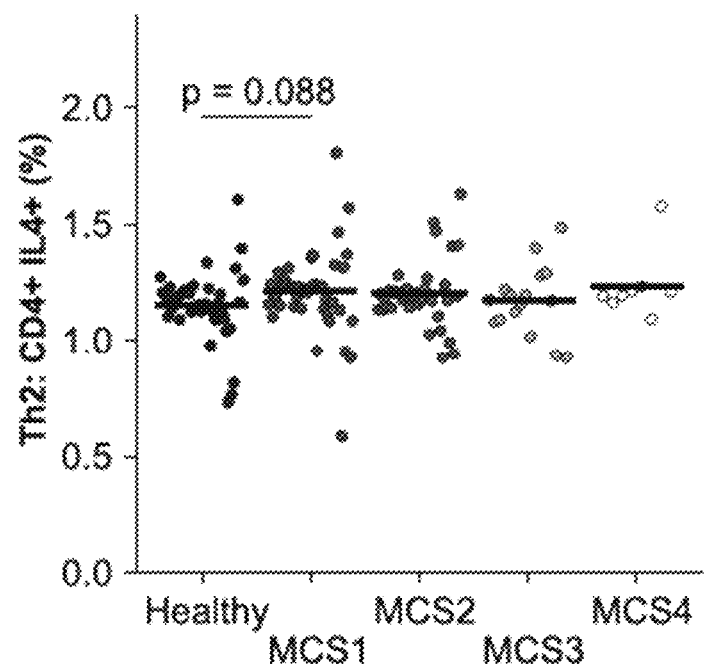
Figure 33H:
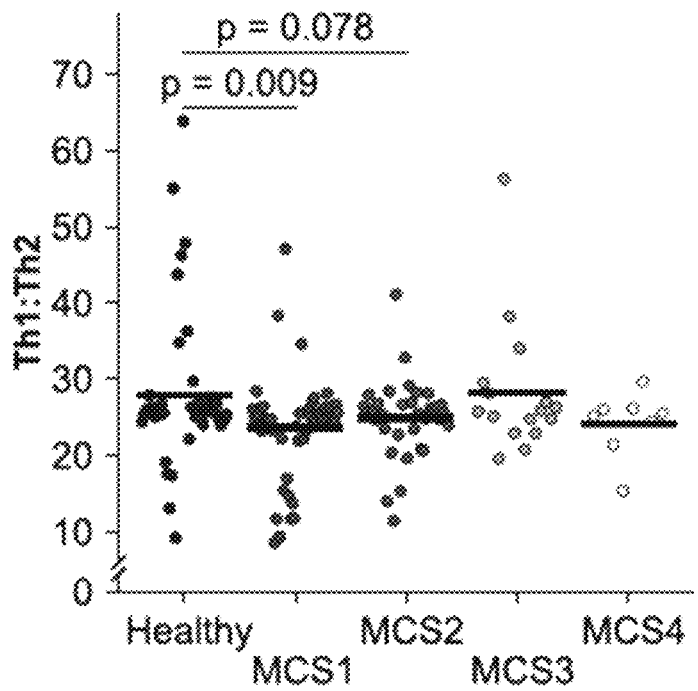
Figure 33I:
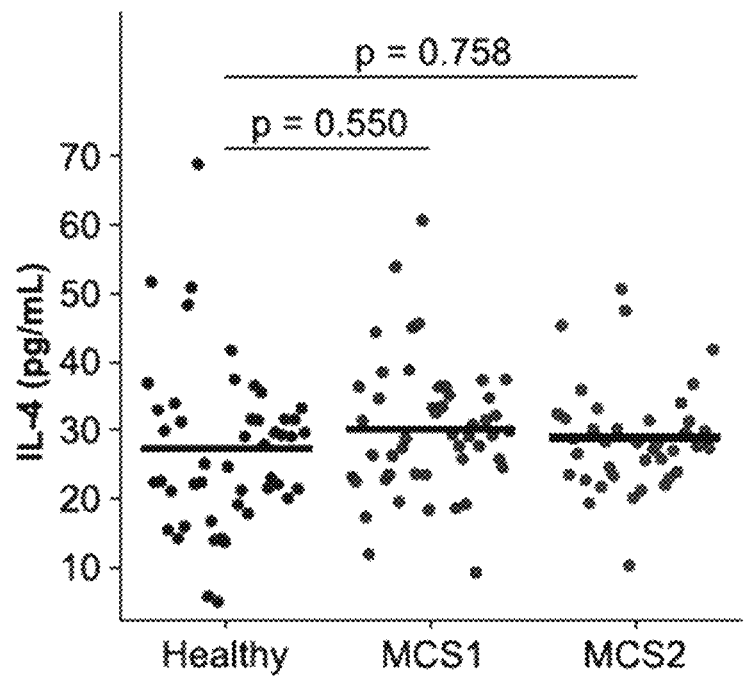
Figure 33J:
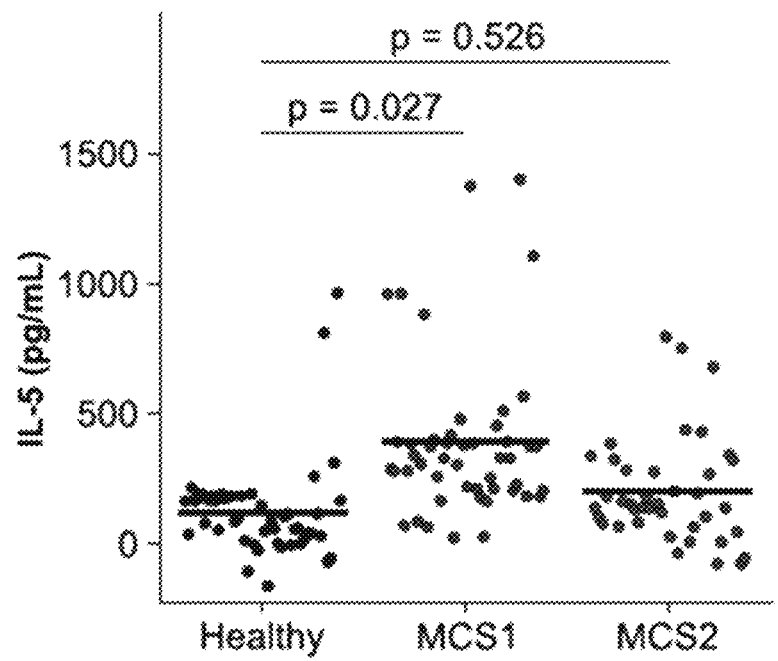
Figure 33K:
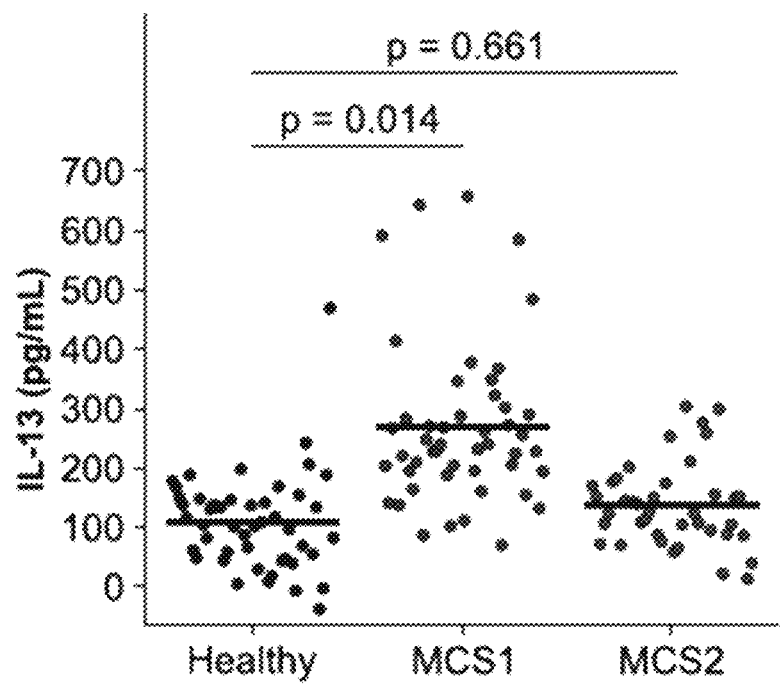

Having demonstrated the Th2-skewing effect of UC-associated fecal water, we next asked if this immune response varied on the basis of MCS and associated differences in symptom severity, focusing specifically on Th1 and Th2 populations. With the exception of a minor significant increase in Th1 populations in response to MCS4 fecal water, no significant differences in overall Th1 or Th2 cell populations were observed between MCS groups and controls (FIG. 33F and FIG. 33G). However, when the Th1-to-Th2 ratio was calculated for each group, the MCS1 group exclusively exhibited a significantly lower Th1-to-Th2 ratio compared with healthy controls (FIG. 33H). Of note, no difference in the Th1-to-Th2 ratio was observed when UC patients were compared on the basis of ethnicity (EU UC versus SA UC, see FIG. 36), providing evidence that patient ethnicity alone is not responsible for the altered T-cell activity observed ex vivo. Furthermore, when considering the two MCSs demonstrating the greatest difference in disease severity (MCS1 and MCS2), only MCS1 fecal water significantly increased secretion of Th2-associated cytokines compared with healthy controls (FIG. 33I-33K). These ex vivo data provide evidence that compositionally and metabolically distinct UC microbiotas are capable of differentially influencing CD4$^+$ T-cell populations in a manner consistent with UC disease severity.

Discussion Heterogeneity among UC patients is poorly understood and represents a significant barrier to more effective therapy. Colitis development necessitates microbial involvement, and gut micro-biome dysbiosis is characteristic of adult UC patients, but while genetic, therapeutic, and environmental factors are related to UC bacterial β diversity, they explain a small proportion of the observed variation in these microbial communities (5, 9). Microbial species engage in inter- and intraspecies interactions that dictate coassociated microbes and their physiology (27, 28). For example, *C. albicans* coaggregates with specific bacterial species in the oral microbiota, facilitating more robust, stress-resistant mixed-species biofilms (27). In turn, the products of these coassociated bacteria induce a physiological shift toward unicellular morphology in *C. albicans* (27). Similarly, because of metabolic cross-feeding, *Streptococcus gordonii* facilitates coassociation with *Fusobacterium nucleatum* (28). Hence, we rationalized that, under the proinflammatory conditions of the colitic gut, distinct patterns of pathogen coassociation occur whose composition and function are relatively conserved across patients and related to immune activation and disease severity. Our data support the existence of four distinct UC MCSs that differ significantly in their prevalence along ethnic divides. Internal and external validation confirmed the existence of the predominant microbiota states, indicating that, despite inherent patient variability, treatment regimens, and geography, conserved patterns of pathogenic microbiota coassociation exist across UC populations within the United States. To improve our understanding of the progression and development of these MCSs, it will be important for future studies to investigate UC patient factors, be they temporal, clinical, genetic, or environmental, that directly drive the microbiome toward these differential microbial states.

Of the four MCSs identified in our study, MCS1 represented the most ill patient group, implicating the composition and metabolism of MCS1 in enhanced immune activation and increased disease severity. MCS1 characteristically exhibited expansion of *Bacteroides* species, which can produce enterotoxin previously associated with UC, stimulate interleukin-8 (IL-8) and tumor necrosis factor alpha (TNF-α) secretion in intestinal epithelial cells, and intensify *colitis* symptoms in a murine model of UC (29-31). MCS1 patients also exhibited the greatest expansion of *C. albicans* and *Debaryomyces* species. Gut microbial expansion of these fungal species has also been described in adult and pediatric Crohn's disease, as well as pediatric IBD (Crohn's disease and UC patients combined) (10, 32, 33). Together with our study, these data indicate that expansion of *Saccharomycetales* fungi in the context of depleted bacterial diversity is a consistent feature of IBD in pediatric and adult populations. Whether *C. albicans* directly influences UC pathology in patients in our study is unclear. However, gastrointestinal colonization by *C. albicans* impairs gastrointestinal healing in both UC patients and a murine model of UC and can induce a Th2 response following gastrointestinal infection of mice with antimicrobial-depleted gut microbiota diversity (34, 35).

The MCS2 subgroup was enriched for both *Blautia* and *Rumi-nococcus* species, which together may produce anti-inflammatory short-chain fatty acids (36-38). *Prevotella* species (enriched in MCS3) are capable of suppressing lymphocyte activity, while *Bifidobacterium* species (enriched in MCS4) can reduce the production of both IL-8 and TNF-α in intestinal epithelial cells (39, 40). It should be noted that one patient in our study, who demonstrated a dramatic enrichment of Porphyromonadaceae (see FIG. 35A and FIG. 35B), was not classified as having one of the four main MCSs identified here and, though removed from our analysis, may represent an additional, clinically relevant MCS that, given additional patient enrollments, future studies may further characterize and draw conclusions from. Though confirmation that the MCSs identified in our study are also present in independent UC microbiome studies indicates the relative durability of these microbial states, their long-term stability cannot be assessed in cross-sectional studies. It is likely that these MCSs represent discrete points along a nonlinear continuum of pathogenic microbial successional states that relate to disease progression and severity, similar to the microbial gradient identified by Gevers et al. in pediatric Crohn's disease (11). Though these cross-sectional studies are informative, more expansive, longitudinal studies are necessary to determine the natural history of the gut microbiome in UC development and progression.

While interkingdom microbial taxonomic states represent an economical means to stratify patients in large studies, the functional capacity and productivity of these compositionally discrete pathogenic microbiota are paramount to dictating host immune responses and clinical disease severity. Indeed, in our study, programs of metabolic productivity idiosyncratic to the predicted pathways encoded by bacteria present in each MCS were identified. In particular, 9-HODE, 13-HODE, 9,10-DiHOME, and lyso-phosphatidylcholines (significantly enriched in MCS1) can increase leukocyte recruitment and proinflammatory cytokine secretion (17-20). Soluble epoxide hydrolase inhibitors, which prevent 9,10-DiHOME formation, attenuate UC in both chemical and genetic murine models (41), underscoring a potential role for these oxylipins as contributors to more severe disease and that treatments inhibiting their production may be especially efficacious in this specific patient subgroup. In addition to enrichment of leukocyte chemotactic metabolites, MCS1 patients also had high fecal concentrations of p-cresol sulfate, a microbe-derived metabolite (42), and putrescine, both of which can stimulate a leukocyte oxidative burst (15, 16). Consistent with these observations, ophthalmate was also enriched in MCS1 patients, indicative of greater oxidative stress due to low or depleted levels of reactive oxygen species (ROS) quenching glutathione (14). While the metabolome of high disease severity MCS1 indicated conditions of high oxidative stress, that of UC MCSs associated with lower disease severity (MCS2 to -4) exhibited an increased capacity for ROS quenching due to enhanced γ-glutamyltransferase activity indicated by enrichment of γ-glutamyl amino acids (critical for maintaining glutathione levels) and high concentrations of superoxide scavenging myo-inositol (23, 24). Metabolic signatures indicative of immunosuppressive activity, such as enrichment of anti-inflammatory dipeptides (i.e., alanyl-glutamine) and myo-inositol (both of which decrease the expression of proinflammatory cytokines and reduce leukocyte recruitment in animal models of colitis) (21, 22, 25), were also observed in MCS2 to −4 with lower disease severity. This suggests that the specific metabolic productivity associated with each MCS may govern host immune activity and resulting differences in UC severity.

MCS-associated luminal products, which include host- and/or microbe-derived immunomodulatory metabolites, provide a multifaceted mechanism by which a pathogenic gut microbiota may influence host physiology and dictate clinical disease severity. Though pathogen-associated molecular patterns (PAMPs) have traditionally been considered paramount to driving host immune responses to microbes, emerging data in the field of immuno-metabolism indicate that microbe-derived metabolites are equally effective in dictating immune cell phenotypes. In addition to the established direct immunomodulatory activity of microbe-derived metabolites such as short-chain fatty acids or p-cresol sulfate (16, 38), recent studies have demonstrated that the gut microbiota-associated metabolites taurine, histamine, and spermine comodulate NLRP6 inflammasome signaling, epithelial IL-18 secretion, and downstream antimicrobial peptide production (43). Indeed, our data suggest that specific programs of microbe-derived metabolism in combination with an array of PAMPs presented by pathogenic bacteria and fungi in the distal gut of UC patients serve as effective drivers of immune dysfunction related to UC disease severity. Support for this concept comes from our demonstration ex vivo that sterile fecal water from the most severely ill MCS1 patients induced the greatest degree of Th2 skewing in T-cell populations and associated cytokine production, a feature not observed among the other subgroups with less severe disease. While this observation does not directly implicate the microbiome as a causative agent of UC, it does provide evidence of the ability of the microbiome to perpetuate the inflammation and symptoms associated with UC in a manner specific to microbiota composition. This finding also indicates that the Th2 skew traditionally considered characteristic of UC patients (26) is not a consistent finding across our cohort and may, in fact, be driven by the most severely ill patients in UC cohorts (i.e., MCS1). Whether or not different inflammatory phenotypes present among UC patients select for phenotype-maintaining microbes or are the result of initial, discrete dysbioses remains to be addressed. Regardless, this raises the possibility that distinct immunological features not examined in this study characterize patients with lower disease activity and distinct gut MCSs. Future larger studies will be important in further characterizing the potential immuno-modulatory contributions of theses MCSs while confirming the observations presented here. Hence, therapies tailored to the specific microbial, metabolic, and immune dysfunctions exhibited by UC patient subgroups may prove a highly efficacious strategy for more effective treatment of this disease.

Materials and Methods. Fecal sample collection and nucleic acid isolation. Stool samples were collected from healthy participants and physician-diagnosed UC patients of either EU or SA ethnicity by using a standardized protocol. Fecal DNA was extracted with a combination of bead beating and the commercially available QIAamp DNA Stool kit (catalog no. 51504; Qiagen, CA).

Bacterial 16S rRNA profiling. Total DNA extracted from fecal samples was used as the template for 16S rRNA gene amplification (in triplicate) with barcoded primers targeting the V4 region as previously described (44). Sequencing libraries were created as previously described (44). Full-length 16S amplicons were also generated and hybridized to the G3 16S rRNA PhyloChip (Affymetrix, CA) as previously described (45).

Fungal ITS2 library preparation. ITS2 sequencing libraries were created with triplicate PCR amplicons per sample.

16S and ITS2 library sequencing Purified sequencing libraries were analyzed with a Bioanalyzer (Agilent), quantified with the Qubit HS ds-DNA Assay kit (Invitrogen), and sequenced with an Illumina MiSeq platform and MiSeq Control Software v2.2.0 according to the manufacturer's instructions (Illumina). FLASH v1.2.7, QIIME 1.8, and usearch software packages were used for sequence read quality filtering, operational taxonomic unit (OTU) picking, and OTU table generation (46-48).

Predicted community metagenome analyses. PICRUSt (picrust.github.io/picrust/) was used to generate in silico bacterial metag-enomes by using 16S rRNA data (13).

Metabolome profiling. To profile fecal metabolites, >200 mg of each frozen stool sample was shipped overnight on dry ice to Metabolon, Inc. (Durham, N.C.), for broad-spectrum gas and liquid chromatography-mass spectrometry.

In vitro DC/T-cell fecal water assay. DCs obtained from anonymous healthy human donors (Blood Centers of the Pacific) were coincubated for 24 h with fecal water prepared from the same fecal samples submitted for metabolite profiling (filter to remove intact cells) prior to stimulation with TNF-$\alpha$, IL-1f3, IL-6, and prostaglandin E2 and incubated for an additional 24 h to induce maturation. DCs were then harvested, washed, and cocultured with autologous T cells at a ratio of 1/10 for 5 days, with medium replenishment every 2 days. The T-cell phenotype was assessed via flow cytometry, and cytokine secretion was assessed by Cytometric Bead Array analysis (BD Biosciences). The assay was repeated in quadruplicate with distinct donors to ensure that observations were not confounded by the peripheral blood mononuclear cell (PBMC) source.

Statistical analysis. (i) Microbial, metagenomic, and metabolomic analyses. Statistical analyses were performed with QIIME v1.8.0 and the R statistical environment (47, 49). For PhyloChip data, fluorescence intensities were log normalized prior to analysis. (ii) Comparison of clinical measurements of disease severity. Clinical measurements of disease severity were compared between UC MCSs by a Kruskal-Wallis test, followed by a pairwise two-tailed Dunn test. (iii) Analysis of T-cell subsets. A linear mixed-effect model was applied with the lme4 package in R to identify significant differences in the abundance of induced T-cell subpopulations based on sample groups (i.e., UC MCSs) while accounting for potential variation introduced by the PBMC source (i.e., donor) (50).

Microarray and nucleotide sequence data accession numbers. All microarray data have been deposited in the Gene Expression Omnibus database (ncbi.nlm.nih.gov/geo) under accession no. GSE78724. All of the sequence data related to this study are available in the Sequence Read Archive database (ncbi.nlm.nih.gov/sra) under accession no. SRP071201.

Fecal sample collection. Study participants were provided detailed instructions and necessary materials for fecal sample collection. Standardized fecal samples (first stool of the morning) were collect at home by defecating onto a sterile stool collection device (Cat. No. Protocult #120; Ability Building Center, MN) placed over a toilet seat and using a sterile collection cup with an attached sterile scoop (Cat. No. 80.734.311; Sarstedt, Germany). Following collection, fecal samples were placed in a pre-paid overnight mailer with a frozen ice pack (Cat. No. S-9902; ULINE, CA) and shipped overnight via USPS in accordance with federal regulations. Upon arrival, fecal sample were immediately stored at −80° C. This study was approved by the Committee on Human Research at the University of California, San Francisco (CHR #10-03092). Physician diagnosed Ulcerative Colitis patients (age 18 to 60 years old) were recruited directly from the gastroenterology clinic at UCSF's Mount Zion Campus. A questionnaire was provided to each patient to assess clinical measures of disease severity [Simple Clinical Colitis Activity index (SCCA), extra-colonic manifestations (arthritis, pyoderma gangrenosum, erythema nodosum, and uveitis), number of first- and second-degree relatives diagnosed with IBD, and duration of disease (years since UC diagnosis)]. Healthy volunteers (age 18 to 60 years old) were drawn from patients' families and by word of mouth. All participants were self-reported to be of either European or South Asian ethnicity (FIG. 37). Additionally, all participants resided within a 70-mile radius of San Francisco, Calif. Any participant experiencing pregnancy or breast feeding, severe concomitant disease involving the liver, heart, lungs or kidneys, or antibiotic treatment within the preceding 2 months were excluded from the study.

Fecal DNA isolation. DNA was extracted from individual fecal samples using a combination of bead beating and the commercially available QIAamp® DNA Stool Kit (Cat. No. 51504; QIAGEN, CA). Initially, 1.6 mL of Buffer ASL was added to approximately 100 mg of feces and bead beat for 30 s at 6.0 m/s in a FastPrep-24 instrument (Cat. No. 116004500; MP Biomedicals). Following bead beating, samples were incubated at 95° C. for 5 minutes to improve lysis efficiency of difficult to lyse microbes. The remainder of the DNA isolation was conducted using a QIAcube (Cat. No. 9001292; QIAGEN, CA) according to the QIAamp® DNA Stool Kit Protocol: Isolation of DNA from Stool for Pathogen Detection. Isolated DNA was stored at −80° C. Blank extractions were included as negative controls to monitor for bacterial contamination.

Bacterial 16S rRNA Gene Library Preparation. Bacterial 16S rRNA gene sequencing libraries were created as previously described (52). PCR amplification of the 16S rRNA gene was conducted in triplicate for each sample using barcoded primers targeting the V4 region as previously described (52). Blank extractions were used as template for negative controls to monitor for 16S rRNA contamination. PCR reactions were performed in 25 µl reactions using 0.025 U Takara Hot Start ExTaq (Takara Mirus Bio Inc, Madison, Wis.), 1× Takara buffer with $MgCl_2$, 0.4 pmol $\mu l^{-1}$ of F515 and R806 primers, 0.56 mg $ml^{-1}$ of bovine serum albumin (BSA; Roche Applied Science, Indianapolis, Ind.), 200 µM of dNTPs, and 10 ng of gDNA. Reactions were performed in triplicate under the following conditions: initial denaturation (98° C. for 2 min) followed by 30 cycles of 98° C. (20 sec), annealing at 50° C. (30 sec), extension at 72° C. (45 sec) and a final extension at 72° C. for 10 min. Following PCR, triplicates were pooled and 16s rRNA amplicon concentrations were determined via gel electrophoresis quantitation. 16S rRNA sequence library was created by pooling all PCR amplicons in equimolar concentrations to a final volume of 75 uL. To remove background, the 16S rRNA sequence library was run on a 2% agarose gel and the 16S amplicon (~380 bp) was purified using the QIAquick Gel Extraction Kit (Cat. No. 28704; QIAGEN, CA). The 16S rRNA primer sequences are provided in Caporaso J G, Lauber C L, Walters W A, Berg-Lyons D, Huntley J, Fierer N, Owens S M, Betley J, Fraser L, Bauer M, Gormley N, Gilbert J A, Smith G, Knight R. 2012. Ultra-high-throughput microbial community analysis on the Illumina HiSeq and MiSeq platforms. ISME J 6:1621-1624. In embodiments, other primer sequences may be used.

Fungal ITS2 Library Preparation. Fungal internal transcribed spacer 2 (ITS2) sequencing libraries were created using similar methods to those used for the 16S rRNA library. PCR amplification of the ITS2 region was conducted in triplicate for each sample using barcoded primers. PCR reactions were performed in 25 µl reaction with 1× Takara buffer (Takara Mirus Bio), 200 nM of each primer, 200 µM dNTPs, 2.75 mM of $MgCl_2$, 0.56 mg $ml^{-1}$ of BSA (Roche Applied Science), 0.025 U Takara Hot Start ExTaq and 50 ng of gDNA. Reactions were conducted under the following conditions: initial denaturation (94° C. for 5 min) followed by 30 cycles of 94° C. (30 sec), annealing at 54° C. (30 sec), extension at 72° C. (30 sec) and a final extension at 72° C. for 7 min. Following PCR, triplicates were pooled and purified using the Agencourt AMPure XP-PCR Purification Kit and associated protocol (Cat. No. A63880, Beckman Coulter). Samples were quantified using the KAPA SYBR FAST qPCR Kit (Cat. No. KK4601, KAPA Biosystems) as recommended by the manufacturers. All purified samples were then pooled in equimolar concentrations based individual sample ITS2 quantification to a final volume of 75 uL.

16S and ITS2 Library Sequencing. Purified sequencing libraries were analyzed using a Bioanalyzer (Aligent), quantified using the Qubit HS dsDNA kit (Invitrogen), and diluted to 2 nM. Diluted sequence libraries were then denatured, diluted to 5.88 pM, and combined with denatured 12.5 pM PhiX spike-in to final concentration of 5 pM. Prepared sequencing libraries were then loaded onto the Illumina MiSeq cartridge (Cat. No. MS-102-3001, Illumina) and sequenced (514 cycles, Read 1: 251 cycles, Index Read: 12 cycles, Read 2: 251 cycles) using a MiSeq platform and MiSeq Control Software v2.2.0 according to the manufacturer's instructions (Illumina). All sequence data related to this study is available in the Sequence Read Archive (SRA) database, ncbi.nlm.nih.gov/sra (accession no. PRJNA313074).

Bacterial 16S rRNA Sequence Processing.

Following paired-end sequencing, paired sequences were assembled using FLASH v1.2.7 with a minimum overlap set at 15 bp (53). Assembled reads were de-multiplexed by barcode and filtered for low quality (Q-score<30) using QIIME 1.8 (54). If the Q-score three consecutive bases were <30, the read was truncated before the low-quality bases. The resulting read was retained in the dataset if it was at least 75% of the original length. Operational taxonomic units (OTUs) were picked at 97% sequence identity using uclust against the GreenGenes 13_8 database (55) (56), retaining OTUs containing >1 sequence read. Reads that failed to hit the reference sequence collection were retained and clustered de novo. Sequences were aligned using PyNAST and taxonomy was assigned using uclust and the GreenGenes 13_8 database (57) (55) (56). PyNAST-aligned sequences were chimera checked using ChimeraSlayer (58), removing putative chimeras and representative sequences that failed PyNAST alignment. A phylogenetic tree was built using FastTree (59). To normalize variation in read depth across samples, data were rarefied to the minimum read depth of 49,518 sequences per sample for bacteria. To ensure that a truly representative community of each sample was used for analysis, sequence sub-sampling at the defined depth was bootstrapped 100 times. The representative community composition for each sample was defined as that which exhibited the minimum average Canberra distance to all other OTU vectors generated from all sub-samplings for that particular sample.

Fungal ITS2 Sequence Processing.

Following paired-end sequencing, paired sequences were assembled using FLASH v1.2.7 with a minimum overlap of 25 bp and a maximum overlap of 290 bp (53). Assembled reads were de-multiplexed by barcode using QIIME 1.8 (54). Assembled reads containing >2 expected errors, as determined by usearch (55), were removed. Singleton reads were removed and OTUs of 97% sequence similarity were generated de novo using usearch8.0 (55). The 8_1_2015 UNITE ITS fungal sequence database and usearch8.0 was used to remove potentially chimeric sequences (60) (55). The ITSx software package was then used to extract the predicted ITS2 region from the reference sequence of non-chimeric OTUs, filtering out OTUs predicted to lack a true ITS2 region in the process (61). Taxonomy was then assigned to non-chimeric. ITS2 extracted OTUs using Bayesian classification with a confidence cut-off of 0.8 in QIIME according to the 8_1_2015 UNITE ITS fungal sequence database (54) (60). OTUs responsible for less that 0.001% of the total sequence reads were removed. To normalize variation in read depth across samples, data were rarefied to the minimum read depth of 6,653 sequences per sample for bacteria. To ensure that a truly representative community of each sample was used for analysis, sequence sub-sampling at the defined depth was bootstrapped 100 times. The representative community composition for each sample was defined as that which exhibited the minimum average Canberra distance to all other OTU vectors generated from all sub-samplings for that particular sample.

Bacterial 16S rRNA Gene Profiling Using PhyloChip. Total DNA extracted from fecal samples was used as template for 16S rRNA gene amplification as previously described (62). PCR amplification was verified on a 1% TBE agarose gel then purified using the QIAquick Gel Extraction kit (Cat. No. 28704. QIAGEN, CA). A total of 500 ng of purified PCR product per sample was then fragmented, biotin-labeled, and hybridized to the G3 16S rRNA PhyloChip (Affymetrix, CA) as previously described (63). Washing, staining, and scanning of arrays were conducted according to standard Affymetrix protocol (63). Background subtraction, detection, taxon quantification criteria and array normalization was performed as previously described (63). Stage 1 thresholds were adjusted, based on quantitative standards to the following: $rQ1 \geq 0.25$, $rQ2 \geq 0.50$, $rQ3 \geq 0.80$. All PhyloChip microarray data reported in this paper has been deposited in the Gene Expression Omnibus (GEO) database, ncbi.nlm.nih.gov/geo (accession no. GSE78724).

Predicted community metagenome analyses. Phylogenetic Investigation of Communities by Reconstruction of Unobserved States (PICRUSt; picrust.github.io/picrust/), a bioinformatics software package used to predict functional metagenomes from a marker gene survey (such as 16S rRNA gene), was used to generate in silico bacterial metagenomes for data generated in this study (64). First, the biom-formatted bacterial OTU table previously generated from the processed 16S rRNA gene MiSeq data was filtered to contain only closed-reference OTUs [i.e. OTUs present in the GreenGenes 16S rRNA 13_8 database (56)]. The closed-reference OTU table was then used to generate predicted metagenomes according to the PICRUSt metagenome prediction tutorial (picrust.github.io/picrust/tutorials/metagenome_prediction.html-metagenome-prediction-tutorial). Briefly, OTU abundance was first normalized according to known or predicted 16s copy number. Following 16s copy number normalization, this normalized OTU table was then used to predicted KEGG Ortholog (KO) abundances for each sample, which were further collapsed into KEGG Pathways (genome.jp/kegg/pathway.html).

Metabolome Profiling. To profile fecal metabolites, >200 mg of frozen stool from each sample was shipped overnight on dry ice to Metabolon (Metabolon, NC). Also included were several technical replicate samples created from a homogeneous pool containing a small amount of all study sample. Upon receipt, samples were inventoried, and immediately stored at −80° C. At the time of analysis, samples were extracted and prepared for analysis using Metabolon's standard solvent extraction method (metabolon.com/). The extracted samples were split into equal parts for analysis on the GC/MS and Q-Exactive accurate mass LC/MS platforms.

Sample Preparation:

The sample preparation process was carried out using the automated MicroLab STAR® system from Hamilton Company. Recovery standards were added prior to the first step in the extraction process for QC purposes. Sample preparation was conducted using a proprietary series of organic and aqueous extractions to remove the protein fraction while allowing maximum recovery of small molecules. The resulting extract was divided into two fractions; one for analysis by LC/MS and one for analysis by GC/MS. Samples were placed briefly on a TurboVap® (Zymark) to remove the organic solvent. Each sample was then frozen and dried under vacuum. Samples were then prepared for the appropriate instrument, either LC/MS or GC/MS.

QA/QC:

For QA/QC purposes, a number of additional samples were included with each day's analysis. Furthermore, a selection of QC compounds was added to every sample, including those under test. These compounds were chosen so as not to interfere with the measurement of the endogenous compounds. FIG. 38 and FIG. 39 describe the QC samples and compounds. These QC samples are primarily used to evaluate the process control for each study as well as aiding in the data curation.

Ultrahigh Performance Liquid Chromatography Mass Spectroscopy (UPLC/MS/MS):

The LC/MS portion of the platform was based on a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in acidic or basic LC-compatible solvents, each of which contained 8 or more injection standards at fixed concentrations to ensure injection and chromatographic consistency. One aliquot was analyzed using acidic positive ion optimized conditions and the other using basic negative ion optimized conditions in two independent injections using separate dedicated columns (Waters UPLC BEH C18-2.1×100 mm, 1.7 μm). Extracts reconstituted in acidic conditions were gradient eluted using water and methanol containing 0.1% formic acid, while the basic extracts, which also used water/methanol, contained 6.5 mM Ammonium Bicarbonate. The MS analysis alternated between MS and data-dependent MS2 scans using dynamic exclusion, and the scan range was from 80-1000 m/z. Raw data files are archived and extracted as described below.

Gas chromatography Mass Spectrometry (GC/MS):

The samples destined for GC/MS analysis were re-dried under vacuum desiccation for a minimum of 24 hours prior to being derivatized under dried nitrogen using bistrimethylsilyl-triflouroacetamide (BSTFA). The GC column was 5% phenyl/95% dimethyl polysiloxane fused silica column and the temperature ramp was from 40° to 300° C. in a 16 minute period. Samples were analyzed on a Thermo-Finnigan Trace DSQ fast-scanning single-quadrupole mass spectrometer using electron impact ionization. The instrument was tuned and calibrated for mass resolution and mass accuracy on a daily basis. The information output from the raw data files was automatically extracted as discussed below.

Data Extraction and Compound Identification:

Raw data was extracted, peak-identified and QC processed using Metabolon's hardware and software. Compounds were identified by comparison to library entries of purified standards or recurrent unknown entities. Metabolon maintains a library based on authenticated standards containing the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, nominal mass match to the library +/−0.4 amu, and the MS/MS forward and reverse scores between the experimental data and authentic standards. The MS/MS scores are based on a comparison of the ions present in the experimental spectrum to the ions present in the library spectrum.

Normalization:

For studies spanning multiple days, a data normalization step was performed to correct variation resulting from instrument inter-day tuning differences. Essentially, each compound was corrected in run-day blocks by registering the medians to equal one (1.00) and normalizing each data point proportionately. For studies that did not require more than one day of analysis, no normalization was necessary.

In vitro DC/T-cell fecal water assay. Fecal Water Preparation. Fecal samples were diluted in sterile 37° C. PBS containing 20% FBS and 2 mM EDTA to a final concentration of 1 g/mL. Diluted fecal samples were then vortex for 1 minutes and incubated at 37° C. for 10 minutes. Following incubation, samples were centrifuged at ~21,000 g for 10 minutes at room temperature to remove insoluble material. Supernatants were then filtered through a 0.2 μm nylon filter to remove intact cells. Sterile fecal water solutions were stored at −20° C.

Dendritic Cell Fecal Water Challenge and T-Cell Co-Culture.

Peripheral blood samples were obtained from anonymous healthy human donors (Blood Centers of the Pacific, San Francisco, Calif.). Peripheral blood mononuclear cells (PBMCs) were isolated by Ficoll-Hypaque gradient centrifugation (Cat. No. Histopaque-10771; Sigma-Aldrich). Dendritic cells (DCs) were purified from isolated PBMCs using the EasySep™ Human Pan-DC Pre-Enrichment Kit (Cat. No. 19251; STEMCELL Technologies, Canada) and cultured in 96-well plates ($0.5×10^6$ cells/ml) in fresh R10 media: RPMI 1640 (Cat. No. 11875; Thermo-Fisher Scientific) supplemented with 10% heat-inactivated FCS (Cat. No. 9871-5244; USA Scientific), 100 U/ml penicillin-streptomycin (Cat. No. 10378016; Life Technologies, CA), 10 ng/ml GM-CSF (Cat. No. 15-GM-010; R&D Systems, MN), and 20 ng/ml IL-4 (Cat. No. 204-IL-010; R&D Systems). Prepared sterile fecal water was added to DC culture at a 1/20 dilution. After a 24 hour incubation, cells were stimulated with 10 ng/ml TNF-α (Cat. No. 300-01A; PeproTech, NJ), 10 ng/ml IL-1β (Cat. No. 200-01B; PeproTech), 10 ng/ml IL-6 (Cat. No. AF-200-06; PeproTech), and 1 μM PGE2 (Cat. No. 72194; STEMCELL Technologies) and incubated for an additional 24 hours to induce DC maturation. T-cells were purified from autologous, monocyte-depleted PBMCs by negative selection using the Human T-Cell Enrichment Column (Cat. No. HTCC-2000; R&D Systems) and were subsequently cultured in TexMACS Medium (Cat. Not. 130-097-196; Miltenyi Biotec, Germany). Following DC stimulation, DCs were harvested, washed, and co-cultured with autologous T-cells at a ratio of 1/10 in the presence of 1 ug/ml soluble anti-CD28 (Cat. No. 555725; BD Biosciences, CA) and 1 μg/ml anti-CD49d (Cat. No. 555501; BD Biosciences) for 5 days, replenishing the media every 2 days. This assay was repeated four times using PBMCs obtained from distinct donors to ensure observations were independent of PBMC source.

Flow Cytometry.

To assess cytokine production, the co-cultures were stimulated with Phorbol Myristate Acetate-Ionomycin (Cat. No. 356150010; Fisher Scientific) and GolgiPlug (Cat. No. 555029; BD Biosciences) for 16 hours. Cells were harvested and single-cell suspensions were stained in two separate antibody panels to assess phenotype. Panel 1: anti-CD3 (Cat. No. 557917, BD Biosciences), anti-CD4 (Cat. No. 563028; BD Biosciences), anti-CD8a (Cat. No. 563821; BioLegend), anti-CD25 (Cat. No. 557741; BD Biosciences), anti-FoxP3 (Cat. No. 14-4776-80; eBioscience), and anti-IL10 (Cat. No. 130-096-043; Miltenyi Biotec). Panel 2: anti-CD3 (Cat. No. 557917; BD Biosciences), anti-CD4 (Cat. No. 563028; BD Biosciences), anti-CD8a (Cat. No. 563821; BioLegend), anti-CD69 (Cat. No. 560737; BD Biosciences), anti-INFγ (Cat. No. 560371; BD Biosciences), anti-IL4 (Cat. No. 130-091-647; Miltenyi Biotec), anti-IL117A (Cat. No. 17-7179-42; eBioscience), and anti-IL22 (Cat. No. 25-7229-42; eBioscience). Cells were permeabilized by either Cytofix/Cytoperm™ (Cat. No. 554714; BD Bioscience) or Fixation/Permeabilization (Cat. No. 00-5523-00; Affymatrix eBioscience). Upon staining, live T-cells were gated as $CD3^+CD4^+$ or $CD3^+CD8^+$ cells. Activated T-cells were surface stained CD69hi. Among the $CD4^+$ T-cell population, subpopulations were defined as Th1: $IFN\gamma^+$, Th2: $IL-4^+$, Th17: $IL-17A^+$, Th22: $IL17A^-$ and $IL-22^+$, and Treg: CD25hi and FoxP3hi. $CD8^+$ T-cells subpopulations were defined as Tc1: $IFN\gamma^+$, Tc2: $IL-4^+$, and Tc17: $IL-17A^+$. Stained cells were assayed via flow cytometry on a BD LSR II (BD Biosciences).

Cytometric Bead Array.

Prior to addition of PMA/Gplug, 100 uL of cell-free supernatant was removed from each co-culture and centrifuged for 1 minute at 3000 rpm. Cytokine secretion was measured using a cytometric bead array (BD Biosciences) and the concentration of IL-4, IL-5, IL-13, and were determined according to the manufacturer's guidelines. Data was acquired by flow cytometry on a BD LSR II (BD Biosciences) and data analysis was performed using the proprietary FCAP Array analysis software (BD Biosciences).

Statistical analysis. Microbial, Metagenomic, and Metabolomic Analysis. Analysis was performed using QIIME v1.8.0 and the R statistical environment (54, 65). Shannon's Diversity and Faith's Phylogenetic Diversity were calculated using QIIME v 1.8.0 and two-tailed t-tests were performed to identify significant between group differences (e.g. UC vs. Healthy) (54). Weighted UniFrac, Canberra, and Bray-Curtis distance matrices were generated using QIIME v 1.8.0 and visualized via NMDS in the R statistical environment using the vegan package (66, 67). For PhyloChip data, fluorescent intensities were log-normalized prior to calculating Canberra distances. Permutational multivariate analysis of variance (PERMANOVA) using calculated distance matrices was used to determine relationships between existing metadata (i.e. Health Status or Ethnicity) and bacterial, fungal, metagenome, or metabolome composition using the *adonis* function found in vegan (67). Hierarchical cluster analysis combined with multi-scale, bootstrap resampling was performed using the pvclust package in R with 1000 bootstrap replications (68). Correlation between distances matrices was calculated using the mantel function found in vegan (67). To identify significantly enriched or depleted bacterial OTUs, fungal OTUs, and KEGG pathways between relevant sample groups (e.g. UC vs. Healthy), the three-model approach described by Romero et al. was applied (69). Briefly, three linear mixed-effect regression models (negative binomial, zero-inflated negative bionomial, and Poisson) were independently fit to each observation (i.e. OTU or KEGG pathway) and the model with lowest Akaike Information Criterion (AIC) was retained. P-values were computed for only the best-fit models (i.e. those that minimized AIC). To account for false discovery, q-values were calculated based on the computed p-values. For PhyloChip data, significantly enriched or depleted OTUs were determined by applying a two-tailed t-test to log-normalized fluorescent intensities. To identify significantly enriched or depleted fecal metabolites, log-normalized relative concentrations were compared using a Welch's t-test.

Comparison of Clinical Measures of Disease Severity.

Clinical measures of disease severity (i.e. SCCA, number of extra-colonic manifestations, number of diagnosed first- and second-degree relatives, and years since diagnosis were compared between UC-MCS by a Kruskal-Wallis Test followed by pairwise tw-tailed Dun's Test.

Analysis of T-Cell Subsets.

Because the T-cell assay described above was repeated four separate times using PBMCs from four different PBMC donors, a linear mixed effects model was applied using the lme4 package in R to identify significant differences in the abundance of induced T-cell subpopulations based on sample group (i.e. UC-MCS) while accounting for potential variation introduced due to PBMC source (i.e. donor) (70). The following linear mixed effects models were applied to identify changes due to health status (Healthy vs. UC) and UC-MCS (Healthy vs. MCS1, MCS2, MCS3, MCS4) respectively:

$$Y \sim \beta((EXP\_GROUP) + \mu(DONOR) + \mu(SAMPLE) + \varepsilon$$

$$Y \sim \beta(MCS) + \mu(DONOR) + \mu(SAMPLE) + \varepsilon$$

Where Y=a measured, dependent variable such as Th1 abundance, EXP_GROUP=health status (Healthy or UC), MCS=microbial community state (Healthy, MCS1, MCS2, MCS3, or MCS4), DONOR=PBMC donor source (Donor #1 to #4), and SAMPLE=fecal sample study participant.

REFERENCES

References for Example 4

1. Arrieta, M. C. et al. Early infancy microbial and metabolic alterations affect risk of childhood asthma. *Sci. Transl. Med.* 7, 307ra152 (2015).
2. Asher, M. I., Montefort, S., Bjorksten, B., Lai, C. K. & Strachan, D. P. W. S. Worldwide time trends in the prevalence of symptoms of asthma, allergic rhinoconjunctivitis, and eczema in childhood. *Lancet* 368, 733-743 (2006).
3. Simpson, A. et al. Beyond atopy: multiple patterns of sensitization in relation to asthma in a birth cohort study. *Am. J. Respir. Crit. Care Med.* 181, 1200-1206 (2010).
4. Aichbhaumik, N. et al. Prenatal exposure to household pets influences fetal immunoglobulin E production. *Clin. Exp. Allergy* 38, 1787-1794 (2008).
5. Havstad, S. et al. Atopic phenotypes identified with latent class analyses at age 2 years. *J. Allergy Clin. Immunol.* 134, 722-727.e2 (2014).
6. Hoffmann, C. et al. Archaea and fungi of the human gut microbiome: correlations with diet and bacterial residents. *PLoS One* 8, e66019 (2013).

7. Holmes, I., Harris, K. & Quince, C. Dirichlet multinomial mixtures: generative models for microbial metagenomics. *PLoS One* 7, e30126 (2012).
8. Langille, M. G. I. et al. Predictive functional profiling of microbial communities using 16S rRNA marker gene sequences. *Nat. Biotechnol.* 31, 814-821 (2013).
9. Morin, C., Blier, P. U. & Fortin, S. Eicosapentaenoic acid and docosapentaenoic acid monoglycerides are more potent than docosahexaenoic acid monoglyceride to resolve inflammation in a rheumatoid arthritis model. *Arthritis Res. Ther.* 17, 142 (2015).
10. Amagai, Y. et al. Dihomo-γ-linolenic acid prevents the development of atopic dermatitis through prostaglandin DI production in NC/Tnd mice. *J. Dermatol. Sci.* 79, 30-37 (2015).
11. Bode, L. Human milk oligosaccharides: every baby needs a sugar mama. *Glycobiology* 22, 1147-1162 (2012).
12. Weichert, S. et al. Bioengineered 2'-fucosyllactose and 3-fucosyllactose inhibit the adhesion of *Pseudomonas aeruginosa* and enteric pathogens to human intestinal and respiratory cell lines. *Nutr. Res.* 33, 831-838 (2013).
13. DeAngelis, K. M. et al. Selective progressive response of soil microbial community to wild oat roots. *ISME J.* 3, 168-178 (2009).
14. Caporaso, J. G. et al Global patterns of 16S rRNA diversity at a depth of millions of sequences per sample. *Proc. Natl. Acad. Sci. U.S.A.* 108 Supplem, 4516-4522 (2011).
15. Caporaso, J. G. et al. Ultra-high-throughput microbial community analysis on the Illumina HiSeq and MiSeq platforms. *ISME J.* 6, 1621-1624 (2012).
16. Magoč, T. & Salzberg, S. L. FLASH: fast length adjustment of short reads to improve genome assemblies. *Bioinformatics* 27, 2957-2963 (2011).
17. Caporaso, J. G. et al. QIIME allows analysis of high-throughput community sequencing data. *Nat. Methods* 7, 335-336 (2010).
18. Edgar, R. C., Haas, B. J., Clemente, J. C., Quince, C. & Knight, R. UCHIME improves sensitivity and speed of chimera detection. *Bioinformatics* 27, 2194-2200 (2011).
19. Edgar, R. C. Search and clustering orders of magnitude faster than BLAST. *Bioinformatics* 26, 2460-2461 (2010).
20. McDonald, D. et al. An improved Greengenes taxonomy with explicit ranks for ecological and evolutionary analyses of bacteria and archaea. *ISME J.* 6, 610-618 (2012).
21. Caporaso, J. G. et al. PyNAST: a flexible tool for aligning sequences to a template alignment. *Bioinformatics* 26, 266-267 (2010).
22. Price, M. N., Dehal, P. S. & Arkin, A. P. FastTree 2-approximately maximum-likelihood trees for large alignments. *PLoS One* 5, e9490 (2010).
23. Martin, M. Cutadapt removes adapter sequences from high-throughput sequencing reads. *EMBnet.journal* 17, 10-12 (2011).
24. Edgar, R. C. UPARSE: highly accurate OTU sequences from microbial amplicon reads. *Nat. Methods* 10, 996-998 (2013).
25. Abarenkov, K. et al. The UNITE database for molecular identification of fungi—recent updates and future perspectives. *New Phytol.* 186, 281-285 (2010).
26. Benjamini, Y. & Hochberg, Y. Controlling the false discovery rate: A practical and powerful approach to multiple testing. *J. Roy. Stat. Soc. B* 57, 289-300 (1995).
27. Obermaier, B. et al. Development of a new protocol for 2-day generation of mature dendritic cells from human monocytes. *Biol. Proced. Online* 5, 197-203 (2003).
28. Lozupone, C. & Knight, R. UniFrac: a new phylogenetic method for comparing microbial communities. *Appl. Environ. Microbiol.* 71, 8228-8235 (2005).
29. Vázquez-Baeza, Y., Pirrung, M., Gonzalez, A. & Knight, R. EMPeror: a tool for visualizing high-throughput microbial community data. *Gigascience* 2, 16 (2013).
30. Letunic, I. & Bork, P. Interactive Tree Of Life v2: online annotation and display of phylogenetic trees made easy. *Nucleic Acids Res.* 39, W475-W478 (2011).
31. Shannon, P. et al. Cytoscape: A software environment for integrated models of biomolecular interaction networks cytoscape. *Genome Res.* 13, 2498-2504 (2003).

References for Example 5

1. Nagalingam N A, Lynch S V. 2012. Role of the microbiota in inflammatory bowel diseases. Inflamm Bowel Dis 18:968-984.
2. Wenzel S E. 2012. Asthma phenotypes: the evolution from clinical to molecular approaches. Nat Med 18:716-725.
3. Neuman M G, Nanau R M. 2012. Inflammatory bowel disease: role of diet, microbiota, life style. Transl Res 160:29-44.
4. Yatsunenko T, Rey F E, Manary M J, Trehan I, Dominguez-Bello M G, Contreras M, Magris M, Hidalgo G, Baldassano R N, Anokhin A P, Heath A C, Warner B, Reeder J, Kuczynski J, Caporaso J G, Lozupone C A, Lauber C, Clemente J C, Knights D, Knight R, Gordon J I. 2012. Human gut microbiome viewed across age and geography. Nature 486: 222-227.
5. Frank D N, Robertson C E, Hamm C M, Kpadeh Z, Zhang T, Chen H, Zhu W, Sartor R B, Boedeker E C, Harpaz N, Pace N R, Li E. 2011. Disease phenotype and genotype are associated with shifts in intestinal-associated microbiota in inflammatory bowel diseases. Inflamm Bowel Dis 17:179-184.
6. Juyal G, Prasad P, Senapati S, Midha V, Sood A, Amre D, Juyal R C, BKT. 2011. An investigation of genome-wide studies reported susceptibility loci for ulcerative *colitis* shows limited replication in north Indians. PLoS One 6:e16565.
7. Trompette A, Gollwitzer E S, Yadava K, Sichelstiel A K, Sprenger N, Ngom-Bru C, Blanchard C, Junt T, Nicod L P, Harris N L, Marsland B J. 2014. Gut microbiota metabolism of dietary fiber influences allergic airway disease and hematopoiesis. Nat Med 20:159-166.
8. Frank D N, St Amand A L, Feldman R A, Boedeker E C, Harpaz N, Pace N R. 2007. Molecular-phylogenetic characterization of microbial community imbalances in human inflammatory bowel diseases. Proc Natl Acad Sci USA 104:13780-13785.
9. Morgan X C, Tickle T L, Sokol H, Gevers D, Devaney K L, Ward D V, Reyes J A, Shah S A, Leleiko N, Snapper S B, Bousvaros A, Korzenik J, Sands B E, Xavier R J, Huttenhower C. 2012. Dysfunction of the intestinal microbiome in inflammatory bowel disease and treatment. Genome Biol 13:R79
10. Lewis J D, Chen E Z, Baldassano R N, Otley A R, Griffiths A M, Lee D, Bittinger K, Bailey A, Friedman E S, Hoffmann C, Albenberg L, Sinha R, Compher C, Gilroy E, Nessel L, Grant A, Chehoud C, Li H, Wu G D, Bushman F D. 2015. Inflammation, antibiotics, and diet as environmental stressors of the gut microbiome in pediatric Crohn's disease. Cell Host Microbe 18:489-500.
11. Gevers D, Kugathasan S, Denson L A, Vazquez-Baeza Y, Van Treuren W, Ren B, Schwager E, Knights D, Song S J, Yassour M, Morgan X C, Kostic A D, Luo C, Gonzalez A, McDonald D. Haberman Y, Walters T, Baker S, Rosh J, Stephens M, Heyman M, Markowitz J. Baldassano R, Griffiths A, Sylvester F, Mack D, Kim S, Crandall W, Hyams J, Hut-tenhower C, Knight R, Xavier R J. 2014. The treatment-naive micro-biome in new-onset Crohn's disease. Cell Host Microbe 15:382-392.
12. Walmsley R S, Ayres R C, Pounder R E, Allan R N. 1998. A simple clinical colitis activity index. Gut 43:29-32.
13. Langille M G, Zaneveld J, Caporaso J G, McDonald D, Knights D, Reyes J A, Clemente J C, Burkepile D E, Vega Thurber R L, Knight R, Beiko R G, Huttenhower C. 2013. Predictive functional profiling of microbial communities using 16S rRNA marker gene sequences. Nat Biotechnol 31: 814-821.
14. Dello S A, Neis E P, de Jong M C, van Eijk H M, Kicken C H, Olde Damink S W, Dejong C H. 2013. Systematic review of ophthalmate as a novel bio-marker of hepatic glutathione depletion. Clin Nutr 32:325-330.
15. Walters J D, Chapman K J. 1995. Polyamines found in gingival fluid enhance the secretory and oxidative function of human polymorphonuclear leukocytes in vitro. J Periodontal Res 30:167-171.
16. Schepers E, Meert N, Glorieux G, Goeman J, Van der Eycken J, Vanholder R. 2007. P-cresylsulphate, the main in vivo metabolite of p-cresol, activates leucocyte free radical production. Nephrol Dial Transplant 22:592-596.
17. Henricks P A, Engels F, van der Vliet H, Nijkamp F P. 1991. 9- and 13-hydroxy-linoleic acid possess chemotactic activity for bovine and human polymorphonuclear leukocytes. Prostaglandins 41:21-27.
18. Rolin J, Al-Jaderi Z, Maghazachi A A. 2013. Oxidized lipids and lysophosphatidylcholine induce the chemotaxis and intracellular calcium influx in natural killer cells. Immunobiology 218:875-883.
19. Totani Y, Saito Y, Ishizaki T, Sasaki F, Ameshima S, Miyamori I. 2000. Leukotoxin and its diol induce neutrophil chemotaxis through signal transduction different from that of fMLP. Eur Respir J 15:75-79.
20. Qin X, Qiu C. Zhao L. 2014. Lysophosphatidylcholine perpetuates macrophage polarization toward classically activated phenotype in inflammation. Cell Immunol 289: 185-190.
21. Young D, Ibuki M, Nakamori T, Fan M, Mine Y. 2012. Soy-derived di- and tripeptides alleviate colon and ileum inflammation in pigs with dex-tran sodium sulfate-induced colitis. J Nutr 142:363-368.
22. Hou Y C, Chu C C, Ko T L, Yeh C L, Yeh S L. 2013. Effects of alanyl-glutamine dipeptide on the expression of colon-inflammatory mediators during the recovery phase of colitis induced by dextran sulfate sodium. Eur J Nutr 52:1089-1098.
23. Mistry D, Stockley R A. 2010. Gamma-glutamyl transferase: the silent partner? COPD 7:285-290.
24. Nascimento N R, Lessa L M, Kerntopf M R, Sousa C M, Alves R S, Queiroz M G. Price J. Heimark D B, Larner J, Du X, Brownlee M, Gow A, Davis C, Fonteles M C. 2006. Inositols prevent and reverse endothelial dysfunction in diabetic rat and rabbit vasculature metabolically and by scavenging superoxide. Proc Natl Acad Sci USA 103:218-223.
25. Liao J. Seril D N, Yang A L, Lu G G, Yang G Y. 2007. Inhibition of chronic ulcerative colitis associated adenocarcinoma development in mice by ino-sitol compounds. Carcinogenesis 28:446-454.
26. Bamias G, Kaltsa G, Ladas S D. 2011. Cytokines in the pathogenesis of ulcerative colitis. Discov Med 11:459-467.
27. Hogan D A, Vik A, Kolter R. 2004. A Pseudomonas aeruginosa quorum-sensing molecule influences Candida albicans morphology. Mol Micro-biol 54:1212-1223.
28. Sakanaka A, Kuboniwa M, Takeuchi H, Hashino E, Amano A. 2015. Arginine-ornithine antiporter ArcD controls arginine metabolism and interspecies biofilm development of Streptococcus gordonii. J Biol Chem 290: 21185-21198.
29. Prindiville T P, Sheikh R A, Cohen S H, Tang Y J, Cantrell M C, Silva J. Jr. 2000. Bacteroides fragilis enterotoxin gene sequences in patients with in-flammatory bowel disease. Emerg Infect Dis 6:171-174.
30. Ohkusa T, Yoshida T, Sato N, Watanabe S, Tajiri H, Okayasu I. 2009. Commensal bacteria can enter colonic epithelial cells and induce proin-flammatory cytokine secretion: a possible pathogenic mechanism of ulcerative colitis. J Med Microbiol 58:535-545.
31. Rath H C, Wilson K H, Sartor R B. 1999. Differential induction of colitis and gastritis in HLA-B27 transgenic rats selectively colonized with Bacte-roides vulgatus or Escherichia coli. Infect Immun 67:2969-2974.
32. Li Q, Wang C, Tang C, He Q, Li N, Li J. 2014. Dysbiosis of gut fungal microbiota is associated with mucosal inflammation in Crohn's disease. J Clin Gastroenterol 48:513-523.
33. Chehoud C, Albenberg L G, Judge C, Hoffmann C, Grunberg S, Bit-tinger K, Baldassano R N, Lewis J D, Bushman F D, Wu G D. 2015. Fungal signature in the gut microbiota of pediatric patients with inflammatory bowel disease. Inflamm Bowel Dis 21:1948-1956.
34. Zwolinska-Wcislo M, Brzozowski T. Budak A, Kwiecien S, Sliwowski Z, Drozdowicz D, Trojanowska D, Rudnicka-Sosin L, Mach T, Konturek S J, Pawlik W W. 2009. Effect of Candida colonization on human ulcerative colitis and the healing of inflammatory changes of the colon in the experimental model of colitis ulcerosa. J Physiol Pharmacol 60:107-118.
35. Noverr M C, Noggle R M, Toews G B, Huffnagle G B. 2004. Role of antibiotics and fungal microbiotain driving pulmonary allergic responses. Infect Immun 72:4996-5003.
36. Park S-K, Kim M-S, Roh S W, Bae J-W. 2012. Blautia stercoris sp. nov., isolated from human faeces. Int J Syst Evol Microbiol 62:776-779.
37. Miller T L, Wolin M J. 1995. Bioconversion of cellulose to acetate with pure cultures of Ruminococcus albus and a hydrogen-using acetogen. Appl Environ Microbiol 61:3832-3835.
38. Park J, Kim M, Kang S G, Jannasch A H, Cooper B, Patterson J, Kim C H. 2015. Short-chain fatty acids induce both effector and regulatory T cells by suppression of histone deacetylases and regulation of the mTOR-S6K pathway. Mucosal Immunol 8:80-93.
39. Shenker B J, Vitale L, Slots J. 1991. Immunosuppressive effects of Pre-votella intermedia on in vitro human lymphocyte activation. Infect Im-mun 59:4583-4589.
40. Riedel C U, Foata F, Philippe D, Adolfsson O, Eikmanns B J, Blum S. 2006. Anti-inflammatory effects of bifidobacteria by inhibition of LPS-induced N F-kappaB activation. World J Gastroenterol 12:3729-3735.
41. Zhang W, Li H, Dong H, Liao J, Hammock B D, Yang G Y. 2013. Soluble epoxide hydrolase deficiency inhibits dextran sulfate sodium-induced colitis and carcinogenesis in mice. Anticancer Res 33:5261-5271.

42. Patel K P, Luo F J, Plummer N S, Hostetter T H, Meyer T W. 2012. The production of p-cresol sulfate and indoxyl sulfate in vegetarians versus omnivores. Clin J Am Soc Nephrol 7:982-988.
43. Levy M, Thaiss C A, Zeevi D, Dohnalovi L, Zilberman-Schapira G, Mahdi J A, David E, Savidor A, Korem T, Herzig Y, Pevsner-Fischer M, Shapiro H, Christ A, Harmelin A, Halpern Z, Latz E, Flavell R A, Amit I, Segal E, Elinav E. 2015. Microbiota-modulated metabolites shape the intestinal microenvironment by regulating NLRP6 inflammasome signaling. Cell 163:1428-1443.
44. Caporaso J G, Lauber C L, Walters W A, Berg-Lyons D, Huntley J, Fierer N, Owens S M, Betley J, Fraser L, Bauer M, Gormley N, Gilbert J A, Smith G, Knight R. 2012. Ultra-high-throughput microbial community analysis on the Illumina HiSeq and MiSeq platforms. ISME J 6:1621-1624
45. Hazen T C, Dubinsky E A, DeSantis T Z, Andersen G L, Piceno Y M, Singh N, Jansson J K, Probst A, Borglin S E, Fortney J L, Stringfellow W T, Bill M, Conrad M E, Tom L M, Chavarria K L, Alusi T R, Lamendella R, Joyner D C, Spier C, Baelum J, Auer M, Zemla M L, Chakraborty R, Sonnenthal E L, D'Haeseleer P, Holman H Y, Osman S, Lu Z, Van Nostrand J D, Deng Y, Zhou J, Mason O U. 2010. Deep-sea oil plume enriches indigenous oil-degrading bacteria. Science 330:204-208.
46. Magoč T, Salzberg S L. 2011. FLASH: fast length adjustment of short reads to improve genome assemblies. Bioinformatics 27:2957-2963.
47. Caporaso J G, Kuczynski J, Stombaugh J, Bittinger K, Bushman F D, Costello E K, Fierer N, Peña A G, Goodrich J K, Gordon J I, Huttley G A, Kelley S T, Knights D, Koenig J E, Ley R E, Lozupone C A, McDonald D, Muegge B D, Pirrung M, Reeder J, Sevinsky J R, Turnbaugh P J, Walters W A, Widmann J, Yatsunenko T, Zaneveld J, Knight R. 2010. QIIME allows analysis of high-throughput community sequencing data. Nat Methods 7:335-336.
48. Edgar R C. 2010. Search and clustering orders of magnitude faster than BLAST. Bioinformatics 26:2460-2461.
49. R Core Team. 2015. R: a language and environment for statistical computing. The R Core Team, Vienna, Austria.
50. Bates D, Machler M, Bolker B, Walker S. 2015. Fitting linear mixed-effects models using lme4. J Stat Softw 67:1-48.
51. Walmsley R S, Ayres R C, Pounder R E, Allan R N. 1998. A simple clinical *colitis* activity index. Gut 43:29-32.
52. Caporaso J G, Lauber C L, Walters W A, Berg-Lyons D, Huntley J, Fierer N, Owens S M, Betley J, Fraser L, Bauer M, Gormley N, Gilbert J A, Smith G, Knight R. 2012. Ultra-high-throughput microbial community analysis on the Illumina HiSeq and MiSeq platforms. ISME J 6:1621-1624.
53. Magoc T, Salzberg S L. 2011. FLASH: fast length adjustment of short reads to improve genome assemblies. Bioinformatics 27:2957-2963.
54. Caporaso J G, Kuczynski J, Stombaugh J, Bittinger K, Bushman F D, Costello E K, Fierer N, Pena A G, Goodrich J K, Gordon J I, Huttley G A, Kelley S T, Knights D, Koenig J E, Ley R E, Lozupone C A, McDonald D, Muegge B D, Pirrung M, Reeder J, Sevinsky J R, Turnbaugh P J, Walters W A, Widmann J, Yatsunenko T, Zaneveld J, Knight R. 2010. QIIME allows analysis of high-throughput community sequencing data. Nat Methods 7:335-336.
55. Edgar R C. 2010. Search and clustering orders of magnitude faster than BLAST. Bioinformatics 26:2460-2461.
56. DeSantis T Z, Hugenholtz P, Larsen N, Rojas M, Brodie E L, Keller K, Huber T, Dalevi D, Hu P, Andersen G L. 2006. Greengenes, a chimera-checked 16S rRNA gene database and workbench compatible with ARB. Appl Environ Microbiol 72:5069-5072.
57. Caporaso J G, Bittinger K, Bushman F D, DeSantis T Z, Andersen G L, Knight R. 2010. PyNAST: a flexible tool for aligning sequences to a template alignment. Bioinformatics 26:266-267.
58. Haas B J, Gevers D, Earl A M, Feldgarden M, Ward D V, Giannoukos G, Ciulla D, Tabbaa D, Highlander S K, Sodergren E, Methe B, DeSantis T Z, Human Microbiome C, Petrosino J F, Knight R, Birren B W. 2011. Chimeric 16S rRNA sequence formation and detection in Sanger and 454-pyrosequenced PCR amplicons. Genome Res 21:494-504.
59. Price M N, Dehal P S, Arkin A P. 2009. FastTree: computing large minimum evolution trees with profiles instead of a distance matrix. Mol Biol Evol 26:1641-1650.
60. Koljalg U, Nilsson R H, Abarenkov K, Tedersoo L, Taylor A F, Bahram M, Bates S T, Bruns T D, Bengtsson-Palme J, Callaghan T M, Douglas B, Drenkhan T, Eberhardt U, Duenas M, Grebenc T, Griffith G W, Hartmann M, Kirk P M, Kohout P, Larsson E, Lindahl B D, Lucking R, Martin M P, Matheny P B, Nguyen N H, Niskanen T, Oja J, Peay K G, Peintner U, Peterson M, Poldmaa K, Saag L, Saar I, Schussler A, Scott J A, Senes C, Smith M E, Suija A, Taylor D L, Telleria M T, Weiss M, Larsson K H. 2013. Towards a unified paradigm for sequence-based identification of fungi. Mol Ecol 22:5271-5277.
61. Bengtsson-Palme J, Ryberg M, Hartmann M, Branco S, Wang Z, Godhe A, De Wit P. Sánchez-Garcia M, Ebersberger I, de Sousa F, Amend A, Jumpponen A, Unterseher M, Kristiansson E, Abarenkov K, Bertrand Y J K, Sanli K, Eriksson K M, Vik U, Veldre V, Nilsson R H. 2013. Improved software detection and extraction of ITS1 and ITS2 from ribosomal ITS sequences of fungi and other eukaryotes for analysis of environmental sequencing data. Methods in Ecology and Evolution 4:914-919.
62. Cox M J, Allgaier M, Taylor B, Baek M S, Huang Y J, Daly R A, Karaoz U, Andersen G L, Brown R, Fujimura K E, Wu B, Tran D, Koff J, Kleinhenz M E, Nielson D, Brodie E L, Lynch S V. 2010. Airway microbiota and pathogen abundance in age-stratified cystic fibrosis patients. PLoS One 5:e11044.
63. Hazen T C, Dubinsky E A, DeSantis T Z, Andersen G L, Piceno Y M, Singh N, Jansson J K, Probst A, Borglin S E, Fortney J L, Stringfellow W T, Bill M, Conrad M E, Tom L M, Chavarria K L, Alusi T R, Lamendella R, Joyner D C, Spier C, Baelum J, Auer M, Zemla M L, Chakraborty R, Sonnenthal E L, D'Haeseleer P, Holman H Y, Osman S, Lu Z, Van Nostrand J D, Deng Y, Zhou J, Mason O U. 2010. Deep-sea oil plume enriches indigenous oil-degrading bacteria. Science 330:204-208.
64. Langille M G, Zaneveld J. Caporaso J G, McDonald D, Knights D. Reyes J A, Clemente J C, Burkepile D E, Vega Thurber R L, Knight R, Beiko R G, Huttenhower C. 2013. Predictive functional profiling of microbial communities using 16S rRNA marker gene sequences. Nat Biotechnol 31:814-821.
65. Team R C. 2015. R: A Language and Environment for Statistical Computing.

66. Lozupone C, Knight R. 2005. UniFrac: a new phylogenetic method for comparing microbial communities. Appl Environ Microbiol 71:8228-8235.
67. Jari Oksanen F G B, Roeland Kindt, Pierre Legendre, Peter R. Minchin, R. B. O'Hara, Gavin L. Simpson, Peter Solymos, M. Henry H. Stevens, and Helene Wagner. 2015. vegan: Community Ecology Package.
68. Suzuki R, Shimodaira H. 2006. Pvclust: an R package for assessing the uncertainty in hierarchical clustering. Bioinformatics 22:1540-1542.
69. Romero R, Hassan S S, Gajer P, Tarca A L, Fadrosh D W, Nikita L, Galuppi M, Lamont R F, Chaemsaithong P, Miranda J, Chaiworapongsa T, Ravel J. 2014. The composition and stability of the vaginal microbiota of normal pregnant women is different from that of non-pregnant women. Microbiome 2:4.
70. Bates D. M. M M, Bolker B. M., Walker S. C. 2015. Fitting Linear Mixed-Effects Models Using {me4. Journal of Statistical Software 67.

What is claimed is:

1. A method of treating or reducing the incidence of allergic inflammation, the method comprising administering a bacterial population comprising isolates of at least: *Lactobacillus* sp., *Faecalibacterium* sp., and *Akkermansia muciniphila* to a subject in need thereof, wherein the bacterial population is present in an effective amount for treating or reducing the incidence of allergic inflammation in the subject.

2. The method of claim 1, wherein the *Lactobacillus* sp. is *Lactobacillus johnsonii*.

3. The method of claim 1, wherein the *Faecalibacterium* sp. is *Faecalibacterium prausnitzii*.

4. The method of claim 1, wherein the *Lactobacillus* sp. is *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus diolivorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae*, or *Lactococcus lactis*; and wherein the *Faecalibacterium* sp., is *Faecalibacterium prausnitzii*.

5. The method of claim 1, wherein the bacterial population further comprises *Bifidobacterium* sp.

6. The method of claim 5, wherein the *Bifidobacterium* sp. is *Bifidobacterium bifidum, Bifidobacterium pseudolongum, Bifidobacterium saeculare*, or *Bifidobacterium subtile*.

7. The method of claim 1, wherein the bacterial population comprises less than 20 species of bacteria.

8. The method of claim 1, wherein the bacterial population is part of a bacterial composition that is not a fecal transplant.

9. The method of claim 1, wherein the bacterial population is part of a bacterial composition that comprises a pharmaceutically acceptable excipient.

10. The method of claim 1, wherein the bacterial population is administered orally or rectally.

11. The method of claim 1, wherein the allergic inflammation is a hypersensitivity, pediatric allergic asthma, allergic asthma, food allergy, or atopic dermatitis.

12. The method of claim 1, wherein the allergic inflammation is pediatric allergic asthma or inflammatory bowel disease.

13. The method of claim 1, wherein the subject has at least 1 relative who has been diagnosed with an inflammatory disease.

14. The method of claim 1, wherein the subject suffers from constipation, diarrhea, bloating, urgency, or abdominal pain.

15. The method of claim 1, wherein the subject has been administered an antibiotic within the last 1 month.

16. The method of claim 1, wherein the subject is a neonate.

17. The method of claim 1, wherein the subject is less than about 24 months old.

18. The method of claim 1, wherein the subject is between about 2 and about 18 years old.

19. The method of claim 1, wherein the subject comprises a gastrointestinal microbiome that
    (a) has an increased proportion of *Streptococcus* spp., and *Enterococcus* spp. compared to a healthy or general population;
    (b) has a reduced proportion of *Alternaria alternata, Aspergillus flavus, Aspergillus cibarius*, and *Candida sojae* compared to a healthy or general population;
    (c) has an increased proportion of *Candida albicans* and *Debaryomyces* spp. compared to a healthy or general population;
    (d) has a reduced proportion of *Bifidobacteria* spp., *Lactobacillus* spp., *Faecalibacterium* spp. and *Akkermansia* spp. compared to a healthy or general population;
    (e) has a reduced proportion of *Malassezia* spp. compared to a healthy or general population;
    (f) has an increased proportion of *Bacterioides* spp. or *Prevotella* spp. compared to a healthy or general population; or (g) has an increased proportion of *Enterococcus fiaecalis, Enterococcus faecium*, or *Clostridium difficile* compared to a healthy or general population.

20. The method of claim 1, further comprising administering a *Cystobacter* sp. or a fungal microorganism to the subject.

21. The method of claim 1, wherein the bacterial population is part of a bacterial composition that is lyophilized.

22. The method of claim 1, wherein the bacterial population is part of a bacterial composition that is in liquid form.

23. The method of claim 1, wherein the inflammation is chronic inflammation.

24. The method of claim 1, wherein the *Lactobacillus* sp. is *Lactobacillus crispatus*, and wherein the *Faecalibacterium* sp., is *Faecalibacterium prausnitzii*.

25. The method of claim 24, wherein the bacterial population consists of three bacterial species.

26. The method of claim 1, wherein the *Lactobacillus* sp. is *Lactobacillus johnsonii*, and wherein the *Faecalibacterium* sp., is *Faecalibacterium prausnitzii*.

27. The method of claim 26, wherein the bacterial population consists of three bacteria species.

\* \* \* \* \*

SEQUENCE LISTING

```
<160> NUMBER OF SEQ ID NOS: 8

<210> SEQ ID NO 1
<211> LENGTH: 153
<212> TYPE: PRT
<213> ORGANISM: Homo sapiens

<400> SEQUENCE: 1

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 2
<211> LENGTH: 178
<212> TYPE: PRT
<213> ORGANISM: Homo sapiens

<400> SEQUENCE: 2

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95
```

```
Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 3
<211> LENGTH: 146
<212> TYPE: PRT
<213> ORGANISM: Homo sapiens

<400> SEQUENCE: 3

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn
145

<210> SEQ ID NO 4
<211> LENGTH: 155
<212> TYPE: PRT
<213> ORGANISM: Homo sapiens

<400> SEQUENCE: 4

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
```

```
                         85                  90                  95
Leu Gly Cys Ile Asn Ala Asp Gly Asn Val Asp Tyr His Met Asn Ser
                    100                 105                 110

Val Pro Ile Gln Gln Glu Ile Leu Val Leu Arg Arg Glu Pro Pro His
                115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 5
<211> LENGTH: 5654
<212> TYPE: PRT
<213> ORGANISM: Homo sapiens

<400> SEQUENCE: 5

Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
                20                  25                  30

Glu Ser Ser Tyr Lys His His Pro Ala Leu Ser Pro Ile Ala Arg Gly
            35                  40                  45

Pro Ser Gly Val Pro Leu Arg Gly Ala Thr Val Phe Pro Ser Leu Arg
        50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
                100                 105                 110

Ala Ala Tyr Glu Asp Phe Asn Ile Gln Leu Arg Arg Ser Gln Glu Ser
            115                 120                 125

Ala Ala Pro Thr Leu Ser Arg Val Leu Met Lys Val Asp Gly Val Val
        130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175

Thr Lys Val Glu Ala Arg Leu Gly Leu Val Leu Met Trp Asn His Asp
            180                 185                 190

Asp Ser Leu Leu Glu Leu Asp Thr Lys Tyr Ala Asn Lys Thr Cys
        195                 200                 205

Gly Leu Cys Gly Asp Phe Asn Gly Met Pro Val Val Ser Glu Leu Leu
    210                 215                 220

Ser His Asn Thr Lys Leu Thr Pro Met Glu Phe Gly Asn Leu Gln Lys
225                 230                 235                 240

Met Asp Asp Pro Thr Asp Gln Cys Gln Asp Pro Val Pro Glu Pro Pro
                245                 250                 255

Arg Asn Cys Ser Thr Gly Phe Gly Ile Cys Glu Glu Leu Leu His Gly
                260                 265                 270

Gln Leu Phe Ser Gly Cys Val Ala Leu Val Asp Val Gly Ser Tyr Leu
            275                 280                 285

Glu Ala Cys Arg Gln Asp Leu Cys Phe Cys Glu Asp Thr Asp Leu Leu
        290                 295                 300
```

```
Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
            325                 330                 335

Lys Cys Pro Asn Asn Met Gln Tyr His Glu Cys Arg Ser Pro Cys Ala
        340                 345                 350

Asp Thr Cys Ser Asn Gln Glu His Ser Arg Ala Cys Glu Asp His Cys
    355                 360                 365

Val Ala Gly Cys Phe Cys Pro Glu Gly Thr Val Leu Asp Asp Ile Gly
370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
            405                 410                 415

Thr Cys Ser Gly Gly Arg Trp Ser Cys Gln Glu Val Pro Cys Pro Gly
        420                 425                 430

Thr Cys Ser Val Leu Gly Gly Ala His Phe Ser Thr Phe Asp Gly Lys
    435                 440                 445

Gln Tyr Thr Val His Gly Asp Cys Ser Tyr Val Leu Thr Lys Pro Cys
450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
            485                 490                 495

Ala Gln Thr Val Val Ile Lys Ala Ser Gly Glu Val Phe Leu Asn
        500                 505                 510

Gln Ile Tyr Thr Gln Leu Pro Ile Ser Ala Ala Asn Val Thr Ile Phe
    515                 520                 525

Arg Pro Ser Thr Phe Phe Ile Ile Ala Gln Thr Ser Leu Gly Leu Gln
530                 535                 540

Leu Asn Leu Gln Leu Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
            565                 570                 575

Ile Gln Ala Asp Asp Phe Arg Thr Leu Ser Gly Val Val Glu Ala Thr
        580                 585                 590

Ala Ala Ala Phe Phe Asn Thr Phe Lys Thr Gln Ala Ala Cys Pro Asn
    595                 600                 605

Ile Arg Asn Ser Phe Glu Asp Pro Cys Ser Leu Ser Val Glu Asn Glu
610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
            645                 650                 655

Cys Met Phe Asp Thr Cys Asn Cys Glu Arg Ser Glu Asp Cys Leu Cys
        660                 665                 670

Ala Ala Leu Ser Ser Tyr Val His Ala Cys Ala Ala Lys Gly Val Gln
    675                 680                 685

Leu Gly Gly Trp Arg Asp Gly Val Cys Thr Lys Pro Met Thr Thr Cys
690                 695                 700

Pro Lys Ser Met Thr Tyr His Tyr His Val Ser Thr Cys Gln Pro Thr
705                 710                 715                 720

Cys Arg Ser Leu Ser Glu Gly Asp Ile Thr Cys Ser Val Gly Phe Ile
```

-continued

```
                725                 730                 735
Pro Val Asp Gly Cys Ile Cys Pro Lys Gly Thr Phe Leu Asp Asp Thr
            740                 745                 750
Gly Lys Cys Val Gln Ala Ser Asn Cys Pro Cys Tyr His Arg Gly Ser
            755                 760                 765
Met Ile Pro Asn Gly Glu Ser Val His Asp Ser Gly Ala Ile Cys Thr
            770                 775                 780
Cys Thr His Gly Lys Leu Ser Cys Ile Gly Gln Ala Pro Ala Pro
785             790                 795                 800
Val Cys Ala Ala Pro Met Val Phe Phe Asp Cys Arg Asn Ala Thr Pro
                805                 810                 815
Gly Asp Thr Gly Ala Gly Cys Gln Lys Ser Cys His Thr Leu Asp Met
                820                 825                 830
Thr Cys Tyr Ser Pro Gln Cys Val Pro Gly Cys Val Cys Pro Asp Gly
                835                 840                 845
Leu Val Ala Asp Gly Glu Gly Gly Cys Ile Thr Ala Glu Asp Cys Pro
                850                 855                 860
Cys Val His Asn Glu Ala Ser Tyr Arg Ala Gly Gln Thr Ile Arg Val
865                 870                 875                 880
Gly Cys Asn Thr Cys Thr Cys Asp Ser Arg Met Trp Arg Cys Thr Asp
                    885                 890                 895
Asp Pro Cys Leu Ala Thr Cys Ala Val Tyr Gly Asp Gly His Tyr Leu
                900                 905                 910
Thr Phe Asp Gly Gln Ser Tyr Ser Phe Asn Gly Asp Cys Glu Tyr Thr
                915                 920                 925
Leu Val Gln Asn His Cys Gly Gly Lys Asp Ser Thr Gln Asp Ser Phe
                930                 935                 940
Arg Val Val Thr Glu Asn Val Pro Cys Gly Thr Thr Gly Thr Thr Cys
945                 950                 955                 960
Ser Lys Ala Ile Lys Ile Phe Leu Gly Gly Phe Glu Leu Lys Leu Ser
                965                 970                 975
His Gly Lys Val Glu Val Ile Gly Thr Asp Glu Ser Gln Glu Val Pro
                980                 985                 990
Tyr Thr Ile Arg Gln Met Gly Ile Tyr Leu Val Val Asp Thr Asp Ile
                995                 1000                1005
Gly Leu Val Leu Leu Trp Asp Lys Lys Thr Ser Ile Phe Ile Asn
            1010                1015                1020
Leu Ser Pro Glu Phe Lys Gly Arg Val Cys Gly Leu Cys Gly Asn
            1025                1030                1035
Phe Asp Asp Ile Ala Val Asn Asp Phe Ala Thr Arg Ser Arg Ser
            1040                1045                1050
Val Val Gly Asp Val Leu Glu Phe Gly Asn Ser Trp Lys Leu Ser
            1055                1060                1065
Pro Ser Cys Pro Asp Ala Leu Ala Pro Lys Asp Pro Cys Thr Ala
            1070                1075                1080
Asn Pro Phe Arg Lys Ser Trp Ala Gln Lys Gln Cys Ser Ile Leu
            1085                1090                1095
His Gly Pro Thr Phe Ala Ala Cys His Ala His Val Glu Pro Ala
            1100                1105                1110
Arg Tyr Tyr Glu Ala Cys Val Asn Asp Ala Cys Ala Cys Asp Ser
            1115                1120                1125
Gly Gly Asp Cys Glu Cys Phe Cys Thr Ala Val Ala Ala Tyr Ala
            1130                1135                1140
```

-continued

```
Gln Ala Cys His Glu Val Gly Leu Cys Val Ser Trp Arg Thr Pro
    1145            1150                1155

Ser Ile Cys Pro Leu Phe Cys Asp Tyr Tyr Asn Pro Glu Gly Gln
    1160            1165                1170

Cys Glu Trp His Tyr Gln Pro Cys Gly Val Pro Cys Leu Arg Thr
    1175            1180                1185

Cys Arg Asn Pro Arg Gly Asp Cys Leu Arg Asp Val Arg Gly Leu
    1190            1195                1200

Glu Gly Cys Tyr Pro Lys Cys Pro Pro Glu Ala Pro Ile Phe Asp
    1205            1210                1215

Glu Asp Lys Met Gln Cys Val Ala Thr Cys Pro Thr Pro Pro Leu
    1220            1225                1230

Pro Pro Arg Cys His Val His Gly Lys Ser Tyr Arg Pro Gly Ala
    1235            1240                1245

Val Val Pro Ser Asp Lys Asn Cys Gln Ser Cys Leu Cys Thr Glu
    1250            1255                1260

Arg Gly Val Glu Cys Thr Tyr Lys Ala Glu Ala Cys Val Cys Thr
    1265            1270                1275

Tyr Asn Gly Gln Arg Phe His Pro Gly Asp Val Ile Tyr His Thr
    1280            1285                1290

Thr Asp Gly Thr Gly Gly Cys Ile Ser Ala Arg Cys Gly Ala Asn
    1295            1300                1305

Gly Thr Ile Glu Arg Arg Val Tyr Pro Cys Ser Pro Thr Thr Pro
    1310            1315                1320

Val Pro Pro Thr Thr Phe Ser Phe Ser Thr Pro Pro Leu Val Val
    1325            1330                1335

Ser Ser Thr His Thr Pro Ser Asn Gly Pro Ser Ser Ala His Thr
    1340            1345                1350

Gly Pro Pro Ser Ser Ala Trp Pro Thr Thr Ala Gly Thr Ser Pro
    1355            1360                1365

Arg Thr Arg Leu Pro Thr Ala Ser Ala Ser Leu Pro Pro Val Cys
    1370            1375                1380

Gly Glu Lys Cys Leu Trp Ser Pro Trp Met Asp Val Ser Arg Pro
    1385            1390                1395

Gly Arg Gly Thr Asp Ser Gly Asp Phe Asp Thr Leu Glu Asn Leu
    1400            1405                1410

Arg Ala His Gly Tyr Arg Val Cys Glu Ser Pro Arg Ser Val Glu
    1415            1420                1425

Cys Arg Ala Glu Asp Ala Pro Gly Val Pro Leu Arg Ala Leu Gly
    1430            1435                1440

Gln Arg Val Gln Cys Ser Pro Asp Val Gly Leu Thr Cys Arg Asn
    1445            1450                1455

Arg Glu Gln Ala Ser Gly Leu Cys Tyr Asn Tyr Gln Ile Arg Val
    1460            1465                1470

Gln Cys Cys Thr Pro Leu Pro Cys Ser Thr Ser Ser Ser Pro Ala
    1475            1480                1485

Gln Thr Thr Pro Pro Thr Thr Ser Lys Thr Thr Glu Thr Arg Ala
    1490            1495                1500

Ser Gly Ser Ser Ala Pro Ser Ser Thr Pro Gly Thr Val Ser Leu
    1505            1510                1515

Ser Thr Ala Arg Thr Thr Pro Ala Pro Gly Thr Ala Thr Ser Val
    1520            1525                1530
```

```
Lys Lys Thr Phe Ser Thr Pro Ser Pro Pro Val Pro Ala Thr
1535             1540             1545

Ser Thr Ser Ser Met Ser Thr Thr Ala Pro Gly Thr Ser Val Val
1550             1555             1560

Ser Ser Lys Pro Thr Pro Thr Glu Pro Ser Thr Ser Ser Cys Leu
1565             1570             1575

Gln Glu Leu Cys Thr Trp Thr Glu Trp Ile Asp Gly Ser Tyr Pro
1580             1585             1590

Ala Pro Gly Ile Asn Gly Gly Asp Phe Asp Thr Phe Gln Asn Leu
1595             1600             1605

Arg Asp Glu Gly Tyr Thr Phe Cys Glu Ser Pro Arg Ser Val Gln
1610             1615             1620

Cys Arg Ala Glu Ser Phe Pro Asn Thr Pro Leu Ala Asp Leu Gly
1625             1630             1635

Gln Asp Val Ile Cys Ser His Thr Glu Gly Leu Ile Cys Leu Asn
1640             1645             1650

Lys Asn Gln Leu Pro Pro Ile Cys Tyr Asn Tyr Glu Ile Arg Ile
1655             1660             1665

Gln Cys Cys Glu Thr Val Asn Val Cys Arg Asp Ile Thr Arg Leu
1670             1675             1680

Pro Lys Thr Val Ala Thr Thr Arg Pro Thr Pro His Pro Thr Gly
1685             1690             1695

Ala Gln Thr Gln Thr Thr Phe Thr Thr His Met Pro Ser Ala Ser
1700             1705             1710

Thr Glu Gln Pro Thr Ala Thr Ser Arg Gly Gly Pro Thr Ala Thr
1715             1720             1725

Ser Val Thr Gln Gly Thr His Thr Thr Leu Val Thr Arg Asn Cys
1730             1735             1740

His Pro Arg Cys Thr Trp Thr Lys Trp Phe Asp Val Asp Phe Pro
1745             1750             1755

Ser Pro Gly Pro His Gly Gly Asp Lys Glu Thr Tyr Asn Asn Ile
1760             1765             1770

Ile Arg Ser Gly Glu Lys Ile Cys Arg Arg Pro Glu Glu Ile Thr
1775             1780             1785

Arg Leu Gln Cys Arg Ala Lys Ser His Pro Glu Val Ser Ile Glu
1790             1795             1800

His Leu Gly Gln Val Val Gln Cys Ser Arg Glu Glu Gly Leu Val
1805             1810             1815

Cys Arg Asn Gln Asp Gln Gln Gly Pro Phe Lys Met Cys Leu Asn
1820             1825             1830

Tyr Glu Val Arg Val Leu Cys Cys Glu Thr Pro Arg Gly Cys His
1835             1840             1845

Met Thr Ser Thr Pro Gly Ser Thr Ser Ser Ser Pro Ala Gln Thr
1850             1855             1860

Thr Pro Ser Thr Thr Ser Lys Thr Thr Glu Thr Gln Ala Ser Gly
1865             1870             1875

Ser Ser Ala Pro Ser Ser Pro Gly Thr Val Ser Leu Ser Thr
1880             1885             1890

Ala Arg Thr Thr Pro Ala Pro Gly Thr Ala Thr Ser Val Lys Lys
1895             1900             1905

Thr Phe Ser Thr Pro Ser Pro Pro Val Pro Ala Thr Ser Thr
1910             1915             1920

Ser Ser Met Ser Thr Thr Ala Pro Gly Thr Ser Val Val Ser Ser
```

```
                  1925                1930                1935
Lys Pro Thr Pro Thr Glu Pro Ser Thr Ser Ser Cys Leu Gln Glu
       1940                1945                1950

Leu Cys Thr Trp Thr Glu Trp Ile Asp Gly Ser Tyr Pro Ala Pro
       1955                1960                1965

Gly Ile Asn Gly Gly Asp Phe Asp Thr Phe Gln Asn Leu Arg Asp
       1970                1975                1980

Glu Gly Tyr Thr Phe Cys Glu Ser Pro Arg Ser Val Gln Cys Arg
       1985                1990                1995

Ala Glu Ser Phe Pro Asn Thr Pro Leu Ala Asp Leu Gly Gln Asp
       2000                2005                2010

Val Ile Cys Ser His Thr Glu Gly Leu Ile Cys Leu Asn Lys Asn
       2015                2020                2025

Gln Leu Pro Pro Ile Cys Tyr Asn Tyr Glu Ile Arg Ile Gln Cys
       2030                2035                2040

Cys Glu Thr Val Asn Val Cys Arg Asp Ile Thr Arg Pro Pro Lys
       2045                2050                2055

Thr Val Ala Thr Thr Arg Pro Thr Pro His Pro Thr Gly Ala Gln
       2060                2065                2070

Thr Gln Thr Thr Phe Thr Thr His Met Pro Ser Ala Ser Thr Glu
       2075                2080                2085

Gln Pro Thr Ala Thr Ser Arg Gly Gly Pro Thr Ala Thr Ser Val
       2090                2095                2100

Thr Gln Gly Thr His Thr Thr Pro Val Thr Arg Asn Cys His Pro
       2105                2110                2115

Arg Cys Thr Trp Thr Thr Trp Phe Asp Val Asp Phe Pro Ser Pro
       2120                2125                2130

Gly Pro His Gly Gly Asp Lys Glu Thr Tyr Asn Asn Ile Ile Arg
       2135                2140                2145

Ser Gly Glu Lys Ile Cys Arg Arg Pro Glu Glu Ile Thr Arg Leu
       2150                2155                2160

Gln Cys Arg Ala Lys Ser His Pro Glu Val Ser Ile Glu His Leu
       2165                2170                2175

Gly Gln Val Val Gln Cys Ser Arg Glu Glu Gly Leu Val Cys Arg
       2180                2185                2190

Asn Gln Asp Gln Gln Gly Pro Phe Lys Met Cys Leu Asn Tyr Glu
       2195                2200                2205

Val Arg Val Leu Cys Cys Glu Thr Pro Lys Gly Cys Pro Val Thr
       2210                2215                2220

Ser Thr Pro Val Thr Ala Pro Ser Thr Pro Ser Gly Arg Ala Thr
       2225                2230                2235

Ser Pro Thr Gln Ser Thr Ser Ser Trp Gln Lys Ser Arg Thr Thr
       2240                2245                2250

Thr Leu Val Thr Thr Ser Thr Thr Ser Thr Pro Gln Thr Ser Thr
       2255                2260                2265

Thr Tyr Ala His Thr Thr Ser Thr Thr Ser Ala Pro Thr Ala Arg
       2270                2275                2280

Thr Thr Ser Ala Pro Thr Thr Arg Thr Thr Ser Ala Ser Pro Ala
       2285                2290                2295

Ser Thr Thr Ser Gly Pro Gly Asn Thr Pro Ser Pro Val Pro Thr
       2300                2305                2310

Thr Ser Thr Ile Ser Ala Pro Thr Thr Ser Ile Thr Ser Ala Pro
       2315                2320                2325
```

```
Thr Thr Ser Thr Thr Ser Ala Pro Thr Ser Ser Thr Thr Ser Gly
    2330            2335                2340

Pro Gly Thr Thr Pro Ser Pro Val Pro Thr Thr Ser Ile Thr Ser
    2345            2350                2355

Ala Pro Thr Thr Ser Thr Thr Ser Ala Pro Thr Thr Ser Thr Thr
    2360            2365                2370

Ser Ala Arg Thr Ser Ser Thr Ser Ala Thr Thr Ser Arg
    2375            2380                2385

Ile Ser Gly Pro Glu Thr Thr Pro Ser Pro Val Pro Thr Thr Ser
    2390            2395                2400

Thr Thr Ser Ala Thr Thr Ser Thr Thr Ser Ala Pro Thr Thr
    2405            2410                2415

Ser Thr Thr Ser Ala Pro Thr Ser Ser Thr Thr Ser Ser Pro Gln
    2420            2425                2430

Thr Ser Thr Thr Ser Ala Pro Thr Thr Ser Thr Thr Ser Gly Pro
    2435            2440                2445

Gly Thr Thr Pro Ser Pro Val Pro Thr Thr Ser Thr Thr Ser Ala
    2450            2455                2460

Pro Thr Thr Arg Thr Thr Ser Ala Pro Lys Ser Ser Thr Thr Ser
    2465            2470                2475

Ala Ala Thr Thr Ser Thr Thr Ser Gly Pro Glu Thr Thr Pro Arg
    2480            2485                2490

Pro Val Pro Thr Thr Ser Thr Thr Ser Ser Pro Thr Thr Ser Thr
    2495            2500                2505

Thr Ser Ala Pro Thr Thr Ser Thr Thr Ser Ala Ser Thr Thr Ser
    2510            2515                2520

Thr Thr Ser Gly Ala Gly Thr Thr Pro Ser Pro Val Pro Thr Thr
    2525            2530                2535

Ser Thr Thr Ser Ala Pro Thr Ser Thr Thr Ser Ala Pro Ile
    2540            2545                2550

Ser Ser Thr Thr Ser Ala Thr Thr Ser Thr Thr Ser Gly Pro
    2555            2560                2565

Gly Thr Thr Pro Ser Pro Val Pro Thr Thr Ser Thr Thr Ser Ala
    2570            2575                2580

Pro Thr Thr Ser Thr Thr Ser Gly Pro Gly Thr Thr Pro Ser Ala
    2585            2590                2595

Val Pro Thr Thr Ser Ile Thr Ser Ala Pro Thr Thr Ser Thr Asn
    2600            2605                2610

Ser Ala Pro Ile Ser Ser Thr Thr Ser Ala Thr Thr Thr Ser Arg
    2615            2620                2625

Ile Ser Gly Pro Glu Thr Thr Pro Ser Pro Val Pro Thr Ala Ser
    2630            2635                2640

Thr Thr Ser Ala Ser Thr Thr Ser Thr Thr Ser Gly Pro Gly Thr
    2645            2650                2655

Thr Pro Ser Pro Val Pro Thr Thr Ser Thr Ile Ser Val Pro Thr
    2660            2665                2670

Thr Ser Thr Thr Ser Ala Ser Thr Thr Ser Thr Thr Ser Ala Ser
    2675            2680                2685

Thr Thr Ser Thr Thr Ser Gly Pro Gly Thr Thr Pro Ser Pro Val
    2690            2695                2700

Pro Thr Thr Ser Thr Thr Ser Ala Pro Thr Thr Ser Thr Thr Ser
    2705            2710                2715
```

```
Ala Pro Thr Thr Ser Thr Ile Ser Ala Pro Thr Thr Ser Thr Thr
2720                2725                2730

Ser Ala Thr Thr Thr Ser Thr Thr Ser Ala Pro Thr Pro Arg Arg
2735                2740                2745

Thr Ser Ala Pro Thr Ser Thr Ile Ser Ala Ser Thr Thr Ser
2750                2755                2760

Thr Thr Ser Ala Thr Thr Thr Ser Thr Thr Ser Ala Thr Thr Thr
2765                2770                2775

Ser Thr Ile Ser Ala Pro Thr Thr Ser Thr Thr Leu Ser Pro Thr
2780                2785                2790

Thr Ser Thr Thr Ser Thr Thr Ile Thr Ser Thr Thr Ser Ala Pro
2795                2800                2805

Ile Ser Ser Thr Thr Ser Thr Pro Gln Thr Ser Thr Thr Ser Ala
2810                2815                2820

Pro Thr Thr Ser Thr Thr Ser Gly Pro Gly Thr Thr Ser Ser Pro
2825                2830                2835

Val Pro Thr Thr Ser Thr Thr Ser Ala Pro Thr Thr Ser Thr Thr
2840                2845                2850

Ser Ala Pro Thr Thr Arg Thr Thr Ser Val Pro Thr Ser Ser Thr
2855                2860                2865

Thr Ser Thr Ala Thr Thr Ser Thr Thr Ser Gly Pro Gly Thr Thr
2870                2875                2880

Pro Ser Pro Val Pro Thr Thr Ser Thr Thr Ser Ala Pro Thr Thr
2885                2890                2895

Arg Thr Thr Ser Ala Pro Thr Thr Ser Thr Thr Ser Ala Pro Thr
2900                2905                2910

Thr Ser Thr Thr Ser Ala Pro Thr Ser Ser Thr Thr Ser Ala Thr
2915                2920                2925

Thr Thr Ser Thr Ile Ser Val Pro Thr Thr Ser Thr Thr Ser Val
2930                2935                2940

Pro Gly Thr Thr Pro Ser Pro Val Pro Thr Thr Ser Thr Ile Ser
2945                2950                2955

Val Pro Thr Thr Ser Thr Thr Ser Ala Ser Thr Thr Ser Thr Thr
2960                2965                2970

Ser Gly Pro Gly Thr Thr Pro Ser Pro Val Pro Thr Thr Ser Thr
2975                2980                2985

Thr Ser Ala Pro Thr Thr Ser Thr Thr Ser Ala Pro Thr Thr Ser
2990                2995                3000

Thr Ile Ser Ala Pro Thr Thr Ser Thr Pro Ser Ala Pro Thr Thr
3005                3010                3015

Ser Thr Thr Leu Ala Pro Thr Thr Ser Thr Thr Ser Ala Pro Thr
3020                3025                3030

Thr Ser Thr Thr Ser Thr Pro Thr Ser Ser Thr Thr Ser Ser Pro
3035                3040                3045

Gln Thr Ser Thr Thr Ser Ala Ser Thr Thr Ser Ile Thr Ser Gly
3050                3055                3060

Pro Gly Thr Thr Pro Ser Pro Val Pro Thr Thr Ser Thr Thr Ser
3065                3070                3075

Ala Pro Thr Thr Ser Thr Thr Ser Ala Ala Thr Thr Ser Thr Ile
3080                3085                3090

Ser Ala Pro Thr Thr Ser Thr Thr Ser Ala Pro Thr Thr Ser Thr
3095                3100                3105

Thr Ser Ala Ser Thr Ala Ser Lys Thr Ser Gly Leu Gly Thr Thr
```

```
            3110            3115              3120
Pro Ser Pro Ile Pro Thr Thr Ser Thr Thr Ser Pro Pro Thr Thr
        3125            3130              3135

Ser Thr Thr Ser Ala Ser Thr Ala Ser Lys Thr Ser Gly Pro Gly
        3140            3145              3150

Thr Thr Pro Ser Pro Val Pro Thr Thr Ser Thr Ile Phe Ala Pro
        3155            3160              3165

Arg Thr Ser Thr Thr Ser Ala Ser Thr Ser Thr Thr Pro Gly
        3170            3175              3180

Pro Gly Thr Thr Pro Ser Pro Val Pro Thr Thr Ser Thr Ala Ser
        3185            3190              3195

Val Ser Lys Thr Ser Thr Ser His Val Ser Ile Ser Lys Thr Thr
        3200            3205              3210

His Ser Gln Pro Val Thr Arg Asp Cys His Leu Arg Cys Thr Trp
        3215            3220              3225

Thr Lys Trp Phe Asp Ile Asp Phe Pro Ser Pro Gly Pro His Gly
        3230            3235              3240

Gly Asp Lys Glu Thr Tyr Asn Asn Ile Ile Arg Ser Gly Glu Lys
        3245            3250              3255

Ile Cys Arg Arg Pro Glu Glu Ile Thr Arg Leu Gln Cys Arg Ala
        3260            3265              3270

Glu Ser His Pro Glu Val Ser Ile Glu His Leu Gly Gln Val Val
        3275            3280              3285

Gln Cys Ser Arg Glu Glu Gly Leu Val Cys Arg Asn Gln Asp Gln
        3290            3295              3300

Gln Gly Pro Phe Lys Met Cys Leu Asn Tyr Glu Val Arg Val Leu
        3305            3310              3315

Cys Cys Glu Thr Pro Lys Gly Cys Pro Val Thr Ser Thr Pro Val
        3320            3325              3330

Thr Ala Pro Ser Thr Pro Ser Gly Arg Ala Thr Ser Pro Thr Gln
        3335            3340              3345

Ser Thr Ser Ser Trp Gln Lys Ser Arg Thr Thr Thr Leu Val Thr
        3350            3355              3360

Thr Ser Thr Thr Ser Thr Pro Gln Thr Ser Thr Thr Ser Ala Pro
        3365            3370              3375

Thr Thr Ser Thr Thr Ser Ala Pro Thr Thr Ser Thr Thr Ser Ala
        3380            3385              3390

Pro Thr Thr Ser Thr Thr Ser Thr Pro Gln Thr Ser Ile Ser Ser
        3395            3400              3405

Ala Pro Thr Ser Ser Thr Thr Ser Ala Pro Thr Ser Ser Thr Ile
        3410            3415              3420

Ser Ala Arg Thr Thr Ser Ile Ile Ser Ala Pro Thr Thr Ser Thr
        3425            3430              3435

Thr Ser Ser Pro Thr Thr Ser Thr Thr Ser Ala Thr Thr Thr Ser
        3440            3445              3450

Thr Thr Ser Ala Pro Thr Ser Ser Thr Thr Ser Thr Pro Gln Thr
        3455            3460              3465

Ser Lys Thr Ser Ala Ala Thr Ser Ser Thr Thr Ser Gly Ser Gly
        3470            3475              3480

Thr Thr Pro Ser Pro Val Thr Thr Thr Ser Thr Ala Ser Val Ser
        3485            3490              3495

Lys Thr Ser Thr Ser His Val Ser Val Ser Lys Thr Thr His Ser
        3500            3505              3510
```

-continued

```
Gln Pro Val Thr Arg Asp Cys His Pro Arg Cys Thr Trp Thr Lys
3515                3520                3525

Trp Phe Asp Val Asp Phe Pro Ser Pro Gly Pro His Gly Gly Asp
3530                3535                3540

Lys Glu Thr Tyr Asn Asn Ile Ile Arg Ser Gly Glu Lys Ile Cys
3545                3550                3555

Arg Arg Pro Glu Glu Ile Thr Arg Leu Gln Cys Arg Ala Lys Ser
3560                3565                3570

His Pro Glu Val Ser Ile Glu His Leu Gly Gln Val Val Gln Cys
3575                3580                3585

Ser Arg Glu Glu Gly Leu Val Cys Arg Asn Gln Asp Gln Gln Gly
3590                3595                3600

Pro Phe Lys Met Cys Leu Asn Tyr Glu Val Arg Val Leu Cys Cys
3605                3610                3615

Glu Thr Pro Lys Gly Cys Pro Val Thr Ser Thr Ser Val Thr Ala
3620                3625                3630

Pro Ser Thr Pro Ser Gly Arg Ala Thr Ser Pro Thr Gln Ser Thr
3635                3640                3645

Ser Ser Trp Gln Lys Ser Arg Thr Thr Thr Leu Val Thr Ser Ser
3650                3655                3660

Ile Thr Ser Thr Thr Gln Thr Ser Thr Thr Ser Ala Pro Thr Thr
3665                3670                3675

Ser Thr Thr Pro Ala Ser Ile Pro Ser Thr Thr Ser Ala Pro Thr
3680                3685                3690

Thr Ser Thr Thr Ser Ala Pro Thr Thr Ser Thr Thr Ser Ala Pro
3695                3700                3705

Thr Thr Ser Thr Thr Ser Thr Pro Gln Thr Thr Thr Ser Ser Ala
3710                3715                3720

Pro Thr Ser Ser Thr Thr Ser Ala Pro Thr Thr Ser Thr Ile Ser
3725                3730                3735

Ala Pro Thr Thr Ser Thr Ile Ser Ala Pro Thr Thr Ser Thr Thr
3740                3745                3750

Ser Ala Pro Thr Ala Ser Thr Thr Ser Ala Pro Thr Ser Thr Ser
3755                3760                3765

Ser Ala Pro Thr Thr Asn Thr Thr Ser Ala Pro Thr Thr Ser Thr
3770                3775                3780

Thr Ser Ala Pro Ile Thr Ser Thr Ile Ser Ala Pro Thr Thr Ser
3785                3790                3795

Thr Thr Ser Thr Pro Gln Thr Ser Thr Ile Ser Ser Pro Thr Thr
3800                3805                3810

Ser Thr Thr Ser Thr Pro Gln Thr Ser Thr Thr Ser Ser Pro Thr
3815                3820                3825

Thr Ser Thr Thr Ser Ala Pro Thr Thr Ser Thr Thr Ser Ala Pro
3830                3835                3840

Thr Thr Ser Thr Thr Ser Thr Pro Gln Thr Ser Ile Ser Ser Ala
3845                3850                3855

Pro Thr Ser Ser Thr Thr Ser Ala Pro Thr Ala Ser Thr Ile Ser
3860                3865                3870

Ala Pro Thr Thr Ser Thr Thr Ser Phe His Thr Thr Ser Thr Thr
3875                3880                3885

Ser Pro Pro Thr Ser Ser Thr Ser Ser Thr Pro Gln Thr Ser Lys
3890                3895                3900
```

```
Thr Ser Ala Ala Thr Ser Ser Thr Thr Ser Gly Ser Gly Thr Thr
    3905            3910            3915

Pro Ser Pro Val Pro Thr Thr Ser Thr Ala Ser Val Ser Lys Thr
    3920            3925            3930

Ser Thr Ser His Val Ser Val Ser Lys Thr Thr His Ser Gln Pro
    3935            3940            3945

Val Thr Arg Asp Cys His Pro Arg Cys Thr Trp Thr Lys Trp Phe
    3950            3955            3960

Asp Val Asp Phe Pro Ser Pro Gly Pro His Gly Gly Asp Lys Glu
    3965            3970            3975

Thr Tyr Asn Asn Ile Ile Arg Ser Gly Glu Lys Ile Cys Arg Arg
    3980            3985            3990

Pro Glu Glu Ile Thr Arg Leu Gln Cys Arg Ala Glu Ser His Pro
    3995            4000            4005

Glu Val Ser Ile Glu His Leu Gly Gln Val Val Gln Cys Ser Arg
    4010            4015            4020

Glu Glu Gly Leu Val Cys Arg Asn Gln Asp Gln Gln Gly Pro Phe
    4025            4030            4035

Lys Met Cys Leu Asn Tyr Glu Val Arg Val Leu Cys Cys Glu Thr
    4040            4045            4050

Pro Lys Gly Cys Pro Val Thr Ser Thr Pro Val Thr Ala Pro Ser
    4055            4060            4065

Thr Pro Ser Gly Arg Ala Thr Ser Pro Thr Gln Ser Thr Ser Ser
    4070            4075            4080

Trp Gln Lys Ser Arg Thr Thr Thr Leu Val Thr Thr Ser Thr Thr
    4085            4090            4095

Ser Thr Pro Gln Thr Ser Thr Thr Ser Ala Pro Thr Thr Ser Thr
    4100            4105            4110

Ile Pro Ala Ser Thr Pro Ser Thr Thr Ser Ala Pro Thr Thr Ser
    4115            4120            4125

Thr Thr Ser Ala Pro Thr Thr Ser Thr Thr Ser Ala Pro Thr His
    4130            4135            4140

Arg Thr Thr Ser Gly Pro Thr Thr Ser Thr Thr Leu Ala Pro Thr
    4145            4150            4155

Thr Ser Thr Thr Ser Ala Pro Thr Thr Ser Thr Asn Ser Ala Pro
    4160            4165            4170

Thr Thr Ser Thr Ile Ser Ala Ser Thr Ser Thr Ile Ser Ala
    4175            4180            4185

Pro Thr Thr Ser Thr Ile Ser Ser Pro Thr Ser Ser Thr Thr Ser
    4190            4195            4200

Thr Pro Gln Thr Ser Lys Thr Ser Ala Ala Thr Ser Ser Thr Thr
    4205            4210            4215

Ser Gly Ser Gly Thr Thr Pro Ser Pro Val Pro Thr Thr Ser Thr
    4220            4225            4230

Thr Ser Ala Ser Thr Thr Ser Thr Thr Ser Ala Pro Thr Thr Ser
    4235            4240            4245

Thr Thr Ser Gly Pro Gly Thr Pro Ser Pro Val Pro Ser Thr
    4250            4255            4260

Ser Thr Thr Ser Ala Ala Thr Thr Ser Thr Thr Ser Ala Pro Thr
    4265            4270            4275

Thr Arg Thr Thr Ser Ala Pro Thr Ser Ser Met Thr Ser Gly Pro
    4280            4285            4290

Gly Thr Thr Pro Ser Pro Val Pro Thr Thr Ser Thr Thr Ser Ala
```

-continued

```
            4295              4300              4305
Pro Thr Thr Ser Thr Thr Ser Gly Pro Gly Thr Thr Pro Ser Pro
    4310              4315              4320
Val Pro Thr Thr Ser Thr Thr Ser Ala Pro Ile Thr Ser Thr Thr
    4325              4330              4335
Ser Gly Pro Gly Ser Thr Pro Ser Pro Val Pro Thr Thr Ser Thr
    4340              4345              4350
Thr Ser Ala Pro Thr Thr Ser Thr Thr Ser Ala Ser Thr Ala Ser
    4355              4360              4365
Thr Thr Ser Gly Pro Gly Thr Pro Ser Pro Val Pro Thr Thr
    4370              4375              4380
Ser Thr Thr Ser Ala Pro Thr Thr Arg Thr Thr Ser Ala Ser Thr
    4385              4390              4395
Ala Ser Thr Thr Ser Gly Pro Gly Ser Thr Pro Ser Pro Val Pro
    4400              4405              4410
Thr Thr Ser Thr Thr Ser Ala Pro Thr Thr Arg Thr Thr Pro Ala
    4415              4420              4425
Ser Thr Ala Ser Thr Thr Ser Gly Pro Gly Thr Thr Pro Ser Pro
    4430              4435              4440
Val Pro Thr Thr Ser Thr Thr Ser Ala Ser Thr Thr Ser Thr Ile
    4445              4450              4455
Ser Leu Pro Thr Thr Ser Thr Thr Ser Ala Pro Ile Thr Ser Met
    4460              4465              4470
Thr Ser Gly Pro Gly Thr Thr Pro Ser Pro Val Pro Thr Thr Ser
    4475              4480              4485
Thr Thr Ser Ala Pro Thr Thr Ser Thr Thr Ser Ala Ser Thr Ala
    4490              4495              4500
Ser Thr Thr Ser Gly Pro Gly Thr Thr Pro Ser Pro Val Pro Thr
    4505              4510              4515
Thr Ser Thr Thr Ser Ala Pro Thr Thr Ser Thr Thr Ser Ala Ser
    4520              4525              4530
Thr Ala Ser Thr Thr Ser Gly Pro Gly Thr Ser Leu Ser Pro Val
    4535              4540              4545
Pro Thr Thr Ser Thr Thr Ser Ala Pro Thr Thr Ser Thr Thr Ser
    4550              4555              4560
Gly Pro Gly Thr Thr Pro Ser Pro Val Pro Thr Thr Ser Thr Thr
    4565              4570              4575
Ser Ala Pro Thr Thr Ser Thr Ser Gly Pro Gly Thr Thr Pro
    4580              4585              4590
Ser Pro Val Pro Thr Thr Ser Thr Thr Pro Val Ser Lys Thr Ser
    4595              4600              4605
Thr Ser His Leu Ser Val Ser Lys Thr Thr His Ser Gln Pro Val
    4610              4615              4620
Thr Ser Asp Cys His Pro Leu Cys Ala Trp Thr Lys Trp Phe Asp
    4625              4630              4635
Val Asp Phe Pro Ser Pro Gly Pro His Gly Gly Asp Lys Glu Thr
    4640              4645              4650
Tyr Asn Asn Ile Ile Arg Ser Gly Glu Lys Ile Cys Arg Arg Pro
    4655              4660              4665
Glu Glu Ile Thr Arg Leu Gln Cys Arg Ala Glu Ser His Pro Glu
    4670              4675              4680
Val Asn Ile Glu His Leu Gly Gln Val Val Gln Cys Ser Arg Glu
    4685              4690              4695
```

```
Glu Gly Leu Val Cys Arg Asn Gln Asp Gln Gln Gly Pro Phe Lys
    4700                4705                4710

Met Cys Leu Asn Tyr Glu Val Arg Val Leu Cys Cys Glu Thr Pro
    4715                4720                4725

Arg Gly Cys Pro Val Thr Ser Val Thr Pro Tyr Gly Thr Ser Pro
    4730                4735                4740

Thr Asn Ala Leu Tyr Pro Ser Leu Ser Thr Ser Met Val Ser Ala
    4745                4750                4755

Ser Val Ala Ser Thr Ser Val Ala Ser Ser Val Ala Ser Ser
    4760                4765                4770

Ser Val Ala Tyr Ser Thr Gln Thr Cys Phe Cys Asn Val Ala Asp
    4775                4780                4785

Arg Leu Tyr Pro Ala Gly Ser Thr Ile Tyr Arg His Arg Asp Leu
    4790                4795                4800

Ala Gly His Cys Tyr Tyr Ala Leu Cys Ser Gln Asp Cys Gln Val
    4805                4810                4815

Val Arg Gly Val Asp Ser Asp Cys Pro Ser Thr Thr Leu Pro Pro
    4820                4825                4830

Ala Pro Ala Thr Ser Pro Ser Ile Ser Thr Ser Glu Pro Val Thr
    4835                4840                4845

Glu Leu Gly Cys Pro Asn Ala Val Pro Pro Arg Lys Lys Gly Glu
    4850                4855                4860

Thr Trp Ala Thr Pro Asn Cys Ser Glu Ala Thr Cys Glu Gly Asn
    4865                4870                4875

Asn Val Ile Ser Leu Arg Pro Arg Thr Cys Pro Arg Val Glu Lys
    4880                4885                4890

Pro Thr Cys Ala Asn Gly Tyr Pro Ala Val Lys Val Ala Asp Gln
    4895                4900                4905

Asp Gly Cys Cys His His Tyr Gln Cys Gln Cys Val Cys Ser Gly
    4910                4915                4920

Trp Gly Asp Pro His Tyr Ile Thr Phe Asp Gly Thr Tyr Tyr Thr
    4925                4930                4935

Phe Leu Asp Asn Cys Thr Tyr Val Leu Val Gln Gln Ile Val Pro
    4940                4945                4950

Val Tyr Gly His Phe Arg Val Leu Val Asp Asn Tyr Phe Cys Gly
    4955                4960                4965

Ala Glu Asp Gly Leu Ser Cys Pro Arg Ser Ile Ile Leu Glu Tyr
    4970                4975                4980

His Gln Asp Arg Val Val Leu Thr Arg Lys Pro Val His Gly Val
    4985                4990                4995

Met Thr Asn Glu Ile Ile Phe Asn Asn Lys Val Val Ser Pro Gly
    5000                5005                5010

Phe Arg Lys Asn Gly Ile Val Val Ser Arg Ile Gly Val Lys Met
    5015                5020                5025

Tyr Ala Thr Ile Pro Glu Leu Gly Val Gln Val Met Phe Ser Gly
    5030                5035                5040

Leu Ile Phe Ser Val Glu Val Pro Phe Ser Lys Phe Ala Asn Asn
    5045                5050                5055

Thr Glu Gly Gln Cys Gly Thr Cys Thr Asn Asp Arg Lys Asp Glu
    5060                5065                5070

Cys Arg Thr Pro Arg Gly Thr Val Val Ala Ser Cys Ser Glu Met
    5075                5080                5085
```

```
Ser Gly Leu Trp Asn Val Ser Ile Pro Asp Gln Pro Ala Cys His
    5090            5095            5100

Arg Pro His Pro Thr Pro Thr Val Gly Pro Thr Thr Val Gly
    5105            5110            5115

Ser Thr Thr Val Gly Pro Thr Val Gly Ser Thr Thr Val Gly
    5120            5125            5130

Pro Thr Thr Pro Pro Ala Pro Cys Leu Pro Ser Pro Ile Cys Gln
    5135            5140            5145

Leu Ile Leu Ser Lys Val Phe Glu Pro Cys His Thr Val Ile Pro
    5150            5155            5160

Pro Leu Leu Phe Tyr Glu Gly Cys Val Phe Asp Arg Cys His Met
    5165            5170            5175

Thr Asp Leu Asp Val Val Cys Ser Ser Leu Glu Leu Tyr Ala Ala
    5180            5185            5190

Leu Cys Ala Ser His Asp Ile Cys Ile Asp Trp Arg Gly Arg Thr
    5195            5200            5205

Gly His Met Cys Pro Phe Thr Cys Pro Ala Asp Lys Val Tyr Gln
    5210            5215            5220

Pro Cys Gly Pro Ser Asn Pro Ser Tyr Cys Tyr Gly Asn Asp Ser
    5225            5230            5235

Ala Ser Leu Gly Ala Leu Pro Glu Ala Gly Pro Ile Thr Glu Gly
    5240            5245            5250

Cys Phe Cys Pro Glu Gly Met Thr Leu Phe Ser Thr Ser Ala Gln
    5255            5260            5265

Val Cys Val Pro Thr Gly Cys Pro Arg Cys Leu Gly Pro His Gly
    5270            5275            5280

Glu Pro Val Lys Val Gly His Thr Val Gly Met Asp Cys Gln Glu
    5285            5290            5295

Cys Thr Cys Glu Ala Ala Thr Trp Thr Leu Thr Cys Arg Pro Lys
    5300            5305            5310

Leu Cys Pro Leu Pro Pro Ala Cys Pro Leu Pro Gly Phe Val Pro
    5315            5320            5325

Val Pro Ala Ala Pro Gln Ala Gly Gln Cys Cys Pro Gln Tyr Ser
    5330            5335            5340

Cys Ala Cys Asn Thr Ser Arg Cys Pro Ala Pro Val Gly Cys Pro
    5345            5350            5355

Glu Gly Ala Arg Ala Ile Pro Thr Tyr Gln Glu Gly Ala Cys Cys
    5360            5365            5370

Pro Val Gln Asn Cys Ser Trp Thr Val Cys Ser Ile Asn Gly Thr
    5375            5380            5385

Leu Tyr Gln Pro Gly Ala Val Val Ser Ser Leu Cys Glu Thr
    5390            5395            5400

Cys Arg Cys Glu Leu Pro Gly Gly Pro Pro Ser Asp Ala Phe Val
    5405            5410            5415

Val Ser Cys Glu Thr Gln Ile Cys Asn Thr His Cys Pro Val Gly
    5420            5425            5430

Phe Glu Tyr Gln Glu Gln Ser Gly Gln Cys Cys Gly Thr Cys Val
    5435            5440            5445

Gln Val Ala Cys Val Thr Asn Thr Ser Lys Ser Pro Ala His Leu
    5450            5455            5460

Phe Tyr Pro Gly Glu Thr Trp Ser Asp Ala Gly Asn His Cys Val
    5465            5470            5475

Thr His Gln Cys Glu Lys His Gln Asp Gly Leu Val Val Val Thr
```

```
                   5480                5485                5490
Thr Lys Lys Ala Cys Pro Pro Leu Ser Cys Ser Leu Asp Glu Ala
       5495                5500                5505

Arg Met Ser Lys Asp Gly Cys Cys Arg Phe Cys Pro Pro Pro
   5510                5515                5520

Pro Pro Tyr Gln Asn Gln Ser Thr Cys Ala Val Tyr His Arg Ser
       5525                5530                5535

Leu Ile Ile Gln Gln Gln Gly Cys Ser Ser Ser Glu Pro Val Arg
       5540                5545                5550

Leu Ala Tyr Cys Arg Gly Asn Cys Gly Asp Ser Ser Met Tyr
       5555                5560                5565

Ser Leu Glu Gly Asn Thr Val Glu His Arg Cys Gln Cys Cys Gln
       5570                5575                5580

Glu Leu Arg Thr Ser Leu Arg Asn Val Thr Leu His Cys Thr Asp
       5585                5590                5595

Gly Ser Ser Arg Ala Phe Ser Tyr Thr Glu Val Glu Glu Cys Gly
       5600                5605                5610

Cys Met Gly Arg Arg Cys Pro Ala Pro Gly Asp Thr Gln His Ser
       5615                5620                5625

Glu Glu Ala Glu Pro Glu Pro Ser Gln Glu Ala Glu Ser Gly Ser
       5630                5635                5640

Trp Glu Arg Gly Val Pro Val Ser Pro Met His
       5645                5650

<210> SEQ ID NO 6
<211> LENGTH: 5762
<212> TYPE: PRT
<213> ORGANISM: Homo sapiens

<400> SEQUENCE: 6

Met Gly Ala Pro Ser Ala Cys Arg Thr Leu Val Leu Ala Leu Ala Ala
 1               5                  10                  15

Met Leu Val Val Pro Gln Ala Glu Thr Gln Gly Pro Val Glu Pro Ser
                20                  25                  30

Trp Glu Asn Ala Gly His Thr Met Asp Gly Gly Ala Pro Thr Ser Ser
            35                  40                  45

Pro Thr Arg Arg Val Ser Phe Val Pro Pro Val Thr Val Phe Pro Ser
        50                  55                  60

Leu Ser Pro Leu Asn Pro Ala His Asn Gly Arg Val Cys Ser Thr Trp
 65                  70                  75                  80

Gly Asp Phe His Tyr Lys Thr Phe Asp Gly Asp Val Phe Arg Phe Pro
                85                  90                  95

Gly Leu Cys Asn Tyr Val Phe Ser Glu His Cys Arg Ala Ala Tyr Glu
            100                 105                 110

Asp Phe Asn Val Gln Leu Arg Arg Gly Leu Val Gly Ser Arg Pro Val
        115                 120                 125

Val Thr Arg Val Val Ile Lys Ala Gln Gly Leu Val Leu Glu Ala Ser
    130                 135                 140

Asn Gly Ser Val Leu Ile Asn Gly Gln Arg Glu Glu Leu Pro Tyr Ser
145                 150                 155                 160

Arg Thr Gly Leu Leu Val Glu Gln Ser Gly Asp Tyr Ile Lys Val Ser
                165                 170                 175

Ile Arg Leu Val Leu Thr Phe Leu Trp Asn Gly Glu Asp Ser Ala Leu
            180                 185                 190
```

```
Leu Glu Leu Asp Pro Lys Tyr Ala Asn Gln Thr Cys Gly Leu Cys Gly
            195                 200                 205

Asp Phe Asn Gly Leu Pro Ala Phe Asn Glu Phe Tyr Ala His Asn Ala
210                 215                 220

Arg Leu Thr Pro Leu Gln Phe Gly Asn Leu Gln Lys Leu Asp Gly Pro
225                 230                 235                 240

Thr Glu Gln Cys Pro Asp Pro Leu Pro Leu Pro Ala Gly Asn Cys Thr
                245                 250                 255

Asp Glu Glu Gly Ile Cys His Arg Thr Leu Leu Gly Pro Ala Phe Ala
            260                 265                 270

Glu Cys His Ala Leu Val Asp Ser Thr Ala Tyr Leu Ala Ala Cys Ala
        275                 280                 285

Gln Asp Leu Cys Arg Cys Pro Thr Cys Pro Cys Ala Thr Phe Val Glu
    290                 295                 300

Tyr Ser Arg Gln Cys Ala His Ala Gly Gly Gln Pro Arg Asn Trp Arg
305                 310                 315                 320

Cys Pro Glu Leu Cys Pro Arg Thr Cys Pro Leu Asn Met Gln His Gln
                325                 330                 335

Glu Cys Gly Ser Pro Cys Thr Asp Thr Cys Ser Asn Pro Gln Arg Ala
            340                 345                 350

Gln Leu Cys Glu Asp His Cys Val Asp Gly Cys Phe Cys Pro Pro Gly
        355                 360                 365

Thr Val Leu Asp Asp Ile Thr His Ser Gly Cys Leu Pro Leu Gly Gln
    370                 375                 380

Cys Pro Cys Thr His Gly Gly Arg Thr Tyr Ser Pro Gly Thr Ser Phe
385                 390                 395                 400

Asn Thr Thr Cys Ser Ser Cys Thr Cys Ser Gly Gly Leu Trp Gln Cys
                405                 410                 415

Gln Asp Leu Pro Cys Pro Gly Thr Cys Ser Val Gln Gly Gly Ala His
            420                 425                 430

Ile Ser Thr Tyr Asp Glu Lys Leu Tyr Asp Leu His Gly Asp Cys Ser
        435                 440                 445

Tyr Val Leu Ser Lys Lys Cys Ala Asp Ser Ser Phe Thr Val Leu Ala
    450                 455                 460

Glu Leu Arg Lys Cys Gly Leu Thr Asp Asn Glu Asn Cys Leu Lys Ala
465                 470                 475                 480

Val Thr Leu Ser Leu Asp Gly Gly Asp Thr Ala Ile Arg Val Gln Ala
                485                 490                 495

Asp Gly Gly Val Phe Leu Asn Ser Ile Tyr Thr Gln Leu Pro Leu Ser
            500                 505                 510

Ala Ala Asn Ile Thr Leu Phe Thr Pro Ser Ser Phe Phe Ile Val Val
        515                 520                 525

Gln Thr Gly Leu Gly Leu Gln Leu Leu Val Gln Leu Val Pro Leu Met
    530                 535                 540

Gln Val Phe Val Arg Leu Asp Pro Ala His Gln Gly Gln Met Cys Gly
545                 550                 555                 560

Leu Cys Gly Asn Phe Asn Gln Asn Gln Ala Asp Asp Phe Thr Ala Leu
                565                 570                 575

Ser Gly Val Val Glu Ala Thr Gly Ala Ala Phe Ala Asn Thr Trp Lys
            580                 585                 590

Ala Gln Ala Ala Cys Ala Asn Ala Arg Asn Ser Phe Glu Asp Pro Cys
        595                 600                 605

Ser Leu Ser Val Glu Asn Glu Asn Tyr Ala Arg His Trp Cys Ser Arg
```

```
                610             615             620
Leu Thr Asp Pro Asn Ser Ala Phe Ser Arg Cys His Ser Ile Ile Asn
625                 630             635                 640

Pro Lys Pro Phe His Ser Asn Cys Met Phe Asp Thr Cys Asn Cys Glu
                645             650             655

Arg Ser Glu Asp Cys Leu Cys Ala Ala Leu Ser Ser Tyr Val His Ala
                660             665             670

Cys Ala Ala Lys Gly Val Gln Leu Ser Asp Trp Arg Asp Gly Val Cys
            675             680             685

Thr Lys Tyr Met Gln Asn Cys Pro Lys Ser Gln Arg Tyr Ala Tyr Val
            690             695             700

Val Asp Ala Cys Gln Pro Thr Cys Arg Gly Leu Ser Glu Ala Asp Val
705             710             715                 720

Thr Cys Ser Val Ser Phe Val Pro Val Asp Gly Cys Thr Cys Pro Ala
                725             730             735

Gly Thr Phe Leu Asn Asp Ala Gly Ala Cys Val Pro Ala Gln Glu Cys
            740             745             750

Pro Cys Tyr Ala His Gly Thr Val Leu Ala Pro Gly Glu Val Val His
            755             760             765

Asp Glu Gly Ala Val Cys Ser Cys Thr Gly Gly Lys Leu Ser Cys Leu
770             775             780

Gly Ala Ser Leu Gln Lys Ser Thr Gly Cys Ala Ala Pro Met Val Tyr
785             790             795             800

Leu Asp Cys Ser Asn Ser Ser Ala Gly Thr Pro Gly Ala Glu Cys Leu
                805             810             815

Arg Ser Cys His Thr Leu Asp Val Gly Cys Phe Ser Thr His Cys Val
            820             825             830

Ser Gly Cys Val Cys Pro Pro Gly Leu Val Ser Asp Gly Ser Gly Gly
            835             840             845

Cys Ile Ala Glu Glu Asp Cys Pro Cys Val His Asn Glu Ala Thr Tyr
850             855             860

Lys Pro Gly Glu Thr Ile Arg Val Asp Cys Asn Thr Cys Thr Cys Arg
865             870             875             880

Asn Arg Arg Trp Glu Cys Ser His Arg Leu Cys Leu Gly Thr Cys Val
            885             890             895

Ala Tyr Gly Asp Gly His Phe Ile Thr Phe Asp Gly Asp Arg Tyr Ser
            900             905             910

Phe Glu Gly Ser Cys Glu Tyr Ile Leu Ala Gln Asp Tyr Cys Gly Asp
            915             920             925

Asn Thr Thr His Gly Thr Phe Arg Ile Val Thr Glu Asn Ile Pro Cys
930             935             940

Gly Thr Thr Gly Thr Thr Cys Ser Lys Ala Ile Lys Leu Phe Val Glu
945             950             955             960

Ser Tyr Glu Leu Ile Leu Gln Glu Gly Thr Phe Lys Ala Val Ala Arg
            965             970             975

Gly Pro Gly Gly Asp Pro Pro Tyr Lys Ile Arg Tyr Met Gly Ile Phe
            980             985             990

Leu Val Ile Glu Thr His Gly Met Ala Val Ser Trp Asp Arg Lys Thr
            995             1000            1005

Ser Val Phe Ile Arg Leu His Gln Asp Tyr Lys Gly Arg Val Cys
    1010            1015            1020

Gly Leu Cys Gly Asn Phe Asp Asp Asn Ala Ile Asn Asp Phe Ala
    1025            1030            1035
```

```
Thr Arg Ser Arg Ser Val Val Gly Asp Ala Leu Glu Phe Gly Asn
    1040            1045                1050

Ser Trp Lys Leu Ser Pro Ser Cys Pro Asp Ala Leu Ala Pro Lys
    1055            1060                1065

Asp Pro Cys Thr Ala Asn Pro Phe Arg Lys Ser Trp Ala Gln Lys
    1070            1075                1080

Gln Cys Ser Ile Leu His Gly Pro Thr Phe Ala Ala Cys Arg Ser
    1085            1090                1095

Gln Val Asp Ser Thr Lys Tyr Tyr Glu Ala Cys Val Asn Asp Ala
    1100            1105                1110

Cys Ala Cys Asp Ser Gly Gly Asp Cys Glu Cys Phe Cys Thr Ala
    1115            1120                1125

Val Ala Ala Tyr Ala Gln Ala Cys His Asp Ala Gly Leu Cys Val
    1130            1135                1140

Ser Trp Arg Thr Pro Asp Thr Cys Pro Leu Phe Cys Asp Phe Tyr
    1145            1150                1155

Asn Pro His Gly Gly Cys Glu Trp His Tyr Gln Pro Cys Gly Ala
    1160            1165                1170

Pro Cys Leu Lys Thr Cys Arg Asn Pro Ser Gly His Cys Leu Val
    1175            1180                1185

Asp Leu Pro Gly Leu Glu Gly Cys Tyr Pro Lys Cys Pro Pro Ser
    1190            1195                1200

Gln Pro Phe Phe Asn Glu Asp Gln Met Lys Cys Val Ala Gln Cys
    1205            1210                1215

Gly Cys Tyr Asp Lys Asp Gly Asn Tyr Tyr Asp Val Gly Ala Arg
    1220            1225                1230

Val Pro Thr Ala Glu Asn Cys Gln Ser Cys Asn Cys Thr Pro Ser
    1235            1240                1245

Gly Ile Gln Cys Ala His Ser Leu Glu Ala Cys Thr Cys Thr Tyr
    1250            1255                1260

Glu Asp Arg Thr Tyr Ser Tyr Gln Asp Val Ile Tyr Asn Thr Thr
    1265            1270                1275

Asp Gly Leu Gly Ala Cys Leu Ile Ala Ile Cys Gly Ser Asn Gly
    1280            1285                1290

Thr Ile Ile Arg Lys Ala Val Ala Cys Pro Gly Thr Pro Ala Thr
    1295            1300                1305

Thr Pro Phe Thr Phe Thr Thr Ala Trp Val Pro His Ser Thr Thr
    1310            1315                1320

Ser Pro Ala Leu Pro Val Ser Thr Val Cys Val Arg Glu Val Cys
    1325            1330                1335

Arg Trp Ser Ser Trp Tyr Asn Gly His Arg Pro Glu Pro Gly Leu
    1340            1345                1350

Gly Gly Gly Asp Phe Glu Thr Phe Glu Asn Leu Arg Gln Arg Gly
    1355            1360                1365

Tyr Gln Val Cys Pro Val Leu Ala Asp Ile Glu Cys Arg Ala Ala
    1370            1375                1380

Gln Leu Pro Asp Met Pro Leu Glu Glu Leu Gly Gln Gln Val Asp
    1385            1390                1395

Cys Asp Arg Met Arg Gly Leu Met Cys Ala Asn Ser Gln Gln Ser
    1400            1405                1410

Pro Pro Leu Cys His Asp Tyr Glu Leu Arg Val Leu Cys Cys Glu
    1415            1420                1425
```

```
Tyr Val Pro Cys Gly Pro Ser Pro Ala Pro Gly Thr Ser Pro Gln
1430            1435                1440

Pro Ser Leu Ser Ala Ser Thr Glu Pro Ala Val Pro Thr Pro Thr
1445            1450                1455

Gln Thr Thr Ala Thr Glu Lys Thr Thr Leu Trp Val Thr Pro Ser
1460            1465                1470

Ile Arg Ser Thr Ala Ala Leu Thr Ser Gln Thr Gly Ser Ser Ser
1475            1480                1485

Gly Pro Val Thr Val Thr Pro Ser Ala Pro Gly Thr Thr Thr Cys
1490            1495                1500

Gln Pro Arg Cys Gln Trp Thr Glu Trp Phe Asp Glu Asp Tyr Pro
1505            1510                1515

Lys Ser Glu Gln Leu Gly Gly Asp Val Glu Ser Tyr Asp Lys Ile
1520            1525                1530

Arg Ala Ala Gly Gly His Leu Cys Gln Gln Pro Lys Asp Ile Glu
1535            1540                1545

Cys Gln Ala Glu Ser Phe Pro Asn Trp Thr Leu Ala Gln Val Gly
1550            1555                1560

Gln Lys Val His Cys Asp Val His Phe Gly Leu Val Cys Arg Asn
1565            1570                1575

Trp Glu Gln Glu Gly Val Phe Lys Met Cys Tyr Asn Tyr Arg Ile
1580            1585                1590

Arg Val Leu Cys Cys Ser Asp Asp His Cys Arg Gly Arg Ala Thr
1595            1600                1605

Thr Pro Pro Pro Thr Thr Glu Leu Glu Thr Ala Thr Thr Thr Thr
1610            1615                1620

Thr Gln Ala Leu Phe Ser Thr Pro Gln Pro Thr Ser Ser Pro Gly
1625            1630                1635

Leu Thr Arg Ala Pro Pro Ala Ser Thr Thr Ala Val Pro Thr Leu
1640            1645                1650

Ser Glu Gly Leu Thr Ser Pro Arg Tyr Thr Ser Thr Leu Gly Thr
1655            1660                1665

Ala Thr Thr Gly Gly Pro Thr Thr Pro Ala Gly Ser Thr Glu Pro
1670            1675                1680

Thr Val Pro Gly Val Ala Thr Ser Thr Leu Pro Thr Arg Ser Ala
1685            1690                1695

Leu Pro Gly Thr Thr Gly Ser Leu Gly Thr Trp Arg Pro Ser Gln
1700            1705                1710

Pro Pro Thr Leu Ala Pro Thr Thr Met Ala Thr Ser Arg Ala Arg
1715            1720                1725

Pro Thr Gly Thr Ala Ser Thr Ala Ser Lys Glu Pro Leu Thr Thr
1730            1735                1740

Ser Leu Ala Pro Thr Leu Thr Ser Glu Leu Ser Thr Ser Gln Ala
1745            1750                1755

Glu Thr Ser Thr Pro Arg Thr Glu Thr Thr Met Ser Pro Leu Thr
1760            1765                1770

Asn Thr Thr Thr Ser Gln Gly Thr Thr Arg Cys Gln Pro Lys Cys
1775            1780                1785

Glu Trp Thr Glu Trp Phe Asp Val Asp Phe Pro Thr Ser Gly Val
1790            1795                1800

Ala Gly Gly Asp Met Glu Thr Phe Glu Asn Ile Arg Ala Ala Gly
1805            1810                1815

Gly Lys Met Cys Trp Ala Pro Lys Ser Ile Glu Cys Arg Ala Glu
```

-continued

```
                1820                1825                1830
Asn Tyr Pro Glu Val Ser Ile Asp Gln Val Gly Gln Val Leu Thr
        1835                1840                1845
Cys Ser Leu Glu Thr Gly Leu Thr Cys Lys Asn Glu Asp Gln Thr
        1850                1855                1860
Gly Arg Phe Asn Met Cys Phe Asn Tyr Asn Val Arg Val Leu Cys
        1865                1870                1875
Cys Asp Asp Tyr Ser His Cys Pro Ser Thr Pro Ala Thr Ser Ser
        1880                1885                1890
Thr Ala Thr Pro Ser Ser Thr Pro Gly Thr Thr Trp Ile Leu Thr
        1895                1900                1905
Lys Pro Thr Thr Thr Ala Thr Thr Ala Ser Thr Gly Ser Thr
        1910                1915                1920
Ala Thr Pro Thr Ser Thr Leu Arg Thr Ala Pro Pro Lys Val
        1925                1930                1935
Leu Thr Thr Thr Ala Thr Thr Pro Thr Val Thr Ser Ser Lys Ala
        1940                1945                1950
Thr Pro Ser Ser Ser Pro Gly Thr Ala Thr Ala Leu Pro Ala Leu
        1955                1960                1965
Arg Ser Thr Ala Thr Thr Pro Thr Ala Thr Ser Val Thr Pro Ile
        1970                1975                1980
Pro Ser Ser Ser Leu Gly Thr Thr Trp Thr Arg Leu Ser Gln Thr
        1985                1990                1995
Thr Thr Pro Thr Ala Thr Met Ser Thr Ala Thr Pro Ser Ser Thr
        2000                2005                2010
Pro Glu Thr Ala His Thr Ser Thr Val Leu Thr Ala Thr Ala Thr
        2015                2020                2025
Thr Thr Gly Ala Thr Gly Ser Val Ala Thr Pro Ser Ser Thr Pro
        2030                2035                2040
Gly Thr Ala His Thr Thr Lys Val Pro Thr Thr Thr Thr Gly
        2045                2050                2055
Phe Thr Ala Thr Pro Ser Ser Pro Gly Thr Ala Leu Thr Pro
        2060                2065                2070
Pro Val Trp Ile Ser Thr Thr Thr Thr Pro Thr Thr Arg Gly Ser
        2075                2080                2085
Thr Val Thr Pro Ser Ser Ile Pro Gly Thr Thr His Thr Ala Thr
        2090                2095                2100
Val Leu Thr Thr Thr Thr Thr Thr Val Ala Thr Gly Ser Met Ala
        2105                2110                2115
Thr Pro Ser Ser Ser Thr Gln Thr Ser Gly Thr Pro Pro Ser Leu
        2120                2125                2130
Thr Thr Thr Ala Thr Thr Ile Thr Ala Thr Gly Ser Thr Thr Asn
        2135                2140                2145
Pro Ser Ser Thr Pro Gly Thr Pro Ile Pro Pro Val Leu Thr
        2150                2155                2160
Thr Thr Ala Thr Thr Pro Ala Ala Thr Ser Asn Thr Val Thr Pro
        2165                2170                2175
Ser Ser Ala Leu Gly Thr Thr His Thr Pro Pro Val Pro Asn Thr
        2180                2185                2190
Met Ala Thr Thr His Gly Arg Ser Leu Pro Pro Ser Ser Pro His
        2195                2200                2205
Thr Val Arg Thr Ala Trp Thr Ser Ala Thr Ser Gly Ile Leu Gly
        2210                2215                2220
```

-continued

```
Thr Thr His Ile Thr Glu Pro Ser Thr Val Thr Ser His Thr Leu
2225                2230                2235

Ala Ala Thr Thr Gly Thr Thr Gln His Ser Thr Pro Ala Leu Ser
2240                2245                2250

Ser Pro His Pro Ser Ser Arg Thr Thr Glu Ser Pro Pro Ser Pro
2255                2260                2265

Gly Thr Thr Thr Pro Gly His Thr Thr Ala Thr Ser Arg Thr Thr
2270                2275                2280

Ala Thr Ala Thr Pro Ser Lys Thr Arg Thr Ser Thr Leu Leu Pro
2285                2290                2295

Ser Ser Pro Thr Ser Ala Pro Ile Thr Thr Val Val Thr Met Gly
2300                2305                2310

Cys Glu Pro Gln Cys Ala Trp Ser Glu Trp Leu Asp Tyr Ser Tyr
2315                2320                2325

Pro Met Pro Gly Pro Ser Gly Gly Asp Phe Asp Thr Tyr Ser Asn
2330                2335                2340

Ile Arg Ala Ala Gly Gly Ala Val Cys Glu Gln Pro Leu Gly Leu
2345                2350                2355

Glu Cys Arg Ala Gln Ala Gln Pro Gly Val Pro Leu Arg Glu Leu
2360                2365                2370

Gly Gln Val Val Glu Cys Ser Leu Asp Phe Gly Leu Val Cys Arg
2375                2380                2385

Asn Arg Glu Gln Val Gly Lys Phe Lys Met Cys Phe Asn Tyr Glu
2390                2395                2400

Ile Arg Val Phe Cys Cys Asn Tyr Gly His Cys Pro Ser Thr Pro
2405                2410                2415

Ala Thr Ser Ser Thr Ala Met Pro Ser Ser Thr Pro Gly Thr Thr
2420                2425                2430

Trp Ile Leu Thr Glu Leu Thr Thr Thr Ala Thr Thr Glu Ser
2435                2440                2445

Thr Gly Ser Thr Ala Thr Pro Ser Ser Thr Pro Gly Thr Thr Trp
2450                2455                2460

Ile Leu Thr Glu Pro Ser Thr Thr Ala Thr Val Thr Val Pro Thr
2465                2470                2475

Gly Ser Thr Ala Thr Ala Ser Ser Thr Gln Ala Thr Ala Gly Thr
2480                2485                2490

Pro His Val Ser Thr Thr Ala Thr Thr Pro Thr Val Thr Ser Ser
2495                2500                2505

Lys Ala Thr Pro Phe Ser Ser Pro Gly Thr Ala Thr Ala Leu Pro
2510                2515                2520

Ala Leu Arg Ser Thr Ala Thr Thr Pro Thr Ala Thr Ser Phe Thr
2525                2530                2535

Ala Ile Pro Ser Ser Ser Leu Gly Thr Thr Trp Thr Arg Leu Ser
2540                2545                2550

Gln Thr Thr Thr Pro Thr Ala Thr Met Ser Thr Ala Thr Pro Ser
2555                2560                2565

Ser Thr Pro Glu Thr Val His Thr Ser Thr Val Leu Thr Thr Thr
2570                2575                2580

Ala Thr Thr Thr Gly Ala Thr Gly Ser Val Ala Thr Pro Ser Ser
2585                2590                2595

Thr Pro Gly Thr Ala His Thr Thr Lys Val Leu Thr Thr Thr Thr
2600                2605                2610
```

-continued

```
Thr Gly Phe Thr Ala Thr Pro Ser Ser Ser Pro Gly Thr Ala Arg
    2615                2620                2625

Thr Leu Pro Val Trp Ile Ser Thr Thr Thr Pro Thr Thr Arg
    2630                2635                2640

Gly Ser Thr Val Thr Pro Ser Ser Ile Pro Gly Thr Thr His Thr
    2645                2650                2655

Pro Thr Val Leu Thr Thr Thr Thr Thr Val Ala Thr Gly Ser
    2660                2665                2670

Met Ala Thr Pro Ser Ser Ser Thr Gln Thr Ser Gly Thr Pro Pro
    2675                2680                2685

Ser Leu Thr Thr Thr Ala Thr Thr Ile Thr Ala Thr Gly Ser Thr
    2690                2695                2700

Thr Asn Pro Ser Ser Thr Pro Gly Thr Thr Pro Ile Pro Pro Val
    2705                2710                2715

Leu Thr Thr Thr Ala Thr Thr Pro Ala Ala Thr Ser Ser Thr Val
    2720                2725                2730

Thr Pro Ser Ser Ala Leu Gly Thr Thr His Thr Pro Pro Val Pro
    2735                2740                2745

Asn Thr Thr Ala Thr Thr His Gly Arg Ser Leu Ser Pro Ser Ser
    2750                2755                2760

Pro His Thr Val Arg Thr Ala Trp Thr Ser Ala Thr Ser Gly Thr
    2765                2770                2775

Leu Gly Thr Thr His Ile Thr Glu Pro Ser Thr Gly Thr Ser His
    2780                2785                2790

Thr Pro Ala Ala Thr Thr Gly Thr Thr Gln His Ser Thr Pro Ala
    2795                2800                2805

Leu Ser Ser Pro His Pro Ser Ser Arg Thr Thr Glu Ser Pro Pro
    2810                2815                2820

Ser Pro Gly Thr Thr Thr Pro Gly His Thr Arg Ala Thr Ser Arg
    2825                2830                2835

Thr Thr Ala Thr Ala Thr Pro Ser Lys Thr Arg Thr Ser Thr Leu
    2840                2845                2850

Leu Pro Ser Ser Pro Thr Ser Ala Pro Ile Thr Thr Val Val Thr
    2855                2860                2865

Met Gly Cys Glu Pro Gln Cys Ala Trp Ser Glu Trp Leu Asp Tyr
    2870                2875                2880

Ser Tyr Pro Met Pro Gly Pro Ser Gly Gly Asp Phe Asp Thr Tyr
    2885                2890                2895

Ser Asn Ile Arg Ala Ala Gly Gly Ala Val Cys Glu Gln Pro Leu
    2900                2905                2910

Gly Leu Glu Cys Arg Ala Gln Ala Gln Pro Gly Val Pro Leu Arg
    2915                2920                2925

Glu Leu Gly Gln Val Val Glu Cys Ser Leu Asp Phe Gly Leu Val
    2930                2935                2940

Cys Arg Asn Arg Glu Gln Val Gly Lys Phe Lys Met Cys Phe Asn
    2945                2950                2955

Tyr Glu Ile Arg Val Phe Cys Cys Asn Tyr Gly His Cys Pro Ser
    2960                2965                2970

Thr Pro Ala Thr Ser Ser Thr Ala Thr Pro Ser Ser Thr Pro Gly
    2975                2980                2985

Thr Thr Trp Ile Leu Thr Glu Gln Thr Thr Ala Ala Thr Thr Thr
    2990                2995                3000

Ala Thr Thr Gly Ser Thr Ala Ile Pro Ser Ser Thr Pro Gly Thr
```

-continued

```
              3005                3010                3015

Ala Pro Pro Pro Lys Val Leu Thr Ser Thr Ala Thr Thr Pro Thr
    3020                3025                3030

Ala Thr Ser Ser Lys Ala Thr Ser Ser Ser Pro Arg Thr Ala
    3035                3040                3045

Thr Thr Leu Pro Val Leu Thr Ser Thr Ala Thr Lys Ser Thr Ala
    3050                3055                3060

Thr Ser Phe Thr Pro Ile Pro Ser Phe Thr Leu Gly Thr Thr Gly
    3065                3070                3075

Thr Leu Pro Glu Gln Thr Thr Thr Pro Met Ala Thr Met Ser Thr
    3080                3085                3090

Ile His Pro Ser Ser Thr Pro Glu Thr Thr His Thr Ser Thr Val
    3095                3100                3105

Leu Thr Thr Lys Ala Thr Thr Thr Arg Ala Thr Ser Ser Met Ser
    3110                3115                3120

Thr Pro Ser Ser Thr Pro Gly Thr Thr Trp Ile Leu Thr Glu Leu
    3125                3130                3135

Thr Thr Ala Ala Thr Thr Thr Ala Ala Thr Gly Pro Thr Ala Thr
    3140                3145                3150

Pro Ser Ser Thr Pro Gly Thr Thr Trp Ile Leu Thr Glu Pro Ser
    3155                3160                3165

Thr Thr Ala Thr Val Thr Val Pro Thr Gly Ser Thr Ala Thr Ala
    3170                3175                3180

Ser Ser Thr Arg Ala Thr Ala Gly Thr Leu Lys Val Leu Thr Ser
    3185                3190                3195

Thr Ala Thr Thr Pro Thr Val Ile Ser Ser Arg Ala Thr Pro Ser
    3200                3205                3210

Ser Ser Pro Gly Thr Ala Thr Ala Leu Pro Ala Leu Arg Ser Thr
    3215                3220                3225

Ala Thr Thr Pro Thr Ala Thr Ser Val Thr Ala Ile Pro Ser Ser
    3230                3235                3240

Ser Leu Gly Thr Ala Trp Thr Arg Leu Ser Gln Thr Thr Thr Pro
    3245                3250                3255

Thr Ala Thr Met Ser Thr Ala Thr Pro Ser Ser Thr Pro Glu Thr
    3260                3265                3270

Val His Thr Ser Thr Val Leu Thr Thr Thr Thr Thr Thr Thr Arg
    3275                3280                3285

Ala Thr Gly Ser Val Ala Thr Pro Ser Ser Thr Pro Gly Thr Ala
    3290                3295                3300

His Thr Thr Lys Val Pro Thr Thr Thr Thr Thr Gly Phe Thr Ala
    3305                3310                3315

Thr Pro Ser Ser Ser Pro Gly Thr Ala Leu Thr Pro Pro Val Trp
    3320                3325                3330

Ile Ser Thr Thr Thr Pro Thr Thr Arg Gly Ser Thr Val Thr
    3335                3340                3345

Pro Ser Ser Ile Pro Gly Thr His Thr Ala Thr Val Leu Thr
    3350                3355                3360

Thr Thr Thr Thr Thr Val Ala Thr Gly Ser Met Ala Thr Pro Ser
    3365                3370                3375

Ser Ser Thr Gln Thr Ser Gly Thr Pro Pro Ser Leu Thr Thr Thr
    3380                3385                3390

Ala Thr Thr Ile Thr Ala Thr Gly Ser Thr Thr Asn Pro Ser Ser
    3395                3400                3405
```

-continued

```
Thr Pro Gly Thr Thr Pro Ile Pro Pro Val Leu Thr  Thr Thr Ala
    3410                3415                3420

Thr Thr Pro Ala Ala Thr Ser Ser Thr Val Thr Pro  Ser Ser Ala
    3425                3430                3435

Leu Gly Thr Thr His Thr Pro Pro Val Pro Asn Thr  Thr Ala Thr
    3440                3445                3450

Thr His Gly Arg Ser Leu Pro Pro Ser Ser Pro His  Thr Val Arg
    3455                3460                3465

Thr Ala Trp Thr Ser Ala Thr Ser Gly Ile Leu Gly  Thr Thr His
    3470                3475                3480

Ile Thr Glu Pro Ser Thr Val Thr Ser His Thr Pro  Ala Ala Thr
    3485                3490                3495

Thr Ser Thr Thr Gln His Ser Thr Pro Ala Leu Ser  Ser Pro His
    3500                3505                3510

Pro Ser Ser Arg Thr Thr Glu Ser Pro Pro Ser Pro  Gly Thr Thr
    3515                3520                3525

Thr Pro Gly His Thr Arg Gly Thr Ser Arg Thr Thr  Ala Thr Ala
    3530                3535                3540

Thr Pro Ser Lys Thr Arg Thr Ser Thr Leu Leu Pro  Ser Ser Pro
    3545                3550                3555

Thr Ser Ala Pro Ile Thr Thr Val Val Thr Thr Gly  Cys Glu Pro
    3560                3565                3570

Gln Cys Ala Trp Ser Glu Trp Leu Asp Tyr Ser Tyr  Pro Met Pro
    3575                3580                3585

Gly Pro Ser Gly Gly Asp Phe Asp Thr Tyr Ser Asn  Ile Arg Ala
    3590                3595                3600

Ala Gly Gly Ala Val Cys Glu Gln Pro Leu Gly Leu  Glu Cys Arg
    3605                3610                3615

Ala Gln Ala Gln Pro Gly Val Pro Leu Arg Glu Leu  Gly Gln Val
    3620                3625                3630

Val Glu Cys Ser Leu Asp Phe Gly Leu Val Cys Arg  Asn Arg Glu
    3635                3640                3645

Gln Val Gly Lys Phe Lys Met Cys Phe Asn Tyr Glu  Ile Arg Val
    3650                3655                3660

Phe Cys Cys Asn Tyr Gly His Cys Pro Ser Thr Pro  Ala Thr Ser
    3665                3670                3675

Ser Thr Ala Thr Pro Ser Ser Thr Pro Gly Thr Thr  Trp Ile Leu
    3680                3685                3690

Thr Lys Leu Thr Thr Thr Ala Thr Thr Thr Glu Ser  Thr Gly Ser
    3695                3700                3705

Thr Ala Thr Pro Ser Ser Thr Pro Gly Thr Thr Trp  Ile Leu Thr
    3710                3715                3720

Glu Pro Ser Thr Thr Ala Thr Val Thr Val Pro Thr  Gly Ser Thr
    3725                3730                3735

Ala Thr Ala Ser Ser Thr Gln Ala Thr Ala Gly Thr  Pro His Val
    3740                3745                3750

Ser Thr Thr Ala Thr Thr Pro Thr Val Thr Ser Ser  Lys Ala Thr
    3755                3760                3765

Pro Phe Ser Ser Pro Gly Thr Ala Thr Ala Leu Pro  Ala Leu Arg
    3770                3775                3780

Ser Thr Ala Thr Thr Pro Thr Ala Thr Ser Phe Thr  Ala Ile Pro
    3785                3790                3795
```

```
Ser Ser Ser Leu Gly Thr Thr Trp Thr Arg Leu Ser Gln Thr Thr
    3800                3805                3810

Thr Pro Thr Ala Thr Met Ser Thr Ala Thr Pro Ser Ser Thr Pro
    3815                3820                3825

Glu Thr Ala His Thr Ser Thr Val Leu Thr Thr Thr Ala Thr Thr
    3830                3835                3840

Thr Arg Ala Thr Gly Ser Val Ala Thr Pro Ser Ser Thr Pro Gly
    3845                3850                3855

Thr Ala His Thr Thr Lys Val Pro Thr Thr Thr Thr Thr Gly Phe
    3860                3865                3870

Thr Val Thr Pro Ser Ser Ser Pro Gly Thr Ala Arg Thr Pro Pro
    3875                3880                3885

Val Trp Ile Ser Thr Thr Thr Thr Pro Thr Thr Ser Gly Ser Thr
    3890                3895                3900

Val Thr Pro Ser Ser Val Pro Gly Thr Thr His Thr Pro Thr Val
    3905                3910                3915

Leu Thr Thr Thr Thr Thr Thr Val Ala Thr Gly Ser Met Ala Thr
    3920                3925                3930

Pro Ser Ser Ser Thr Gln Thr Ser Gly Thr Pro Pro Ser Leu Ile
    3935                3940                3945

Thr Thr Ala Thr Thr Ile Thr Ala Thr Gly Ser Thr Thr Asn Pro
    3950                3955                3960

Ser Ser Thr Pro Gly Thr Thr Pro Ile Pro Pro Val Leu Thr Thr
    3965                3970                3975

Thr Ala Thr Thr Pro Ala Ala Thr Ser Ser Thr Val Thr Pro Ser
    3980                3985                3990

Ser Ala Leu Gly Thr Thr His Thr Pro Pro Val Pro Asn Thr Thr
    3995                4000                4005

Ala Thr Thr His Gly Arg Ser Leu Ser Pro Ser Ser Pro His Thr
    4010                4015                4020

Val Arg Thr Ala Trp Thr Ser Ala Thr Ser Gly Thr Leu Gly Thr
    4025                4030                4035

Thr His Ile Thr Glu Pro Ser Thr Gly Thr Ser His Thr Pro Ala
    4040                4045                4050

Ala Thr Thr Gly Thr Thr Gln His Ser Thr Pro Ala Leu Ser Ser
    4055                4060                4065

Pro His Pro Ser Ser Arg Thr Thr Glu Ser Pro Pro Ser Pro Gly
    4070                4075                4080

Thr Thr Thr Pro Gly His Thr Thr Ala Thr Ser Arg Thr Thr Ala
    4085                4090                4095

Thr Ala Thr Pro Ser Lys Thr Arg Thr Ser Thr Leu Leu Pro Ser
    4100                4105                4110

Ser Pro Thr Ser Ala Pro Ile Thr Thr Val Val Thr Thr Gly Cys
    4115                4120                4125

Glu Pro Gln Cys Ala Trp Ser Glu Trp Leu Asp Tyr Ser Tyr Pro
    4130                4135                4140

Met Pro Gly Pro Ser Gly Gly Asp Phe Asp Thr Tyr Ser Asn Ile
    4145                4150                4155

Arg Ala Ala Gly Gly Ala Val Cys Glu Gln Pro Leu Gly Leu Glu
    4160                4165                4170

Cys Arg Ala Gln Ala Gln Pro Gly Val Pro Leu Gly Glu Leu Gly
    4175                4180                4185

Gln Val Val Glu Cys Ser Leu Asp Phe Gly Leu Val Cys Arg Asn
```

-continued

```
            4190           4195              4200

Arg Glu Gln Val Gly Lys Phe Lys Met Cys Phe Asn Tyr Glu Ile
    4205            4210             4215

Arg Val Phe Cys Cys Asn Tyr Gly His Cys Pro Ser Thr Pro Ala
    4220            4225             4230

Thr Ser Ser Thr Ala Met Pro Ser Ser Thr Pro Gly Thr Thr Trp
    4235            4240             4245

Ile Leu Thr Glu Leu Thr Thr Thr Ala Thr Thr Thr Ala Ser Thr
    4250            4255             4260

Gly Ser Thr Ala Thr Pro Ser Ser Thr Pro Gly Thr Ala Pro Pro
    4265            4270             4275

Pro Lys Val Leu Thr Ser Pro Ala Thr Thr Pro Thr Ala Thr Ser
    4280            4285             4290

Ser Lys Ala Thr Ser Ser Ser Ser Pro Arg Thr Ala Thr Thr Leu
    4295            4300             4305

Pro Val Leu Thr Ser Thr Ala Thr Lys Ser Thr Ala Thr Ser Val
    4310            4315             4320

Thr Pro Ile Pro Ser Ser Thr Leu Gly Thr Thr Gly Thr Leu Pro
    4325            4330             4335

Glu Gln Thr Thr Thr Pro Val Ala Thr Met Ser Thr Ile His Pro
    4340            4345             4350

Ser Ser Thr Pro Glu Thr Thr His Thr Ser Thr Val Leu Thr Thr
    4355            4360             4365

Lys Ala Thr Thr Thr Arg Ala Thr Ser Ser Thr Ser Thr Pro Ser
    4370            4375             4380

Ser Thr Pro Gly Thr Thr Trp Ile Leu Thr Glu Leu Thr Thr Ala
    4385            4390             4395

Ala Thr Thr Thr Ala Ala Thr Gly Pro Thr Ala Thr Pro Ser Ser
    4400            4405             4410

Thr Pro Gly Thr Thr Trp Ile Leu Thr Glu Leu Thr Thr Thr Ala
    4415            4420             4425

Thr Thr Thr Ala Ser Thr Gly Ser Thr Ala Thr Pro Ser Ser Thr
    4430            4435             4440

Pro Gly Thr Thr Trp Ile Leu Thr Glu Pro Ser Thr Thr Ala Thr
    4445            4450             4455

Val Thr Val Pro Thr Gly Ser Thr Ala Thr Ala Ser Ser Thr Gln
    4460            4465             4470

Ala Thr Ala Gly Thr Pro His Val Ser Thr Thr Ala Thr Thr Pro
    4475            4480             4485

Thr Val Thr Ser Ser Lys Ala Thr Pro Ser Ser Ser Pro Gly Thr
    4490            4495             4500

Ala Thr Ala Leu Pro Ala Leu Arg Ser Thr Ala Thr Thr Pro Thr
    4505            4510             4515

Ala Thr Ser Phe Thr Ala Ile Pro Ser Ser Ser Leu Gly Thr Thr
    4520            4525             4530

Trp Thr Arg Leu Ser Gln Thr Thr Thr Pro Thr Ala Thr Met Ser
    4535            4540             4545

Thr Ala Thr Pro Ser Ser Thr Pro Glu Thr Val His Thr Ser Thr
    4550            4555             4560

Val Leu Thr Ala Thr Ala Thr Thr Gly Ala Thr Gly Ser Val
    4565            4570             4575

Ala Thr Pro Ser Ser Thr Pro Gly Thr Ala His Thr Thr Lys Val
    4580            4585             4590
```

```
Pro Thr Thr Thr Thr Thr Gly Phe Thr Ala Thr Pro Ser Ser Ser
    4595                4600                4605

Pro Gly Thr Ala Leu Thr Pro Pro Val Trp Ile Ser Thr Thr Thr
    4610                4615                4620

Thr Pro Thr Thr Thr Thr Pro Thr Thr Ser Gly Ser Thr Val Thr
    4625                4630                4635

Pro Ser Ser Ile Pro Gly Thr Thr His Thr Ala Arg Val Leu Thr
    4640                4645                4650

Thr Thr Thr Thr Thr Val Ala Thr Gly Ser Met Ala Thr Pro Ser
    4655                4660                4665

Ser Ser Thr Gln Thr Ser Gly Thr Pro Pro Ser Leu Thr Thr Thr
    4670                4675                4680

Ala Thr Thr Ile Thr Ala Thr Gly Ser Thr Thr Asn Pro Ser Ser
    4685                4690                4695

Thr Pro Gly Thr Thr Pro Ile Thr Pro Val Leu Thr Ser Thr Ala
    4700                4705                4710

Thr Thr Pro Ala Ala Thr Ser Ser Lys Ala Thr Ser Ser Ser Ser
    4715                4720                4725

Pro Arg Thr Ala Thr Thr Leu Pro Val Leu Thr Ser Thr Ala Thr
    4730                4735                4740

Lys Ser Thr Ala Thr Ser Phe Thr Pro Ile Pro Ser Ser Thr Leu
    4745                4750                4755

Trp Thr Thr Trp Thr Val Pro Ala Gln Thr Thr Thr Pro Met Ser
    4760                4765                4770

Thr Met Ser Thr Ile His Thr Ser Ser Thr Pro Glu Thr Thr His
    4775                4780                4785

Thr Ser Thr Val Leu Thr Thr Thr Ala Thr Met Thr Arg Ala Thr
    4790                4795                4800

Asn Ser Thr Ala Thr Pro Ser Ser Thr Leu Gly Thr Thr Arg Ile
    4805                4810                4815

Leu Thr Glu Leu Thr Thr Thr Ala Thr Thr Ala Ala Thr Gly
    4820                4825                4830

Ser Thr Ala Thr Leu Ser Ser Thr Pro Gly Thr Thr Trp Ile Leu
    4835                4840                4845

Thr Glu Pro Ser Thr Ile Ala Thr Val Met Val Pro Thr Gly Ser
    4850                4855                4860

Thr Ala Thr Ala Ser Ser Thr Leu Gly Thr Ala His Thr Pro Lys
    4865                4870                4875

Val Val Thr Thr Met Ala Thr Met Pro Thr Ala Thr Ala Ser Thr
    4880                4885                4890

Val Pro Ser Ser Ser Thr Val Gly Thr Thr Arg Thr Pro Ala Val
    4895                4900                4905

Leu Pro Ser Ser Leu Pro Thr Phe Ser Val Ser Thr Val Ser Ser
    4910                4915                4920

Ser Val Leu Thr Thr Leu Arg Pro Thr Gly Phe Pro Ser Ser His
    4925                4930                4935

Phe Ser Thr Pro Cys Phe Cys Arg Ala Phe Gly Gln Phe Phe Ser
    4940                4945                4950

Pro Gly Glu Val Ile Tyr Asn Lys Thr Asp Arg Ala Gly Cys His
    4955                4960                4965

Phe Tyr Ala Val Cys Asn Gln His Cys Asp Ile Asp Arg Phe Gln
    4970                4975                4980
```

-continued

```
Gly Ala Cys Pro Thr Ser Pro Pro Val Ser Ser Ala Pro Leu
         4985                4990            4995

Ser Ser Pro Ser Pro Ala Pro Gly Cys Asp Asn Ala Ile Pro Leu
    5000            5005                5010

Arg Gln Val Asn Glu Thr Trp Thr Leu Glu Asn Cys Thr Val Ala
    5015            5020                5025

Arg Cys Val Gly Asp Asn Arg Val Val Leu Leu Asp Pro Lys Pro
    5030            5035                5040

Val Ala Asn Val Thr Cys Val Asn Lys His Leu Pro Ile Lys Val
    5045            5050                5055

Ser Asp Pro Ser Gln Pro Cys Asp Phe His Tyr Glu Cys Glu Cys
    5060            5065                5070

Ile Cys Ser Met Trp Gly Gly Ser His Tyr Ser Thr Phe Asp Gly
    5075            5080                5085

Thr Ser Tyr Thr Phe Arg Gly Asn Cys Thr Tyr Val Leu Met Arg
    5090            5095                5100

Glu Ile His Ala Arg Phe Gly Asn Leu Ser Leu Tyr Leu Asp Asn
    5105            5110                5115

His Tyr Cys Thr Ala Ser Ala Thr Ala Ala Ala Arg Cys Pro
    5120            5125                5130

Arg Ala Leu Ser Ile His Tyr Lys Ser Met Asp Ile Val Leu Thr
    5135            5140                5145

Val Thr Met Val His Gly Lys Glu Glu Gly Leu Ile Leu Phe Asp
    5150            5155                5160

Gln Ile Pro Val Ser Ser Gly Phe Ser Lys Asn Gly Val Leu Val
    5165            5170                5175

Ser Val Leu Gly Thr Thr Thr Met Arg Val Asp Ile Pro Ala Leu
    5180            5185                5190

Gly Val Ser Val Thr Phe Asn Gly Gln Val Phe Gln Ala Arg Leu
    5195            5200                5205

Pro Tyr Ser Leu Phe His Asn Asn Thr Glu Gly Gln Cys Gly Thr
    5210            5215                5220

Cys Thr Asn Asn Gln Arg Asp Asp Cys Leu Gln Arg Asp Gly Thr
    5225            5230                5235

Thr Ala Ala Ser Cys Lys Asp Met Ala Lys Thr Trp Leu Val Pro
    5240            5245                5250

Asp Ser Arg Lys Asp Gly Cys Trp Ala Pro Thr Gly Thr Pro Pro
    5255            5260                5265

Thr Ala Ser Pro Ala Ala Pro Val Ser Ser Thr Pro Thr Pro Thr
    5270            5275                5280

Pro Cys Pro Pro Gln Pro Leu Cys Asp Leu Met Leu Ser Gln Val
    5285            5290                5295

Phe Ala Glu Cys His Asn Leu Val Pro Pro Gly Pro Phe Phe Asn
    5300            5305                5310

Ala Cys Ile Ser Asp His Cys Arg Gly Arg Leu Glu Val Pro Cys
    5315            5320                5325

Gln Ser Leu Glu Ala Tyr Ala Glu Leu Cys Arg Ala Arg Gly Val
    5330            5335                5340

Cys Ser Asp Trp Arg Gly Ala Thr Gly Gly Leu Cys Asp Leu Thr
    5345            5350                5355

Cys Pro Pro Thr Lys Val Tyr Lys Pro Cys Gly Pro Ile Gln Pro
    5360            5365                5370

Ala Thr Cys Asn Ser Arg Asn Gln Ser Pro Gln Leu Glu Gly Met
```

```
            5375                5380                5385

Ala Glu Gly Cys Phe Cys Pro Glu Asp Gln Ile Leu Phe Asn Ala
    5390                5395                5400

His Met Gly Ile Cys Val Gln Ala Cys Pro Cys Val Gly Pro Asp
    5405                5410                5415

Gly Phe Pro Lys Phe Pro Gly Glu Arg Trp Val Ser Asn Cys Gln
    5420                5425                5430

Ser Cys Val Cys Asp Glu Gly Ser Val Ser Val Gln Cys Lys Pro
    5435                5440                5445

Leu Pro Cys Asp Ala Gln Gly Gln Pro Pro Cys Asn Arg Pro
    5450                5455                5460

Gly Phe Val Thr Val Thr Arg Pro Arg Ala Glu Asn Pro Cys Cys
    5465                5470                5475

Pro Glu Thr Val Cys Val Cys Asn Thr Thr Cys Pro Gln Ser
    5480                5485                5490

Leu Pro Val Cys Pro Pro Gly Gln Glu Ser Ile Cys Thr Gln Glu
    5495                5500                5505

Glu Gly Asp Cys Cys Pro Thr Phe Arg Cys Arg Pro Gln Leu Cys
    5510                5515                5520

Ser Tyr Asn Gly Thr Phe Tyr Gly Val Gly Ala Thr Phe Pro Gly
    5525                5530                5535

Ala Leu Pro Cys His Met Cys Thr Cys Leu Ser Gly Asp Thr Gln
    5540                5545                5550

Asp Pro Thr Val Gln Cys Gln Glu Asp Ala Cys Asn Asn Thr Thr
    5555                5560                5565

Cys Pro Gln Gly Phe Glu Tyr Lys Arg Val Ala Gly Gln Cys Cys
    5570                5575                5580

Gly Glu Cys Val Gln Thr Ala Cys Leu Thr Pro Asp Gly Gln Pro
    5585                5590                5595

Val Gln Leu Asn Glu Thr Trp Val Asn Ser His Val Asp Asn Cys
    5600                5605                5610

Thr Val Tyr Leu Cys Glu Ala Glu Gly Gly Val His Leu Leu Thr
    5615                5620                5625

Pro Gln Pro Ala Ser Cys Pro Asp Val Ser Ser Cys Arg Gly Ser
    5630                5635                5640

Leu Arg Lys Thr Gly Cys Cys Tyr Ser Cys Glu Glu Asp Ser Cys
    5645                5650                5655

Gln Val Arg Ile Asn Thr Thr Ile Leu Trp His Gln Gly Cys Glu
    5660                5665                5670

Thr Glu Val Asn Ile Thr Phe Cys Glu Gly Ser Cys Pro Gly Ala
    5675                5680                5685

Ser Lys Tyr Ser Ala Glu Ala Gln Ala Met Gln His Gln Cys Thr
    5690                5695                5700

Cys Cys Gln Glu Arg Arg Val His Glu Glu Thr Val Pro Leu His
    5705                5710                5715

Cys Pro Asn Gly Ser Ala Ile Leu His Thr Tyr Thr His Val Asp
    5720                5725                5730

Glu Cys Gly Cys Thr Pro Phe Cys Val Pro Ala Pro Met Ala Pro
    5735                5740                5745

Pro His Thr Arg Gly Phe Pro Ala Gln Glu Ala Thr Ala Val
    5750                5755                5760
```

<210> SEQ ID NO 7

```
<211> LENGTH: 19
<212> TYPE: DNA
<213> ORGANISM: Artificial Sequence
<220> FEATURE:
<223> OTHER INFORMATION: fITS7 Primer

<400> SEQUENCE: 7
gtgartcatc gaatctttg                                                 19

<210> SEQ ID NO 8
<211> LENGTH: 20
<212> TYPE: DNA
<213> ORGANISM: Artificial Sequence
<220> FEATURE:
<223> OTHER INFORMATION: ITS4 Primer

<400> SEQUENCE: 8
tcctccgctt attgatatgc                                                20
```